US005830713A

United States Patent [19]

Ferrari et al.

[11] Patent Number: 5,830,713
[45] Date of Patent: *Nov. 3, 1998

[54] METHODS FOR PREPARING SYNTHETIC REPETITIVE DNA

[75] Inventors: Franco A. Ferrari, La Jolla; Joseph Cappello, San Diego; John W. Crissman, San Diego; Mary A. Dorman, San Diego, all of Calif.

[73] Assignee: Protein Polymer Technologies, Inc., San Diego, Calif.

[*] Notice: The term of this patent shall not extend beyond the expiration date of Pat. No. 5,641,648.

[21] Appl. No.: 707,237

[22] Filed: Sep. 3, 1996

Related U.S. Application Data

[63] Continuation-in-part of Ser. No. 175,155, Dec. 29, 1993, Pat. No. 5,641,648, which is a continuation-in-part of Ser. No. 53,049, Apr. 22, 1993, abandoned, which is a continuation-in-part of Ser. No. 609,716, Nov. 6, 1990, Pat. No. 5,514,581, which is a continuation-in-part of Ser. No. 269,429, Nov. 9, 1988, abandoned, which is a continuation-in-part of Ser. No. 114,618, Oct. 19, 1987, Pat. No. 5,243,038, which is a continuation-in-part of Ser. No. 927,258, Nov. 4, 1986, abandoned.

[51] Int. Cl.$^6$ .......................... C12P 19/34; C12P 21/02; C07H 21/04; C12Q 1/68
[52] U.S. Cl. .......................... 435/91.1; 435/6; 435/69.1; 435/252.8; 435/320.1; 536/23.1; 536/24.1; 536/25.3
[58] Field of Search .......................... 435/6, 172.3, 69.1, 435/91.1, 71.2, 172.1, 320.1, 252.8; 536/23.1, 24.1, 25.3

[56] References Cited

U.S. PATENT DOCUMENTS

| | | |
|---|---|---|
| 5,023,171 | 6/1991 | Ho et al. . |
| 5,089,406 | 2/1992 | Williams et al. .................. 435/172.3 |
| 5,641,648 | 6/1997 | Ferrari et al. ...................... 435/69.1 |

FOREIGN PATENT DOCUMENTS

| | | |
|---|---|---|
| 88/03533 | 5/1988 | WIPO . |
| 88/05082 | 7/1988 | WIPO . |
| 90/05177 | 5/1990 | WIPO . |
| 93/03151 | 2/1993 | WIPO . |
| 93/10154 | 5/1993 | WIPO . |
| 94/12632 | 6/1994 | WIPO . |
| 96/04403 | 2/1996 | WIPO . |
| 96/05296 | 2/1996 | WIPO . |

OTHER PUBLICATIONS

Wosnick et al., "Total Chemical Sysnthesis and Expression in *Escherichia coli* of a maize glutathione–transferase (GST) gene," *Gene*, 76:153–160 (1989).
Newton and Graham, "4. Klonierung von PCR Produkten," *PCR*, Spektrum Akademischer Verlag:Heidelberg, pp. 63–70 (1994).
White et al., "Concatemer Chain Reaction: A Taq DNA Polymerase–Mediated Mechanism for Generating Long Tandemly Repetitive DNA Sequences," *Analytical Biochemistry*, 199:184–190 (1991).
Rudert and Trucco, "DNA Polymers of Protein Binding Sequences Generated by PCR," *Nucleic Acids Research*, 18(21):6460 (1990).
Ijdo et al., "Improved Telomere Detection Using a Telomere Repeat Probe (TTAGGG)$_n$ generated by PCR," *Nucleic Acids Research*, 19(17):4780 (1991).
Dougherty et al., "Biosynthesis of New Polymers of Controlled Molecular Structure," *Makromol. Chem.; Macromol. Symp.* 62:225–229 (1992).
Doel, M.T., et al., "The Expression in *E. Coli* of Synthetic Repeating Polymeric Genes Coding for Poly(L–Aspartyl–L–Phenylalanine)," *Nucleic Acids Research*, 8(20):4575–4592 (1980).
White, T.J., et al., "The Polymerase Chain Reaction," *Trends in Genetics*, 5(6):(Jun. 1989).
Kempe, T., et al., "Multiple–Copy Genes: Production and Modification of Monomerica Peptides from Large Multimeric Fusion Proteins," *Gene*, 39:239–245 (1985).
Kangas, T.T., et al., "Expression of a Proline–Enriched Protein in *Escherichia coli*," 43(3):629–635 (1982).
White et al Trends in Genetics 5(6) 185–189, 1989.
Doel et al Nucleic Acids Research 8 4575–4592, 1980.
Hein et al Nucleosides & Nucleotides 7 497–510, 1988.
Cserpan et al Acta Chemica Scandinavica 45 265–272, 1991.
McClain et al. Nucleic Acids Research 14 6670, 1986.
Kempe et al. Gene 39 239–245, 1985.

*Primary Examiner*—Nancy Degen
*Attorney, Agent, or Firm*—Richard F. Trecartin; Mark T. Kresnak; Flehr Hohbach Test Albritton and Herbert

[57] ABSTRACT

Methods are provided for the production of large polypeptides containing repeating sequences of amino acids utilizing biochemical techniques, specifically DNA sequences coding for the expression of the large polypeptides. Systems utilizing exogenous transcriptional and translational regions to control the production of the large polypeptides are also provided.

37 Claims, 10 Drawing Sheets

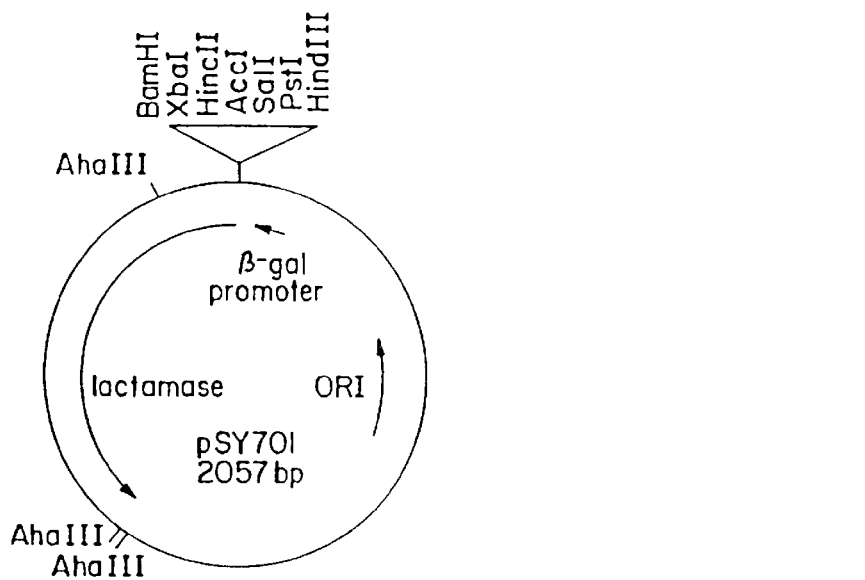
FIG._1

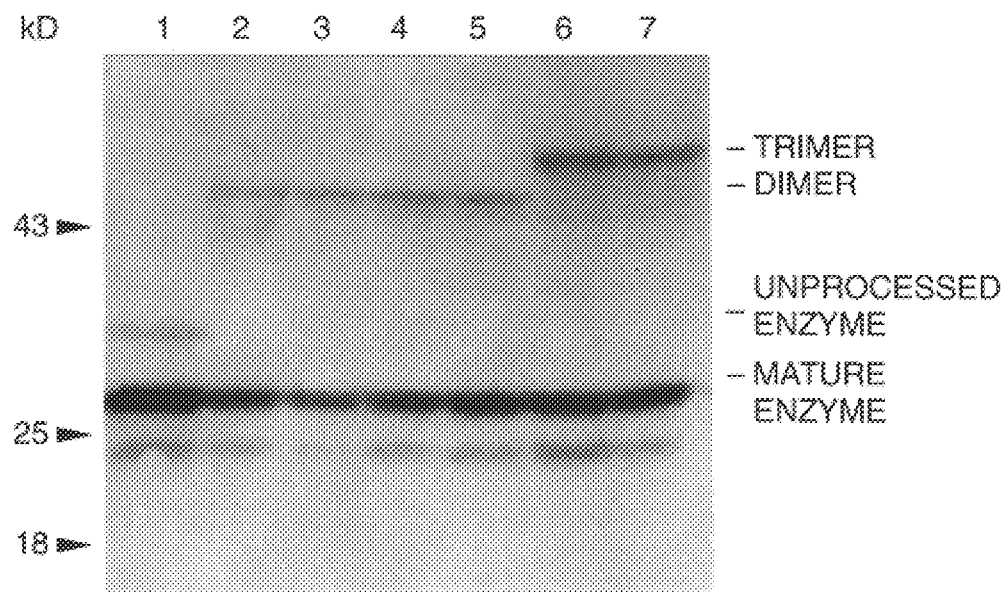
FIG._2A
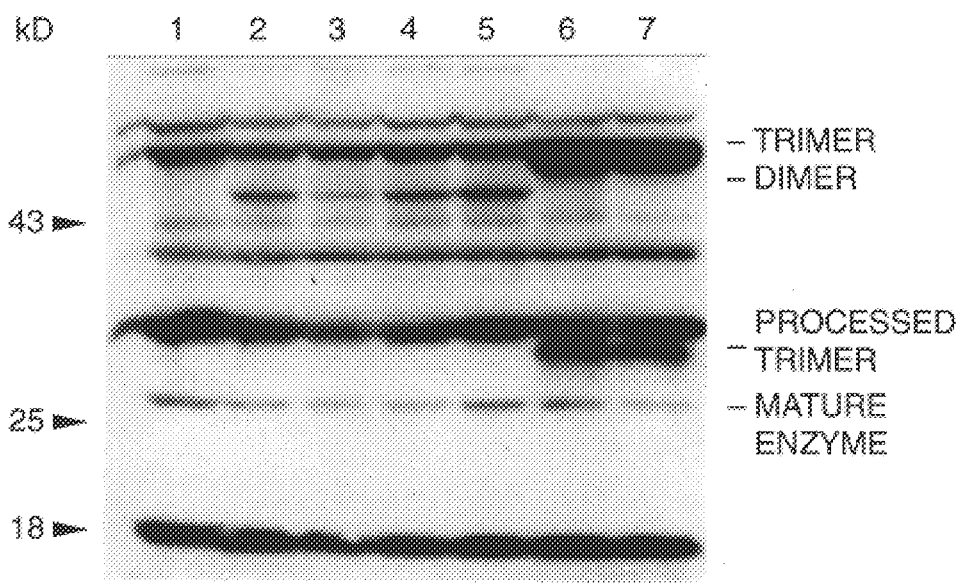
FIG._2B

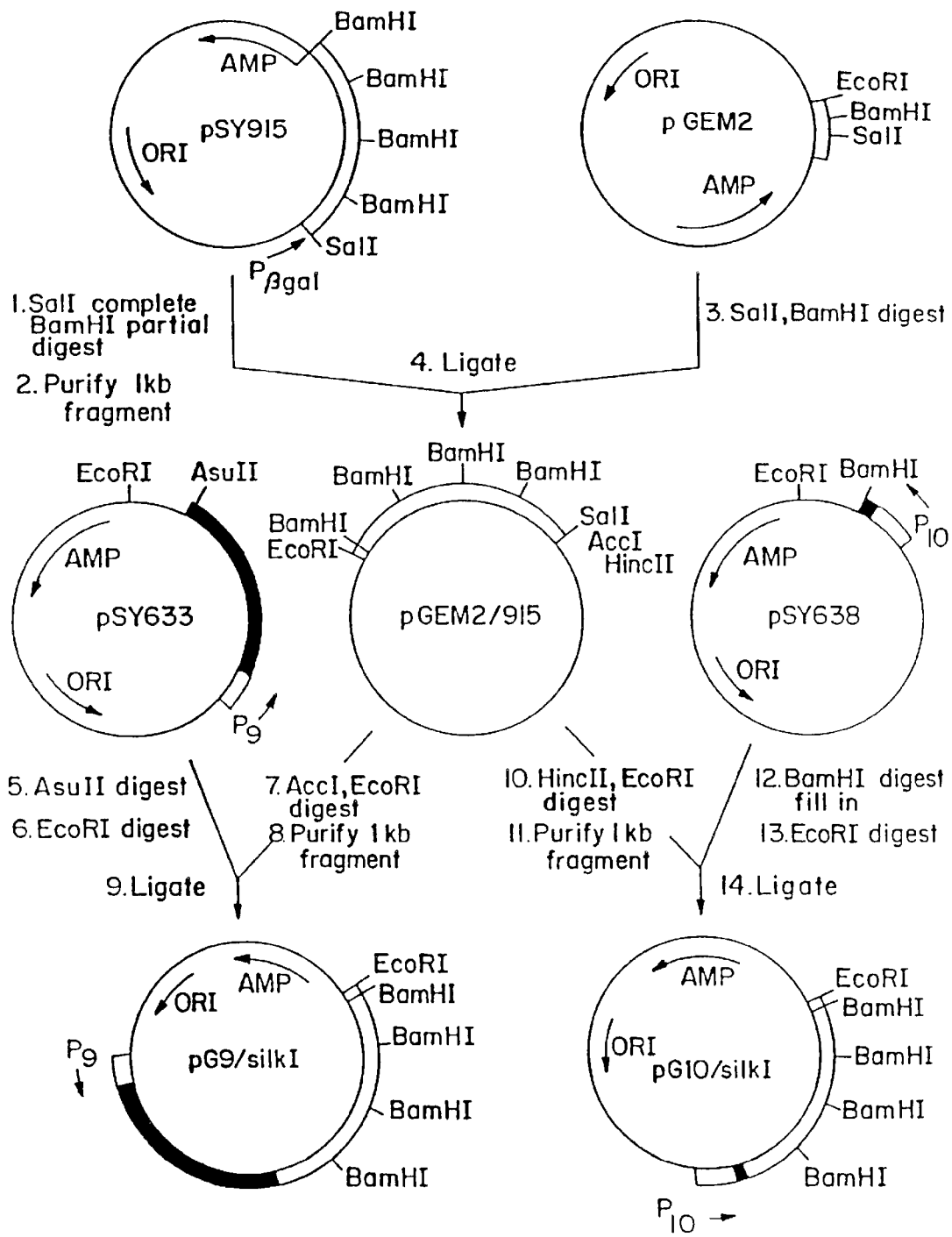
FIG._3

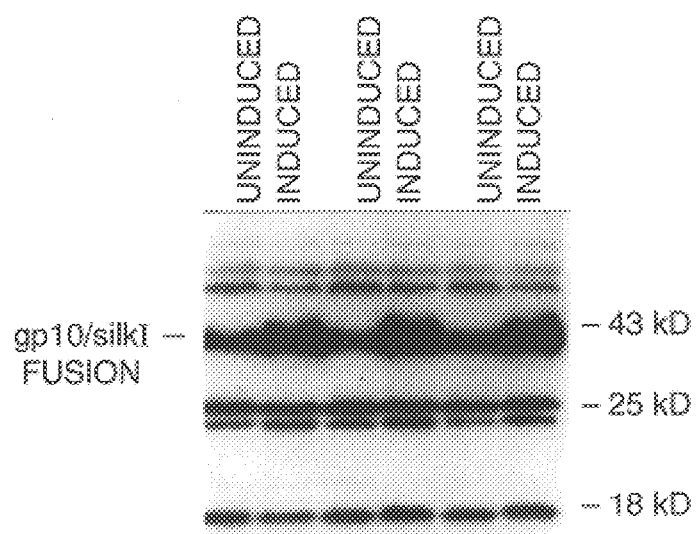
FIG._4A
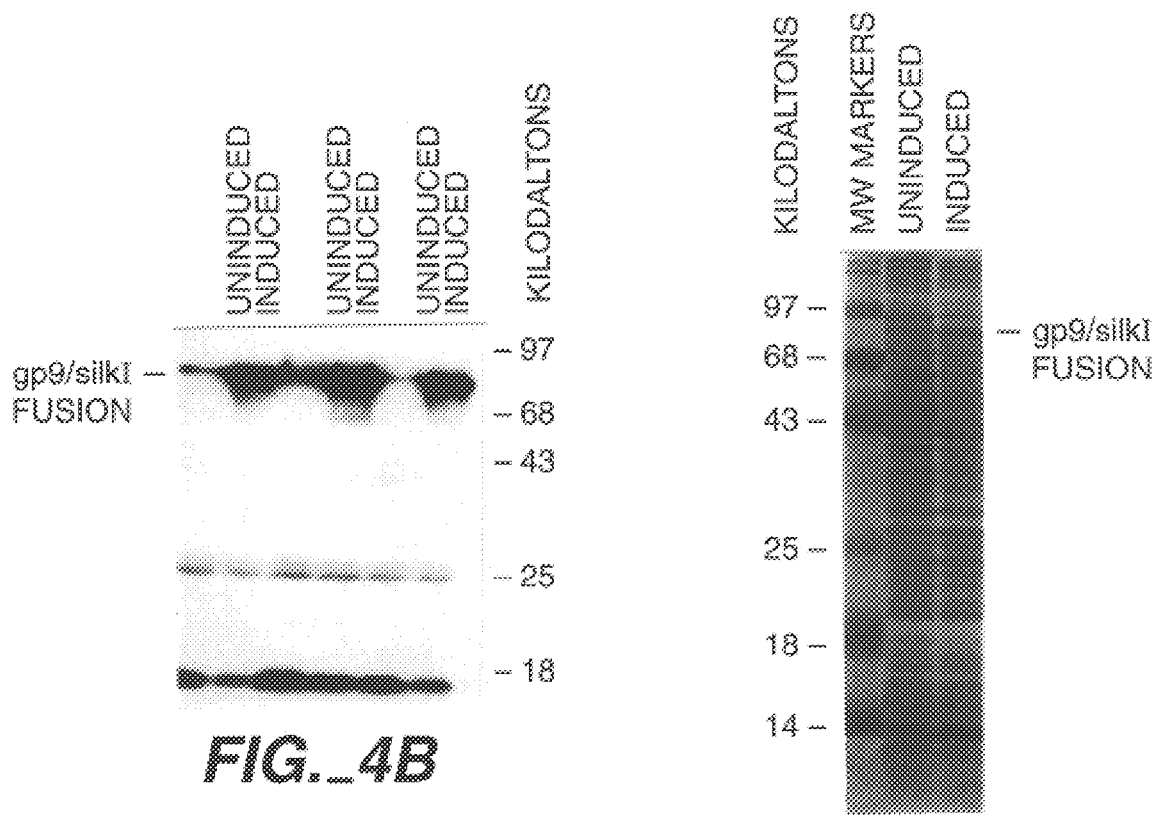
FIG._4B
FIG._4C

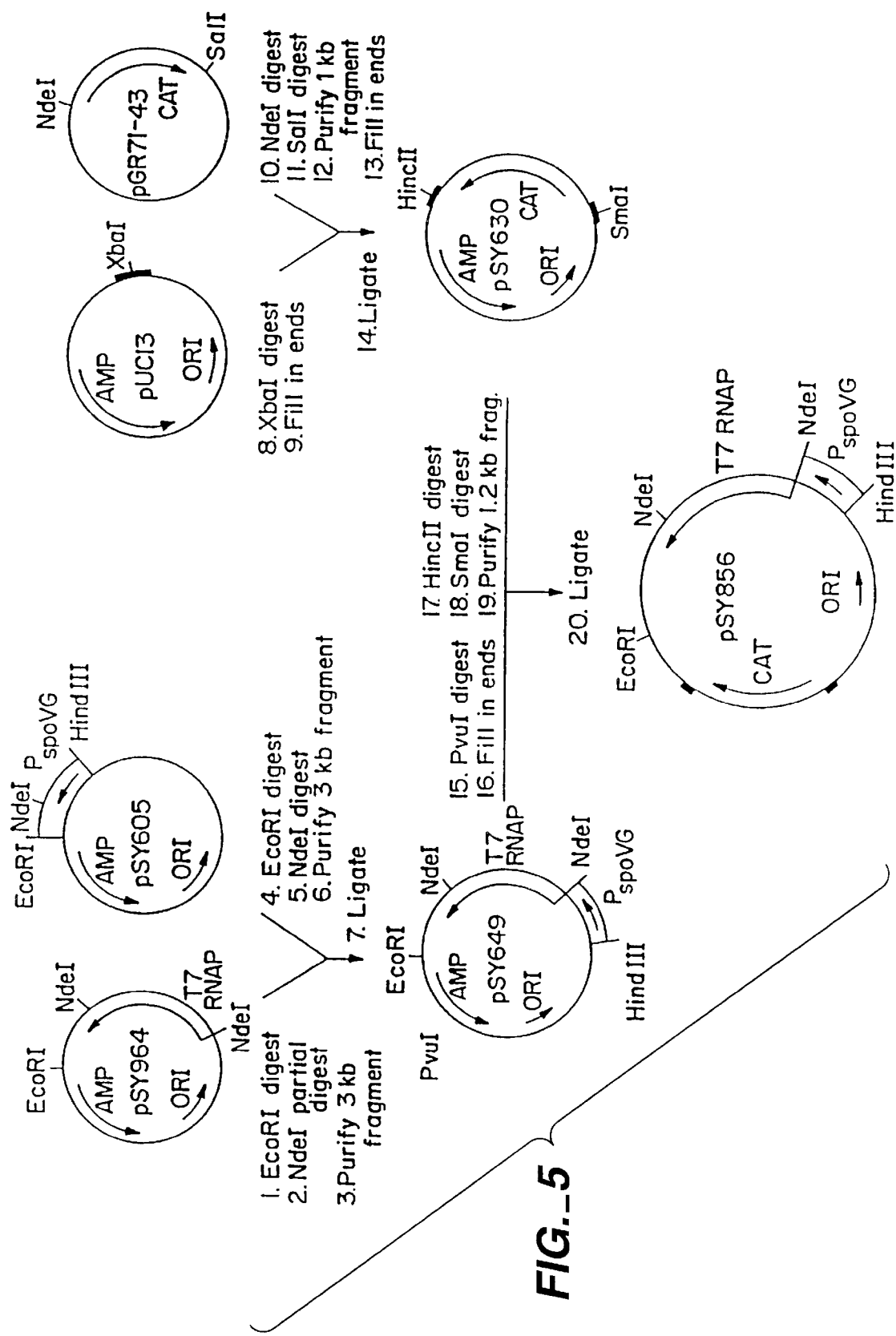
FIG._5

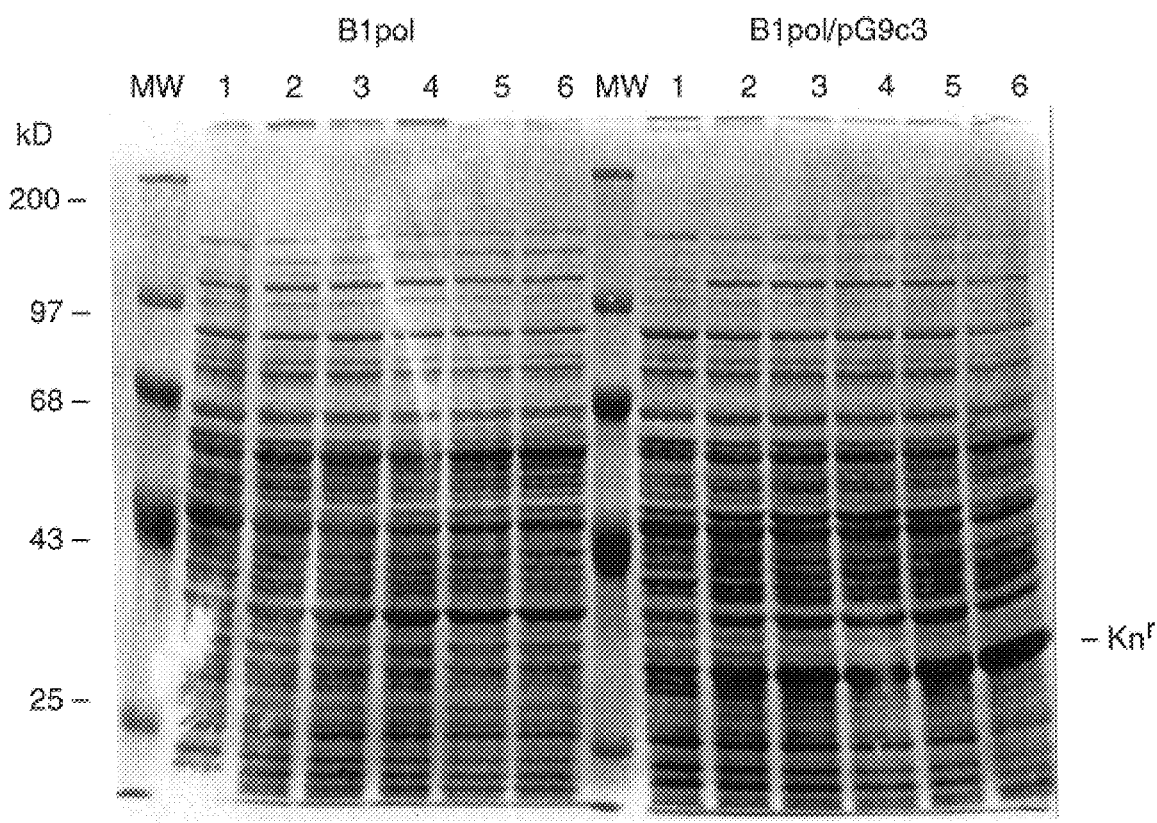
FIG._6

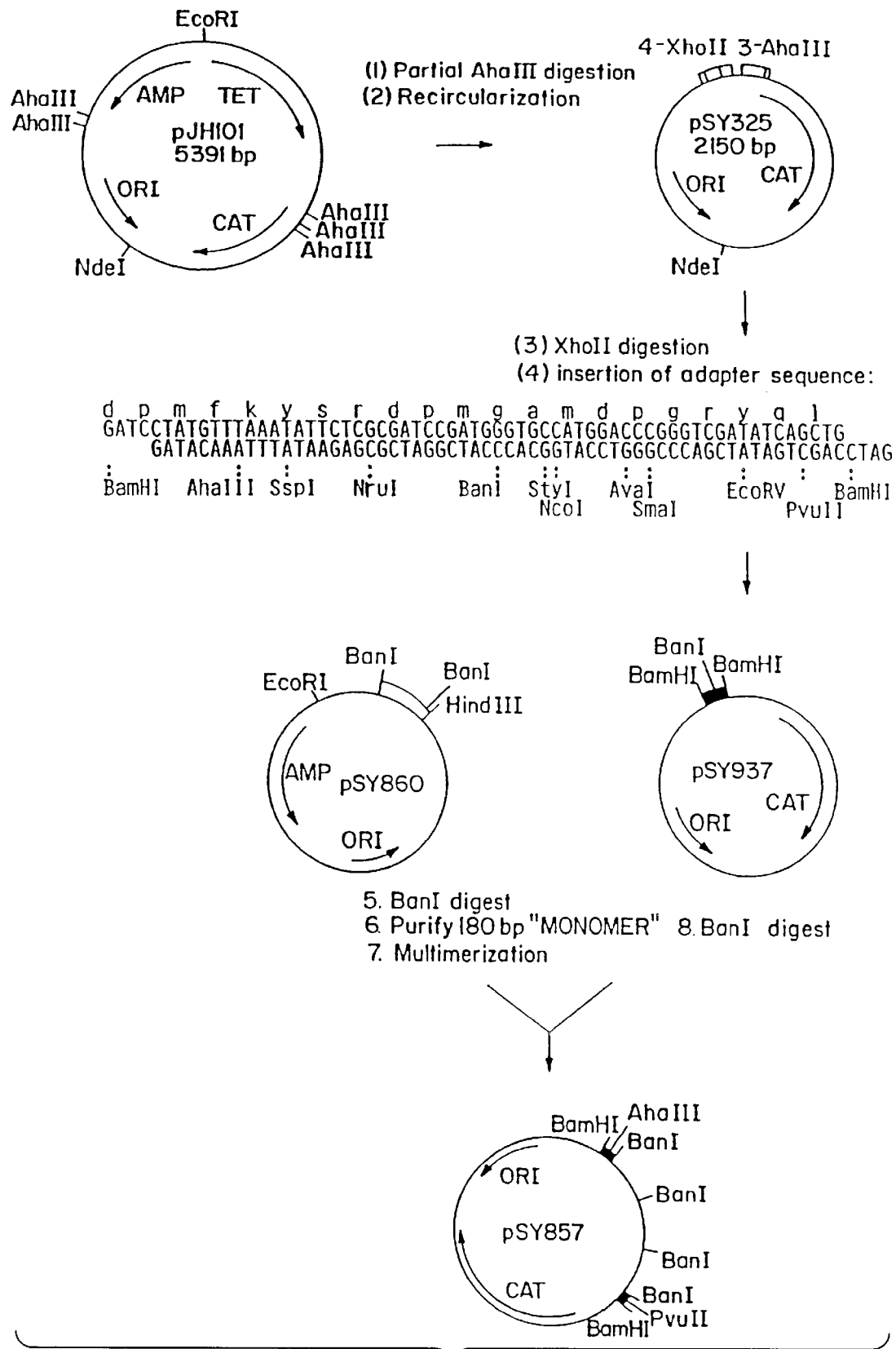
FIG._7

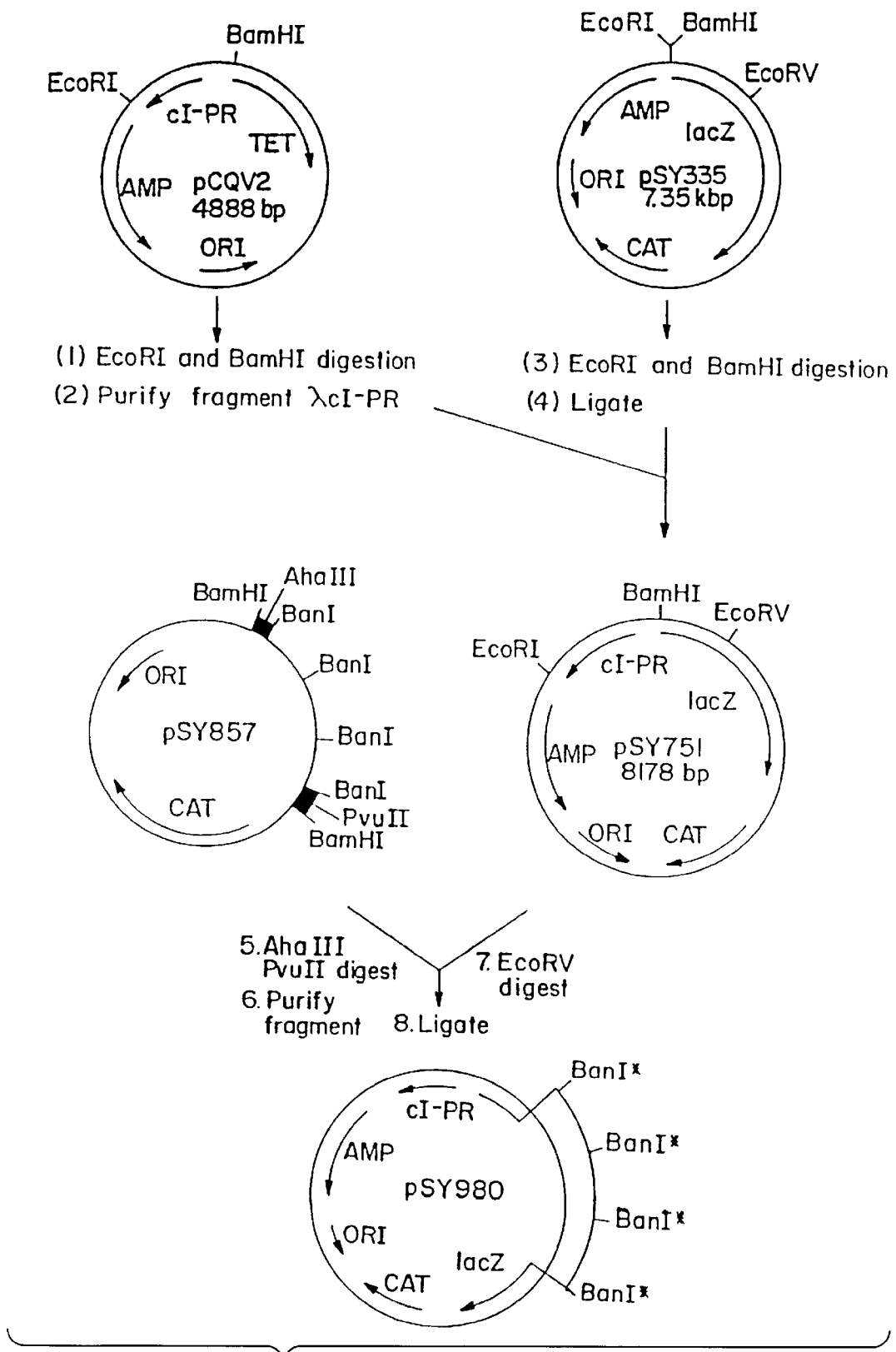
FIG._8

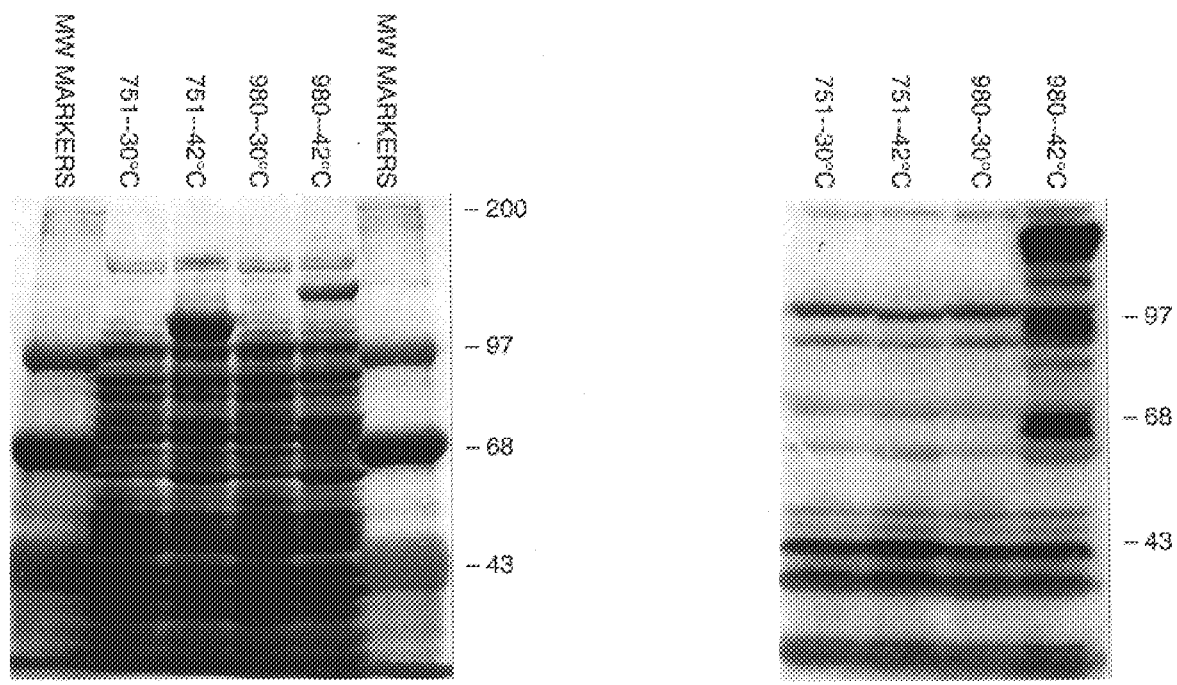
FIG._9A  FIG._9B

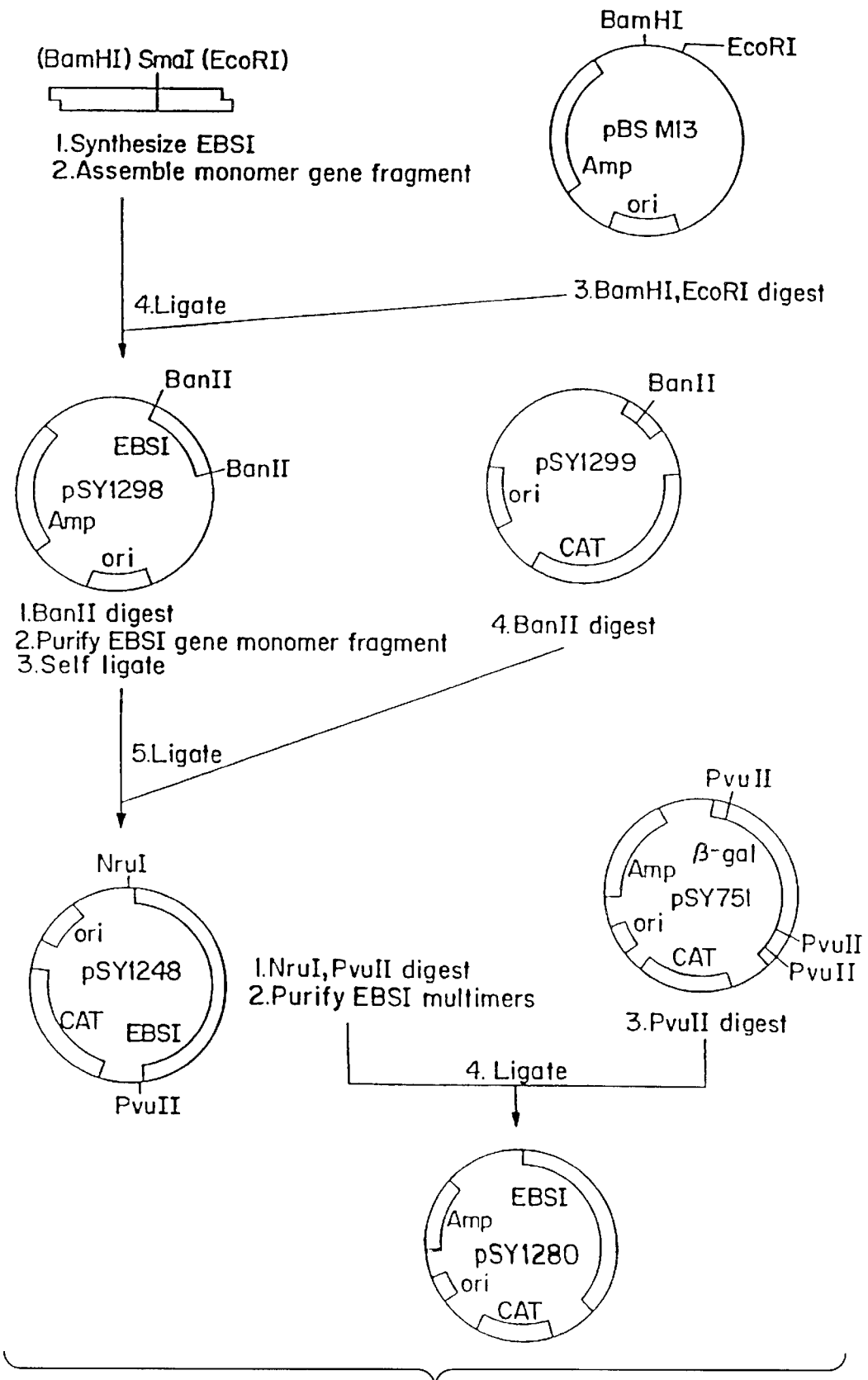
FIG._10

METHODS FOR PREPARING SYNTHETIC REPETITIVE DNA

CROSS-REFERENCE TO RELATED APPLICATIONS

This application is a continuation-in-part of application Ser. No. 08/175,155, filed Dec. 29, 1993, now U.S. Pat. No. 5,641,648 issued on Jun. 24, 1997, which is a continuation-in-part of application Ser. No. 08/053,049, now abandoned, filed Apr. 22, 1993 which is a continuation-in-part of application Ser. No. 07/609,716, filed on Nov. 6, 1990, now U.S. Pat. No. 5,514,581 issued on May 7, 1996, which is a continuation-in-part of application Ser. No. 07/269,429, filed on Nov. 9, 1988, abandoned, which is a continuation-in-part of application Ser. No. 07/114,618, filed Oct. 29, 1987, now U.S. Pat. No. 5,243,038 issued on Sep. 7, 1993, which is a continuation-in-part of application Ser. No. 06/927,258, filed on Nov. 4, 1986, abandoned.

The government has certain rights in this invention as a result of support provided by the Department of the Navy for the work leading to the present invention.

INTRODUCTION

1. Technical Field

The field is related to the production of high-molecular-weight polymers, either nucleic acids or peptides that are the expression products of the nucleic acids, and is particularly related to the production of high-molecular-weight peptides containing repeating sequences by biochemical processes, the peptides finding use as structural materials.

2. Background

Recombinant DNA technology has been applied in the isolation of natural genes and the expression of these genes in a variety of host cells. Typically, this technology has had utility in producing biologically active polypeptides, such as interferons or peptide hormones, which were impractical to produce in useful amounts by other means. It was also possible to produce modified proteins by isolating natural genes and utilizing the techniques of site specific, in vitro mutagenesis to alter these genes and thereby change the polypeptides produced. Other polypeptides have been created by combining sections of various native genes to produce new polypeptides that are chimeric molecules of the several naturally occurring molecules.

With the advent of efficient and automated methods for the chemical synthesis of DNA, it has become possible to synthesize entire genes and to modify such synthetic genes at will during the course of synthesis. However, these various technologies have been applied to the production of natural or modified versions of natural polypeptides. There have been very few attempts to use these technologies to create substantially new polypeptides. In nature, polypeptides have a wide range of chemical, physical and physiological characteristics. Nevertheless, there are commercial applications for which known, naturally occurring polypeptides are not appropriate.

While biotechnology is versatile, usually it has been limited in its applications to naturally occurring products or modifications of naturally occurring molecules. One great strength of organic chemical synthesis, by contrast, has been the ability to transform inexpensive carbon materials to a wide variety of polymeric molecules, including naturally occurring molecules, but most importantly entirely new chemical structures, such as polypropylene and polyacrylates, which have defined and predicted chemical properties not associated with naturally occurring molecules.

Such materials, particularly high-molecular-weight polymers containing repeating sequences of amino acids, have proven difficult to produce by biochemical means. The genes necessary for producing large peptides containing repeating units of amino acids were unstable and often underwent intermolecular recombination causing deletions of repeating units in the gene. The development of a biotechnology which would produce polymeric molecules by biological processes similar to those available by organic synthesis would significantly broaden the range of applications of biotechnology.

3. Brief Description of the Relevant Literature

The cloning of multiple lactose operators up to four in tandem is disclosed by Sadler et al., *Gene* (1980) 8: 279–300. Hybrid bacterial plasmids containing highly repeated satellite DNA is disclosed by Brutlag et al., *Cell* (1977) 10: 509–519. The synthesis of a poly(aspartyl-phenylalanine) in bacteria is disclosed by Doel et al., *Nucleic Acids Research* (1980) 8: 4575–4592. A method for enriching for proline content by cloning a plasmid which codes for the production of a proline polymer was disclosed by Kangas et al., *Applied and Environmental Microbiology* (1982) 43: 629–635. The biological limitations on the length of highly repetitive DNA sequences that may be stably maintained within plasmid replicons is discussed by Gupta et al. in *Bio/Technology*, p. 602–609, September 1983.

SUMMARY OF THE INVENTION

Methods are provided for the production of protein polymers having extended stretches of small repeating units by expression of a synthetic gene. The amino acid repeating units are sequences that provide a motif for the protein polymer and comprise a major portion of the gene encoding the protein polymer. There may be more than one type of amino acid repeating unit in a single protein polymer. According to the design of the protein polymer, one or more different amino acid repeating units and, optionally, one or more amino acid interrupting linker or spacer sequences are organized into a "monomer". In the final protein polymer, the amino acid monomer is sequentially replicated to achieve the desired molecular weight.

To construct the gene encoding the protein polymer, a DNA monomer sequence encoding the amino acid monomer sequence is first designed and synthesized. There are three different approaches to synthesizing the DNA monomer: (1) synthesizing a plurality of dsDNA segments, which when ligated either in conjunction with their synthesis or after cloning and subsequent restriction enzyme digestion correspond to the desired DNA monomer sequence. Each dsDNA segment will typically encode a few amino acid repeating units, although the segment may encode an amino acid interrupting linker or spacer sequence. The dsDNA segments are synthesized by synthesizing single stranded oligomers which at least partially overlap and hybridizing pairs of oligomers to provide dsDNA. The dsDNA monomer is then assembled by independently cloning each dsDNA segment in a cloning vector and then sequentially inserting into a cloning vector containing all or a portion of a first segment all or a portion of each additional dsDNA segment by restriction enzyme digestion and ligation, by simultaneously cloning in a cloning vector all of the dsDNA segments where each individual segment has a 3' or 5' terminus complementary to the 5' or 3' terminus of a second segment, and so forth, or by combining convenient elements of these methods whereby a monomer is obtained with an open reading frame with the proper sequence, which monomer is sequenced; or (2) synthesizing a single strand of all or a portion of the DNA monomer and making the complementary strand, conveniently using the polymerase chain reaction (PCR) in which case the synthesized PCR template comprises the appropriate sequence of the ssDNA monomer flanked by appropriate primer binding site sequences. The resulting dsDNA segment(s) are then digested by restriction enzyme digestion to remove the primer binding sites, cloned in a cloning vector, and if more than one segment has been synthesized, assembled in a cloning vector as described above to form the monomer, which is sequenced; or (3) using the appropriate restriction enzymes, deleting a portion of a DNA monomer or combining all or part of DNA monomers previously prepared as in (1) and/or (2) above, optionally including new dsDNA segments synthesized as above, and characterizing the monomer. Generally, the dsDNA segments will be sequenced after each cloning step. dsDNA segments prepared as in (1) and/or (2) above can be combined to form a monomer, which is sequenced. In those cases where new DNA is synthesized and introduced into a monomer, at least the new DNA and usually the entire monomer, will be sequenced.

The monomers have predetermined termini for oligomerization. The monomer is then concatenated or oligomerized under ligating conditions to form multimers of the monomer, where the multimers may have different numbers of monomers resulting in a plurality of genes having different numbers of monomers. At least one multimer is inserted into an expression vector for introducing the vector into an appropriate expression host for expression of the gene. The expression host is then grown under conditions whereby the protein is expressed and may be isolated.

BRIEF DESCRIPTION OF THE FIGURES

FIG. 1: Plasmid pSY701 structure (SEQ ID NOS: 1 and 2).

FIGS. 2A–B: Immunoblots of polypeptide products using antibody to (a) beta-lactamase or to (b) gly-ala-peptide.

FIG. 3: Construction flowchart for plasmid pG10/SlpI.

FIGS. 4A–C: Immunoblots of polypeptide products (a) T7gp10/SlpI with anti-SlpAb, (b) T7gp9/SlpI with anti-Slp ab or (c) staining with Coomassie blue.

FIG. 5: Construction flowchart for plasmid pSY856.

FIG. 6: Time course for accumulation of the kanamycin-resistance gene product with the T7 system.

FIG. 7: Construction flowchart for plasmid pSY857 (SEQ ID NOS: 3–5).

FIG. 8: Construction flowchart for plasmid pSY980.

FIGS. 9A–B: (A) Amido black stain or gel containing the product of beta-galactosidase/SlpIII gene fusion; (b) immunoblot of same product with anti-Slp antibody.

FIG. 10: Construction flowchart for plasmid pSY1280.

DESCRIPTION OF SPECIFIC EMBODIMENTS

Novel polypeptides are provided which are block polymers of repeating, relatively short, amino acid sequence units. The blocks of repeating units (oligomers) may be linked by spacers of different amino acid sequences. The polypeptides may contain only one or a plurality of repetitive amino acid sequences (having the same or different amino acid sequences). The novel polypeptides are particularly useful as fibrous or structural proteins, including crystalline, elastomeric, tough and bony materials, e.g. proteins similar to, but different from, silk, elastin, collagen, keratin or other naturally occurring structural polymers having a repetitive amino acid sequence motif. The gene encoding the repeating-unit-containing peptides is produced to particularly avoid problems previously associated with genes containing multiple repeating units.

Genes produced according to the methods described herein will generally be at least 900 nt in length, usually at least 1200 nt in length, preferably at lest 1500 nt in length, usually not more than 20 knt in length, more usually not more than 12 knt in length, frequently not more than about 6 knt in length. This will usually result in a protein of from about 30 kDal, usually at least 35 kDal, and not more than about 250 kDal, more usually not more than about 125 kDal. The methods for production of the synthetic genes encoding the protein polymer involve preparation of a dsDNA "monomer", which is an extended segment of DNA principally encoding amino acid repeating units, where the dsDNA monomer is generally a repeating segment of the final product, where the final product will have from 2, frequently at least 3, and up to 50, usually not more than about 30, more usually not more than about 20, monomeric units. There is one exception, to be described below, where the monomer may be the entire final repeating unit gene. The monomer will be a dsDNA whose sequence is, with one exception, established prior to its multimerization to provide the gene.

The size of the dsDNA monomer is dependent upon the desired amino acid monomer sequence as well as the way in which the monomer is obtained. If the monomer is constructed using any newly synthesized and ligated DNA, then the monomer is always sequenced prior to multimerization and the practical limitations of DNA sequencing technology limit the monomer size to about 500 nt, usually about 400 nt. If the gene monomer is constructed solely from digestion fragments of previously constructed and sequenced monomers, then the final gene monomer is typically characterized by restriction digests. Therefore, the gene monomer can be as large as the final gene, depending upon the desired amino acid repeating unit sequences and periodicity.

Because of the nature of the subject genes, which involve long tracts of repetitive units encoding the same amino acid sequence, the manner in which the monomer gene may be successfully prepared is restricted and requires that there be certainty as to the fidelity of the sequence. In the initial methods of preparation, there were a number of stages: preparation of ssDNA pairs, which overlapped and when hybridized provided segments; cloning of segments; sequencing of segments to ensure the fidelity of the sequence; and combining the segments to form the monomer. The order and manner in which these various operations were carried out could be varied, depending on the nature of the gene and the protein it encoded. In order to reduce the possibility of undesirable recombination events, different nucleic acid sequences are used to encode the same repetitive unit.

There are three ways to obtain the monomer. The first way relies on synthesis and assembly of single stranded deoxynucleotide oligomers encoding from about 1 to 12, more usually 1 to 9, frequently 1 to 6 repeating amino acid units into a dsDNA monomer sequence. Each repeat unit will have about 3 to 30 codons (9 to 90 bases), usually about 3 to 25 codons, more usually about 3 to 15 codons, frequently not more than 9 codons, particularly when mimicking a naturally occurring motif. The number of amino acid repeat units in a dsDNA monomer sequence will depend to a substantial degree on the size of the repeating unit. Conveniently, ssDNA oligomers may be prepared having from about 15 to 120 bases, usually about 21 to 90 bases, more usually about 39 to 72 bases, although oligomers may be prepared with up to 300 bases, more usually up to about 252 bases. For repeating units having a few amino acids, usually in the range of 3 to 15 amino acids, more usually in the range of 3 to 9 amino acids, the single stranded oligomer will conveniently have from about 2 to 12 amino acid repeating units.

The number of different single stranded oligomers will usually be at least 2, forming 1 pair, more usually about 6, forming 3 pairs, or may be 8 or more, forming 4 or more pairs, where the protein polymer has the same repeating unit. Where block copolymers are prepared, the number of oligomers will depend on the number of different blocks and the size of the blocks. The dsDNA segments formed by the pairs of oligomers of the different ssDNA oligomers may encode the same amino acid sequence or a different amino acid sequence, but where more than one dsDNA segment is synthesized, at least two segments will have different nucleotide sequences. Each pair of oligomers forming a dsDNA segment are complementary and at least partially overlap, providing blunt or cohesive (protruding) ends, preferably protruding ends, to allow for ease of assembly and ligation of the dsDNA to form a "monomer".

The dsDNA segments are desirably assembled in a prokaryotic vector by linearizing a vector having an origin and convenient restriction sites, which may involve a polylinker, for insertion of one or more dsDNA segments. The vector will also have a marker gene for selection, which will usually impart antibiotic resistance, but may afford another distinguishing characteristic, e.g. chromophore or fluorophore formation. The marker will preferably provide antibiotic resistance, there being a wide variety of antibiotic reagents, e.g. tetracycline, chloramphenicol, actinomycin, neomycin, ampicillin, hygromycin, heavy metals, etc. Other markers include β-galactosidase, which, with the substrate X-gal, provides a blue color. Numerous vectors are commercially available for cloning in E. coli and need not be exemplified here. The vector is then introduced into an appropriate cloning host by any convenient means, including calcium phosphate precipitated DNA, fusion, transfection, conjugation or the like. The cells are then grown in an appropriate selective nutrient medium. Surviving cells are harvested, lysed and the plasmid isolated.

By having a multiplicity of dsDNA segments, the termini may be designed that the first segment has a 3' or 5' terminus complementary to the 5' or 3' terminus of a second segment and so on, where the termini may have different consensus sequences for different restriction enzymes or not be recognized by any known restriction enzyme. The termini of the dsDNA segments may be selected to have protruding 5' ends, protruding 3' ends, or a protruding 5' and a protruding 3' end on the same strand, either the coding strand or the non-coding strand. Complementation of the protruding ends may destroy the sequence of the restriction site or retain the sequence, when different dsDNA segments are ligated.

Restriction enzymes are used to digest the dsDNA of the cloning vector and insert dsDNA segments. Restriction enzyme digestion of the vector, whether or not already having inserted dsDNA segments, will provide termini which are complementary to the termini of the next dsDNA segment being inserted, which may already be a combination of two or more synthesized dsDNA segments. In selecting dsDNA segment sequences, one generally selects the terminal sequences to allow for linearization of the vector and insertion of the next dsDNA segment, proximal to a terminus of a segment. However, sometimes it is convenient in creating a monomer to insert a dsDNA segment within a previously cloned segment. The final dsDNA segment sequence which is inserted into the cloning vector may not be the entire dsDNA segment which was synthesized, but will have the appropriate complementary termini that allow for insertion formed by the restriction enzyme digestion. Similarly, digestion of the vector may create the appropriate termini for insertion of the next dsDNA segment by restriction enzyme digestion that deletes a portion of the originally synthesized and cloned DNA. Generally, in building a monomer it is preferable to cleave the vector with a single restriction enzyme corresponding to a single restriction enzyme recognition site so that the use of partial enzyme digestions can be avoided.

By having different termini at each end of each dsDNA segment, the individual segments cannot oligomerize, even if they have been phosphorylated. In this way, when the different segments are combined, the ends of the combination of the segments may have complementary termini, so that they can be oligomerized. The 3' and 5' termini of each dsDNA segment are generally selected so that only one copy of the segment can be cloned in one orientation into a cloning vector. However, sometimes it is convenient to have complementary 3' and 5' termini, so that a segment can be cloned into an existing monomer or portion of a monomer even though it is then necessary to select a clone having the segment inserted in the correct orientation and number. During the construction of the monomer, some combinations of dsDNA segments may not be in reading frame, one to the other. However, by appropriate selection of the dsDNA segment sequences and the restriction enzymes used in the monomer construction, the final combination of dsDNA segments comprising the monomer will be in a continuous open reading frame coding for the desired amino acid sequence. The above-described approach may be used with the other methods of forming the monomer, as will be described hereafter.

Using these techniques and design strategies, it is possible to construct the dsDNA monomer in a variety of ways, as described in the examples that follow. In one variation, a first dsDNA segment is cloned into the cloning vector after it has been linearized by restriction enzyme digestion. After cloning, the first dsDNA segment is characterized, such as by restriction analysis and sequencing. Where the dsDNA segment is relatively small, sequencing can be performed rapidly and substantially error free.

Once the first dsDNA segment has been shown to have the correct sequence, the vector may then be used in the next stage in the preparation of the gene. The vector is linearized at the 5' or 3' terminus of the first dsDNA segment cloned. By employing a polylinker in the vector at the 5' and/or 3' terminus of the dsDNA segment cloned, the vector may be digested by using a restriction enzyme which cleaves in the polylinker to provide a terminus at the 5' or 3' terminus of the vector complementary to the 3' or 5' terminus of the next dsDNA segment. Alternatively, one may use restriction enzymes which cleave distal from the consensus sequence. In this way the vector may be repeatedly cleaved and ligated, without cleavage of the monomer DNA being constructed. After cloning, the combined dsDNA segments may be characterized as described above. The process may be repeated until all of the dsDNA segments have been inserted and verified for sequence and being in the proper order and reading frame.

In another variation, two or more dsDNA segments may be sequentially cloned as described above, with each new insertion at the 3' or 5' terminus of the previously cloned segment, and then another dsDNA segment may be inserted between the previously cloned segments. In another variation, a first dsDNA segment may be cloned as described above and then another dsDNA segment may be inserted internal to the cloned segment. In another variation, two or more dsDNA segments may be cloned simultaneously into a vector, with additional dsDNA segments sequentially inserted a) at the 3' or 5' termini of the previously cloned DNA segments, b) between the previously cloned DNA segments, or c) internal to a previously cloned segment. In another variation, all dsDNA segments comprising the monomer may be simultaneously ligated into the cloning vector. In another variation, each dsDNA segment comprising the monomer may be individually cloned and characterized. The individual dsDNA segments are then purified and ligated in a single cloning step to construct the monomer, which is sequenced.

An essential element in this method for constructing the monomer is that the pairs of ssDNA be annealed into dsDNA segments prior to further manipulation. Generally, each dsDNA or combination of segments, once cloned, is sequenced prior to further manipulation. The monomer is always sequenced prior to multimerization.

A second approach depends on the synthesis of a single strand of all or a portion of the monomer. Synthetic techniques allow reasonably accurate oligonucleotide synthesis of 300 bases or more. For the most part the single strand will be in the range of about 100 to 300 bases, usually in the range of about 100 to 250 bases. The single strand is then used to produce a complementary strand, conveniently using the polymerase chain reaction ("PCR"). The synthesized PCR template comprises the appropriate sequence of the ssDNA monomer flanked by appropriate primer binding site sequences.

The primers which are used for PCR are designed not to hybridize readily to the repeat sequences, having overall a nucleotide sequence substantially different from the nucleotide sequence of the sequence being amplified, although a portion of the primer desirably includes a sequence common with the repetitive sequence being amplified, this will be not more than about 30 nucleotides, usually not more than about 25 nucleotides and at least 10 nucleotides, usually at least 12 nucleotides. The total number of nucleotides in the primers will generally be in the range of about 15 to 50, more usually 20 to 45. In the portion of the primer hybridizing with the target, all or a portion of a restriction enzyme consensus sequence is included in the primer which binds to the target ssDNA, where only a portion is present, the target will complete the consensus sequence. Restriction enzyme digestion allows for cleavage at the terminus or proximal to the terminus of the primer sequence hybridizing to the target ssDNA. Preferably, not more than about 5 nt, usually not more than about 3 nt, preferably not more than 2 nt, will be left from the primer after clevage by restriction enzyme digestion. Usually, the consensus sequence will be 6 to 8, usually 6 nucleotides for the restriction enzyme.

The 3' and 5' primers will be different, so as not to hybridize with each other. In order for the primers to work efficiently, the primers must have similar $T_m$ and $\Delta G$ characteristics, both as to hybridizing with the complementary member of the primer pair and hybridizing with the target DNA. These characteristics can be controlled by the length of the primers, the length of the sequence hybridizing with the target ssDNA, and the proportion of GC binding that occurs. Generally the primers will have at least 40%, more usually at least 45% G and C, and may be 50% or more, usually, not greater than about 75%, more usually not greater than about 65%. For hybridizing between complementary primers, the $T_m$ will generally be in the range of about 88 to 92. usually about 90° C.±1. The $T_m$ difference between the primer pairs will usually be less than about 1°, more usually less than about 0.75° C. The $T_m$ for hybridizing of the primer to the target ssDNA will generally be in the range of about 68 to 73, usually about 71° C.±1, having similar restrictions as regard the whole primer.

In addition, because the primers will be selected so that not more than a small portion of the primer will participate in the final gene sequence, a restriction site will be present to permit removal of the primer sequence, leaving the resulting sequence with ends which will allow for multimerization, particularly cohesive ends, where the ends may recreate the restriction site or the restriction site may be destroyed. Thus, the cleavage site may occur within the consensus sequence or away from the consensus sequence, while providing for complementary termini.

The resulting dsDNA segment(s) are then digested by restriction enzyme digestion to remove the primer binding sites, cloned in a cloning vector, and if more than one segment has been synthesized, assembled in a cloning vector as described above to form the monomer. The resulting dsDNA monomer is cloned, purified and sequenced to ensure that it has the correct sequence. The monomer prepared this way will have the same limitations as to size and the number of amino acid repeating units which are encoded as the monomer prepared by the sequential and/or simultaneous cloning of dsDNA segments as described above.

After the monomer has been prepared, characterized and the desired sequence confirmed, the monomer may then be excised from the vector and purified in accordance with conventional procedures. At this time the "monomer" synthesis has been completed. The monomer may then be used to produce the gene. As is evident from the above descriptions, dsDNA segments prepared as in (1) and/or (2) above can be combined to form a monomer, which is sequenced.

The third approach relies on the use of fully characterized dsDNA which is already present in a monomer, previously prepared by either of the methods described above. Using this approach allows for great flexibility in constructing new monomers, particularly where copolymers comprising different amino acid repeating units are desired. Using the appropriate restriction enzymes, all or part of the dsDNA comprising a monomer may be purified. In some instances, all or a portion of a previously synthesized monomer is then used as a new monomer in combination with newly synthesized dsDNA segments prepared as in (1) and/or (2) above or a portion of a previously synthesized monomer is then used as a new monomer by itself. In other instances, the desired dsDNA from two or more separate monomers may be combined to construct a new monomer encoding the amino acid repeating units of interest, either by themselves or in combination with newly synthesized dsDNA segments prepared as in (1) and/or (2) above. The digested monomer DNA fragments which are to be combined may have complementary or non-complementary ends. If the termini of the monomer sequences are not complementary, as required, the termini may be made so by employing adapters, filling in, nuclease digestion, or the like. Once the appropriate monomer sequences have been cloned together, sequentially and/or simultaneously, to make the new monomer, the monomer is then characterized and sequenced, if necessary. If newly synthesized adapters or filling in reactions or nuclease digestion or the like are employed, the region comprising the modified monomer DNA is sequenced.

When the gene encoding the desired protein product is a homooligomer of the monomer, desirably the termini have cohesive ends and may retain the same restriction site consensus sequence or result in a sequence other than the consensus sequence. By appropriate choice of the restriction enzymes or polylinker, the termini of the monomer may have the same or different terminal restriction sites, but will have complementary ends, if the monomer is to be multimerized. Preferably, a single restriction enzyme that cleaves the monomer from the vector at asymmetric consensus sites will be employed. However, restriction enzymes that cleave outside of the recognition sites may also be used. By having a monomer with different, yet complementary termini, the monomer may be ligated in vitro with the monomers only assembling in one orientation.

As evidenced by the above description, the monomer is a molecule which will normally be comprised of a plurality of previously prepared dsDNA segments, normally being formed from at least two different dsDNA segments, which may or may not encode the same amino acid sequence, but generally providing for blocks of the same pattern of repeat amino acid units throughout the final polymer gene (the exception is when the monomer is the gene). Thus the monomer may provide for a homopolymer, copolymer, or polymer having a defined motif, where the amino acid repeating units vary, e.g. collagen.

The monomer is then multimerized by ligation, conveniently employing from about 0.01 to 100 µg of the monomer under ligating conditions, where multimers having different numbers of monomers are obtained. The multimers may then be segregated by size, selecting multimers of a predetermined size. Any of the original mixture, the partially purified mixture, or size segregated fractions thereof, may then be introduced into a vector. Either an adapter vector or an appropriate expression vector is employed. The adapter vector has a polylinker which will allow for insertion into the polylinker, so as to be capable of being read in any reading frame. In this way one may introduce different unique restriction sites which allow for excision and transfer of the multimer gene from the expression vector. The multimer gene may be characterized and purified before transfer to the expression vector. The multimer will have appropriate termini which will allow for insertion into the vector and, as appropriate, have end groups which are present in the vector or be inserted with termini which will allow for the exact excision of the gene. One may select a particular sized multimer or a plurality of multimers of different size for expression, so that one has a family of protein polymers, sharing the same repeating motif.

The expression vector will be characterized by having an origin of replication which is functional in an appropriate expression host, usually for episomal maintenance, and a marker for selection. Markers as described above may find use. For unintegrated vectors or constructs, the origin of replication will usually provide for multicopies, usually greater than about 5 copies on the average.

The expression vector will also have a promoter which is functional in the expression host. Various promoters can find use, which provide for a high level of transcription, either inducible or constitutive transcription. Illustrative promoters include β-lactamase, β-galactosidase, $\lambda P_L$ or $\lambda P_R$ promoters, trpE promoter, trp-lac promoter, T7 promoter (particularly genes 9 and 10), $cI^{ts}$, etc. The multimer gene and the linearized vector may be combined under hybridizing, usually including ligating, conditions. Where the multimer gene does not have an initiation codon, such a codon can be added. More conveniently, the multimer gene may be inserted into a coding sequence present in the vector, under the transcriptional control of a promoter. The coding sequence in the vector will generally not exceed 200 bp, usually not exceeding about 60 bp, where the site into which the multimer gene is inserted has the coding sequence and multimer gene in proper reading frame. Generally, the coding sequence present in the vector will be not more than 20%, usually fewer than 10%, preferably fewer than about 5% of the total number of bases in the coding sequence.

A signal sequence may be present at the 5' terminus of the coding sequence to allow for secretion of the protein polymer into the periplasmic space. For the most part, the product will be produced intracellularly.

Instead of a vector, DNA constructs may be employed for transformation of the expression host, with integration of the construct into the genome of the expression host. The construct will differ from the vector primarily by lacking an origin which provides for episomal maintenance. Thus, the construct will provide at least transcriptional and translational initiation and termination regions, the gene encoding the protein polymer between the initiation and termination regions and under their regulatory control, a marker for selection as described above, and other functional sequences, such as homologous sequences for integration into the host genome, sequences for priming for the polymerase chain reaction, restriction sites, and the like.

For the most part, the expression host will normally be unicellular, prokaryotic or eukaryotic, but may be from a multicellular organism. The organism may be selected from bacteria, algae, fungi, insect cells, plant cells, etc. Illustrative hosts include E. coli, B. subtilis, B. stearothermophilus, S. cerevisiae, and the like.

The expression host is then grown in accordance with conventional ways in an appropriate medium in culture, e.g. fermentation. After the cells have been grown to an appropriate density, the cells may be harvested, lysed and the product isolated by appropriate means, in accordance with the physical and chemical characteristics of the product. In some instances, the product is insoluble at moderate temperatures in an aqueous medium, and may be purified by detergent extraction at mildly elevated temperatures, above about 60° C., see U.S. Pat. No. 5,235,041. As appropriate, the crude or purified product may then be used for its intended purpose.

The genes of the subject invention generally comprise concatenated monomers of DNA encoding the same amino acid sequence, where all or a part of two or more different monomers encoding different amino acid repeating units may be joined together to form a new monomer encoding a block copolymer. The individual amino acid units will have from 3 to 30 amino acids (9 to 90 nt), usually 3 to 25 amino acids (9 to 75 nt), more usually 3 to 15 (9 to 45 nt) amino acids, usually having the same amino acid appear at least twice in the same unit, generally separated by at least one amino acid. In some instances, the minimum number of amino acids will be 4. Within a monomer, dsDNA encoding the same amino acid repeating unit may involve two or more nucleotide sequences, relying on the codon redundancy to achieve the same amino acid sequence.

For the most part the DNA compositions of this invention may be depicted by the following formula:

$$K_k(W\ M_r X_x N_s Y_y)_i L_l$$

wherein:

K is a DNA sequence encoding an amino acid sequence of from about 1 to 125 amino acids, usually 1 to 60 amino acids, which may be any sequence depending upon the manner of preparation of the construct and the purpose of the protein product, generally being fewer than about 20% of the total number of amino acids, more generally being fewer than about 10% of the total number of amino acids, which may be any sequence, particularly a naturally occurring sequence where the multimer structural gene has been fused to another DNA sequence in reading frame. K, if present, will have the initiation methionine codon. L may be the same or different from K, coming within the definition of K, but lacking the initiation methionine codon.;

k and l are the same or different and are 0 or 1;

W has the formula:

$$[(A)_n(B)_p]_q$$

wherein:

A is a DNA sequence coding each time that it appears for the same amino acid repeating unit normally having at least one amino acid appear at least twice in the sequence, where A will generally be from about 9 to 90 nucleotides (nt), more usually from about 9 or 12 to 75 nt, preferably from about 9 or 12 to 45 nt, more preferably from about 9 or 12 to 30 nt, and in some instances may be as few as 24 nt;

where there will usually be at least two different A's, usually not more than ten different A's, more usually not more than six different A's, which code for the same amino acid sequence but differ from each other by at least one nucleotide and may differ by as many as ten nucleotides, usually not differing by more than about five nucleotides from another A sequence, each of the different A's usually being repeated at least twice; at least two different codons are employed for the same amino acid, e.g. GGC and GGA for glycine, in different A's coding for the same amino acid sequence unit;

n will be an integer of at least 2, usually at least about 4, more usually at least about 8, and not more than about 250, usually not more than about 200, frequently not more than about 125, and in some instances may not exceed about 50;

B is a DNA sequence different from A coding for an amino acid sequence other than the amino acid sequence unit coded by the A unit and serves as a linking unit between oligomers of A units. B will generally have from about 3 to 45 nt, (1 to 15 amino acids) more usually from about 3 to 30 nt (1 to 10 amino acids);

where the B units appearing in the gene may be the same or different, there usually not being more than about 10 different B units, more usually not more than about 5 different B units, where the B units may differ from about 1 to 45 nt, more usually from about 1 to 15 nt, where the different B's may code for the same or different amino acid sequence;

p is 0 or 1 and may differ each time there is a successive A unit;

q is an integer of at least 1 and will vary with the number of nucleotides in A and B, as well as the values of n and p. The variable q will be selected so as to provide for at least 90 nt for the multimeric portion of the structural gene, preferably at least about 150 nt, more preferably at least 450 nt, and most preferably at least 900 nt, and the number of nucleotides will usually not exceed about 10,000 nt, more usually not exceeding about 8,000 nt, generally being in the range of about 900 to 6,000 nt, more usually to about 5,000 nt; and M is a DNA nucleotide sequence of about 12 to 150 nt, usually being 18 to 150 nt, more usually not more than about 90 nt, which may encode any amino acid sequence, usually encoding a functional sequence which provides for a natural or synthetic sequence resulting in a biological or chemical function or activity;

r and s are the same or different, being 0 to 3, usually 0 to 2, depending on whether a functional group is present in the polymer, usually being 1 to 2, where different, the same or similar functional groups may be combined in a contiguous manner;

N is the same or different from M and comes within the same definition as M;

X may be the same as or different from W, usually different, and will have the formula:

$$[A^1)_{n^1}(B^1)_{p^1}]_{q^1}$$

wherein:

$A^1$, $B^1$, $N^1$, $p^1$ and $q^1$ are the same as or different from A, B, n, p and q respectively, at least one being different, wherein the analogous symbols come within the same definition as their counterparts;

x is 0 or 1;

Y may be the same as or different from W, usually different, and will have the formula:

$$[A^2)_{n^2}(B^2)_{p^2}]_{q^2}$$

wherein:

$A^2$, $B^2$, $n^2$, $p^2$ and $q^2$ are the same as or different from A, B, n, p and q respectively, at least one being different, wherein the analogous symbols come within the same definitions as their counterparts.

y is 0 or 1;

i is 1 to 100, usually 1 to 50, more usually 1 to 30, particularly 1, when x, y, r and s are 0;

when x or y are 1, q, $q^1$ and $q^2$ will be a total of at least 2, usually at least 5 and not more than about 50, usually not more than about 33.

The total number of nucleotides will be at least 900 nucleotides, usually at least about 1200 nt, preferably at least about 1500 nt and may be 20 knt (kilonucleotides), usually not more than about 6 knt, more usually not more than about 4 knt.

The polypeptide encoded by the above DNA sequence will have the following formula:

$$K'_k(W'M'_rX'_xN'_sY'_y)_iL'_1$$

wherein:

W' will have the following formula $$[(D)_n(E)_p]_q$$

wherein:

D is the amino acid sequence encoded for by A and therefore has the numerical limitations based on 3 nucleotides defining a codon that codes for one amino acid;

E is the amino acid sequence encoded for by B, and therefore has the numerical limitations based on 3 nucleotides defining a codon, where each E may be the same or different, depending upon the coding of B;

and, wherein, likewise K', W', M', X', N', Y' and L' is the amino acid sequence encoded for by K, W, M, X, N, Y and L respectively. However, in the case of K and L, subsequent processing, such as protease treatment, cyanogen bromide treatment, etc. may result in partial or complete removal of the N- or C-terminal non-multimeric chains.

n, p, q, k, r, s, x, i and l have the same definitions as previously indicated.

Particular polymeric compositions having amino acid repeating units having the same compositions (A) will have the following formula where x and y are 0,

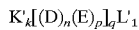
$$K'_k[(D)_n(E)_p]_q L'_1$$

where all of the symbols have been defined previously; and the DNA sequence will have the formula

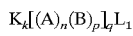
$$K_k[(A)_n(B)_p]_q L_1$$

where all of the symbols have been defined previously.

Particular DNA sequences encoding copolymeric compositions having a repeating unit of two to three multimeric blocks will have the following formula:

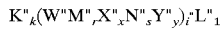
$$K''_k(W''M'',X''_xN''_s,Y''_y)_{i'} L''_1$$

wherein:
W" is a multimer having the formula

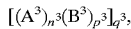
$$[(A^3)_{n^3}(B^3)_{p^3}]_{q^3},$$

where $A^3$ is of 3 to 15, usually 4 to 6 codons, otherwise coming within the definition of A;

$n^3$ will be from about 2 to 40, usually 2 to 32;

$B^3$ is of from 2 to 20, usually 4 to 6 codons;

$p^3$ is 0 or 1;

$q^3$ is of from about 2 to 50, usually 2 to 30, depending on the value of $n^3$, as discussed previously for n and q;

X" and Y" are the same as or different from W", usually different, coming within the same definitions as W";

M" and N" come within the definitions of M' and N';

i" is at least 2, usually at least 5 and not more than about 75, usually not more than about 50, generally not exceeding 30;

with the other symbols as defined previously, wherein at least one of x and y is 1.

The compositions of the invention will usually have a molecular weight of at least about 30 kDal, usually 50 kdal, frequently at least about 60 kDal and may have molecular weights as high or higher than 500 kdal, usually not exceeding 300 kDal, more usually not exceeding about 250 kDal, and in many instances not exceeding 125 kDal, the higher ranges generally being the multimer combinations, with the individual multimer usually being less than about 150 kDal, usually less than about 100 kDal.

The nucleotide sequences which are employed will be synthesized, so that the repetitive units will have different codons for the same amino acid as described above. Usually, at least about 25%, more usually at least about 40%, and generally at least about 60%, but not greater than about 95%, preferably not greater than about 90% of the nucleotide sequences encoding the repetitive units will be the same. Greater diversity within those ranges will be employed where the initial constructs are experimentally shown to undergo spontaneous recombination events.

Of particular interest are polypeptides which have as a repeating unit SGAGAG (SEQ ID NO: 6) (G=glycine; A=alanine; S=serine), where the choice of the S as the initial amino acid of the repeating unit is arbitrary, since except for the first and last units, all the other units will be the same. This repeating unit is found in a naturally occurring silk fibroin protein, which can be represented as GAGAG (SGAGAG)$_8$SGAAGY(Y=tyrosine) (SEQ ID NO: 7). In the subject invention, the repeating unit is designed where the N-terminus may be MGAGAG (SEQ ID NO: 8) or any other sequence of generally at least about 3 amino acids, usually at least about 5 amino acids, more usually 12 amino acids and not greater than 235, usually not greater than 100 amino acids, which may be different from the repetitive unit. Generally, a different N-terminus will be the result of insertion of the gene into a vector in a manner that results in expression of a fusion protein. Any protein which does not interfere with the desired properties of the product may provide the N-terminus. Particularly, endogenous host proteins, e.g. bacterial proteins, may be employed. The choice of protein may depend on the nature of the transcriptional initiation region. Similarly, the C-terminus may have an amino acid sequence different from the repeat sequence. Conveniently, there may be from 1 to 125, frequently 1 to 100, usually 1 to 25 amino acids, which may be the C-terminus of a naturally occurring structural gene, which again typically results from the formation of a fusion product.

A silk-like-protein (Slp) gene may be produced by providing oligomers of from about 5 to 25 repeat units as described above, more usually of about 10 to 20 repeat units. By having different cohesive ends, the oligomers may be concatemerized to provide for the polymer having 2 or more of the oligomeric units, usually not more than about 50 oligomeric units, more usually not more than about 30 oligomeric units, and frequently not more than about 25 oligomeric units.

The silk-like proteins may be varied by having alternate multimers with the same or different handedness. For example, in the formula, $(B)_p$ may provide an even or odd number of amino acids. In silk, the hydrogens of the glycine may align on one side and the methyls and hydroxyls of alanine and serine on the other. If $(B)_p$ is even, there will be continuous alignment, if odd, there will be alternating alignment of $(A)_n$. Thus, different properties can be achieved by changing the number of amino acids encoded by $(B)_p$.

Of particular interest are polypeptides which mimic the composition and physical properties of silks found in nature, e.g. *Bombyx mori*.

Also of interest are polypeptides which have as a base repeating unit GVGVP(G=glycine, V=valine, P=proline) (SEQ ID NO: 9), which may be found in naturally occurring elastin; also VPGVG (SEQ ID NO: 10) and/or APGVGV (SEQ ID NO: 11) units, where again the choice of the initial amino acid in the repeating unit is arbitrary. In the subject invention, the N-terminus may be any convenient sequence and, if desired, may be in whole or in part removed by a protease. Usually the N-terminal sequence which does not have the subject motif will be less than about 125, frequently less than about 100 amino acids, more usually less than about 60 amino acids.

Of particular interest is a base sequence of about 2 to 32, preferably 8, units separated by a sequence of about 3 to 50 amino acids, usually 12 to 48 amino acids, which may include an internal repeat of from 3 to 15 amino acids different from the basic repeating unit. For example, the second repeat sequence could be GAGAGS (SEQ ID NO: 12), repeated twice. The total number of base repeating units will generally be in the range of about 150 to 500, more usually 150 to 300, and more usually 175 to 250. The C-terminus may terminate with a repetitive unit or portion thereof or a different sequence of from 1 to 125, usually 1 to 50 amino acids. The C-terminus is not critical to the invention and will be selected primarily for convenience. As with the N-terminus, it may be designed for proteolytic cleavage. As in the case of the silk protein, the subject elastin-like protein may be similarly engineered.

Of particular interest are proteins which mimic the properties of elastin and provide for elastomeric properties and the use of elastin blocks to impart different physical properties, e.g. elastic properties or to modify the solubility properties of a different repetitive unit polymer.

Of particular interest are collagen like proteins which have the sequence $G\alpha\beta$, where $\alpha$ and $\beta$ may be any amino acid, particularly one being proline. Usually in the protein $\alpha$ and $\beta$ will be selected so that the total percent proline in the protein is between about 10 to 45 number % of the amino acids in the protein. The amino acids of particular interest other than glycine and proline are alanine, isoleucine, leucine, valine, serine, threonine, asparagine, glutamine, lysine, arginine, aspartic acid, glutamic acid, histidine. By known procedures after production of the protein, one or more prolines may be oxidized to hydroxyproline.

Also of interest are the polypeptides which have as a repeating unit K-L-(1)-L-A-E-A (SEQ ID NO: 13) where 1 is a basic or acidic amino acid, particularly K or E and the repeating units alternate as to whether I is a basic or acidic amino acid. This structure is commonly found in keratin.

The copolymer involving repeating units is a powerful method for varying properties, by appropriate choice of the different units, the number of units in each multimer, the spacing between them, and the number of repeats of the multimer combination assembly. Thus, by varying the number and arrangement of primary monomers, a variety of different physical and chemical properties can be achieved.

Exemplary of the use of the block copolymers are combinations of silk units and elastin units to provide products having properties distinctive from polymers only having the same monomeric unit.

The repetitive proteins can find a variety of uses. The Slp proteins may be used in producing fibers having unique properties, as a substitute for silk, and the like. Collagen proteins can be produced, where the collagen is free of the telopeptide or contains the telopeptide, depending upon its function. Atelopeptide collagen should have little if any immunogenicity, so as to be a useful structural element for a variety of prosthetic devices or for use as a collagen substitute in other applications. Similarly, other proteins having repetitive sequences, such as keratin, can also be prepared in accordance with the subject invention. Other useful repetitive proteins can be prepared based on sequences of spider silks and other repetitive animal fibers. Artificial peptides useful for immunization could also be prepared based on repeating sequences present in various surface antigens of disease-causing microorganisms, such as parasites, bacteria, and viruses.

The following examples are offered by way of illustration and not by way of limitation.

EXAMPLE 1

DNA Preparation Methods

1. Preparation of plasmid DNA from *E. coli:*

A. Small scale: Plasmid DNA was prepared from 1.5 ml cultures by either the boiling procedure or the alkaline lysis method (Maniatis, et al., Molecular Cloning: A Laboratory Manual. Cold Spring Harbor Laboratory, Cold Spring Harbor. (1982)).

B. Large scale: A plasmid-carrying strain was grown overnight in 1 liter of Luria broth with the appropriate antibiotic. The cells were collected by centrifugation at 10,000×g for 5 min and resuspended in 10 ml of ice cold TE (10 mM Tris-HCl pH 8, 1 mM EDTA). The cells were centrifuged again, resuspended in 4 ml of TES (TE and 25% w/v sucrose) and homogenized by vortexing. The samples were kept on ice for the following steps. Lysozyme (1 ml of 10 mg/ml) was added to the cell suspension and incubated for 5 min before the addition of 2 ml of 0.5M EDTA pH 8. After 10 min incubation, 50 ml of proteinase K (40 mg/ml) were added followed 10 min later with 15 ml of lysing buffer (0.1% Triton X-100, 1 mM EDTA, 50 mM tris-HCl pH 8). After 15–20 min, the cell lysate was centrifuged at 35,000×g for 90–120 minutes. The supernatant (19.8 ml) was transferred to a plastic tube with 20 mg of CsCl and 400 µl of ethidium bromide (10 mg/ml). After dissolution, the mixture was divided into two polyallomer ultracentrifuge tubes, sealed with heat and centrifuged in a Beckman Ti 65 rotor at 60,000 rpm for 24 hr. The lower plasmid DNA band was removed from the tube with a hypodermic needle. The ethidium bromide was extracted three times with an equal volume of NaCl-saturated isopropanol. Two volumes of $H_2O$ were added to the DNA solution, and then the DNA was precipitated with ethanol.

2. Preparation of double-stranded DNA:

A culture of JM103 was grown to an $OD_{600}$ of about 0.2 and then divided into aliquots of 2 ml. Each aliquot was infected with a fresh plaque of M13 and incubated at 37° C. for about 6 hours with vigorous shaking. Then the cells were pelleted and the supernatant was saved for subsequent infections. The double-stranded phage DNA was extracted by the boiling method (Maniatis et al.).

3. Deproteinization:

Phenol extraction was performed on a convenient volume of DNA sample, typically between 100 µl to 10 ml. The DNA sample was diluted in 0.01M Tris-HCl pH 7.5, 1 mM EDTA and an equal volume of water-saturated phenol was added. The sample was vortexed briefly and placed on ice for 3 minutes. After centrifugation for 3 min in a microfuge, the aqueous layer was removed to a new tube and extracted once with an equal volume of chloroform:isoamylalcohol (24: 1).

4. Ethanol precipitation:

DNA in an aqueous buffer was concentrated by ethanol precipitation. To the DNA sample was added ¹⁄₁₀ volume of 3M sodium acetate pH 7.5 and 2–3 volumes of cold ethanol. The DNA was precipitated for 30 min at −70° C. or overnight at −20° C. and then pelleted by centrifugation in the microfuge for 15 min at 4° C. The pellet was washed once with 200 µl of cold 80% ethanol and pelleted again for 10 min at 4° C. After air drying or lyophilization, the pellets were resuspended in the appropriate buffer.

5. Phosphatase treatment of DNA:

A. Phosphatase treatment of DNA was performed by adding 1 µl (25 units) of calf intestinal phosphatase (Boehringer Mannheim) directly to the restriction enzyme digestion reaction and continuing the incubation for 30 minutes at 37° C. The phosphatase was inactivated for 60 min at 65° C. prior to deproteinization by phenol extraction.

B. Phosphatase treatment of DNA was also performed by resuspending ethanol precipitated DNA from the restriction enzyme digest in 20 mM Tris-HCl pH 8.0, 10 mM $MgCl_2$ to a final DNA concentration of 20 µg/ml. Shrimp alkaline phosphatase ("SAP") was added at 2 U/µg of DNA and the mixture was incubated at 37° C. for one hour, heat inactivated for 20 min at 65° C. and then passed through a Probind filter (Millipore) and subsequently a Bio-Spin column. The DNA was then ethanol precipitated and resuspended in suitable buffer.

6. Phophorylation of DNA:

Phosphorylation before annealing was performed by using Polynucleotide Kinase 3'-phosphatase-free (Boerhinger Mannheim). The reaction was carried out at 37° C. for 30 min in a 50 µl reaction volume containing: 12.5 µg DNA, 5 µl 10× kinase buffer (0.5M Tris pH 7.5, 10 mM Spermidine, 0.1M $MgCl_2$, 150 mM DTT, 1 mM EDTA), and 2 µl Polynucleotide Kinase (10 U/µl). After phosphorylation, salts and glycerol were removed from the DNA strands using a Bio-Spin 6 column (BioRad) equilibriated in TEAB.

7. Fill-in reaction with DNA polymerase I:

DNA was resuspended in buffer containing 50 mM Tris-HCl pH 7.4, 50 mM KCl, 5 mM $MgCl_2$, and 400 µM each of the four deoxynucleotide triphosphates. Ten units of Klenow DNA polymerase (BRL) were added, and the reaction was allowed to proceed for 15 min at room temperature. The DNA was then phenol extracted and ethanol precipitated.

8. T4 polynucleotide kinase reaction:

The reaction (10 µl) contained: T4 polynucleotide kinase (BRL), 150 ng of DNA, 1 µl of 10×kinase buffer (0.7M Tris-HCl pH 7.6, 0.1M $MgCl_2$, 50 mM DTT) and [$^{32}$P]-ATP (200–300 nCi). This was incubated at 37° C. for 30 minutes and then the DNA was purified using a NACS column (Bethesda Research Labs).

9. Digestion with restriction endonucleases:

DNA was digested with restriction endonucleases (REN) in 1×"AA" buffer [10×AA buffer is 330 mM Tris-acetate, pH 7.9, 660 mM potassium acetate, 100 mM magnesium acetate, 50 mM dithiothreitol (DTT) and 1 mg/ml bovine serum albumin (nuclease free)]. Whenever possible, the concentration of DNA was kept below 1 µg/25 µl. Incubation was at 37° C. for 1–4 hrs for most restriction endonucleases except for BalI, BanI and NaeI digestions which were incubated overnight.

10. Analytical agarose gel electrophoresis of DNA:

To DNA samples for gel analysis we added 0.2 volumes of loading buffer (5×electrophoresis buffer, 0.01% bromphenol blue dye, 50 mM EDTA, and 50% glycerol). Then the samples were loaded into lanes of a horizontal submerged electrophoresis unit containing a 1.0% (w/v) agarose gel. The electrophoresis buffer was either 1×TAC or ½×TBE. The 1×TAC is 40 mM Tris-base, 10 mM EDTA, adjusted to pH 7.8 with acetic acid. The ½×TBE is 0.045M Tris-base, 0.045M boric acid, 1 mM EDTA, pH 8. The gel was run at 40–50V for 18 hr, then removed and stained with 0.5 µg/ml ethidium bromide for 30 minutes. The DNA bands were visualized on a long wavelength UV transilluminator.

11. Preparative agarose gel electrophoresis:

The procedures and materials are the same as for the analytical agarose gel electrophoresis. The only difference is the use of low melting point ("LMP") agarose, ranging in concentration from 0.5 to 2.5% (w/v) depending on the size of the DNA fragment to be purified. DNA restriction fragments were excised from the LMP agarose gels after visualization with ethidium bromide. For agarose ligation, the buffer used was 1×TAE (50 mM Tris-acetate, pH 7.8).

12. NACS purification:

Gel fragments containing DNA were melted at 70° C. for 5 min and diluted approximately 5 fold with TE1 (10 mM Tris-HCl pH 7.5, 0.2M NaCl). The gel solution was applied to a NACS column (BRL). The column was washed with 5 ml of the same buffer. The bound DNA was eluted with 300 µl of either TE2 (10 mM Tris-HCl pH 7.5, 1.0M NaCl) for DNA fragments smaller than 1000 bp or TE3 (10 mM Tris-HCl pH 7.5, 2M NaCl) for larger fragments. The eluted DNA was concentrated by ethanol precipitation.

13. DNA lipation:

Reactions for ligating cohesive ends contained: 1 µg DNA, 1×AA buffer (see step 9, above) 1 mM ATP and 20 units of T4 DNA ligase (BRL) in a 20 µl final reaction volume. The ligation was allowed to proceed for 16–18 hr at 15° C. or 1–2 hr at room temperature. For blunt-ended ligations the reactions contained 1 µg DNA, 25 mM Tris-KCl pH 7.5, 5 mM $MgCl_2$, 5 mM DTT, 0.25 mM spermidine, 200 mg BSA, 1 mM hexamine cobalt chloride (HCC), 0.5 mM ATP and 400 units T4 DNA ligase (NEB) in a 20 µl reaction volume. The ligation was allowed to proceed for 30 min to 1 hr at room temperature.

14. Agarose DNA Ligation

The agarose was melted at 65° C., the temperature was then lowered to 37° C. and ligation buffer (5×=100 mM Tris-HCl, pH 7.5, 50 mM $MgCl_2$, 50 mM DTT, 1 mM ATP) was added; the tube was then placed at room temperature and ligase was added (1000 units T4 DNA ligase (NEB)), the reaction volume was usually 50 µl. The reaction was incubated at 15° C. for 16–18 hours.

15. Use of Filters and Columns for DNA Purification.

A. Ultrafree®-Probind filter unit ("Probind", Millipore): the DNA containing solution was applied to the filter unit and spun at 12,000 RPM for 30 seconds in a Sorvall Microspin 24S.

B. Microcon-30 filter (Amicon): the DNA containing solution was washed by applying to the filter and exchanging twice with $H_2O$ by spinning at 12,000 RPM for 6 min in a microfuge.

C. Bio-Spin 6 column ("Bio-Spin", BioRad): Salts and glycerol were removed from the DNA solution by applying to the column, previously equilibrated in TEAB (triethyl ammonium bicarbonate pH 7.0), and spinning in a Sorvall RC5B centrifuge using an HB4 rotor at 2,500 RPM for 4 min.

16. Agarose DNA Purification Using Ultrafee®-MC Filter Unit:

This procedure can be used for agarose slices up to 400 µl in size. After agarose gel electrophoresis the DNA is visualized by ethidium bromide staining and the agarose block containing the DNA band of interest is excised. The agarose is then frozen at −20° C. for 1 hour; then quickly thawed at 37° C. for 5 minutes. The agarose is then thoroughly inacerated. The pieces are then transferred into the sample cup of the filter unit and spun at 5,000×g in a standard microfuge for 20 mins. The agarose is then resuspended in 200 µl of Tris-EDTA, or other buffer, and incubated at room temperature for 30 mins. to allow for elution of additional DNA from the gel. The mixture is then centrifuged for an additional 20 min at 10,000 RPM. The DNA is, at this point, in the filtrate tube separated from the agarose fragments and ready for subsequent DNA manipulations.

Bacterial Transformation Methods

1. Preparation of transformation-competent E. coli cells:

A culture of 200 ml of sterile L broth was inoculated with a small loopful of E. coli cells. This was incubated with shaking at 37° C. until the $OD_{600}$ was approximately 0.5. The culture was placed on ice for 10 min and centrifuged at 6,000×g for 10 minutes. The cell pellet was resuspended in 100 ml of ice-cold 0.1M $MgCl_2$, kept on ice for 30–40 min and centrifuged again. The pellet was resuspended in 2 ml of ice-cold 100 mM $CaCl_2$, transferred to a sterile test tube and incubated on ice for 24 hours. The competent cells were then aliquoted and stored at −70° C..

2. Transformation of *E. coli*;

An aliquot of frozen competent cells were thawed on ice. To 50 μl of cells 0.1 to 1 μg of DNA was added and the mixture was incubated on ice for 30 minutes. The tube was removed from ice and placed in a 42° C.. bath for 2 minutes. L broth (1 ml) was added and the transformation mix incubated with shaking at the desired temperature (usually 30° C.. or 37° C..) for 2 hours. Then on-tenth of the transformation was plated on L broth plates containing the appropriate antibiotic and, when necessary, XGAL and IPTG were added.

DNA transformation of *B. subtilis*;

*B. subtilis* cells were grown to early stationary phase (change in Klett units of ≦5% in 15 min). Transformation followed established procedures (Anagnostopoulos et al., 1981) (ref. 8). Cells (0.45 ml) were incubated with 1–10 μg of DNA at 37° C.. for 80 minutes with shaking, and then plated on TBAB agar plates with an appropriate antibiotic.

4. Isolation of plasmid DNA from *B. subtilis*;

Plasmid DNA from *B. subtilis* was obtained by a method similar to the alkaline-lysis method except that pelleted cells were resuspended in 8 ml of solution 1 (50 m M glucose, 10 mM EDTA, 25 mM Tris-HCl (pH 8.0), 10 mg/ml lysoyme) and incubated at room temperature for 30 minutes. Then 16 ml of solution 2 (0.2N NaOH, 1% (w/v) SDS) was added and incubated on ice for 10 minutes. Finally, 12 ml of 3M potassium acetate (pH 4.8) was added and incubated an additional 20 min on ice. The lysed cells were centrifuged 15 min at 15,000 rpm in a Sorval SS-34 rotor. The DNA was precipitated by adding an equal volume of isopropyl alcohol and centrifuged at 7,000 rpm. The pellet was resuspended in 5 ml of 10 mM Tris-HCl (pH 7.5), 1 mM EDTA (TE). The solution was phenol extracted once and chloroform extracted. DNA was precipitated with ethanol and resuspended in 3 ml of TE. The volume was adjusted to 5.2 ml by adding 4.2 g CsCl, 400 μl of ethidium bromide at 10 mg/ml and TE. The solution was transferred to a Beckman quickseal polyallomer centrifuge tube and centrifuged at 45,000 rpm in a Beckman vti65 rotor for 18 hours.

Antibody Production, Protein Chemistry and Electrophoresis of Proteins

1. Preparation of antibody to artificially synthesized peptides:

Synthetic peptide of sequence (GAGAGS)$_8$GGAAGY (SEQ ID NO: 14) was coupled to BSA using the glutaraldehyde procedure of Kagen and Glick (1979). The degree of coupling was monitored using trace amounts of radioactive iodinated synthetic peptide.

A peptide of 53 amino acids corresponding to the SlpIII sequence was prepared on an Applied Biosystems peptide synthesizer. The yield of this material, which has a molecular weight of 3640 was approximately 0.5 grams. The peptide was coupled to bovine serum albumin. The material was sent to Antibodies, Inc. for preparation of antibodies in rabbits. Peptide conjugates at a concentration of 1 mg/ml in complete Freund's adjuvant were used to immunize rabbits at day 0. Animals were re-injected with antigen in Freund's incomplete adjuvant at day 30 and titered at day 60. Positive sera was detected using a microtiter RIA using the synthetic peptide as antigen. Kagen and Glick (1979), in Methods of Radioimmunoassay, Jaffe and Berman (eds.), Academic Press, p 328. Antisera was obtained that reacted with synthetic peptides of both the SlpI and SlpIII sequences. These antisera have been useful for the detection of fusion peptides containing gly-ala (SLP) sequences.

Following the procedure described above an antigen was synthesized having the formula (V-P-G-V-G)$_8$ (SEQ ID NO: 15), which was coupled to keyhole limpet hemocyanin. Polyclonal antisera was then prepared as described above which bound to the ELP peptide.

Following the same procedure, additional antigens were synthesized having the formula YTITVYAVTGRGD-SPASSKPISINYC (SEQ ID NO: 16) of fibronectin (the FCB portion) and the formula (GAPGAPGSQGAPGLQ)$_2$YMK (SEQ ID NO: 17) (a repeat unit of the collagen-like protein (CLP) sequence) which were coupled to keyhole limpet hemocyanin for use as immunogens. Polyclonal antisera were then prepared as described above which bound, respectively, to the FCB peptide, and to the synthetic peptide of the CLP 3.7 sequence and PPAS sequence described below.

2. Polyacrylamide gel electrophoresis of proteins:

Approximately $10^9$ *E. coli* cells from growing cultures were pelleted by centrifugation at 10,000×g for 5 minutes. The cell pellets were resuspended in 100 to 500 μl of 2× sample buffer (100 mM Tris-HCl pH 6.8, 4% SDS, 10% β-mercaptoethanol, 60% glycerol or sucrose) and sonicated for 30 sec using a Tekmar sonic disrupter. Samples were boiled for approximately 5 min and 20 to 100 μl of the cell lysates were loaded on an SDS-polyacrylamide gel (7.5 to 16% w/v). The gels were prepared following the procedure of Laemmli, Nature (1970) 227: 680–685. The proteins in the gels were stained with 2% Coomassie brilliant blue in 10% methanol, 7.5% acetic acid for 1 hr and destained in 10% methanol, 7.5% acetic acid overnight.

3. Protein expression analysis:

An overnight culture which had been grown at 30° C. was used to inoculate 50 ml of the LB media contained in a 250 ml flask. Kanamycin was added at a final concentration of 50 μg/ml and the culture was incubated with agitation (200 RPM) at 30° C.. When the culture reached an OD$_{600}$ of 0.8, 40 ml were transferred to a new flask prewarmed at 42° C.. And incubated at the same temperature for approximately 2 hours. The cultures (30° C. and 42° C..) were chilled on ice and OD$_{600}$ was taken. Cells were collected by centrifugation and then divided in 1.0 OD$_{600}$ aliquots and used to perform western analysis using the appropriate antibodies.

4. Immunoblotting of proteins in gels:

After protein electrophoresis, one of the flanking glass plates was removed from the polyacrylamide gel. The gel surface was wetted with transfer buffer (25 mM Tris-HCl, 192 mM glycine, 20% methanol). A piece of nitrocellulose paper (Sartorius, SM 11307) was saturated with transfer buffer and laid on the gel. Air bubbles between the filter and the gel were removed. The gel and nitrocellulose filter were placed in the transfer unit as specified by manufacturer (BioRad). Transfer was allowed to proceed at 200 mA for 3–4 hours. Then the nitrocellulose filter was removed and stained with Amido-Schwartz for 3 min (0.05% Amido black, 45% deionized H$_2$O, 45% methanol, 10% acetic acid) and destained in H$_2$O. The filter was incubated for at least 10 min at room temperature in "BLOTTO" (5% w/v nonfat dry milk, 50 mM Tris-HCl pH 7.4, 0.9% w/v NaCl, 0.2% w/v sodium azide). The filter was placed in serum appropriately diluted (1:50 to 1:500) in 0.5×Blotto (2.5% nonfat dry milk, 50 mM Tris-HCl pK 7.4, 0.9% NaCl, 0.2% sodium azide) and was gently agitated for approximately 16 hr at room temperature. The filter was washed for 1 hr with 5 changes of TSA (50 mM Tris-HCl pH 7.4, 0.9% NaCl, 0.2% sodium azide). The blot was placed in 15 ml of 0.5×BLOTTO solution containing 1×10$^7$ cpm of the $^{125}$I-protein A and gently agitated for 2 hr at room temperature. The filter was washed for 2 hr with a minimum of 7 changes of TSA, rinsed once with deionized H$_2$O and air dried. The blot was covered with Saran® wrap and autoradiographed.

An alternative to the [125]I-Protein A detection method was also used. This method relied on a chemiluminescent signal activated by horseradish peroxidase (HRP). The chemiluminescent reagents are readily available from several suppliers such as Amersham and DuPont NEN. The western blot was prepared and blocked with BLOTTO. A number of methods were used to introduce the HRP reporter enzyme including, for example, a hapten/anti-hapten-HRP, a biotinylated antibody/streptavidin-HRP, a secondary reporter such as a goat or mouse anti-rabbit IgG-biotinylated/ streptavidin-HRP, or a goat or mouse-anti rabbit IgG-HRP. These reagents were bought from different sources such as BioRad or Amersham and occasionally biotinylated antibodies were prepared in our laboratory using Biotin NHS from Vector Laboratories, Burlingame, Calif. (Cat. #SP-1200) following the procedure accompanying the product. The following is an example of a procedure used to detect the expression of protein polymers.

The blot was placed in 15 ml of BLOTTO solution containing biotinylated goat anti-rabbit IgG (BioRad) diluted in BLOTTO (1:7500) and gently agitated for 2 hrs at room temperature. The filter was then washed for 30 minutes with 3 changes of TSA (50 mM Tris-HCl pH 7.4, 0.9% NaCl, 0.2% sodium azide). The blot was then incubated for 20 minutes at room temperature with gentle rotation, in 20 ml of TBS (100 mM Tris Base, 150 mM NaCl, pH 7.5) HRP-Streptavidin (Amersham) diluted 1:1000 in TBS with 0.1% Tween 20. The blot was then washed three times for 5 minutes each in TBS with 0.3% Tween 20 and then three times for 5 minutes each in TBS with 0.1% Tween 20. The blot was then incubated for 1 minute with gentle agitation in 12 ml of development solutions #1 an #2 (Amersham) equally mixed. The blot was removed from the development solution and autoradiographed.

5. Amino Acid Analysis:

Amino acid compositions are determined by the PTC derivitization procedure of Henrickson and Meredith (1984). Protein samples were hydrolysed with 5.7N constant boiling KCl at 108° C. for 24 hours in vacuo. After reaction with PITC, amino acid derivatives were detected at 254 nm by HPLC reverse phase chromatography using a Hewlett Packard 1090 or Waters 600E system and a Supelco C18 column (4.6 mm×25 cm) with a linear gradient of 0–50% acetonitrile in 0.1M NH$_4$OAc pH 6.78 as a mobile base. Henrickson, R. L. and Meredith, S. C. (1984) Amino Analysis by Reverse Phase High Performance Liquid Chromatography. *Anal. Biochem.* 137: 65–74.

6. Amino Acid Sequence Analysis:

The N-terminal amino acid sequence was determined by automated Edman degradation using an Applied Biosystems Model 470A gas phase protein sequenator. The PTH amino acid derivatives were analyzed by reverse phase HPLC using a Hewlett Packard 1090 or Waters 600E system and an Altex C18 column (2 mm×25 cm) with a complex gradient buffer system.

7. Peptide Synthesis:

Synthetic peptides were prepared by solid phase synthesis on an Applied Biosystems Model 430A Peptide Synthesizer using the standard symmetric anhydride chemistry as provided by the manufacturer. The coupling yield at each step was determined by the quantitative ninhydrin procedure of Sarin et al., (1981). The synthetic peptide was cleaved from the solid support and amino acid blocking groups were removed using anhydrous HF (Stewart and Young, 1984). Crude peptides were desalted by chromatography over Sephadex G-50. Sarin, V. K., Kent, S. B. H., Tam, J. P. and Merrifield, R. B. (1981). *Anal. Biochem.* 237: 927–936.

Stewart, J. M. and Young, J. D. (1984). Solid Phase Peptide Synthesis, Pierce Chemical Company, Rockford, Ill. pp 85–89.

Synthetic DNA Methods

1. In vitro DNA synthesis:

The N,N-diisopropylphosphoramidites or β-cyanoethylphosphoramidites, controlled-pore glass columns and all synthesis reagents were obtained from Applied Biosystems, Foster City, Calif.

Synthetic oligonucleotides were prepared by the phosphite triester method with an Applied Biosystems Model 380A or 381A DNA synthesizer using a 10-fold excess of protected phosphoramidites and 0.2 or 1 μmole of nucleotide bound to the synthesis support column. The chemistries used for synthesis are the standard protocols recommended for use with the synthesizer and have been described (Matteucci, et al., *Journal Amer. Chem. Soc.,* 103: 3185–3319 (1981)). Deprotection and cleavage of the oligomers from the solid support were performed according to standard procedures as described by McBride, et al., *Tetrahedron Letters,* 24: 245–248 (1983) and as provided by Applied Biosystems. The repetitive yield of the synthesis as measured by the optical density of the removed protecting group as recommended by Applied Biosystems (1984) was greater than 97.5%.

The crude oligonucleotide mixture was purified by preparative gel electrophoresis as described by the Applied Biosystems protocols of Nov. 9, 1984 (User Bulletin No. 13) and as updated in the Applied Biosystems protocols in Evaluating and Isolating Synthetic Oligonucleotides, 1992. The acrylamide gel concentration varied from 10 to 20% depending upon the length of the oligomer. The purified oligomer was identified by UV shadowing, excised from the gel and extracted by the crush and soak procedure (Smith, *Methods in Enzymology,* 65: 371–379 (1980)).

For DNA synthesis of oligonucleotides longer than 100 bases, the synthesis cycle was changed from the protocol recommended by Applied Biosystems for the 381A DNA synthesizer. All the reagents used were fresh. All the reagents were supplied by Applied Biosystems except for the acetonitrile (Burdick and Jackson Cat#017-4 with water content less then 0.001%) and the 2000 Å pore size column (Glen Research). Due to the length of the oligo, interrupt pauses had to be inserted during the synthesis to allow changing the reagent bottles that emptied during synthesis. This interrupt pause was done at the cycle entry step and the pause was kept as short as possible. The washes after detritylation by TCA, through the beginning of each synthesis cycle, were increased from about 2×to 3× over the recommended time. The time allocated for the capping was also increased to limit truncated failure sequences. After the synthesis the deprotection was done at 55° C.. for 6 hours. After desalting the synthesized DNA was amplified using PCR.

2. Sequencing of DNA:

DNA sequences were determined by the following methods. Fragments containing the region of interest were cloned into the multiple cloning site of M13mp18 or M13mp19 and single-stranded DNA was prepared and sequenced by the primer extension method as described in the literature. (Sanger et al. 1977; Maniatis et al., 1982; Norrander et al. 1983. *Gene,* 26: 101–106 ; Sanger et al. 1977 *Proc. Natl. Acad. Sci. USA,* 74: 5463–5467 and Biggin 1983 *Proc. Natl. Acad. Sci. USA,* 80: 3963–3965; Sanger et al. 1978, *FEBS Letters,* 87: 107–110) using $^{35}$S-deoxyadenosine 5' (alpha-thio)-triphosphate (New England Nuclear) as label. In some cases, reverse transcriptase (Molecular Genetics) was used to extend the primer, using the dideoxy:deoxynucleoside tri-phosphate ratios utilized by Zagursky et al., *Gene Anal. Techn.* (1985) 2: 89–94.

Deoxyadenosine triphosphate labeled with either $^{32}P$ or $^{35}S$ was used in these reactions. Compression artifacts which appeared in some G-C rich sequences were overcome by eliminating deoxyguanosine triphosphate from the G reaction, and using deoxyinosine triphosphate (P-L Biochemicals) at a final concentration of 37.5 µM instead. In the other mixes, the concentration of dideoxyGTP in the G reaction was 0.5 mM. All sequences were run on 6 or 8% polyacrylamide gels containing 8M urea (Sanger et al. 1978). Primers used for sequencing were purchased from P-L Biochemicals. Storage and analysis of data utilized software from both DNAstar and International Biotechnologies, Inc for IBM personal computer and DNA Strider, DNA Inspection IIe or DNAid for Apple Macintosh personal computer.

3. In vitro mutagenesis of cloned DNA:

Plasmid DNA (1 µg) containing the sequence to be mutated was digested in two separate reactions. One reaction contained either one or two restriction endonucleases which cleave at sites immediately flanking the region of interest. In the second reaction, the DNA was digested with a restriction endonuclease which cleaves only once at a site distant from the sequence to be mutated. The DNA fragments generated in the first reaction were separated by agarose gel electrophoresis and the large fragment which lacks the sequence to be mutated was excised and purified. DNA from the second reaction, the large fragment of DNA from the first reaction, and a synthetic oligodeoxynucleotide of 20–30 bases in length containing the mutant sequence were mixed in a molar ratio of 1:1:250. The mixture was denatured by heating at 100° C.. for 3 min in 25 to 100 µl of 100 mM NaCl, 6.5 mM Tris-HCl pH 7.5, 8 mM $MgCl_2$, and 1 mM β-mercaptoethanol. The denatured mixture was reannealed by gradually lowering the temperature as follows: 37° C. for 30 min, 4° C. for 30 min, and 0° C. for 10 minutes. The reaction was supplemented with 0.5 mM deoxyribonucleotide triphosphates, 1 mM ATP, 400 units of T4 DNA ligase and 5 units of *E. coli* DNA polymerase large fragment and incubated at 15° C. for 12–16 hours. The reaction mixture was then transformed into *E. coli* and antibiotic-resistant colonies were selected.

4. Dideoxy DNA Sequencing of Double Stranded Plasmid DNA:

Plasmid DNA was prepared as described previously (Preparation of plasmid DNA from *E. coli*, Small Scale, Maniatis et al.). Primers were synthesized using a DNA synthesizer as described previously, and were annealed to the plasmid DNA following the procedure described above for M13 sequencing. The sequencing reactions were done using Sequenase (United States Biochemicals) and the conditions were as recommended by the supplier. All sequences were run on polyacrylamide gels as described above.

5. PCR amplification:

The PCR reaction was performed in a 100 µl volume in a Perkin Elmer thin-walled Gene Amp™ reaction tube. Approximately 1 µl of each primer DNA was added to 1×PCR buffer (supplied by Perkin Elmer as 10× solution), 200 µM of each dNT, 5U AmpliTaq, and several concentrations of the target DNA. Amplification was performed in a Perkin Elmer DNA Thermal cycler model 480 for 30 cycles with the following step cycles of 12 min each: 95° C., 62° C., and 72° C.. Aliquots from the different reactions were analyzed by Agarose Gel Electrophoresis using 1.5% Low Melting Point agarose in 0.5× Ta buffer. The reaction mixtures that gave the desired band were pooled and spun through an Ultrafree-Probind filter unit (Millipore) at 12,000 Rpm for 30 seconds in a Sorvall Microspin 24S to remove the AmpliTaq enzyme. The buffer was then exchanged with $H_2O$ two times, using a Microcon-30 filter (Amicon) by spinning at 12,000 RPM for 6 min in a microfuge. Salts and glycerol were removed from the amplified dsDNA using a Bio-Spin 6 column (from BioRad) equilibrated in TEAB, in a Sorvall RC5B centrifuge using an HB4 rotor at 2,500 RPM for 4 minutes. The DNA was then concentrated in vacuo.

Fermentation Conditions

The fermentor is a 15 L Chemap, 10 L working volume. The culture conditions are: temperature=30° C., pH 6.8; NaOH 2.5M is used for pH regulation. The headspace pressure is below 0.1 bar. The dissolved oxygen is regulated at 50%. The air flow varies from 0.5 L/min to 20 L/minute. The agitation rate varies between 200 to 1500 rpm. The fermentor is inoculated with a 10% (v/v) inoculum grown in medium A for 15 hours at 30° C. under agitation.

Medium B, C or D was the fermentor medium. The starting volume in the case of 10 liter fermentation, is no less than 3 L, and in the case of a 1 liter fermentation, is no less than 0.5 liters.

If the fermentor starting volume is less than the final volume desired, then when the carbon source concentration reaches 1%, a concentrated solution (5×) of medium B, C, or D, respectively, is added to the fermentor in order to keep the carbon source concentration approximately 1%.

When the culture reached an $OD_{600}$ of 60.0, the temperature was increased to 42° C. for 10 min, then lowered to 39° or 40° C. for 2–3 hours. The cells were then harvested by centrifugation and, if necessary, frozen at −70° C. until processed.

Other fermentors used for the expression of protein polymers were usually a 15 l MBR, 10 l working volume, or a 13 l Braun Biostat E, 8.5 l working volume. The choice of the fermentor and its size is not critical. Any media used for the growth of *E. coli* can be used. The nitrogen source ranged from NZAmine to inorganic salts and the carbon source generally used was glycerol or glucose. All fermentations were done with the appropriate selection conditions imposed by the plasmid requirements (e.g. kanamycin, ampicillin, etc.). The fermentation method used to express protein polymers in *E. coli* was the fed-batch method. This is the preferred method for the fermentation of recombinant organisms even if other methods can be used.

The fed-batch method exploits the stage of cell growth where the organisms make a transition from exponential to stationary phase. This transition is often the result of either depletion of an essential nutrient or accumulation of a metabolic byproduct. When the transition is the result of nutrient depletion, the addition of nutrients to the system causes cell division to continue. One or more essential nutrients can incrementally be added to the fermentation vessel during the run, with the net volume increasing during the fermentation process. The result is a controlled growth rate where biomass and expression levels can be optimized. When the cell number in the culture has reached or is approaching a maximum, protein polymer production is induced by providing an appropriate physical or chemical signal, depending upon the expression system used. Production will then continue until the accumulated product reaches maximum levels (Fiestchko, J., and Ritch, T., *Chem. Eng. Commun.* (1986), 45: 229–240. Seo, J. H.; Bailey, J. E., *Biotechnol. Bioeng.* (1986), 28: 1590–1594.

TABLE 1

Medium Table

| Constituent | g/L |
|---|---|
| Medium A: LB Medium | |
| NaCl | 10 |
| tryptone | 10 |
| yeast extract | 5 |
| kanamycin | $5 \times 10^{-3}$ |
| Medium B | |
| $NH_4Cl$ | 4.5 |
| $KH_2PO_4$ | 0.76 |
| $MgSO_4 \cdot 7H_2O$ | 0.18 |
| $K_2SO_4$ | 0.09 |
| $CaCl_2$ | $24 \times 10^{-3}$ |
| $FeSO_4 \cdot 7H_2O$ | $7.6 \times 10^{-3}$ |
| TE | 0.5 ml |
| casamino acids | 25 |
| yeast extract | 5 |
| glucose | 20 |
| kanamycin | $5 \times 10^{-3}$ |
| Medium D | |
| $(NH_4)SO_4$ | 5.6 |
| $K_2HPO_4$ | 6.7 |
| $MgSO_4 \cdot 7H_2O$ | 7.8 |
| $NaH_2PO_4 \cdot H_2O$ | 3.8 |
| EDTA | 0.98 |
| Trace Elements | 1 ml |
| Yeast Extract or NZ Amine | 50 |
| Glucose or glycerol | 20 |
| Kanamycin or ampicillin | $5 \times 10^{-3}$ |

EXAMPLE 2
Assembly and Expression of the SlpI Gene

1. Summary of the scheme for assembling the SlpI gene:

An 18 bp DNA sequence that codes for the most frequent repeating oligopeptide in the silk fibroin protein made by *Bombyx mori* [Lucas, F. and K. M. Rudall (1986) Extracellular Fibrous Proteins: The Silks. p. 475–558, in Comprehensive Biochemistry, vol. 26, part B., M. Florkin and F. H. Stotz (eds.) Elsevier, Amsterdam] was synthesized in vitro. Two single-strands were synthesized, annealed together and then the resulting double-stranded segments were multimerized head-to-tail to generate concatamers of up to and exceeding 13 repeats. The structural gene for silk I that we proceeded to work with had 13 repeats that coded for the oligopeptide GAGAGS, where g=glycine, a=alanine and s=serine. We refer to this structural gene as the "monomer". We constructed "dimeric, trimeric, tetrameric, pentameric and hexameric" SlpI genes containing 26 (SlpI-2), 39 (SlpI-3), 52 (SlpI4), 65 (SlpI-5) and 78 (SlpI-6) repeats. There is a short intervening sequence between each monomer unit. The assembly is pictured as follows:

Repeating DNA Sequence 5'-GGTGCGGGCGCAGGAAGT
                                  CGCCCGCGTCCTTCACCA-5'

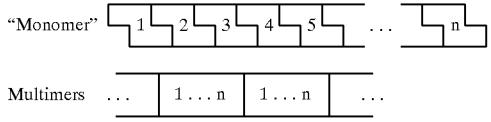

2. Assembly of the "monomeric" SlpI structural gene:

The two single-strands shown above were synthesized as previously described. The strands were separately purified by gel electrophoresis, phosphorylated using T4 polynucleotide kinase and then mixed together and allowed to anneal. This resulted in the double-stranded segments aligning spontaneously head-to-tail in long concatamers. The phosphodiester bonds between segments were formed with T4 DNA ligase. The reaction was stopped by filling in the terminal cohesive ends using the Klenow fragment of DNA polymerase I. The blunt-ended repeating DNA was then ligated to the HincII REN site in plasmid vector pUC12 (Veiera, et al., *Gene* 19: 259–268 (1982)). The ligated DNA was transformed into *E. coli* HB101 and transformants were selected for their ability to grow in the presence of ampicillin. The DNA of potential clones was analyzed; for size and orientation by REN digestion and gel electrophoresis. DNA sequences were determined for isolates with large inserts that were oriented properly. The "monomer" clone selected for subsequent multimerization had 13 repeats coding for the oligopeptide AGAGSG (SEQ ID NO: 20), and was named pSY708. The DNA sequence, deduced amino acid sequence and REN sites of the SlpI insert and flanking regions of pSY708 are shown in Table 2.

TABLE 2

```
H                   P           A  S
I                   S           V  M
N                   T           A  A
3                   1           1  1
|                   |           |  |
|                   |           |  |
AAGCTTGGGCTGCAGGTCACCCGGGCGGGCGCAGGAAGTGGTGCGGGCGCAGGAAGTGGT
TTCGAACCCGACGTCCAGTGGGCCCGCCCGCGTCCTTCACCACGCCCGCGTCCTTCACCA    60
 K   L   G   L   Q   V   T   R   A   G   A   G   S   G   A   G   A   G   S   G

GCGGGCGCAGGAAGTGGTGCGGGCGCAGGAAGTGGTGCGGGCGCAGGAAGTGGTGCGGGC
CGCCCGCGTCCTTCACCACGCCCGCGTCCTTCACCACGCCCGCGTCCTTCACCACGCCCG    120
 A   G   A   G   S   G   A   G   A   G   S   G   A   G   A   G   S   G   A   G

GCAGGAAGTGGTGCGGGCGCAGGAAGTGGTGCGGGCGCAGGAAGTGGTGCGGGCGCAGGA
CGTCCTTCACCACGCCCGCGTCCTTCACCACGCCCGCGTCCTTCACCACGCCCGCGTCCT    180
 A   G   S   G   A   G   A   G   S   G   A   G   A   G   S   G   A   G   A   G

AGTGGTGCGGGCGCAGGAAGTGGTGCGGGCGCAGGAAGTGGTGCGGGCGCAGGAAGTGGT
TCACCACGCCCGCGTCCTTCACCACGCCCGCGTCCTTCACCACGCCCGCGTCCTTCACCA    240
 S   G   A   G   A   G   S   G   A   G   A   G   S   G   A   G   A   G   S   G
```

TABLE 2-continued

```
      X        B       A S             E
      B        A       V M             C
      A        M       A A             R
      1        1       1 1             1
      |        |       | |             |
      |        |       | |             |
GCGGGCGCAGGAAGTGGGACTCTAGAGGATCCCCGGGCGAGCTCGAATTC (SEQ ID NO: 21)
CGCCCGCGTCCTTCACCCTGAGATCTCCTAGGGGCCCGCTCGAGCTTAAG (SEQ ID NO: 22)  290
 A  G  A  G  S  G  T  L  O  D  P  R  A  S  S  N  S
```

3. Construction of the expression vector, pSY701:

Plasmid pSP65 (10 μg, Boehringer Mannheim) was digested with AatII REN, phenol extracted and ethanol precipitated. The DNA was resuspended in 10 μl of H$_2$O. One-half of this DNA was digested with exonuclease III in the following mix: 5 μg DNA, 10 μl 10× exonuclease III buffer (600 mM Tris-HCl pH 8.0, 6.6 mM MgCl$_2$, 10 mM β-mercaptoethanol) and 9 units of exonuclease III in a total volume of 200 μl. Samples of 20 μl were taken at 0, 1, 2.5, 5 and 7.5 min and diluted immediately in 100 μl of the following buffer (30 mM sodium acetate, pH 4.5, 0.25M NaCl, 1 mM ZnSO$_4$) containing 5 μg tRNA and 36 units of S1 nuclease. Incubation was at 30° C.. for 45 min and then the reaction was terminated by the addition of 15 μl of stop buffer (0.5M Tris pH 9.0, 125 mM EDTA, 1% w/v SDS, 200 μg/ml tRNA). The samples were phenol extracted and ethanol precipitated. The resuspended DNA was digested with SmaI REN and electrophoresed through a 1% gel of low melting point agarose. The gel band corresponding to the DNA fragment carrying the β-lactamase gene, the plasmid origin and the β-galactosidase promoter was excised from the gel and melted at 65° C.. One volume of H$_2$O was added. The DNA in each sample (timepoint) was recircularized by ligation in the presence of agarose. The reaction included 8 μl melted gel, 2 μl of ligation buffer (100 mM Tris-HCl pH 7.5, 50 mM MgCl$_2$, 50 mM DTT, 1 mM ATP), 10 units T4 DNA ligase and was incubated at 15° C.. for 3 hours. Competent cells of JM101 were transformed with the ligated DNA and transformants were selected by growth on L broth plates containing ampicillin (40 μg/ml). Plasmid DNA was prepared from four transformants. The DNA was digested with BamHI REN, labeled with $^{32}$P-dGTP using the Klenow fragment of DNA Polymerase I, digested with Pvu I and then the smallest fragment was gel purified. The fragment from one transformant was sequenced using the Maxam and Gilbert technique. The fragments of the other three plasmids were further digested with TaqI and electrophoresed on the same gel. The sequenced plasmid had a fusion between the multiple cloning site and a position upstream from the N-terminal ATG of β-lactamase. The size of the BamHI-TaqI fragment of two of the other plasmids indicated a fusion between the multiple cloning site and the 4th amino acid of the β-lactamase gene. The DNA and corresponding amino acid sequences of the N-terminal region of the altered β-lactamase are given below, along with a circular map of REN sites for pSY701 are shown in FIG. 1. The amino acid sequence of FIG. 1 is met-thr-met-ile-thr-pro-ser-leu-gly-cys-arg-ser-thr-leu-glu-asp-pro-his-phe-arg-val-ala-leu-ile-pro-phe-phe-ala-ala-phe-cys-leu-pro-val-phe-ala-his. (SEQ ID NO: 1).

4. Insertion of "monomer" SlpI From pSY708 into pSY701:

Plasmid pSY708 was digested with HindIII, the cohesive ends were filled in using the Klenow fragment of DNA polymerase I and then digested with BamHI. Plasmid pSY701 was digested with XbaI, filled in as above and then digested with BamHI. The DNA fragment from pSY708 and the backbone of pSY701 were then purified by electrophoresis through a low melting temperature agarose gel and purified with NACS (BRL) columns. The appropriate fragments were mixed, ligated, and then transformed into E. coli JM109. Transformed cells were selected by growth on L plates containing ampicillin (40 mg/ml), IPTG (5×10$^{-4}$M) and XGAL (20 mg/ml). Transformants were analyzed for plasmid contents and one (pSY756) was selected for further study since it carried the insert of the monomer SlpI-1 sequences in the proper orientation, as determined by mapping of REN sites. Although the entire DNA sequence was not determined for pSY756, the junctions between the insert and vector were verified as correct restriction sequences for XbaI, upstream and BamHI, downstream.

5. Multimerization of the SlpI gene of pSY756:

Plasmid pSY708 was digested with the REN SmaI and the DNA fragment carrying the coding sequence for the polypeptide arg(ala-gly-ala-gly-ser-gly)$_{13}$ thr-leu-glu-asp-pro (R(AGAGSG)$_{13}$TLEDP) (SEQ ID NO: 23) was purified as in 4 above. Plasmid pSY756 was digested with SmaI, deproteinized and then ligated with the purified DNA fragment from pSY708. Transformants of E. coli JM109 were selected on medium containing ampicillin. Clones were found to contain 2 units (dimer pSY882), 3 units (trimer pSY883), and 4 units (tetramer pSY915) of the original monomer sequence of the pSY708 clone. Similarly, pentamers and hexamers have also been constructed. All of these plasmids are genetically stable and produce the gly-ala peptide as a fusion with β-lactamase.

6. Expression of the SlpI gene fusion to the β-lactamase protein:

Synthesis in E. coli cells of the SlpI peptide as a fusion protein with β-lactamase was detected by immunoblotting (Western) analysis. Anti-"Slp" antibodies were raised against a synthetic silk peptide. Fusions between β-lactamase and SlpI were also detected with antibodies raised against the E. coli β-lactamase. As shown in FIG. 2, this antibody reacts with dimers and trimers of SlpI fused to the E. coli β-lactamase. The SlpI insert precedes the fifth amino acid of the signal sequence for this enzyme. The β-lactamase antibody (FIG. 2A) detects both the unprocessed fusion proteins as well as the processed mature enzyme which appears as the major antigenic band in this figure, at about the 28 kDal position. The mobilities of all Slp-containing polypeptides are anomalously slow and the proteins are not as large as they appear on the gels.

The anti-Slp antibody also is useful in detecting these fusion products. Lanes 2–5 of FIG. 2B represent 4 separate clones that contain dimer fusions of SlpI with β-lactamase, while lanes 6 and 7 are from two clones containing trimer fusions. As can be seen the antigenicity of the trimer is considerably greater than for the dimer. It is known from prior experiments that fusion proteins containing only a monomer of SlpI are not detected at all with this anti-Slp antibody. The increased antigenicity of the trimer peptide allows it to be detected as a processed fusion with the β-lactamase signal peptide. The processed form is seen at about the 33 kDal position in lanes 6 and 7 of FIG. 2B. The appearance of normally processed β-lactamase mature enzyme (detected with β-lactamase antibody) as well as a peptide corresponding to the fusion between the SlpI-3 trimer and the signal peptide of β-lactamase (detected with gly-ala antibody) suggests that despite the insertion of SlpI sequences within the signal sequence, normal proteolytic processing of the enzyme occurs in E. coli.

7.a. Expression of the SlpI gene by fusion to T7 genes:

The SlpI sequence has also been expressed as a fusion protein with both the gene 9 and gene 10 proteins from bacteriophage T7 in E. coli. The construction is diagrammed in FIG. 3. Plasmid pSY915 (containing the SlpI-4 tetramer) was digested to completion with REN SalI and partially with BamHI. The DNA fragment containing the SlpI-4 tetramer was purified and then cloned in plasmid pSY114 (pG2 of Promega Biotech) which had been digested with RENs SalI and BamHI. From this intermediate plasmid, the tetramer insert of SlpI was removed with the RENs AccI and EcoRI. This fragment was then cloned in pSY633 (pBR322 containing the complete T7 gene 9 sequence; pAR441 of Studier et al., (1986)) which was digested with EcoRI and AsuII. In the resulting plasmid the SlpI tetramer is fused to the gene 9 translational reading frame near the C-terminus of gene 9. This plasmid was then used to transform E. coli strain 0–48 (strain HMS174 (λDE3) of Studier, et al., 1986) which contains the T7 RNA polymerase gene inserted into the chromosome under transcriptional control of the IPTG-inducible β-galactosidase promoter. In this configuration, expression of the SlpI-4 sequence is dependent upon production of the T7 RNA polymerase which itself is controlled by the IPTG inducible β-galactosidase promoter. As shown in FIGS. 4B and 4C, when these cells are induced with IPTG a protein product of the gene 9/SlpI-4 fusion gene is synthesized and is detected with antibody to the synthetic Slp peptide. The fusion product migrates in the gel as if it was 82 kDal in size. The size expected is only 65 kdal. The anomalous mobility is characteristic of the unusual amino acid composition (rich in glycine and alanine) and is seen for all Slp-containing products.

In like manner, plasmid pSY638 (pAR2113 of Studier) containing the promoter region and the first 13 amino acids of the T7 gene 10 protein, was digested with REN BamHI, filled in with the Klenow fragment of DNA polymerase and then digested with REN EcoRI. Into this linearized plasmid was cloned the AsuII-EcoRI fragment of pSY633, containing the SlpI-4 tetramer. This ligation creates an in-frame fusion of the silk tetramer following the thirteenth amino acid of T7 gene 10. The latter fusion product may be used for spinning without further processing since the N-terminal 13 amino acids are only a small part of the large SlpI protein. Although the fusion product is about 30 kDal in size, it has an anomalous mobility and migrates as if it was larger, 50 kDal. This is shown in FIG. 4A.

The plasmids pG9/SlpI-4 and pG10/SlpI-4 were further improved by inserting a kanamycin-resistance gene in the β-lactamase gene in the orientation opposite to the T7 expression system. Thus, any low level expression from the T7 system does not lead to elevated β-lactamase activity. Such activity eliminated the ampicillin in the medium that was added to select for maintenance of the plasmid. When the ampicillin was depleted the plasmids were lost from the culture. The kanamycin-resistance gene circumvents this problem and represents a significant improvement in the T7 expression system, especially for large scale cultures. The kanamycin-resistance gene (originally from Tn903) was isolated from a plasmid pUC4K (Veira, J. and J. Messing (1982) Gene 19: 259–268) as a HincII fragment. The plasmid containing pG10/SlpI-4 and the kanamycin resistance gene was designated pSY997.

7.b. Fermentation and purification of SlpI-4:

E. coli strain 0–48 carrying pSY997 was grown at 37° C., using a Chemap or a Braun fermentor, in 10 L of LB to an OD (Klett units) of 300 ($3\times10^9$ cells/ml). The T7 system was then induced with the addition of 3.5 mM IPTG. After 150 min the cells were concentrated 10× using a Millipore filter unit (Pellicon cassette system, 100,000 molecular weight cut off filter). The cell suspension was then frozen at −70° C. until processing.

The cell suspension was melted in a water bath at 42° C. and lysed in a french press, and the lysate was spun at 125,000×g for 1 hour at 25° C.. The cleared supernatant was treated with DNAase (250 µm/ml) for 15 min at room temperature, then filtered through a 0.45 µm sterile filter. The filtrate volume was measured and incubated in ice with slow stirring. Then 231 mg of ammonium sulphate were added for each ml of filtrate over a period of 45 minutes. One ml of NaOH for each 10 g of ammonium sulphate was added to neutralize the pH.

After 2 hours of continuous stirring the mixture was spun at 9,000×g for 10 minutes. The pellet was resuspended in ⅒ of the original filtrate volume using distilled water. The centrifugation and resuspension was repeated three times. The pellet was resuspended in ⅒ of the original filtrate volume in distilled water. Samples were analyzed for protein concentration, amino acid composition and protein sequence by standard methods. This is one of several methods for obtaining the product. This method results in a SlpI-4 product that is greater than 90% pure. The amino acid composition is almost entirely gly, ala and ser, as expected, and the N-terminal amino acid sequence is that of the gene 10 leader.

8. Controlled expression of the T7 RNA polymerase gene in Bacillus subtilis:

The coding sequence of the T7 RNA polymerase gene (T7 gene 1, T7 nucleotides 3128 to 5845) from plasmid pSY558 (pARI151 of Studier, et al., 1986) was modified by in vitro mutagenesis of cloned DNA. We inserted the recognition sequence for the restriction endonuclease NdeI at position 3171. Using an oligodeoxynucleotide which was synthesized as previously described, the T7 gene 1 sequence was changed from its natural sequence, TAAATG (SEQ ID NO: 24), to the modified sequence, CATATG (SEQ ID NO: 25).

Similarly, the upstream regulatory sequence of the Bacillus subtilis gene spoVG, obtained from plasmid pCB1291 (Rosenblum, et al., J. Bacteriology, 148: 341–351 (1981)), was modified by in vitro mutagenesis at position 85 (Johnson, et al., Nature, 302: 800–804 (1983)) such that it also includes an NdeI cleavage site. The upstream regulatory sequences of the spoVG gene were then ligated with the coding sequence of the T7 RNA polymerase gene via these novel NdeI cleavage sites. After transformation of E. coli HB101, the plasmid contents of individual ampicillin-resistant isolates were checked by restriction mapping. The correct construction was named pSY649.

Plasmid DNA containing the spoVG:T7 RNA polymerase fusion gene (pSY649) was further modified to include a chloramphenicol-resistance gene that functions in B. subtilis. First the NdeI to SalI fragment of about 1200 base pairs from plasmid pGR71-P43 (Goldfarb, et al., Nature, 293:

309–311 (1981)) was isolated. This fragment carries the P43 promoter of *B. subtilis* and an adjacent chloramphenicol acetyltransferase gene from Tn9. After filling in all the cohesive ends using the Klenow DNA polymerase reaction, this fragment was inserted into the XbaI site within the multiple-cloning site of pUC13 (Veiera, et al., *Gene,* 19: 259–268 (1982)). Ampicillin and chloramphenicol-resistant transformants were selected for further use. The correct plasmid construction was named pSY630. The SmaI to HincII endonuclease cleavage fragment from plasmid pSY630 containing the chloramphenicol acetyltransferase gene fused to the P43 promoter sequence was gel purified and blunt-end ligated to the PvuI site of plasmid pSY649 that had been treated first with T4 DNA polymerase. The resulting plasmid, pSY856, was then transformed into *B. subtllis* 1168. Because plasmid pSY856 is unable to replicate autonomously in *B. subtilis,* stable transformants resistant to chloramphenicol must result from the integration of the plasmid into the *B. subtilis* chromosome (Ferrari, et al., *J. Bacteriology,* 154: 1513–1515 (1983)). The integration event, facilitated by homologous recombination, most likely occurred at either the spoVG or the P43 loci of the bacterial chromosome (pSY856 contains DNA sequences homologous to the *B. subtilis* chromosome at only these two sites). The resulting strain, "BIPoL," was grown both in the presence and absence of chloramphenicol in order to determine the stability of the selectable marker. Expression of the T7 polymerase was obtained and this has no apparent effect on the growth or viability of this strain.

9.a. Expression of a plasmid-borne target gene (kanamycin-resistance) in *B. subtilis* strain BIPoL:

The *Staphylococcus aureus* plasmid pUB110 (Lacey, et al., *J. Med. Microbiology,* 7: 285–297, 1974) which contains the gene coding for resistance to the antibiotic kanamycin was used to test the expression of the growth-regulated spoVG:T7 RNA polymerase gene of strain BIPoL. An EcoRI-BamHI fragment of phage T7 DNA (positions 21, 402 to 22,858) containing the T7 gene 9 promoter sequence was purified from plasmid pAR441 (Studier, et al., 1986). This DNA fragment was ligated into pUB110 between the EcoRI and BamHI restriction endonuclease sites. The resulting plasmid, pSY952, contains the T7-specific promoter in the same orientation as the kanamycin-resistance gene. Plasmid pSY952 was transformed into *B. subtilis* 1168 and BIPoL and these strains were analyzed for the level of expression of the polypeptide encoded by the plasmid derived kanamycin-resistance gene. Approximately $10^9$ cells from growing cultures of 1168, 1168 containing pUB11O, 1168 containing pSY952, BIPoL, BIPoL containing pUB110, and BIPoL containing pSY952 were obtained at several times during the growth and sporulation cycle. The proteins in these cell samples were processed and analyzed by polyacrylamide gel electrophoresis.

Because the rate of transcription from the spoVG promoter increases as a function of cell density and reaches a maximum during early sporulation, an accelerated accumulation of the target protein is expected in the BIPoL strain containing pSY952 during growth as the culture enters sporulation. The results show that a protein of molecular weight 34 kDal increases in abundance as the culture approaches and enters stationary phase. The size of the protein is in agreement with the predicted size of the kanamycin-resistance gene product (Sadaie, et al., *J. Bacteriology,* 141: 1178–1182 (1980)) encoded in pSY952. This protein is not present in BIPoL or 1168 containing pSY952 which lacks the spoVG-regulated T7 RNA polymerase gene or in BIPoL containing pUB110 which lacks the T7 promoter sequence. The maximum accumulated level of target protein after 24 hours of growth in BIPoL containing pSY952 was 20% of the total cellular protein as determined by densitometry.

9.b Expression of SlpI-4 in *B. subtilis:*

Plasmid pG10SlpI was digested with EcoRI REN. After filling in the cohesive ends using the Klenow DNA polymerase reaction, the DNA was digested with BglII REN. Plasmid pSY662 was digested with SmaI and BamHI RENs. The two plasmids were then purified by electrophoresis through a low melting temperature agarose gel and purified with NACS (BRL) columns. The DNA fragment of pG10SlpI was ligated to the backbone of pSY662 and transformed into *E. coli* containing ampicillin (40 µg/ml). Transformants were analyzed for plasmid contents and one (pSY662/G10/SlpI-4) was selected for further study.

Competent cells of *B. subtilis* BIPol were transformed with pSY662/G10/SlpI-4 and incubated at 37° C. with shaking for 90 minutes. The transformation mixture was then diluted 1:100 in fresh LB containing 10 µg/ml of tetracycline and incubated at 37° C. with shaking. Samples were taken and equal numbers of cells were lysed and loaded on gels for separation by SDS-PAGE. Immunoblot analysis was performed using anti-Slp antibodies to detect the synthesis of the gene 10/SlpI-4 fusion protein.

The expression of the SlpI-4 polypeptide in *B. subtilis* was detected by its seroreactivity with anti-Slp antibody, after transfer of the cellular proteins from the polyacrylamide gel to a nitrocellulose filter. We verified that the seroreactive protein was the product of the SlpI-4 gene by exhaustively treating the cellular proteins with CNBr. This should cleave after methionine residues, but since SlpI-4 lacks methionine it will remain intact. The CNBr treatment eliminated greater than 98% of the proteins stainable with Coomassie blue dye. And as expected for a protein lacking methionine, SlpI-4 remained intact and still reacted with anti-Slp serum.

EXAMPLE 3

Assembly and Expression of the SlpIII Gene

1. Summary of the scheme for assembling the SlpIII gene:

The synthetic SlpIII gene codes for a protein similar to the SlpI gene and to the crystalline region of the silk fibroin protein made by the silkworm, *Bombyx mori.* SlpIII more closely resembles the silk fibroin molecule because it includes the amino acid tyrosine at regular intervals (about 50 residues), whereas multimers of SlpI do not. The SlpIII gene was assembled from smaller parts. First, three doublestranded sections of DNA of about 60 bp in length were chemically synthesized. Each section was cloned by insertion into bacteriophage H13 and the DNA sequence was verified. These sections were then removed from the vector and linked together in a specific order. This linkage of about 180 bp is named the SlpIII "monomer". "Monomers" were then linked in a specific order to yield dimers, trimers, tetramers, etc. of SlpIII. The multimers were then cloned either directly into plasmid expression vectors to detect the SlpIII protein or initially into an adapter plasmid. Insertion of the SlpIII DNA into the adapter allows for further gene manipulation and is further described later. The assembly scheme is pictured as follows:

2. Synthesis of double-stranded DNA sections

The assembly Scheme is pictured as follows:

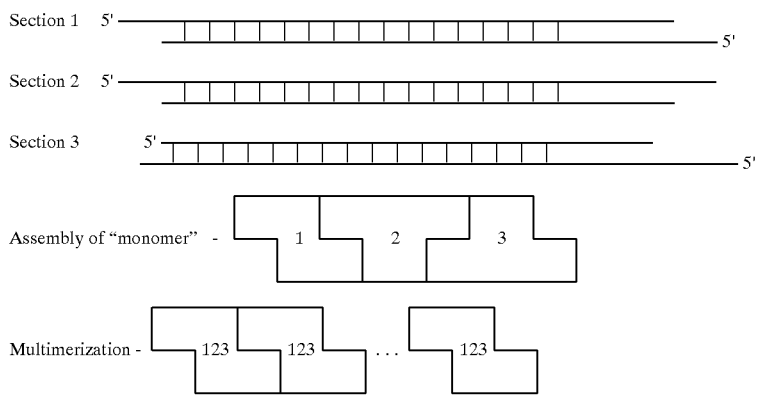
The DNA and corresponding amino acid sequences of the three sections of the SlpIII gene are shown in Table 3.

```
Ban1            Kae1
 |               |
GGT GCC GGC AGC GGT GCA GGA GCC GGT TCT GGA GCT GGC GCG GGC GCA G           61bs
CCA CGG CCG TCG CCA CGT CCT CGG CCA AGA CCT CGA CCG CGC CCG CGT CCT AG      65bs
 G   A   G   S   G   A   G   A   G   S   G   A   G   A   G   A   G   S

Ban1                            Pst1
                                      |                               |
 GA TCC GGC GCA GGC GCT GGT TCT GGC GCA GGC GCG GGA GCG GGG TCT GGA GCT GCA    68bs
    G   CCG CGT CCG CCA AGA CCG CGT CCG CGC CCT CGC CCC AGA CCT CG             60bs
     S   G   A   G   A   G   S   G   A   G   A   G   A   G   S   G   A

Pst1                              Ban1        Hin3
                    |                                 |           |
              A CGT GGC TAT GGA GCT GGC GCT GGC TCA GGT GGT GGA AGC GGA GCG GGT GCC A    55bs
                A   ATA CCT CGA CCG CGA CCG AGT CCA CCA CCT TCG CCT CGC CCA CGG TTC GA   63bs
                 A   G   Y   G   A   G   A   G   S   G   G   G   S   G   A   G   A
```

The double-stranded DNA sequence is shown in the 5' to 3' direction. The amino acids (g=glycine, a=alanine, s=serine, y=tyrosine) coded by the sequence are shown immediately below each section. Recognition sequences for cleavage by restriction endonucleases are shown above each section.

The above six single-strands were synthesized. After synthesis, the strands of DNA were purified and the homologous strands were annealed. About 1 μl (0.5 μg) of each strand was mixed with 2 μl of 10× AA (description) buffer and 16 μl of sterilized deionized H$_2$O in a 1.5 ml polypropylene Eppendorf tube. The tube was placed in a boiling water bath (500 ml in a 1 liter beaker) for 10 min and than the beaker was removed from the hot plate and allowed to cool on the bench to room temperature. This required about 1–2 hours.

Each of the three double-stranded sections was cloned separately into M13mp18. Section 1 was ligated between the SmaI and BamHI restriction sites of the multiple-cloning site. Section 2 was ligated between the BamHI and PstI sites. And section 3 was inserted between the PstI and HindIII sites. The respective clones are: M13mp18.1, M13mp18.2, M13mp18.3. The DNA sequence was determined for each cloned section. One representative of each section that had the correct DNA sequence was recovered and became the material for the next step: assembly of the "imonomer".

3. Assembly of the "monomer" of SlpIII:

The DNA sections 2 and 3 were isolated by digestion of the M13 clones with restriction enzymes: for section 2, M13mp18.2 was digested with BamHI and PstI; for section 3, M13mp18.3 was digested with PstI and HindIII. The two sections were purified and mixed together in equal molar amounts with M13mp18.1 that had been first digested with BamHI and HindIII. T4 DNA ligase was added to link the homologous overlapping ends in the order 1-2-3. Due to the hybridization specificity of the cohesive ends, the three sections are efficiently linked in only this order. The DNA sequence of the cloned "monomer" in the assembly named M13mp18.1.2.3 was determined to be correct and as shown in 2 above.

4. Multimerization of the "monomer" of SlpI:

In order to prepare large amounts of the "monomer" structural gene we first subcloned the "monomer" into the plasmid vector pUC12. M13mp18.1.2.3 was digested with EcoRI and HindIII restriction enzymes. The SlpIII "monomer"was gel purified and ligated into pUC12 digested with EcoRI and HindIII. The resulting plasmid DNA was prepared, the "monomer" was released from the vector by digestion with BanI REN and the fragment was gel purified.

To create multimers, "monomer" DNA with BanI ends were linked by ligation. The nonpalindromic terminal BanI recognition sequence allows linkage only in a head-to-tail order. The extent of multimerization is monitored by gel electrophoresis and staining the DNA with ethidium bromide. Multimers of more than 20 units have been obtained by this method.

5. Cloning of the multimers of SlpIII:

Plasmid pCQV2 (Queen, et al., *J. Appl. Mol. Gen.*, 2: 1–10 (1983)) was digested with EcoRI and BamHI restriction endonucleases and a fragment of about 900 bp was purified. This DNA fragment contains the bacteriophage lambda cI-857 repressor gene, the closely linked rightward promoter, P$_R$, and the beginning of the cro gene. Plasmid pSY335 (described as pJF751 in Ferrari, et al., *J. Bacteriology*, 161: 556–562 (1985)) was digested with EcoRI and BamHI restriction enzymes and subsequently ligated to the DNA fragment of approximately 900 bp of pCQV2. The plasmid obtained from this construction, pSY751, expresses the β-galactosidase gene at 37° C.. and 42° C.., but not at 30° C.. (FIG. 8).

In this approach the SlpIII gene is first cloned into an "adapter" sequence in an intermediate plasmid and then subcloned to the expression systems. The adapter sequence has the following useful features: a unique central BanI REN site, three unique REN sites to either side of BanI, information coding for protein cleavage at either methionine, aspartate-proline or arginine amino acids and small size. The BanI site is the point of insertion for the SlpIII multimers with BanI ends.

The adapter was synthesized with the Applied Biosystems 380A Synthesizer, cloned in M13mp18 and the DNA sequence verified. The adapter was then subcloned into a specially-constructed plasmid vector that lacked BanI REN sites. The recipient plasmid was made as follows. Plasmid pJH101 (Ferrari, et al., 1983) was partially digested with AhaIII restriction enzyme and religated. Transformants of *E. coli* HB101 were selected on medium containing chloramphenicol (12.5 mg/ml). After restriction analysis of several isolates one plasmid was chosen, pSY325 (FIG. 7). This plasmid contains only the chloramphenicol-resistance gene and the replication origin (from pBR322) of pJH101. After digestion to completion with XhoII, pSY325 was ligated with the gel-purified adapter. The result was the adapter-plasmid, pSY937. The new pSY937 REN sites were verified.

The SlpIII multimers were cloned into the BanI site of pSY937 (FIG. 7). Positive clones were identified by colony hybridization and with the lower strand of section 1 of SlpIII as the DNA probe for hybridization (probe sequence shown in Table 2). Positive clones were characterized by gel electrophoresis for the size of the inserted multimer. Finally, the SlpIII sequences were subcloned using the REN site in the flanking adapter regions to specific locations of expression plasmids.

The SlpIII protein had the following amino acid composition:

SlpIII    1178 AA    MW    83,000

(fm) DPVVLQRRDWENPGVTQLNRLAAHPPFASDPM
GAGS (GAGAGS)$_6$GAAGY
[(GAGAGS)$_9$GAAGY]$_{18}$
GAGAGSGAGAGSGAGAMDPGRYQLSAGRYHYQLVWCQK (SEQ ID NO: 35)

(fm) intends the initiation codon.

SlpI Expression Vector

Plasmid DNA pSY1086 is a pSY937 derivative containing 19 repeats of SlpIll (3.5 kb). This plasmid DNA was digested with NruI and PvuII and the fragments separated by agarose gel electrophoresis. The purified SlpIII multimer was then cloned in plasmid pSY751 digested with PvuIII REN. Several clones were analyzed and one (pSY1008) was chosen to be used in expression experiments and SlpIII purification.

The ampicillin drug resistance gene of pSY1008 was substituted with the kanamycin marker from pSY1010 (produced by digestion of pSY633 with DraI and SspI and insertion of Kan$^R$ obtained by HincII digestion of pUC4K) and the subsequent plasmid was called pSY1186. By removing the SlpIII portion of plasmid pSY1186 with BanI, a new plasmid, pSY1262, was generated. This plasmid contains a unique BanI site which allows for the direct ligation of fragments containing BanI ends obtained by polymerization of monomers. This plasmid has been used to generate plasmids containing inserts for the following proteins: SELP1, 2, 3, and Slp4.

Production and Purification of SlpIII Cell Culture

*E. coli* are cultured in the following medium:

| Medium C | |
|---|---|
| | g/l |
| yeast extract | 20 |
| casamino acids | 20 |
| peptone | 20 |
| gelatin peptone | 20 |
| $KH_2PO_4$ | 2 |
| $K_2HPO_4$ | 2 |
| $Na_2HPO_4 7H_2O$ | 2 |
| glucose | 2 |
| ampicillin | 0.1 |

An overnight culture (500 ml–1 l) which had been grown at 30° C.. was used to inoculate 375 l of media contained in a 500 l fermentor. Fermentor conditions include a tachometer reading of 100 rpm, vessel back pressure of 5 psi and an air flow of 170 l/min in order to maintain dissolved $O_2$ at greater than 50%.

Glucose (1 g/l) and ampicillin (0.05 g/l) were added to the fermentation when the culture reached an $OD_{650}$ of 1.0 and again at 2.0. When the culture reached an $OD_{650}$ of 2.0 the temperature was increased to 42° C. for 10 minutes and then lowered to 38° C.. for 2 hours. The culture was then chilled to 10° C.. and cells were harvested by centrifugation in a continuous centrifuge and frozen at −70° C.. until processed. Yields from two separate fermentations were 7.3 kg and 5.2 kg wet weight of cells.

It should be noted that other media can be used and, with different plasmids, various selection conditions can be imposed (i.e., substitution of kanamycin selection for ampicillin). These conditions have been used in laboratory scale fermentations (10 l volumes).

Cell Lysis

Method 1. Cells were thawed and suspended to a concentration of 1 kg wet weight/6 l in 50 mM Tris-HCl pH 7.0, 1 mM EDTA and broken by 2 passages through an APR Gaulin cell disrupter at 8000 psi. During this lysis procedure the cells were kept cold with an ice bath. The cell lysate was then centrifuged at 26,000×g with a continuous centrifuge, such as the T2-28 rotor in a Sorvall RC5B refrigerated centrifuge operated at 4° C.. Under these conditions greater than 90% of the SlpIII produced can be found in the pellet. The supernatant did contain some product which could be recovered by $NH_4SO_4$ precipitation as described below. The pellet was extracted with LiBr as described below.

Method 2. Frozen cells were thawed and resuspended to a concentration of 1 kg wet weight in 6 L in 50 mM Tris-KCl pH 7.0, 10 mM EDTA, and 5 mM PMSF to inhibit protease activity. Cells were stirred in this buffer at room temperature for 0.5 to 2 hours, then lysozyme was added to a concentration of 1 g/l and incubation is continued for 20 minutes. β-Mercaptoethanol was then added to 70 mM and the detergent NP4O was then added to a final concentration of 1% for 20 min while continuously stirring the cell suspension. Then $MgCl_2$ was added to 50 mM followed by DNAse at a concentration of 1 mg/l and incubation was continued at room temperature for 20 minutes. The cell lysate was then centrifuged as in method 1 at 26,000×g in a continuous centrifuge and the supernatant was collected and passed through the continuous centrifuge a second time at 26,000× g. The supernatant resulting from this second centrifugation contained <5% of the total SlpIII, but what was there could be recovered with $NH_4SO_4$ as described below. The pellets resulting from the 1st and 2nd 26,000×g centrifugations were combined and extracted with LiBr as described below.

Method 3. For this method, a strain of *E. coli* was used that contains a second plasmid which encodes the T7 phage lysozyme. This plasmid is compatible with the plasmid encoding the SlpIII gene and the drug resistance determinant. The strain was grown in the same medium and under the same conditions as in the first two methods. However, due to the production of the T7 lysozyme inside the cells, their cell wall was weakened and they could be easily lysed at the completion of the fermentation by the addition of EDTA to >100 mM and NP4O to a concentration of from 0.5 to 1.0% v/v. Lysis could also be achieved by the addition of chloroform (20 ml per liter) of fermentation broth instead of NP4O. Alternatively, cells could be collected by centrifugation prior to lysis, resuspended to 1 kg wet weight in 6 L in Tris-EDTA as described in the first two methods and then lysed by the addition of NP4O or chloroform. Following cell lysis by either method the lysate was centrifuged in a continuous rotor at 26,000×g as described in the first two methods. As with those methods, LiBr extraction of the pellet and $NH_4SO_4$ precipitation of the supernatant was used to recover the product.

Purification of SlpIII

The pellet obtained by centrifugation of the cell lysate at 26,000×g as described above was extracted with an equal volume of 9M LiBr. The salt solution was added and the pellet was evenly suspended by stirring at room temperature (RT). The mixture was stirred for 1 hour at RT after an even suspension was obtained. The mixture was then centrifuged at 26,000×g in a continuous rotor at 4° C.. or at RT to generate a pellet and a supernatant fraction. The supernatant was saved and the pellet was re-extracted with another equal volume of 9M LiBr as above. After mixing for 1 hour the mixture was centrifuged at 26,000×g and the supernatant from this centrifugation was combined with the supernatant from the first LiBr extraction and allowed to stand at 4° C.. overnight. Approximately 90% of the SlpIII contained in the cell lysate 26,000×g pellet was extracted by LiBr using this procedure.

After the LiBr extract stands overnight at 4° C.. a precipitate formed, was removed by centrifugation at 26,000×g and was discarded. The supernatant was then placed in dialysis bags and dialyzed against several changes of $dH_2O$ for 2 days. As the LiBr was removed by dialysis the SlpIII product precipitated in the dialysis bags. The precipitate was collected by centrifugation and washed 2–3 times with $dH_2O$. The final washed product was centrifuged and dried by lyophilization.

For the recovery of SlpIII from the 26,000×g supernatant fractions, $NH_4SO_4$ precipitation was used. Solid $NH_4SO_4$ was slowly added to the sample which was maintained at 4° C.., until 38% saturation was achieved (231 g/l). The mixture is then stirred at 4° C.. for 2–3 hours. The precipitate was recovered by centrifugation in a continuous flow centrifuge and washed 4–5 times with an equal volume of distilled $H_2O$ or with 0.5% SDS in $H_2O$. After each wash the precipitate was recovered by continuous centrifugation. The pellet became increasingly white with successive washes as contaminating protein was removed. SlpIII was recovered as a washed pellet and was dried by lyophilization.

Trypsin Treatment Step of SlpIII

SlpIII was suspended in 50 mM Tris HCl, pH 8.0, 0.1M NaCl buffer, and was placed in a 37° C. water bath, and TPCK treated trypsin solution was mixed into the suspension. The final trypsin concentration was 0.1%. After 3 hours, the solution was centrifuged at 16,000×g for 15 min, the pellet was washed with a half equal volume of 0.5% SDS in $H_2O$ first, then with distilled water. After each wash the pellet was recovered by centrifugation. The final product was resuspended in water and kept at 4° C. for further analysis.

TABLE 4

| Material | a (A) | b (A) | c (A) |
|---|---|---|---|
| $(AG)_n$ | 9.42 | 6.95 | 8.87 |
| $(AGAGSG)_n$ (SEQ ID NO: 20) | 9.39 | 6.85 | 9.05 |
| CTP fraction | 9.38 | 6.87 | 9.13 |
| Native fibroin | 9.40 | 6.97 | 9.20 |
|  | 9.44 | 6.95 | 9.30 |
| SlpIII | 9.38 | 6.94 | 8.97 |

Referenced in Fraser et al., *J. Mol. Biol.* (1966) 19: 580.

EXAMPLE 4

EBSI Gene Construction:

Six oligonucleotide strands were synthesized and purified as described previously.

```
         (HIII)      BanII           StuI
 i.   5'AGCTGGGCTCTGGAGTAGGCCTG3' (SEQ ID NO: 36)

ii.  5'AATTCAGGCCTACTCCAGAGCCC3' (SEQ ID NO: 37)
         (ER1)    StuI              BanII (HIII)
 iii. 5'AGCTTGGTGCCAGGTGTAGGAGTTCCGGGTGTAGGCGTTCCGGGAGTTGG
         TGTACCTGGAGTGGGTGTTCCAGGCGTAGGTGTGC3'   (SEQ ID NO: 38)

(XmaI)
 iv.  5'CCGGGCACACCTACGCCTGGAACACCCACTCCAGGTACACCAACTCCCGGA
         ACGCCTACACCCGGAACTCCTACACCTGGCACCA3' (SEQ ID NO: 39)
                                          BanI (XmaI)                           AhaII
 v.   5'CCGGGGTAGGAGTACCAGGGGTAGGCGTCCCTGGAGCGGGTGCTGGTAG
         CGGCGCAGGCGCGGGCTCCGGAGTAGGGGTGCCG5'
                          BanII           BanI (ERI)  BanI              BanII
 vi.  5'AATTCGGCACCCCTACTCCGGAGCCCGCGCCTGCGCCGCTACCAGCACCCG
         CTCCAGGGACGCCTACCCCTGGTACTCCTACC3' (SEQ ID NO: 41)
         AhaII
```

With the trypsin treatment, SlpIII was purified to 99.4% purity.

Physical Measurements of SlpIII

Physical measurements of the purified silk-like proteins have been compared with those of *Bombyx mori* silk in order to establish that the repetitive amino acid polymers produced microbiologically accurately mimic the properties of naturally occurring polymers. Physical measurements were performed to confirm the model of anti-parallel chain pleated sheet conformation for the crystalline regions of *Bombyx mori* silk fibroin (Marsh, Corey and Pauling, *Biochem. Biophys. Acta* (1955) 16; Pauling and Corey, *Proc. Natl. Acad. Sci. USA* (1953) 39: 247). Preliminary analysis of x-ray diffraction patterns obtained from Slp films are consistent with those described by Fraser, MacRai, and Steward (1966) (Table 4). Circular Dichroic (CD) and Fourier transform infrared (FTIR) spectroscopic analysis of SlpIII were consistent with a high degree of extended β and β-turn conformations. Comparisons of the spectra obtained from SlpIII with that of naturally occurring silk fibroin in various solvents (Isuka and Young, Proc. *Natl. Acad. Sci. USA* (1966) 55: 1175) indicated that SlpIII in solution consists of a mixture of the random and highly ordered structures seen in silk fibroins.

Oligonucleotide strands (iii), (iv), (v) and (vi) were annealed and ligated with the DNA of plasmid pBSm13(+) (Stratagene) which had been digested with HindIII and EcoRI. The products of this ligation reaction were transformed into *E. coli* strain JM109. Transformant colonies were selected for resistance to ampicillin. Colonies were screened for their hybridization with $^{32}$P-labelled oligonucleotides (iii), (v). Plasmid DNA from several positively hybridizing clones was purified and sequenced. Two of the plasmids, pSY1292 and pSY1293, contained the sequence shown for oligonucleotides (iii), (v) and (iv), (vi). These sequences contained all of the nucleotides present in these synthetic oligonucleotides except one. A G:C basepair was missing at position 7 (iii). The lack of this basepair obstructed one of the BanI sites. In order to introduce a second BanII site at the 5' end of the gene fragment, oligonucleotides (i) and (ii) were annealed and ligated with plasmid pBSm13(+) which had been digested with HindIII and EcoRI. Plasmid DNA from the transformant colonies resistant to ampicillin was purified. Two plasmids, pSY1295 and pSY1296, which were digestible with StuI, a unique site contained in the oligonucleotide sequence, were sequenced. They were both shown to contain the sequence shown for oligonucleotides (i) and (ii). Plasmid DNA From pSY1292 was digested sequentially with HindIII, SI nuclease, and EcoRI. The digestion products were separated by electrophoresis in an agarose gel and the DNA fragment of approximately 150 basepairs was excised from the gel. This DNA fragment was ligated with plasmid DNA pSY1296 which had been digested with StuI and EcoRI. The products of this ligation reaction were transformed into E. coli strain JM109 and were selected for resistance to ampicillin. Colonies were screened for hybridization to $^{32}$P-labelled oligonucleotide (v). The plasmid DNA from two positively hybridizing clones was purified and sequenced. These plasmids were named pSY1297 and pSY1298. They contained the following sequence:

```
      (HindIII)       BanII
           AGCTGGGCTCTGGAGTAGGTGTGCCAGGTGTAGGAGTTCCGGGTGTAGGCGTTCCGGGAG    60
           TCGACCCGAGACCTCATCCACACGGTCCACATCCTCAAGGCCCACATCCGCAAGGCCCTC XmaI
           TTGGTGTACCTGGAGTGGGTGTTCCAGGCGTAGGTGTGCCCGGGGTAGGAGTACCAGGGG    120
           AACCACATGGACCTCACCCACAAGGTCCGCATCCACACGGGCCCCATCCTCATGGTCCCC BanII
           TAGGCGTCCCTGGAGCGGGTGCTGGTAGCGGCGCAGGCGCGGGCTCCGGAGTAGGGGTGC    180
           ATCCGCAGGGACCTCGCCCACGACCATCGCCGCGTCCGCGCCCGAGGCCTCATCCCCACG EcoRI
           CGAATTC (SEQ ID NO: 42)
           GCTTAAG
```

EBSI Multimer Gene Assembly:

The BanI acceptor plasmid pSY937 was modified in order to accept BanII terminal cohesive DNA fragments. Two oligonucleotides were synthesized for this purpose.

insertions. Ten clones (pSY1240–1249) with inserts ranging in size from 1.5 Kbp to 4.4 Kbp were obtained.

Expression of EBSI Multimer Gene:

One of these clones, pSY1248, which contained a 4 Kb EBSI multimer gene was recloned in the $\lambda P_R$ expression vector, pSY751. Plasmid DNA from pSY1248 was digested with NruI and PvuII, separated by agarose gel electrophoresis, and the DNA band corresponding to the EBSI multimer gene was excised and purified by NACS purification. DNA from plasmid pSY751 was digested with PvuII and ligated with the NruI-PvuII fragment from pSY1248. The products of this ligation were transformed into E. coli HB101, and the transformants selected for resistance to ampicillin. Two clones were isolated containing the new plasmid pSY1280. E. coli cells containing pSY1280 were grown at 30° C.. to an OD$_{600}$ of 0.7 and then shifted

```
       (BamHI)      DraI      SspI       NruI               BanII
vii.  5'GATCCTATGTTTAAATATTCTCGCGAACGTTTTTCTATGGGCTCGATGTGT
         TACCGTGCGCATGGATATCAGCTG3' (SEQ ID NO: 43)
             FspI       EcoRV      PvuII (BamHI)  PvuII EcoRV       FspI              BanII
viii. 5'GATCCAGCTGATACCATGCGCAGGGTAACACATCGAGCCCATACAAAAA
         CGTTCGCGAGAATATTTAAACATAG3' (SEQ ID NO: 44)
             NruI     SspI    DraI
```

Oligonucleotides (vii) and (viii) were annealed and ligated with plasmid DNA pSY937 which was digested with BamHI. The products of this ligation were transformed into E. coli strain JM109 and colonies were selected for resistance to chloramphenicol. Transformant colonies were screened by hybridization to $^{32}$P-labelled oligonucleotide (vii). Plasmid DNA from two positively hybridizing clones, pSY1299 and pSY1300, contained the sequence shown for oligonucleotides (vii) and (viii), as determined by DNA sequencing.

Plasmid DNA pSY1298 was digested with BanII and the digestion fragments separated by agarose gel electrophoresis. The EBSI gene fragment, approximately 150 base pairs, was excised and purified by electro-elution and ethanol precipitation. Approximately 1 μg of purified fragment was self-ligated in order to produce multimers ranging in size from 450 bp to 6,000 bp. The products of the self-ligation were then ligated with plasmid DNA pSY1299 which had been digested with BanII. The products of this ligation reaction were transformed into E. coli strain HB101. Transformants were selected for resistance to chloramphenicol. Plasmid DNA from individual transformants was purified and analyzed for increased size due to EBSI multimer DNA to 42° C.. for 1.5 hours. The proteins produced by these cells was analyzed by SDS-PAGE. The separated proteins were transferred to nitrocellulose paper and detected by immunoreactivity with anti-ELP rabbit serum. A strongly reactive protein band was observed with an apparent molecular weight of 120 kDal.

The Ampicillin drug resistance gene of pSY1280 was substituted with the Kanamycin marker and the subsequent plasmid was called pSY1332. This plasmid was used in fermentation for the purification of EBSI (see Methods).

pSY1332/pSY1280    EBSI Protein    1413 AA    MW 113,159

MDPVVLQRRDWENPGVTQLNRLAAHPPFASERFCMGS
   [(GVGVP)$_8$(GAGAGSGAGAGS)$_1$]$_{26}$
   MCYRAHGYQLSAGRYHYQLVWCQK (SEQ ID NO: 45)

Purification of EBSI Protein:

E. coli strain HB101 containing plasmid pSY1280 was fermented in 10 L volume. The cells were concentrated by filtration and further harvested by centrifugation. Pelleted cells were stored frozen at −70° C.. until processed. Frozen cells were thawed on ice and suspended in 4 ml of 50 mM Tris-HCl pH 7.0, 10 mM EDTA, 5 mM PMSF per gram wet weight of cells. The cells were broken by French pressing twice at 15,000 psi and then cooled to 0° C.. The crude lysate

```
                   (EcoRI)      BanI                                    SmaI
i)    5' AATTCGGTGCCCGGTGTAGGAGTTCCGGGTGTAGGCGTTCCCGGGGTAG
         GCGTTCCGGGAGTAGGGGTGCCA3' (SEQ ID NO: 46)
                                BanI

BanI                                             SmaI
ii)   3'GCCACGGGCCACATCCTCAAGGCCCACATCCGCCAGGGCCCCATCCGCA
         AGGCCCTCATCCCCACGGTTCGA5'
                   BanI   (HindIII)
``` was cleared by centrifugation at 26,000×g for 20 minutes. The supernatant proteins were precipitated by addition of solid ammonium sulfate to 20% of saturation (114 g/l). The precipitate was collected by centrifugation at 10,000×g for 10 minutes. The pellet was resuspended in 10 ml of H₂O and dialyzed against 10 mM Tris pH 8.0, 0.15M NaCl at 4° C.. The dialyzed solution was digested with 0.1% Trypsin (Sigma) for 1.5 hours at room temperature, and reprecipitated with 20% ammonium sulfate. The precipitated protein was resuspended in H₂O and dialyzed against 10 mM Tris pH 7.0, 1 mM EDTA at 4° C.. The protein purity of this sample was analyzed by amino acid composition and determined to be 83%.

Elastic Properties of EBSI Protein:

The soluble preparation of semi-purified EBSI protein described above was incubated at 37° C. for 30 minutes and centrifuged at 10,000×g for 10 min at room temperature. This treatment caused the EBSI protein to aggregate, become insoluble, and pellet into a translucent solid. The solid was resistant to mechanical disruption either by vortexing or by maceration using a glass rod. The solid could be cut with a razor blade into strips which exhibited a high degree of elasticity. These strips fully retained their shape after repeated extensions and relaxations. They resisted compression with no apparent irreversible deformation of structure.

EBSI Purification

EBSI sample (~70% pure) was dialyzed in 50 mM Tris HCl, 50 mM NaCl, pH 8.0 at 4° C. overnight with one change of buffer. If precipitation was observed, the sample was centrifuged at 27,000×g for 15 min at 4° C.. All remaining steps were performed at 4° C.. The supernatant was applied to a DEAE-Sephacel column which had been equilibrated with 50 mM Tris HCl, 50 mM NaCl, pH 8.0. The flow through fractions which contained EBSI were collected and pooled. NaCl was added to the pooled fractions from DEAE-Sephacel column to make a final concentration of 2M NaCl in the sample. Insoluble material was removed by centrifugation at 27,000×g for 20 minutes. The supernatant was then loaded onto Phenyl-Sepharose column which was equilibrated with 50 mM sodium phosphate buffer, pH 7.0, with 2M NaCl. The column was washed extensively with buffer until no eluting protein was detected by $A_{280}$. The column was then eluted stepwise with 50 mM sodium phosphate buffer, pH 7.0 and finally with water. The EBSI active fractions were pooled and stored at 4° C. for further analysis.

With the addition of these steps to the previous procedures, 100% pure EBSI was obtained.

EXAMPLE 5

ELPI Construction and Expression

Two oligonucleotide strands were synthesized and purified as described in the Methods section.

The two oligonucleotide strands were annealed and ligated with the DNA of plasmid pBS m13(+) (Stratagene) which had been digested with RENs HindIII and EcoRI.

The products of this ligation reaction were transformed into E. coli strain JM109. Transformant colonies were screened for their hybridization with $^{32}$P-labeled oligonucleotide (i). Plasmid DNA from positively hybridizing clones was purified and sequenced. One plasmid, pSY1287, contained the sequence shown for oligonucleotides (i) and (ii).

Plasmid DNA from pSY1287 was digested with BanI REN and the digestion fragments were separated by agarose gel electrophoresis. The ELPI gene fragment, approximately 60 bp, was excised and purified by NACS column. Approximately 1 μg of purified fragment was self-ligated in order to produce multimers ranging in size from 300 bp to 5000 bp.

The products of the self-ligation were then ligated with plasmid DNA pSY937 which had been digested with REN BanI. The product of this ligation reaction was transformed into E. coli strain HB101. Transformants were selected for resistance to chloramphenicol. Plasmid DNA from individual transformants was purified and analyzed for increased size due to ELPI multiple DNA insertions. Four clones (pSY1388–1391) with inserts ranging in size from 1.0 kbp to 2.5 kbp were obtained. These clones were recloned in the APR expression vector pSY751. The clones obtained (pSY1392–1395) were used for expression of ELPI.

The ELPI protein had the following amino acid composition:

pSY1395    ELPI Protein    859 AA    MW 72,555
MDPVVLQRRDWENPGVTQLNRLAAHPPFARNILAIRW
[(VPGVG)₄]₄₀VPWTRVDLSAGRYHYQLVWCQK (SEQ ID NO: 48)

SELP1 Gene Construction and Expression

Two oligonucleotide strands were synthesized and purified as described in the Methods section.

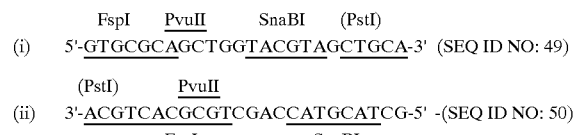

```
      FspI      PvuII    SnaBI   (PstI)
(i)   5'-GTGCGCAGCTGGTACGTAGCTGCA-3' (SEQ ID NO: 49)

(PstI)     PvuII
(ii)  3'-ACGTCACGCGTCGACCATGCATCG-5' -(SEQ ID NO: 50)
                FspI           SnaBI
```

These oligonucleotide strands were annealed and ligated with plasmid pSY1304 which had been digested with PstI REN (pSY1304 differs from pSY857 by having a monomeric unit in place of the trimeric unit of pSY857). Plasmid DNA from transformant colonies resistant to chloramphenicol was purified. One plasmid, pSY1365, which was digestible with REN SnaBI, was sequenced and proven to be correct.

ELPI gene fragment purified as described (ELPI construction and expression) was treated with Mung Bean Nuclease as described by supplier (Stratagene). The DNA fragments mixture was then ligated with plasmid DNA pSY1365 which had been digested sequentially with RENs FspI, SnaBI and calf intestinal phosphatase. The products of this ligation reaction were transformed into *E. coli* strain HB101 and were selected for resistance to chloramphenicol. Plasmid DNA from individual transformants was purified and analyzed for the ELPI monomer DNA insertion. Two plasmids, pSY1366 A and B, were sequenced. They were both shown to contain the ELPI DNA sequence in the correct orientation.

Plasmid DNA pSY1365 was digested with REN BanI and the DNA fragment containing the SELP1 monomer was gel purified. To create multimers, 1 μg of the SELP1 DNA fragment was self-ligated. Multimers were obtained ranging in size from 500 bp to 10 kbp. The SELP1 multimers were cloned into the BanI site of pSY1262. Positive clones were characterized by gel electrophoresis for the size of the inserted multimer and used for expression and protein analysis.

50 mM Tris-HCl, pH 7.0, 10 mM EDTA, 5 mM PMSF per gram wet weight of cells. The cells were broken by passing through a Gaulin cell disrupter at 8,000 psi. The crude lysate was cleared by centrifugation at 26,000×g for 20 minutes. The supernatant, which contained >75% of the SELP2 protein, was precipitated by addition of 20% ammonium sulfate (114 g/L). The precipitate was collected by centrifugation at 10,000×g for 10 minutes. The pellet was resuspended in 10 ml of $H_2O$ and dialyzed against 10 mM Tris pH 8.0, 0.15M NaCl at 4° C.. The dialyzed material was centrifuged at 26,000×g for 15 min in order to collect the insoluble fraction of protein which contained approximately 10% of the SELP2 protein. This insoluble protein pellet was washed twice in 0.2% SDS at 50° C. for 30 min with occasional shaking. The insoluble protein was collected each time by centrifugation at 26,000×g for 15 min followed by a wash of 50% ethanol. The final protein pellet was resuspended in water and analyzed by Western blot analysis

```
pSY1396 SELP1 Protein 2025 AA MW 148,212
MDPVVLQRRDWENPGVTQLNRLAAHPPFASDPMGAGS (GAGAGS)6
[GAA(VPGVG)4VAAGY (GAGAGS)9]24
GAA(VPGVG)4VAAGY (GAGAGS)2GAGAMDPGRYQLSAGRTHYQLVWCQK (SEQ ID NO: 51)
```

SELP2—Monomer Construction

Plasmid DNA pSY1298 was digested with BanII REN and the EBSI gene fragment was purified as described previously. The EBSI monomer fragment was ligated into pSY1304 (pSY937 containing a monomer of SlpIII, constructed as pSY857) which had been digested with BanII REN and treated with calf intestinal phosphatase).

The products of the ligation mixture were transformed in *E. coli* strain HB101. Transformants were selected for resistance to chloramphenicol. After restriction analysis of several isolates, one plasmid was chosen, pSY1301 containing a DNA fragment corresponding to the SELP2 monomer gene.

SELP2—Multiple Gene Assembly and Expression

Plasmid DNA pSY1301 was digested with REN BanI and the DNA fragment containing the SELP2 "monomer" was gel purified. To create multimers, 1 μg of the SELP2 DNA fragment was self-ligated. Multimers were obtained greater than 12 kb in size.

The SELP2 multimers were cloned into the BanI site of pSY1262. Positive clones were characterized by gel electrophoresis for the size of the inserted multimer. The clones with inserts ranging in size from 1.5 kb to 11 kb were selected. Plasmid DNA pSY1372 containing an insert of 6 kb (18 repeats) was used for further analysis and protein purification.

SELP2—Protein Purification

*E. coli* strain HB101 containing plasmid pSY1372 was fermented according to the procedure described in Methods for fermentation. The cells were harvested by centrifugation. Pelleted cells were stored frozen at −70° C. until processed. Frozen cells were thawed on ice and suspended in 4 ml of and amino acid composition. By Western blot the SELP2 protein appears to be homogeneous in size consistent with its large molecular weight (>150 kDal). By amino acid composition the SELP2 preparation is approximately 80% pure and the observed molar ratio of amino acids (Ser:Gly:Ala:Pro:Val:Tyr) agrees very closely with the expected composition as predicted from the SELP2 sequence present in pSY1372.

```
pSY1372 SELP2 Protein 2055 AA MW 152,354
MDPVVLQRRDWENPGVTQLNRLAAHPPFASDPMGAGS(GAGAGS)2(GVGVP)8
[(GAGAGS)6GAAGY (GAGAGS)5(GVGVP)8]17
(GAGAGS)6GAAGY (GAGAGS)2GAGAMDPGRYQLSAGRYHYQLVWCQK (SEQ ID NO: 52)
```

SELP3—Construction and Expression

Plasmid DNA pSY1301 was partially digested with REN HaeII and the digestion fragments separated by agarose gel electrophoresis. The larger DNA fragments were excised and purified by NACS column. The purified fragments were self-ligated, the ligation reaction was heated at 70° C. for 15 min to inactivate the T4 DNA ligase and eventually digested with REN PstI. The digestion mixture was then transformed into *E. coli* strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1377) satisfied both requirements. Plasmid DNA from pSY1377 was digested with REN BanI and the DNA fragment containing the SELP3 monomer was gel purified. To create multimers, 1 μg of the SELP3 DNA fragment was self-ligated. Multimers were obtained ranging in size from 500 bp to 10 kbp. The SELP3 multimers were cloned into the BanI site of pSY 1262. Positive clones were characterized by gel electrophoresis for the size of the inserted multimer and used for expression and protein analysis.

pSY1397 SELP3 Protein 2257 AA MW 168,535
MDPVVLQRRDWENPGVTQLNRLAAHPPFASDPMGAGS (GAGAGS)$_2$
[(GVGVP)$_8$ (GAGAGS)$_8$]$_{24}$
(GVGVP)$_8$ (GAGAGS)$_5$GAGAMDPGRYQLSAGRYHYQLVWCQK (SEQ ID NO: 53)

SLP4—Construction and Expression

Plasmid DNA from pSY1304 was partially digested with REN HaeII and the digestion fragments separated by agarose gel electrophoresis. The larger DNA fragments were excised and purified by NACS column. The purified fragments were self-ligated, the ligation reaction was heated at 70° C. for 15 min to inactivate the T4 DNA ligase and eventually digested with REN PstI. The digestion mixture was then transformed into E. coli strain JM109. Transformants were selected for resistance to chloramphenicol. Plasmid DNA from individual transformants was purified and analyzed for: (1) resistance to REN PstI; and (2) deletion of 60 bp HaeII fragment contained within the SELP2 gene fragment. One clone (pSY1378) satisfied both requirements. Plasmid DNA pSY1378 was digested with REN BanI and the DNA fragment containing the SLP4 monomer was gel purified. To create multimers, 1 μg of SLP4 DNA was self-ligated. Multimers were obtained ranging in size from 300 bp to 6 kbp. The SLP4 multimers were cloned into the BanI site of pSY1262. Positive clones were characterized by gel electrophoresis for the size of the inserted multimer and used for expression and protein analysis.

pSY1398 SLP4 Protein 1101 AA MW 76,231
MDPVVLQRRDWENPGVTQLNRLAAHPPFASDPMGAGS
[(GAGAGS)$_6$]$_{27}$
(GAGAGS)$_4$GAGAMDPGRYQLSAGRYHYQLVWCQK
(SEQ ID NO: 54)

FCB-SLPIII (SLPF) Construction and Expression:

The SLPIII polymer was chosen as a backbone structure for insertion of a biologically functional sequence because of its predicted structure, allowing for fabrication of useful products; having good structural properties for use in a wide variety of applications; having B-turn structures between interactive strands; and allowing for substitution of the turn sequences with other sequences. The fibronectin cell-binding domain, amino acids 1405–1512, has a strong turn propensity, with the tripeptide RGD providing for cell attachment, predicted to be present within a hydrophilic loop between adjacent B-strands. A 10 amino acid sequence spanning this proposed loop structure (referred to as fibronectin cell-binding or FCB sequence) was chosen to constitute the functional block of amino acids to be inserted within the SLPIII backbone. The insertion site within the SLPIII backbone was chosen to correspond with the amino-acid sequence GAAGY (SEQ ID NO: 55) which is also predicted to provide a turn structure (Chou and Fassman, *Biochemestry*, 13: 222–244 (1974)). The design allows for conservation of the FCB structure while causing minimal disruption of the SLPIII (GAGAGS)$_9$ (SEQ ID NO: 56) B-strand crystal-packing domains.

The SLPIII gene monomer contains a PstI restriction endonuclease site within the sequence encoding the proposed turn structure, GAAGY (SEQ ID NO: 56). This site was used to insert the synthetic DNA encoding the 10 amino acids of the FCB sequence. Two complementary DNA strands comprising the FCB site, 36 bases in length, were synthesized consisting of the sequence shown below:

```
5' -      GTGACTGGCCGTGGTGATAGCCCGGCTAGCGCTGCA -3' (SEQ ID NO: 57)
3' - ACGTCACTGACCGGCACCACTATCGGGCCGATCGCG          -5' (SEQ ID NO: 58)
```

These oligonucleotides were purified according to the procedures described in Example 1, and cloned into the PstI site of pSY1304. pSY1304 DNA was digested with PstI and ligated with a mixture of the FCB oligonucleotides. The ligation reaction products were transformed into E. coli cells. Colonies containing the plasmid were selected on bacterial culture plates containing the antibiotic chloramphenicol. Individual colonies were grown and plasmid DNA purified and analyzed for the presence of the FCB oligonucleotide sequence by restriction digestion with NheI. Plasmids containing this restriction site were subjected to DNA sequencing and two candidates were shown to be correct. The partial nucleotide sequence of one of these, pSY1325, and the encoded amino-acid sequence were as follows:

```
Ban I
GGT GCC GGC AGC GGT GCA GGA GCC GGT TCT GGA GCT GGC
G    A   G   S   G   A   G   A   G   S   G   A   G
                                Bam H I
GCG GGC TCT GGC GCG GGC GCA GGA TCC GGC GGA GGC GCT
A    G   S   G   A   G   A   G   S   G   A   G   A
GGT TCT GGC GCA GGG GCA GGC TCT GGC GCA GGA GCG GGG
G    S   G   A   G   A   G   S   G   A   G   A   G
        Pst I
TCT GGA GCT GCA GTG ACT GGC CGT GGT GAT AGC CCG GCT
S    G   A   A   V   T   G   R   G   D   S   P   A
        Pst I
AGC GCT GCA GGC TAT GGA GCT GGC GCT GGC TCA GGT GCT
S    A   A   G   Y   G   A   G   A   G   S   G   A
```

```
                    Ban I
GGA GCA GGA AGC GGA GCG GGT GCC          (SEQ ID NO: 59)
 G   A   G   S   G   A   G              (SEQ ID NO: 60)
```

The FCB-SLP monomer gene fragment was purified from pSY1325 by digestion with BanI, agarose-gel electrophoresis, and NACS purification (Example 1). The monomer gene fragment was self-ligated and cloned into pSY937 which had been digested with BanI. The products of this ligation were transformed into E. coli and selected for growth on chloramphenicol. Plasmid DNA from individual colonies was analyzed for inserts containing multiple FCB-SLP monomer fragments by digestion with NruI and EcoRV and electrophoresis on agarose gels. One clone was identified containing two inserts, one of approximately 2.1 kb and the other of 2.8 kb. Both inserts were cloned individually and transferred to the expression vector pSY751. Plasmid pSY1325 was digested with NruI and PvuII and the 2.1 and 2.8 kb insert bands were purified. These DNA fragments were ligated with pSY751 that had been digested with PvuII. The products of this reaction were transformed into E. coli and selected for growth on the antibiotic ampicillin. Plasmid DNA from individual colonies was analyzed by restriction digestion for the presence of the FCB-SLP polymer gene. Two clones were identified, pSY1520 and 1521, containing the 2.1 and the 2.8 kb inserts, respectively.

E. coli cells containing pSY1520 and pSY1521 were grown at 30° C.. in LB medium containing 50 μg/ml ampicillin to an $OD_{600}$ of 0.7. Production of the FCB-SLP polymer proteins were induced by increasing the culture temperature to 42° C. for 1.5 hours. The cells were harvested by centrifugation and lysed in sample buffer containing sodium dodecylsulfate (SDS) and β-mercaptoethanol by heating at 100° C. for 5 minutes. Samples of these lysates corresponding to $5\times10^8$ cells were applied to an 8% polyacrylamide gel containing SDS, electrophoresed, and transferred to nitrocellulose filters by electroblotting. The filters were incubated either with anti-SLP or anti-FCB peptide antibody. Specific immunoreactivity with the anti-SLP antibody was observed for a protein band of approximately 75 kd in lysates of pSY1520, 95 kd in lysates of pSY1521, and 120 kd in lysates of the SLPIII clone pSY1186. Reactivity with the anti-FCB antibody was observed only for the two FCB-SLP polymer bands.

```
pSY1520 FCB-SLPIII  767 AA  MW 57,467
(fM) DPVVLQRRDWENPGVTQLNRLAAHPPFASDPM
GAGS(GAGAGS)6GAAVTGRGDSPASAAGY
[(GAGAGS)9GAAVTGRGDSPASAAGY]9
GAGAGSGAGAGSGAGAMDPGRYQLSAGRYHYQLVWCQK
(SEQ ID NO: 61)
```

Plasmid pPT0134 Construction:

Two oligonucleotide strands containing multiple cloning sites (MCS) were synthesized and purified as described in Example 1.

```
       FokI   FokI   ScaI

0.A) 5'- GTGCTGCGGATGCTCGAGATGGTGCATGCATGTACATCCGAGTACTTCGAT (SEQ ID NO: 62)
0.B) 3'-     ACGCCTACGAGCTCTACCACGTACGTACATGTAGGCTCATGAAGCTA (SEQ ID NO: 63)
```

After annealing, the two oligonucleotide strands were ligated with pSY937 which had been digested with BanI and EcoRV RENs. The product of the ligation mixture was transformed into E. coli and selected on bacterial plates containing the antibiotic chloramphenicol. Plasmid DNA from individual colonies was analyzed on agarose gel electrophoresis after digestion with ScaI and StuI RENs. One plasmid, pPT0124, contained the expected DNA fragment.

The new MCS were then moved to plasmid pSY1367. This plasmid is a derivative of pSY1299, which was digested with NciI REN and the large DNA fragment was purified by agarose gel electrophoresis and NACS purification. The purified DNA fragment was treated with DNA Polymerase (Example 1), ligated, then digested with FokI prior to transformation in E. coli strain HB101. Plasmid DNA from single colonies was purified and analyzed by restriction digests. One plasmid, pSY1366, was found to be correct and lacking the only FokI site present in pSY1299.

Two oligonucleotide strands were synthesized and purified as described in Example 1:

```
              (BanII)                FokI

1.A) 5'-    CTACATGTGTTACACATCCCGTGC(SEQ ID NO:64)
1.B) 3'- CCGAGATGTACACAATGTGTAGGGCACG(SEQ ID NO:65)
```

Oligonucleotide strands 1.A and 1.B were annealed and ligated with the DNA of plasmid pSY1366 which had been digested with BanII and FspI RENs. The products of this ligation reaction were transformed into E. coli strain HB101. Plasmid DNA from transformed colonies was purified and digested with FokI. Clones which linearized with FokI were sequenced. Plasmid pSY1367 contained the desired MCS sequence and was chosen for subsequent constructions.

Plasmids pPT0124 and pSY1367 were digested with NruI and NcoI and the DNA fragments were purified by agarose gel electrophoresis and NACS purification. The small fragment (approximately 500 bp) from pPT0124 was ligated with the large fragment from pSY1367. The product of the ligation mixture was transformed into E. coli. Plasmid DNA from single colonies was purified and analyzed by restriction digests and DNA sequencing. One plasmid, pPT0134, contained the desired sequence and was used as the acceptor vector for further DNA constructions.

SELPF Construction and Expression:

Plasmid DNA pSY1521 was digested with BanI REN and the SLPF (FCB-SlpIII) monomer was purified using NACS column (see Example 1). The DNA fragment was ligated with pPT0134 previously digested with FokI REN, treated with calf intestinal phosphatase (see Example 1), and subsequently purified using NACS column. The product of this ligation reaction was transformed into E. coli strain HB101. Transformants were selected for resistance to chloramphenicol. Plasmid DNA from transformed colonies was purified and digested with FokI. Clones with the correct restriction pattern were sequenced. Plasmid pPT0141 contained the desired SLPF monomer sequence and was chosen for subsequent constructions.

Plasmid pSY1377 was digested with BanI REN and the SELP3 gene monomer DNA fragment was purified by agarose gel electrophoresis followed by NACS column. The purified SELP3 gene monomer, 268 bp, was ligated with plasmid DNA pPT0141 previously digested with BanI REN and purified using NACS column. The product of this ligation reaction was transformed into *E. coli* strain HB101. Transformants were selected for resistance to chloramphenicol. Plasmid DNA from transformed colonies was purified and digested with FokI. Clones with the correct restriction pattern were sequenced. Plasmid pPT0146 contained the desired SELPF monomer DNA.

Plasmid DNA from pPT0146 was digested with FokI REN and the digestion fragments were separated by agarose gel electrophoresis. The SELPF gene fragment, 477 bp, was excised and purified by NACS column (see Example 1). The purified fragment was ligated with plasmid pSY1262 which had been digested with REN BanI. The product of this ligation reaction was transformed into *E. coli* strain HB101. Transformants were selected for resistance to kanamycin. Plasmid DNA from individual transformants was purified and analyzed for increased size due to SELPF multiple DNA insertion. Several clones were obtained ranging in size from 1 kbp to 6 kbp. One clone pPT0183, with an insert of approximately 2.9 kbp was chosen for expression and protein analysis.

*E. coli* strain HB101 containing plasmid pPT0183 was grown as described in Example 1. The protein produced by these cells was analyzed by SDS-PAGE for detection of reactivity to SLP and ELP antibodies. In every analysis a strong reactive band was observed with an apparent molecular weight of approximately 100 kD.

PPT0183 SELPF 1011 AA MW 79,597
MDPVVLQRRDWENPGVTQLNRLAAHPPFASDPM
GAGS(GAGAGS)$_2$(GVGVP)$_8$
[(GAGAGS)$_{12}$GAAVTGRGDSPASAAGY(GAGAGS)$_5$(GVGVP)$_8$]$_6$
(GAGAGS)$_{12}$GAAVTGRGDSPASAAGY(GAGAGS)$_2$
GAGAMDPGRYQLSAGRYHYQLVWCQK (SEQ ID NO: 66)

EXAMPLE 6

Plasmid pPT0285 Construction:

Plasmid pACYC184 (Chang, A. Y. C. and Cohen, S. N., *J. Bacteriol.,* 134: 1141–1156 (1978)) was digested with BanI REN, purified by agarose gel electrophoresis, and the DNA fragment corresponding to approximately 2,000 bp was further purified using a NACS column. This DNA fragment was filled in using DNA polymerase (see Example 1) and then self-ligated. The products of the ligation mixture were transformed into *E. coli* strain HBO1 and selected on bacterial plates containing chloramphenicol at 30 $\mu$g/ml. Plasmid DNA from individual colonies was linearized by digestion with Eco47III. One clone, pPT0235, was used as the acceptor vector for subsequent DNA manipulations.

Two oligonucleotide strands were synthesized and purified as described in Example 1:

```
    (Eco47III)PmeI        Pm1I              NruI            BanI
 StuIEcoRV          SnaBI(SnaI)
1.5'- GCTATGTTTAAACCACGTGTTCGCGATCCGGGTGCCGATCCAGGCCTGCGATATCAGTACGTA   (SEQ ID NO:67)

2.3'- CGATACAAATTTGGTGCACAAGCGCTAGGCCCACGGCTAGGTCCGGACGCTATAGTCATGCAT   (SEQ ID NO:68)
      A  M  F  K  P  R  V  R  D  P  G  A  D  P  G  L  R  Y  Q  Y  V       (SEQ ID NO:69)
```

The two oligonucleotide strands were annealed and ligated with the DNA of plasmid pPT0235 which had been digested with Eco47III and SnaI RENs. The product of this ligation reaction was transformed into *E. coli* strain HB101. Plasmid DNA from transformants was purified and digested with EcoRI in combination with Eco47III or Snal or NruI RENs. Plasmid DNA from two clones that gave the correct digestion pattern was sequenced. One plasmid, designated pPT0285, was found to be correct and chosen for further constructions.

CLP3.7 Construction and Expression:

One oligonucleotide strand coding for the CLP 3.7 gene monomer (see Table 5) was synthesized using an Applied Biosystems DNA synthesizer model 381A and a 2000 Å synthesis column supplied by Glen Research. After the synthesis, the 226 base DNA fragment was deprotected and cleaved from the column support by treatment in $NH_4OH$ at 55° for 6 hours.

TABLE 5

| |
|---|
| 5'-<br>ATGGCAGCGAAAGGGGACCGGTGCCCCGGGTACTCCTGGTCCACAAGGTCTGCCGGGAAGCCCAGGG |
| GCTCCGGGTACTCCAGGTCCGCAAGGCCTGCCGGGTTCACCGGGTGCTCCGGGAACTCCTGGCCCGC |
| AGGGCTTGCCGGGATCCCCAGGTGCACCAGGAACGCCGGGACCTCAGGGTCTTCCGGGTAGCCCTGG |
| TGCCTTTCCGCTAAAGTCCTGCCGT -3' (SEQ ID NO:70) |

Two additional DNA strands were synthesized to be used as primers for PCR amplification. The synthesis and purification of these DNA primers was performed as described in Example 1. The two strands are:

1. 5' - AAG AAG GAG ATA TCA TAT GGC AGC GAA AGG GGA CC -3' (SEQ ID NO:71)

-continued 2. 5' - CGC AGA TCT TTA AAT TAC GGC AGG ACT TTA GCG AAA A   -3'   (SEQ ID NO:72)

The PCR reaction was performed as described in Example 1.

The DNA was resuspended and digested with BanI REN as described in Example 1. The digested DNA was purified as described in Example 1, and then ligated with pPT0285 previously digested with BanI, treated with SAP, and purified as described in Example 1. The product of the ligation reaction was transformed into *E. coli* strain HB101. Plasmid DNA from transformants was purified and analyzed as described below. Colonies were picked and transferred onto a plate and into a 0.5 ml microfuge tube containing 50 μl of lysis buffer (1% Tween 20, 10 Tris-HCl pH 8.0, 1 mM EDTA). The tube was closed, incubated at 95° C. for 10 minutes. And then cooled to room temperature. 5 μl of lysate was added to 45 μl MasterMix (1×PCR buffer as described previously, 5 U Amplitaq, 200 μM dNTPs) in a 0.5 ml Perkin Elmer thin-walled Gene Amp™ reaction tube. Amplification was performed in a Perkin Elmer DNA Thermal cycler model 480 for 30 cycles with the following step cycle of 1 minute each: 95° C., 52° C., and 72° C.. Aliquots from different reactions were analyzed by agarose gel electrophoresis using 1.5% Low Melting Point agarose in 0.5×TAE buffer. Plasmid DNA from the clones showing the correct size insert was purified and analyzed by DNA sequencing. Plasmid pPT0310 contained the desired CLP 3.7 monomer sequence (see Table 6).

mately 1.25 kbp and 2.6 kbp (pPT0314 and pPT0312 respectively) were chosen to be used for expression of CLP 3.7.

CLP 3.7 Analysis:

*E. coli* strain HB101 containing plasmid pPT0312 or pPT0314 were grown as described in Example 1. The proteins produced by these cells were analyzed by SDS-PAGE for detection of reactivity to CLP antibodies. In every analysis a strong reactive band was observed with an apparent molecular weight of 130 kD and 50 kD respectively.

pPT0312       CLP 3.7             837 AA    MW 72,637
  MDPVVLQRRDWENPGVTQLNRLAAHPPFASDPM
  [(GAPGTPGPQGLPGSP)$_4$]$_{13}$
  GAMDPGRYQLSAGRYHYQLVWCQK   (SEQ ID NO:75)

pPT0314       CLP 3.7             417 AA    MW 37,060
  MDPVVLQRRDWENPGVTQLNRLAAHPPFASDPM
  [(GAPGTPGPQGLPGSP)$_4$]$_6$
  GAMDPGRYQLSAGRYHYQLVWCQK   (SEQ ID NO:76)

PPAS1-A Polymer Construction

The Protein Polymer Adhesive Substrate (PPAS) polymer was designed to include a 17 amino acid oligopeptide block of human fibrin gamma chain within a structural backbone consisting of 3 complete repeats of a 15 amino acid peptide block of human collagen type I (GAPGTPGPQGLPGSP (SEQ ID NO: 77), the CLP3.7 monomer repeating amino acid sequence).

TABLE 6

```
    BanI    AvaI/SmaI
5'- GGTGCCCCGGGTACTCCTGGTCCACAAGGTCTGCCGGGAAGCCCA
3'- CCACGGGGCCCATGAGGACCAGGTGTTCCAGACGGCCCTTCGGGT
    G  A  P  G  T  P  G  P  Q  G  L  P  G  S  P

BanII           GsuI                StuI              DraIII
    GGGGCTCCGGGTACTCCAGGTCCGCAAGGCCTGCCGGGTTCACCG
    CCCCGAGGCCCATGAGGTCCAGGCGTTCCGAACGGCCCAAGTGGC
    G  A  P  G  T  P  G  P  Q  G  L  P  G  S  P

BG1I          BAMHI
    GGTGCTCCGGGAACTCCTGGCCCGCAGGGCTTGCCGGGATCCCCA
    CCACGAGGCCCTTGAGGACCGGGCTGCCCGAACGGCCCTAGGGGT
    G  A  P  G  T  P  G  P  Q  G  L  P  G  S  P

Eco0109I                         BanI
    GGTGCACCAGGAACGCCGGGACCTCAGGGTCTTCCGGGTAGCCCTGGTGCC  -3  (SEQ ID NO:73)
    CCACGTGGTCCTTGCGGCCCTGGAGTCCCAGAAGGCCCATCGGGACCACGG  -5' (SEQ ID NO:74)
    G  A  P  G  T  P  G  P  Q  G  L  P  G  S  P  G  A
```

CLP3.7 Polymer Construction:

Plasmid DNA from pPT0310 was digested with BanI REN and the digestion fragments were separated by agarose gel electrophoresis. The CLP 3.7 gene fragment, 180 bp, was excised and purified by NACS column (see Methods). The purified fragment was ligated with plasmid pSY1262 which had been prepared as follows: pSY1262 plasmid DNA was digested with BanI REN and subsequently treated with Shrimp Alkaline Phosphatase (SAP) as described in Example 1.

The product of this ligation reaction was transformed into *E. coli* strain HB101. Transformants were selected for resistance to kanamycin. Plasmid DNA from individual transformants was purified and analyzed for increased size due to CLP 3.7 multiple DNA insertion. Several clones were obtained and two of them containing inserts of approxi- PPAS1-A Gene Monomer Synthesis and Construction The PPAS1-A amino acid monomer sequence with the fibrin gamma sequence shown in bold is as follows:

(GAPGTPGPQGLPGSP)$_3$GAPGTPGEGQQHHLGGAKQAGDVGSP
(SEQ ID NO:78)

One oligonucleotide strand (see Table 7) was synthesized using an Applied Biosystems DNA synthesizer model 381A and a 2000 Å pore resin synthesis column supplied by Glen Research. During the synthesis, the required interrupt-pause steps for reagent bottle changes were minimized. After the synthesis, the 123 base DNA fragment was deprotected and cleaved from the column support by treatment in ammonium hydroxide at 55° C.. for 6 hrs.

TABLE 7

5'- ATGGCAGCGAAAGGGGACCGTGCACCAGGAACGCC
GGGAGAAGGTCAACAGCACCATCTTGGTGGAGCGAAAC
AGGCAGGCGACGTCGGTAGCCCTGGTGCCTTTCCGCTA
AAGTCCTGCCGT -3'(SEQ ID NO:79)

The PCR reaction was then performed as previously described using the same primers as were used in the construction of the CLP3.7 monomer. The amplified DNA was then resuspended and digested with ApaLI and DraI RENs. The digested DNA was then purified using a Probind filter followed by a Bio-Spin column and then ligated with pPT0310 previously digested with ApaLI and EcoRV RENs and purified by NACS column. The products of the ligation reaction were transformed into E. coli strain HB101. Plasmid DNA from transformants was purified and analyzed by digestion using EcoO109, HincII and HindIII RENs. Plasmid DNA from the clones showing the correct size insert was purified and analyzed by DNA sequencing. Plasmid pPT0318 contained the desired PPAS1-A gene monomer sequence (see Table 8).

was purified and analyzed by digestion using BstYI and Bst1107I RENs. Plasmid DNA from the clones showing the correct restriction pattern was purified and analyzed by DNA sequencing. Plasmid pPT0317 contained the desired DNA insert and was used for further DNA manipulations.

PPAS1-A Polymer Construction

Plasmid DNA from pPT0318 was digested with BanI REN and the digestion fragments were separated by agarose gel electrophoresis. The PPAS1-A gene fragment, 216 bp, was excised and purified using the Ultrafree-MC filter. The purified fragment was ligated with plasmid pPT0317 which had been prepared as follows. Plasmid DNA pPT0317 was digested with BanI REN, then passed through a Probind filter and then a Bio-Spin column. The DNA was then treated with SAP.

The products of the ligation reaction were transformed into E. coli strain HB101. Transformants were selected for resistance to kanamycin. Plasmid DNA from individual transformants was purified and analyzed using EcoRI and EcoRV RENs for the presence of PPAS1-A multimer gene inserts. Several clones were obtained with insert sizes ranging from 200 bp to approximately 4 kb. Several clones containing from 10 to 20 repeats were chosen for use in expression of the PPAS1-A polymer.

TABLE 8

```
       BanI    AvaI/SmaI
5'- GGTGCCCCGGGTACTCCTGGTCCACAAGGTCTGCCGGGAAGCCCA
3'- CCACGGGCCCCATGAGGACCAGGTGTTCCAGACGGCCCTTCGGGT
       G  A  P  G  T  P  G  P  Q  G  L  P  G  S  P

BanII          GsuI              StuI          DraIII
    GGGGCTCCGGGTACTCCAGGTCCGCAAGGCCTGCCGGGTTCACCG
    CCCCGAGGCCCATGAGGTCCAGGCGTTCCGGACGGCCCAAGTGGC
       G  A  P  G  T  P  G  P  Q  G  L  P  G  S  P

BglI                BamHI
    GGTGCTCCGGGAACTCCTGGCCCGCAGGGCTTGCCGGGATCCCCA
    CCACGAGGCCCTTGAGGACCGGGCGTCCCGAACGGCCCTAGGGGT
       G  A  P  G  T  P  G  P  Q  G  L  P  G  S  P

GGTGCACCAGGAACGCCGGGAGAAGGTCAACAGCACCATCTTGGT
    CCACGTGGTCCTTGCGGCCCTCTTCCAGTTGTCGTGGTAGAACCA
       G  A  P  G  T  P  G  E  G  Q  Q  H  L  G

AatII           BanI
    GGAGCGAAACAGGCAGGCGACGTCGGTAGCCCTGGTGCC   -3' (SEQ ID NO:80)
    CCTCGCTTTGTCCGTCCGCTGCAGCCATCGGGACCACGG   -5' (SEQ ID NO:81)
       G  A  K  Q  A  G  D  V  G  S  P  (G  A)
```

Construction of Expression Plasmid pPT0317

Plasmid DNA pSY1262 was linearized with PvuII REN, then passed through a Probind filter followed by a Bio-Spin column. The DNA was then treated with SAP and ligated with a DNA fragment from pQE-17 (QIAGEN Catalog #33173 ) prepared as follows. Plasmid DNA pQE-17 was digested with BglII and HindIII RENs and the 36 bp fragment (see Table 9) was purified using a Probind filter and then a Bio-Spin column. The DNA was purified further using a Microcon-30 filter and the filtrate containing the 36 bp was kept. The DNA was then treated with DNA Polymerase I and purified through a Probind filter and then a Bio-Spin column.

TABLE 9

5'- GATCTTCGATCTCATCACCATCACCATCACTA
                                        (SEQ ID NO:82)
3'-        AAGCTAGAGTAGTGGTAGTGGTAGTGATTCGA
                                        (SEQ ID NO:83)

The products of the ligation reaction were transformed into E. coli strain HB101. Plasmid DNA from transformants PPAS1-A Expression Analysis E. coli strain HB101 containing plasmid pPT0321, pPT0325, pPT0326, or pPT0327 was cultured as previously described. The proteins produced by these cells showed strong reactive bands of apparent molecular weights ranging from 80 kD to 180 kD when analyzed by western blot for reactivity to CLP antibody. One clone, pPT0321, containing 10 repeats of the PPAS1-A monomer was selected for further study.

pPT0321   PPAS1-A   762 AA   MW   68,056
MDPVVLQRRDWENPGVTQLNRLAAHPPFASDPM
[(GAPGTPGPQGLPGSP)$_3$GAPGTPGEGQQHHLGGAKQAGDVGSP]$_{10}$
GAMDPGRYQDLRSHHHHHH   (SEQ ID NO:84)

EXAMPLE 7
Construction of SELP8K and SELP8E

Polymers were prepared designated SELP8K and SELP8E, which are characterized by having specific chemically reactive functional groups within the elastin-like block. The construction of these polymers is described below starting from the previous gene monomer, SELP0 (see U.S. Pat. No. 5,243,038, pSY1298, where SELP0 is termed EBSI).

SELP8K and SELP8E amino acid monomer sequence design:

SELP8K MONOMER (GAGAGS)₄ (GVGVP)₄ GKGVP (GVGVP)₃
(SEQ ID NO:85)

SELP8E MONOMER (GAGAGS)₄ (GVGVP)₄ GEGVP (GVGVP)₃
(SEQ ID NO:86)

Construction of SELP8 Gene Monomer

Plasmid pSY1378 (see U.S. Pat. No. 5,243,038) was digested with BanI REN, purified using agarose gel electrophoresis followed by NACS column, and the DNA was then ethanol precipitated in 2.5M ammonium acetate and ligated with pPT0134 (See PCT\US92\09485) previously digested with FokI REN, phenol/chloroform extracted and ethanol precipitated.

The products of the ligation mixture were transformed into *E. coli* strain HB101. Plasmid DNA from transformants was purified and analyzed by digestion using NruI and XmnI RENs. Plasmid pPT0255 containing the desired restriction pattern was obtained and was used for subsequent constructions.

Plasmid DNA pPT0255 was treated with Cfr10I REN followed by RNAse. The digestion fragments were separated by agarose gel electrophoresis, the DNA was excised and self-ligated. The products of the ligation mixture were transformed into *E. coli* strain HB101. Plasmid DNA from transformants was purified and analyzed by digestion using NaeI and StuI RENs. Plasmid pPT0267 containing the desired deletion was used for subsequent constructions.

Two oligonucleotide strands as shown in Table 10 were synthesized and purified as described in Example 1.

The products of this ligation reaction were transformed into *E. coli* strain HB101. Plasmid DNA from transformants was purified and digested with DraI. Plasmid DNA from two clones that gave the correct digestion pattern was sequenced. One plasmid DNA, designated pPT0287, was found to be correct and chosen for further constructions.

Plasmid DNA pSY1298 (see U.S. Pat. No. 5,243,038) was digested with BanII REN, and the SELP0 gene fragment was purified by agarose gel electrophoresis followed by NACS and then ligated to pPT0287 digested with BanII. The enzyme was then removed using phenol/chloroform extraction and ethanol precipitation.

The products of the ligation mixture were transformed into *E. coli* strain HB101. Plasmid DNA from transformants was purified and analyzed by digestion using DraI REN. Plasmid DNA from the clones showing the correct restriction pattern was further digested with BanII, AhaII and StuI RENs. Plasmid pPT0289 contained the desired SELP8 monomer sequence (see Table 11).

TABLE 10

| | |
|---|---|
| 5'- CTGGAGCGGGTGCCTGCATGTACATCCGAGT -3' | (SEQ ID NO:87) |
| 3'- CCGAGACCTCGCCCACGGACGTACATGTAGGCTCA -5' | (SEQ ID NO:88) |

The two oligonucleotide strands were annealed and ligated with the DNA of plasmid pPT0267 which had been previously digested with BanIII and ScaI RENs, and purified by agarose gel electrophoresis followed by NACS column.

TABLE 11

| BanI | | | | | | | | BanII | | | | | | | |
|---|---|---|---|---|---|---|---|---|---|---|---|---|---|---|---|
| GGT | GCC | GGT | TCT | GGA | GCT | GGC | GCG | GGC | TCT | GGA | GTA | GGT | GTG | CCA | GGT |
| CCA | CGG | CCA | AGA | CCT | CGA | CCG | CGC | CCG | AGA | CCT | CAT | CCA | CAC | GGT | CCA |
| G | A | G | S | G | A | G | A | G | S | G | V | G | V | P | G |
| GTA | GGA | GTT | CCG | GGT | GTA | GGC | GTT | CCG | GGA | GTT | GGT | GTA | CCT | GGA | GTG |
| CAT | CCT | CAA | GGC | CCA | CAT | CCG | CAA | GGC | CCT | CAA | CCA | CAT | GGA | CCT | CAC |
| V | G | V | P | G | V | G | V | P | G | V | G | V | P | G | V |
| | | | | | | SmaI | | | | | | | | | |
| GGT | GTT | CCA | GGC | GTA | GGT | GTG | CCC | GGG | GTA | GGA | GTA | CCA | GGG | GTA | GGC |
| CCA | CAA | GGT | CCG | CAT | CCA | CAC | GGG | CCC | CAT | CCT | CAT | GGT | CCC | CAT | CCG |
| G | V | P | G | V | G | V | P | G | V | G | V | P | G | V | G |
| | | | | | | | | | | | | BanII | | | |
| GTC | CCT | GGA | GCG | GGT | GCT | GGT | AGC | GGC | GCA | GGC | GCG | GGC | TCT | GGA | GCG | (SEQ ID NO:89) |
| CAG | GGA | CCT | CGC | CCA | CGA | CCA | TCG | CCG | CGT | CCG | CGC | CCG | AGA | CCT | CGC | (SEQ ID NO:90) |
| V | P | G | A | G | A | G | S | G | A | G | A | G | S | G | A |

Construction of SELP8K and SELP8E Gene Monomers

One oligonucleotide strand coding for a portion of the SELP8 gene monomer was synthesized with a single base polymorphism at position 90. The use of both adenine and guanidine at this position produced oligonucleotides from a single synthesis that encoded the amino acids lysine and glutamic acid (see Table 12). The synthesis was conducted using an Applied Biosystems DNA synthesizer model 381A and a 2000 Å synthesis column supplied by Glen Research. During the synthesis the required interrupt-pauses for bottle changes were minimized. After the synthesis the 202 base DNA fragment was deprotected and cleaved from the column support by treatment in 30% ammonium hydroxide at 55° C. for 6 hrs.

TABLE 12

5'- ATGGCAGCGAAAGGGGACCGGGCTCTGGTGTTGGA
GTGCCAGGTGTCGGTGTTCCGGGTGTAGGCGTTCCGGG
AGTTGGTGTACCTGGA(A/G)AAGGTGTTCCGGGGGTAGG
TGTGCCGGGCGTTGGAGTACCAGGTGTAGGCGTCCCGG
GGAGCGGGTGCTGGTAGCGGCGCAGGCGCGGGCTCTTT
CCGCTAAAGTCCTGCCGT -3' (SEQ ID NO:91)

Two additional DNA strands were used as primers for PCR amplification. The two strands were:

1. 5'-AAGAAGGAGATATCATATGGCAGCGAAAGGGGACC-3'
(SEQ ID NO:71)

2. 5'-CGCAGATCTTTAAATTACGGCAGGACTTTAGCGGAAA-3'
(SEQ ID NO:72)

The PCR reaction was carried out and the reaction product was purified as described in Example 1.

The DNA was resuspended and digested with BanIII REN as described in Example 1. The digested DNA was then separated by low-melting agarose gel electrophoresis and ligated with pPT0289 previously digested with BanII RENs and purified by NACS column. The products of the ligation reaction were transformed into E. coli strain HB101. Plasmid DNA from isolated transformants was purified and analyzed by digestion using ApaLI and EcoNI RENs. Plasmid DNA from the clones showing the correct restriction pattern were further analyzed by digestion using Asp700 REN to distinguish between clones encoding a lysine or glutamic acid at the polymorphic position. Plasmid DNA from clones containing each of the polymorphs was purified and analyzed by DNA sequencing. Plasmid pPT0340 contained the desired SELP8K monomer sequence and pPT0350 contained the desired SELP8E monomer sequence (see Tables 13 and 14, respectively).

TABLE 13

```
BanI                             BanII
GGT GCC GGT TCT GGA GCT GGC GCG GGC TCT GGT GTT GGA GTG CCA GGT
CCA CGG CCA AGA CCT CGA CCG CGC CCG AGA CCA CAA CCT CAC GGT CCA
G   A   G   S   G   A   G   A   G   S   G   V   G   V   P   G

EcoNI
GTC GGT GTT CCG GGT GTA GGC GTT CCG GGA GTT GGT GTA CCT GGA AAA
CAG CCA CAA GGC CCA CAT CCG CAA GGC CCT CAA CCA CAT GGA CCT TTT
V   G   V   P   G   V   G   V   P   G   V   G   V   P   G   K

GGT GTT CCG GGG GTA GGT GTG CCG GGC GTT GGA GTA CCA GGT GTA GGC
CCA CAA GGC CCC CAT CCA CAC GGC CCG CAA CCT CAT GGT CCA CAT CCG
G   V   P   G   V   G   V   P   G   V   G   V   P   G   V   G

SmaI                                 BanII
GTC CCG GGA GCG GGT GCT GGT AGC GGC GCA GGC GCG GGC TCT GGA GCG   (SEQ ID NO:92)
CAG GGC CCT CGC CCA CGA CCA TCG CCG CGT CCG CGC CCG AGA CCT CGC   (SEQ ID NO:93)
V   P   G   A   G   A   G   S   G   A   G   A   G   S   G   A
```

TABLE 14

```
BanI                             BanII
GGT GCC GGT TCT GGA GCT GGC GCG GGC TCT GGT GTT GGA GTG CCA GGT
CCA CGG CCA AGA CCT CGA CCG CGC CCG AGA CCA CAA CCT CAC GGT CCA
G   A   G   S   G   A   G   A   G   S   G   V   G   V   P   G

EcoNI
GTC GGT GTT CCG GGT GTA GGC GTT CCG GGA GTT GGT GTA CCT GGA GAA
CAG CCA CAA GGC CCA CAT CCG CAA GGC CCT CAA CCA CAT GGA CCT CTT
V   G   V   P   G   V   G   V   P   G   V   G   V   P   G   E

Asp700
GGT GTT CCG GGG GTA GGT GTG CCG GGC GTT GGA GTA CCA GGT GTA GGC
CCA CAA GGC CCC CAT CCA CAC GGC CCG CAA CCT CAT GGT CCA CAT CCG
G   V   P   G   V   G   V   P   G   V   G   V   P   G   V   G

SmaI                                 BanII
GTC CCG GGA GCG GGT GCT GGT AGC GGC GCA GGC GCG GGC TCT GGA GCG   (SEQ ID NO:94)
CAG GGC CCT CGC CCA CGA CCA TCG CCG CGT CCG CGC CCG AGA CCT CGC   (SEQ ID NO:95)
V   P   G   A   G   A   G   S   G   A   G   A   G   S   G   A
```

SELP8K Polymer Construction

Plasmid DNA from pPT0340 was digested with BanI REN and the digestion fragments were separated by agarose gel electrophoresis. The SELP8K gene fragment, 192 bp, was excised and purified by NACS column. The purified fragment was ligated with plasmid pPT0317 which had been digested with BanI REN, passed through a Millipore Probind and a Bio-Spin 6 column. The DNA was then treated with shrimp alkaline phosphatase (SAP) as described in Example 1.

The products of this ligation reaction were transformed into E. coli strain HB101. Transformants were selected for resistance to kanamycin. Plasmid DNA from individual transformants was purified and analyzed for increased size due to SELP8K monomer multiple DNA insertion. Several clones were obtained with insert sizes ranging from 200 bp to approximately 7 kb. Clones containing from 6 to 32 repeats, were used for expression of the SELP8K protein polymer (pPT0341, pPT0343, pPT0344, pPT0345 and pPT0347).

SELP8K Expression Analysis

E. coli strain HB11 containing plasmids pPT0341, pPT0343, pPT0344, pPT0345 and pPT0347 were grown as described in Example 1. The proteins produced by these cells were analysed by Western blot for detection of proteins reactive to SLP antibodies. Each clone produced a strongly reactive band. The apparent molecular weights of the products ranged from approximately 35 kD to greater than 250 kD. Strain pPT0345 produced an SLP antibody reactive band of apparent molecular weight 80,000. The expected amino acid sequence of the SELP8K polymer encoded by plasmid pPT0345 is shown below.

```
pPT0345    SELP8K    884 AA    MW 69,772
MDPVVLQRRDWENPGVTQLNRLAAHPPFASDPMGAGSGAGAGS
[(GVGVP)4GKGVP (GVGVP)3(GAGAGS)4]12
(GVGVP)4GKGVP (GVGVP)3(GAGAGS)2
GAGAMDPGRYQDLRSHHHHHH   (SEQ ID NO:96)
```

The Construction of SELP0K Polymers

The copolymer structure of SELP8K consists of silk-like blocks (SLP block) and elastin-like blocks (ELP block) in the following sequence: [(SLP block)$_4$ (ELP block)$_8$]. Additional polymers were designed to have different resorption and solution properties by adjusting their silk-like to elastin-like block lengths while maintaining their reactive properties. SELP0K contains half the length of crystallizable silk-like blocks than SELP8K while maintaining the dispersion frequency with respect to the elastin-like blocks.

A polymer with intervening sequences to promote in vivo resorption through proteolytic cleavage by collagenase (92 kd) was also designed. SELP0K-CS1 contains two adjacent cleavage sites for collagenase (PLGP) (SEQ ID NO: 97) within a six amino acid insert (GAGAGS GVGVP L G P L G P GVGVP) (SEQ ID NO: 98).

Construction of Plasmid pPT0317

Plasmid DNA pSY1262 (see U.S. Pat. No. 5,243,038) was linearized with PvuII REN, then passed through a Probind filter and a Bio-Spin 6 column. The DNA was then treated with Shrimp Alkaline Phosphatase (SAP). The linearized pSY1262 DNA was then ligated with a DNA fragment from pQE-17 (QIAGEN Catalog #33173) prepared as follows. Plasmid DNA pQE-17 was digested with BglII and HindIII RENs and the 36 bp fragment shown in Table 15 was purified using a Probind filter and a Biospin column. The DNA was purified further using a Microcon-30 filter and the filtrate, containing the 36 bp fragment, was kept. The DNA was then treated with DNA Polymerase I and purified using a Probind filter and a Biospin column (see Example 1).

TABLE 15

5'-GATCTTCGATCTCATCACCATCACCATCACTA
(SEQ ID NO:82)
3'-AAGCTAGAGTAGTGGTAGTGGTAGTGATTCGT
(SEQ ID NO:99)

The product of the ligation reaction was transformed into E. coli strain HBO101. Plasmid DNA from transformants was purified and analyzed by digestion using Bst1107I and EcoRV RENs. The clones containing the desired DNA fragment were further digested with Bst1107I and BstYI RENs to determine the orientation of the insert. Plasmid DNA from the clones showing the correct restriction pattern was purified and analyzed by DNA sequencing. Plasmid pPT0317 contained the desired DNA insert and was used for further DNA constructions.

SELP0K Polymer Construction

One oligonucleotide strand as shown in Table 16 was synthesized using an Applied Biosystems DNA synthesizer model 381A and a 2000 Å synthesis column supplied by Glen Research. After the synthesis the 93 base DNA fragment was deprotected and cleaved from the column support by treatment in ammonium hydroxide at 55° C. for 6 hours.

TABLE 16

5'- ATGGCAGCGAAAGGGGACCGGTGCCGGCGCAGGTA
GCGGAGCCGGTGCGGGCTCAAAAAGGGCTCTGGTGCCT
TTCCGCTAAAGTCCTGCCGT -3'    (SEQ ID NO:100)

The PCR reaction was performed using the same two DNA primer strands as described for the construction of the SELP8K gene monomer and the reaction product was purified. The DNA was resuspended and digested with BanI REN. The digested DNA was then separated by low-melting agarose gel and ligated with pPT0285 (see PCT/US92/09485) previously digested with BanI REN and purified by NACS column. The product of the ligation reaction was transformed into E. coli strain HB101. Plasmid DNA from transformants was purified and analyzed by digestion using EcoRI and BanII RENs. Plasmid DNA from the clones showing the correct restriction pattern was then purified and analyzed by DNA sequencing. Plasmid pPT0358 contained the desired sequence and was used for subsequent DNA constructions.

Plasmid DNA from pPT0340 was digested with BanII REN and the digestion fragments were separated by agarose gel electrophoresis. The SELP0K gene fragment, 156 bp, (see Table 17), was excised and purified using an Ultrafree-MC filter followed by Bio-Spin 6 column.

TABLE 17

BanII
G GGC TCT GGT GTT GGA GTG CCA GGT GTC GGT GTT CCG GGT GTA GGC GTT
C CCG AGA CCA CAA CCT CAC GGT CCA CAG CCA CAA GGC CCA CAT CCG CAA
   G   S   G   V   G   V   P   G   V   G   V   P   G   V   G   V

CCG GGA GTT GGT GTA CCT GGA AAA GGT GTT CCG GGG GTA GGT GTG CCG
GGC CCT CAA CCA CAT GGA CCT TTT CCA CAA GGC CCC CAT CCA CAC GGC
 P   G   V   G   V   P   G   K   G   V   P   G   V   G   V   P

GGC GTT GGA GTA CCA GGT GTA GGC GTC CCG GGA GCG GGT GCT GGT AGC
CCG CAA CCT CAT GGT CCA CAT CCG CAG GGC CCT CGC CCA CGA CCA TCG
 G   V   G   V   P   G   V   G   V   P   G   A   G   A   G   S

BanII
A GGC GCCA GGC GCG GGC TC (SEQ ID NO: 101)
A CCG CGT CCG CGC CCG AG
   G   A   G   A   G     S (SEQ ID NO: 102)

The purified fragment was ligated with plasmid pPT0358 which had been digested with BanII REN, then passed through a Probind filter and a Microcon-30 filter. The digestion fragments were then separated by agarose gel electrophoresis. The plasmid DNA was then excised and purified using an Ultrafree-MC filter followed by Bio-Spin 6 column (see Example 1).

The product of this ligation reaction was transformed into E. coli strain HB101. Transformants were selected for resistance to chloramphenicol. Plasmid DNA from individual transformants was purified and analyzed for increased size due to SELP0K multiple DNA insertion. Several clones were obtained with inserts of different sizes. Plasmid pPT0359, pPT0360 and pPT0374 containing respectively 18, 2 and 6 repeats of the SELP0K gene monomer were used for subsequent constructions.

Plasmid DNA from pPT0359 and pPT0374 was digested with BanI REN and the digestion fragments were separated by agarose gel electrophoresis. The SELP0K gene fragments, approximately 2800 bp and 1000 bp, were excised and purified by NACS column. The purified fragments were then ligated with plasmid pPT0317 which had been digested with BanI REN, then passed through a Probind filter and a Bio-Spin 6 column. The DNA was then treated with Shrimp Alkaline Phosphatase (SAP), passed through a Probind filter and then a Bio-Spin 6 column (see Example 1).

The product of these ligation reactions was transformed into E. coli strain HB101. Transformants were selected for resistance to kanamycin. Plasmid DNA from individual transformants was purified and analyzed for increased size due to SELP0K multiple DNA insertion. Several clones were obtained. Plasmid pPT0364 and pPT0375 were chosen to be used for expression of SELP0K.

SELP0K Expression Analysis

E. coli strain HB101 containing plasmid pPT0364 and pPT0375 were grown as described in Example 1. The proteins produced by these cells were analysed by SDS-PAGE for detection of reactivity to ELP antibodies. In every analysis a strong reactive band was observed of an apparent molecular weight of approximately 95 kD and 35 kD respectively.

pPT0364           SELPOK          1000 AA    MW 80,684
MDPVVLQRRDWENPGVTQLNRLAAHPPFASDPM
[(GAGAGS)$_2$ (GVGVP)$_4$ GKGVP (GVGVP)$_3$]$_{18}$
(GAGAGS)$_2$ GAGAMDPGRYQDLRSHHHHHH (SEQ ID NO: 103)

pPT0375           SELPOK          376 AA    MW 31,445
MDPVVLQRRDWENPGVTQLNRLAAHPPFASDPM
[(GAGAGS)$_2$ (GVGVP)$_4$ GKGVP (GVGVP)$_3$]$_6$
(GAGAGS)$_2$ GAGAMDPGRYQDLRSHHHHHH (SEQ ID NO: 104)

SELP0K-CS1 Polymer Construction

Plasmid pPT0360 was digested with BanI REN and the digestion fragments were separated by agarose gel electrophoresis. The SELP0K gene fragment, approximately 300 bp, was excised and purified using an Ultrafree-MC filter followed by Bio-Spin 6 column. The purified fragment was ligated with plasmid pPT0134 (see PCT/US92/09485) which had been digested with FokI REN. The enzyme was heat inactivated at 65° C. for 20 minutes and the ligation mixture was then passed through a Probind filter. The DNA was then treated with Shrimp Alkaline Phosphatase (SAP), passed through a Probind filter and then a Bio-Spin 6 column.

The product of this ligation reaction was transformed into E. coli strain HBO101. Transformants were selected for resistance to chloramphenicol. Plasmid DNA from individual transformants was purified and analyzed by digestion using DraI REN. One plasmid, pPT0363, showed the correct restriction pattern and was used for subsequent DNA constructions.

One oligonucleotide strand as shown in Table 18 was synthesized using an Applied Biosystems DNA synthesizer model 381A and a 2000 Å synthesis column supplied by Glen Research. After the synthesis the 141 base DNA fragment was deprotected and cleaved from the column support by treatment in ammonium hydroxide at 55° C. for 6 hours.

TABLE 18

5'-ATGGCAGCGAAAGGGGACCGCCGGTGCGGGCTCTGGTGTTGGAGTGCCGCTGGGTCCTCTTGG
CCCAGGTGTCGGTGTTCCGGGTGTAGGCGTTCCGGGAGTTGGTGTACCTGGAAAAGGTTTCCGCTAA
AGTCCTGCCGT-3' (SEQ ID NO: 105)

The PCR reaction was performed using the same two DNA primer strands as described for the construction of the SELP8K gene monomer and the reaction product was purified. The DNA was then resuspended and digested with BsrFI and EcoNI RENs. The digested DNA was treated with Probind and Microcon-30 filters, a Bio-Spin 6 column, and then ligated with pPT0363 previously digested with BsrFI REN, treated with a ProBind filter and a Bio-Spin 6 column and then further digested with EcoNI REN. The digestion fragments were separated by agarose gel electrophoresis. The larger DNA band, approximately 2000 bp, was excised and purified using an Ultrafree-MC filter followed by Bio-Spin 6 column (see Example 1).

The product of the ligation reaction was transformed into E. coli strain HB101. Plasmid DNA from individual transformants was purified and analyzed by digestion using Asp7001 and Eco0109I RENs. Plasmid DNA from the clones showing the correct restriction pattern was then purified and analyzed by DNA sequencing. Plasmid pPT0368 (see Table 19) contained the desired sequence and was used for subsequent DNA constructions.

TABLE 19

```
BanII
G GGC TCT GGT GTT GGA GTG CCG CTG GGT CCT CTT GGC CCA GGT GTC
C CCG AGA CCA CAA CCT CAC GGC GAC CCA GGA GAA CCG GGT CCA CAG
    G   S   G   V   G   V   P   L   G   P   L   G   P   G   V

GGT GTT CCG GGT GTA GGC GTT CCG GGA GTT GGT GTA CCT GGA AAA
CCA CAA GG C CCA CAT CCG CAA GGC CCT CAA CCA CAT GGA CCT TTT
  G   V   P   G   V   G   V   P   G   V   G   V   P   G   K

GGT GTT CCG GGG GTA GGT GTG CCG GGC GTT GGA GTA CCA GGT GTA
CCA CAA GGC CCC CAT CCA CAC GGC CCG CAA CCT CAT GGT CCA CAT
  G   V   P   G   V   G   V   P   G   V   G   V   P   G   V

BanII
GGC GTC CCG GGA GCG GGT GCT GGT AGC GGC GCA GGC GCG GGC TCT (SEQ ID NO: 106)
CCG CAG GGC CCT CGC CCA CGA CCA TCG CCG CGT CCG CGC CCG AGA
  G   V   P   G   A   G   A   G   S   G   A   G   A   G   S    (SEQ ID NO: 107)
```

Plasmid DNA pPT0368 was digested with BanII REN, and the digestion fragments were separated by agarose gel electrophoresis. The SELP0K-CS1 gene fragment, 174 bp, was excised and purified using an Ultrafree-MC filter followed by Bio-Spin 6 column. The purified fragment was ligated with plasmid pPT0358 which had been digested with BanII REN, then passed through a Probind filter and a Microcon-30 filter. Subsequently the digestion fragments were separated by agarose gel electrophoresis. The plasmid DNA was then excised and purified using an Ultrafree-MC filter followed by Bio-Spin 6 column (see Example 1).

The product of this ligation reaction was transformed into E. coli strain HB101. Transformants were selected for resistance to chloramphenicol. Plasmid DNA from individual transformants was purified and analyzed for increased size due to SELP0K-CS1 multiple DNA insertion. Several clones were obtained with insert sizes ranging from 1000 bp to approximately 3000 bp. Plasmid pPT0369 containing 16 repeats of the SELP0K-CS1 gene monomer was used for subsequent constructions.

Plasmid DNA from pPT0369 was digested with BanI REN, followed by a Probind filter and then the digestion fragments were separated by agarose gel electrophoresis. The SELP0K-CS1 gene fragment, approximately 2800 bp, was excised and purified by an Ultrafree-MC filter and desalted using a Bio-Spin 6 column. The purified fragments were then ligated with plasmid pPT0317 which had been digested with BanI REN and then passed through a Probind filter and a Bio-Spin 6 column. The DNA was then treated with Shrimp Alkaline Phosphatase (SAP), passed through a Probind filter and then a Bio-Spin 6 column (see Example 1).

The product of these ligation reactions was transformed into E. coli strain HB101. Transformants were selected for resistance to kanamycin. Plasmid DNA from individual transformants was purified and analyzed for increased size due to SELP0K-CS1 multiple DNA insertion. Several clones were obtained. Plasmid pPT0370 was chosen to be used for expression of SELP0K-CS 1.

SELP0K-CS 1 Expression Analysis

E. coli strain HB101 containing plasmid pPT0370 was grown as described in Example 1. The proteins produced by these cells were analysed by SDS-PAGE for detection of reactivity to ELP antibodies. In every analysis a strong reactive band was observed with an apparent molecular weight of approximately 90 kD.

pPT0370    SELPOK-CS1    934 AA    MW 76,389
MDPVVLQRRDWENPGVTQLNRLAAHPPFASDPM
[(GAGAGS)$_2$ (GVGVP)$_1$ LGPLGP (GVGVP)$_3$ GKGVP (GVGVP)$_3$]$_{15}$
(GAGAGS)$_2$ GAGAMDPGRYQDLRSHHHHHH (SEQ ID NO: 108)

As is evident from the above results, highly repetitive sequences can be prepared, cloned, and used for expression to produce a wide variety of products which may mimic natural products, such as silk and other proteins and antigens. In addition, novel systems are provided for controlling the expression of the peptide under inducible conditions in a variety of hosts. In this manner, new proteinaceous products can be provided which provide for new properties or may closely mimic the properties of naturally occurring products.

Bibliography

1. Maniatis, T., Fritsch, E. F. and Sambrook, J. 1982. Molecular Cloning: A Laboratory Manual. Cold Spring Harbor Laboratory, Cold Spring Harbor, N.Y.
2. Laemmli, U. K., 1970, *Nature* (London), 227: 680–685.
3. Applied Biosystems User Bulletin, 1984, No. 13.
4. Matteucci, M. D. and Caruthers, M. H., 1981, *Journal Amer. Chem. Soc.,* 103: 3185–3319.
5. McBride, L. J. and Caruthers, M. H., 1933, *Tetrahedron Letters,* 24: 245–248.
6. Smith, 1980, *Methods in Enzymology,* 65: 371–379.

7. Vieira, J. and Messing, J., 1982, *Gene,* 19: 259–268.
8. Anagnostopouls, C. and Spizizen, J., 1981, *J. Bacteriol.,* 81: 741–746.
9. Davanloo, P., Rosenberg, A. H. Dunn, J. J. and Studier, F. W., 1984, *Proc. Natl. Acad. Sci. USA,* 81: 2035–2039.
10. Rosenbluh, A., Banner, C. D. B., Losick, R. and Fitz-James, P. C., 1981, *J. Bacteriol.,* 148: 341–351.
11. Sadaie, Y., Burtis, K. C. and Doi, R., 1980, *J. Bacteriol.,* 141(1): 178–1182.
12. Queen, C., 1983, *J. Applied Molecular Genetics,* 2: 1–10.
13. Ferrari, F. A., Trach, K. and Hoch, J. A., 1985, *J. Bacteriol.,* 161: 556–562.
14. Johnson, W. C., Moran, C. P. and Losick, T. R., 1983, *Nature* (London), 302: 800–804.
15. Studier, W. F. and Moffat, B. A., 1986, *J. Mol. Biol.,* 189: 113–130.
16. Goldfarb, D. S., DoI, R. H. and Rodriguez, R. L., 1981, *Nature* (London), 293: 309–311.
17. Ferrari, F. A., Nguyen, A., Lang, D. and Hoch, J. A., 1983, *J. Bacteriol.,* 154: 1513–1515.
18. Lacey, R. W. and Chopra, I., 1974, *J. Med. Microbiology,* 7: 285–297.
19. Norrander, J., Kempe, T. and Messing, J., 1983, *Gene,* 26: 101–106.
20. Sanger, F., Nicklen, 5. and Coulson, A. R., 1977, *Proc. Natl. Acad. Sci. USA,* 74: 5463–5467.
21. Biggin, M. D., Gibson, T. J. and Hong, G. F., 1983, *Proc. Natl. Acad. Sci. USA,* 80: 3963–3965.
22. Zagursky, R. J., Baumeister, K., Lomax, N. and Berman, M. L., 1985, *Gene Anal. Techn.,* 2: 89–94.
23. Sanger, F. and Coulson, A. R., 1978, *FEBS Letters,* 87: 107–110.
24. Sadler, J. R., Techlenburg, M. and J. L. Betz., 1980, Plasmids containing many tandem copies of a synthetic lactose operator, *Gene,* 8: 279–300.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of preparing a synthetic DNA sequence having repeating units of from about 3 to 30 codons and encoding a protein of at least about 30 kDal, said method comprising:
   (1) synthesizing at least two different pairs of single stranded oligomers wherein each of the oligomers of a pair overlap except as to any protruding ends;
   (2) hybridizing each pair of single stranded oligomers to provide double stranded segments;
   (3) combining said segments or amplified copies thereof in a cloning vector to form a monomer, where the combined segments are in reading frame;
   (4) excising said monomer from said cloning vector by restriction enzyme digestion; and
   (5) oligomerizing said monomer to provide a multimer comprising at least two monomers.

2. A method according to claim 1, wherein at least one said restriction enzyme cuts at an asymmetric consensus sequence or at a site distal from the consensus sequence.

3. A method according to claim 1, wherein said monomer has protruding termini which are complementary to each other.

4. A method according to claim 1, wherein said pairs of oligomers includes at least two different pairs encoding the same amino acid sequence.

5. A method according to claim 1, wherein said pairs of oligomers includes at least two different pairs encoding different amino acid sequences.

6. A method according to claim 1, wherein the number of pairs of oligomers is in the range of 2 to 4 and at least one oligomer has protruding ends on the same strand.

7. A method according to claim 1, wherein said repeating units have from 3 to 15 codons.

8. A method according to claim 1, wherein at least a portion of said monomer is sequenced prior to oligomerizing to provide said multimer.

9. A method of preparing a synthetic DNA sequence having repeating units of from about 3 to 30 codons and encoding a protein of at least about 30 kDal, said method comprising:
   (1) synthesizing at least three different pairs of single stranded oligomers wherein each of the oligomers of a pair overlap except as to any protruding ends;
   (2) hybridizing each pair of single stranded oligomers to provide double stranded segments each having from 21 to 90 bases to provide at least three segments, each segment having a different nucleic acid sequence and having complementary ends to contiguous segments;
   (3) combining said segments or amplified copies thereof in a cloning vector to form a monomer, where the combined segments are in reading frame;
   (4) excising said monomer from said cloning vector by restriction enzyme digestion; and
   (5) oligomerizing said monomer to provide a multimer comprising at least two monomers.

10. A method according to claim 9, including the additional step of analyzing said monomer prior to said oligomerizing.

11. A method according to claim 9, wherein at least one repeating unit encodes an amino acid sequence selected from the group consisting of:
   Gaβ, GAGAGS (SEQ ID NO:6), GVGVP (SEQ ID NO:3), VPGVG (SEQ ID NO:4), SGAGAG (SEQ ID NO:1), and AGAGSG (SEQ ID NO:20),
wherein α and β are any amino acid, α and β being selected so that from about 10 to 45 number % of the total number of amino acid residues of the protein are proline.

12. A method of preparing a DNA sequence having repeating units of from about 3 to 30 codons and encoding a protein of at least about 30 kDal, said method comprising:
   (1) synthesizing at least three different pairs of single stranded oligomers of from about 30 to 100 bases, wherein each of the oligomers of a pair overlap except as to any protruding ends;
   (2) hybridizing said pairs of oligomers to provide segments;
   (3) inserting a first segment into a linearized cloning vector;
   (4) sequencing said first segment to ensure the fidelity of said sequence;
   (5) sequentially linearizing said vector with a restriction enzyme cleaving proximal to a terminus of said segment, and adding additional segments at a terminus of the prior segment, by digesting said cloning vector with a restriction enzyme cutting at a site proximal to a terminus of the preceding segment, inserting each successive segment in reading frame with the prior segment, and cloning the cloning vector comprising said next segment, to provide a monomer;

(6) excising said monomer from said cloning vector;

(7) oligomerizing said monomer to provide at least one multimer comprising at least two monomers;

wherein the sequences of said segments and vector are selected to permit insertion of said segments and excision of said monomer by restriction enzyme digestion with restriction enzymes which cleave at asymmetric consensus sequences or distal from the consensus sequence.

13. A method according to claim 12, including the additional step of analyzing said monomer prior to said oligomerizing.

14. A method according to claim 12, wherein at least one repeating unit encodes an amino acid sequence selected from the group consisting of:

Gaβ, GAGAGS (SEQ ID NO:6), GVGVP (SEQ ID NO:3), VPGVG (SEQ ID NO:4), SGAGAG (SEQ ID NO:1), and AGAGSG (SEQ ID NO:20), wherein α and β are any amino acid, α and β being selected so that from about 10 to 45 number % of the total number of amino acid residues of the protein are proline.

15. A method of preparing a synthetic DNA sequence having repeating units of from about 3 to 30 codons and encoding a protein of at least about 30 kDal, said method comprising:

(1) synthesizing at least two different pairs of single stranded oligomers wherein each of the oligomers of a pair overlap except as to any protruding ends;

(2) hybridizing each pair of single stranded oligomers to provide double stranded segments;

(3) cloning a first segment in a cloning vector and analyzing the cloned first segment to determine the fidelity of the sequence, discarding any segment having an erroneous sequence;

(4) either:
(a) adding each successive segment in reading frame to prior segments to provide a monomer and determining the fidelity of the sequence of each successive segment; or
(b) cloning each successive segment in a cloning vector and analyzing each successive segment to determine the fidelity of the sequence and combining said segments or amplified copies thereof in a cloning vector to form a monomer, where the combined segments are in reading frame;

(5) excising said monomer from said cloning vector by restriction enzyme digestion; and (6) oligomerizing said monomer to provide a multimer comprising at least two monomers.

16. A method according to claim 15, including the additional step of analyzing said monomer prior to said oligomerizing.

17. A method according to claim 15, wherein at least one repeating unit encodes an amino acid sequence selected from the group consisting of:

Gaβ, GAGAGS (SEQ ID NO:6), GVGVP (SEQ ID NO:3), VPGVG (SEQ ID NO:4), SGAGAG (SEQ ID NO:1), and AGAGSG (SEQ ID NO:20), wherein α and β are any amino acid, α and β being selected so that from about 10 to 45 number % of the total number of amino acid residues of the protein are proline.

18. A method of preparing a synthetic DNA sequence having repeating units of from about 3 to 30 codons and encoding a protein of at least about 30 kDal, said method comprising:

(1) synthesizing at least two different pairs of single stranded oligomers wherein each of the oligomers of a pair overlap except as to any protruding ends;

(2) hybridizing each pair of single stranded oligomers to provide double stranded segments;

(3) isolating at least one double stranded segment from a previously synthesized monomer;

(4) combining said segments or amplified copies thereof in a cloning vector to form a monomer, where the combined segments are in reading frame;

(5) excising said monomer from said cloning vector by restriction enzyme digestion; and (6) oligomerizing said monomer to provide a multimer comprising at least two monomers;

wherein synthesized segments are sequenced to ensure the fidelity of replication.

19. A method according to claim 18, including the additional step of analyzing said monomer prior to said oligomerizing.

20. A method according to claim 18, wherein at least one repeating unit encodes an amino acid sequence selected from the group consisting of:

Gaβ, GAGAGS (SEQ ID NO:6), GVGVP (SEQ ID NO:3), VPGVG (SEQ ID NO:4), SGAGAG (SEQ ID NO:1), and AGAGSG (SEQ ID NO:20), wherein α and β are any amino acid, α and β being selected so that from about 10 to 45 number % of the total number of amino acid residues of the protein are proline.

21. A method of preparing a synthetic DNA sequence having repeating units of from about 3 to 30 codons and encoding a protein of at least about 30 kDal, said method comprising:

(1) synthesizing a single strand encoding a monomer comprising from about 100 to 300 bases comprising repeating units of from about 3 to 30 codons, wherein said single strand comprises 5' and 3' flanking primer binding site sequences;

(2) preparing a complementary strand and amplifying the resultant dsDNA monomer by polymerase chain reaction using primers of from 1 5 to 50 nt having a sequence comprising a sequence which hybridizes with the respective flanking primer binding site sequences, wherein said primers are different for each end of the dsDNA;

(3) cloning said dsDNA monomer and selecting for a monomer having the correct sequence; and (4) oligomerizing said monomer to provide at least one multimer comprising at least two monomers.

22. A method according to claim 21, wherein at least one repeating unit encodes an amino acid sequence selected from the group consisting of:

Gaβ, GAGAGS (SEQ ID NO:6), GVGVP (SEQ ID NO:3), VPGVG (SEQ ID NO:4), SGAGAG (SEQ ID NO:1), and AGAGSG (SEQ ID NO:20), wherein α and β are any amino acid, α and β being selected so that from about 10 to 45 number % of the total number of amino acid residues of the protein are proline.

23. A method according to claim 21, comprising the further steps of removing said primers with a restriction enzyme resulting in protruding ends and excising said dsDNA monomer after cloning with a restriction enzyme resulting in protruding ends.

24. The method according to claim 21, wherein said primers have at least 40% GC content.

25. The method according to claim 21, wherein the $T_m$ of the primers for hybridizing to their respective target sequence differs by not more than 1° C.

26. The method according to claim 21, wherein the primers have a $T_m$ for hybridizing to their respective target sequence of less than 95° C.

27. A method of preparing a synthetic DNA sequence having repeating units of from about 3 to 30 codons and encoding a protein of at least about 30 kDal, said method comprising:
   (1) synthesizing at least two different pairs of single stranded oligomers of wherein each of the oligomers of a pair overlap except as to any protruding ends;
   (2) hybridizing each pair of single stranded oligomers to provide double stranded segments;
   (3) combining said segments or amplified copies thereof in a cloning vector to form a monomer, where the combined segments are in reading frame;
   (4) excising said monomer from said cloning vector by restriction enzyme digestion;
   (5) oligomerizing said monomer to provide a multimer comprising at least two monomers;
   wherein the sequences of said segments and vector are selected to permit insertion of said segments and excision of said monomer by restriction enzyme digestion;
   (6) inserting said multimer in an expression vector functional for expression in an expression host;
   (7) introducing said expression vector into said expression host; and
   growing said expression host, whereby said protein polymer is expressed.

28. A method according to claim 27, including the additional step of purifying said expressed protein polymer.

29. A method according to claim 27, wherein at least one repeating unit encodes an amino acid sequence selected from the group consisting of:
   Gαβ, GAGAGS (SEQ ID NO:6), GVGVP (SEQ ID NO:3), VPGVG (SEQ ID NO:4), SGAGAG (SEQ ID NO:1), and AGAGSG (SEQ ID NO:20),
   wherein α and β are any amino acid, α and β being selected so that from about 1 0 to 45 number % of the total number of amino acid residues of the protein are proline.

30. A method according to claim 27, wherein said expression host is *E. coli*.

31. A method of preparing a synthetic DNA sequence having repeating units of from about 3 to 30 codons and encoding a protein of at least about 30 kDal, said method comprising:
   (1) synthesizing a single strand encoding a monomer comprising from about 100 to 300 bases comprising repeating units of from about 3 to 30 codons, wherein said single strand comprises 5' and 3' flanking primer binding site sequences;
   (2) preparing a complementary strand and amplifying the resultant dsDNA monomer by polymerase chain reaction using primers of from 20 to 45 nt having a sequence which hybridizes with the respective flanking primer binding site sequences, wherein said primers are different for each end of the dsDNA;
   (3) cloning said dsDNA monomer and selecting for a monomer having the correct sequence; (4) oligomerizing said monomer to provide at least one multimer comprising at least two monomers; (5) inserting said multimer in an expression vector functional for expression in an expression host; (6) introducing said expression vector into said expression host; and
   growing said expression host, whereby said protein polymer is expressed.

32. A method according to claim 31, including the additional step of purifying said expressed protein polymer.

33. A method according to 31, wherein at least one repeating unit encodes an amino acid sequence selected from the group consisting of:
   Gαβ, GAGAGS (SEQ ID NO:6), GVGVP (SEQ ID NO:4), VPGVG (SEQ ID NO:3), SGAGAG (SEQ ID NO:1), and AGAGSG (SEQ ID NO:20),
   wherein α and β are any amino acid, α and β being selected so that from about 10 to 45 number % of the total number of amino acid residues of the protein are proline.

34. A method according to claim 31, wherein said expression host is *E. coli*.

35. The method according to claim 31, wherein said primers have at least 40% GC content.

36. The method according to claim 31, wherein the $T_m$ of the primers for hybridizing to their respective target sequence differs by not more than 1° C.

37. The method according to claim 31, wherein the primers have a $T_m$ for hybridizing to their respective target sequence of less than 95° C.

* * * * *

SEQUENCE LISTING ( 1 ) GENERAL INFORMATION:

( i i i ) NUMBER OF SEQUENCES: 108

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:1:

```
Met  Thr  Met  Ile  Thr  Pro  Ser  Leu  Gly  Cys  Arg  Ser  Thr  Leu  Glu  Asp
 1              5                           10                          15

Pro  His  Phe  Arg  Val  Ala  Leu  Ile  Pro  Phe  Phe  Ala  Ala  Phe  Cys  Leu
                20                         25                      30

Pro  Val  Pro  Ala  His
                35
```

( 2 ) INFORMATION FOR SEQ ID NO:2:

( i ) SEQUENCE CHARACTERISTICS:
        ( A ) LENGTH: 111 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:2:

```
ATGACCATGA  TTACGCCAAG  CTTGGGCTGC  AGGTCGACTC  TAGAGGATCC  CCATTTCGT     60

GTCGCCCTTA  TTCCCTTTTT  TGCGGCATTT  TGCCTTCCTG  TTTTTGCTCA  C            111
```

( 2 ) INFORMATION FOR SEQ ID NO:3:

( i ) SEQUENCE CHARACTERISTICS:

(A) LENGTH: 21 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:3:

Asp Pro Met Phe Lys Tyr Ser Arg Asp Pro Met Gly Ala Met Asp Pro
1               5                   10                  15

Gly Arg Tyr Gln Leu
            20

(2) INFORMATION FOR SEQ ID NO:4:

(i) SEQUENCE CHARACTERISTICS:
(A) LENGTH: 63 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:4:

GATCCTATGT TTAAATATTC TCGCGATCCG ATGGGTGCCA TGGACCCGGG TCGATATCAG    60

CTG    63

(2) INFORMATION FOR SEQ ID NO:5:

(i) SEQUENCE CHARACTERISTICS:
(A) LENGTH: 63 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:5:

GATACAAATT TATAAGAGCG CTAGGCTACC CACGGTACCT GGGCCCAGCT ATAGTCGACC    60

TAG    63

(2) INFORMATION FOR SEQ ID NO:6:

(i) SEQUENCE CHARACTERISTICS:
(A) LENGTH: 6 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:6:

Ser Gly Ala Gly Ala Gly
1               5

(2) INFORMATION FOR SEQ ID NO:7:

(i) SEQUENCE CHARACTERISTICS:
(A) LENGTH: 59 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:7:

Gly Ala Gly Ala Gly Ser Gly Ala Gly Ala Gly Ser Gly Ala Gly Ala
1               5                   10                  15

Gly Ser Gly Ala Gly Ala Gly Ser Gly Ala Gly Ala Gly Ser Gly Ala
                20                      25                      30
Gly Ala Gly Ser Gly Ala Gly Ala Gly Ser Gly Ala Gly Ala Gly Ser
            35                      40                      45
Gly Ala Gly Ala Gly Ser Gly Ala Ala Gly Tyr
            50                  55

( 2 ) INFORMATION FOR SEQ ID NO:8:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:8:

Met Gly Ala Gly Ala Gly
1                   5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:9:

Gly Val Gly Val Pro
1               5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:10:

Val Pro Gly Val Gly
1               5

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:11:

Ala Pro Gly Val Gly Val
1                   5

( 2 ) INFORMATION FOR SEQ ID NO:12:

( i ) SEQUENCE CHARACTERISTICS:
        ( A ) LENGTH: 6 amino acids
        ( B ) TYPE: amino acid (C) STRANDEDNESS: unknown
(D) TOPOLOGY: unknown (i i) MOLECULE TYPE: protein (x i) SEQUENCE DESCRIPTION: SEQ ID NO:12:

Gly Ala Gly Ala Gly Ser
1               5

(2) INFORMATION FOR SEQ ID NO:13:

(i) SEQUENCE CHARACTERISTICS:
(A) LENGTH: 7 amino acids
(B) TYPE: amino acid
(C) STRANDEDNESS: unknown
(D) TOPOLOGY: unknown (i i) MOLECULE TYPE: protein (i x) FEATURE:
(A) NAME/KEY: Modified-site
(B) LOCATION: 3..4
(D) OTHER INFORMATION: /note= "X = a basic or acidic amino
acid, particularly K or E."

(x i) SEQUENCE DESCRIPTION: SEQ ID NO:13:

Lys Leu Xaa Leu Ala Glu Ala
1               5

(2) INFORMATION FOR SEQ ID NO:14:

(i) SEQUENCE CHARACTERISTICS:
(A) LENGTH: 53 amino acids
(B) TYPE: amino acid
(C) STRANDEDNESS: unknown
(D) TOPOLOGY: unknown (i i) MOLECULE TYPE: protein (x i) SEQUENCE DESCRIPTION: SEQ ID NO:14:

Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
                20                  25                  30
Gly Ala Gly Ser Gly Ala Gly Ala Gly Ser Gly Ala Gly Ala Gly Ser
                35                  40                  45
Gly Ala Ala Gly Tyr
                50

(2) INFORMATION FOR SEQ ID NO:15:

(i) SEQUENCE CHARACTERISTICS:
(A) LENGTH: 40 amino acids
(B) TYPE: amino acid
(C) STRANDEDNESS: unknown
(D) TOPOLOGY: unknown (i i) MOLECULE TYPE: protein (x i) SEQUENCE DESCRIPTION: SEQ ID NO:15:

Val Pro Gly Val Gly Val Pro Gly Val Gly Val Pro Gly Val Gly Val
1               5                   10                  15
Pro Gly Val Gly Val Pro Gly Val Gly Val Pro Gly Val Gly Val Pro
                20                  25                  30
Gly Val Gly Val Pro Gly Val Gly
                35                  40

( 2 ) INFORMATION FOR SEQ ID NO:16:

( i ) SEQUENCE CHARACTERISTICS:
        ( A ) LENGTH: 26 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:16:

```
Tyr Thr Ile Thr Val Tyr Ala Val Thr Gly Arg Gly Asp Ser Pro Ala
  1           5                  10                  15
Ser Ser Lys Pro Ile Ser Ile Asn Tyr Cys
            20                  25
```

( 2 ) INFORMATION FOR SEQ ID NO:17:

( i ) SEQUENCE CHARACTERISTICS:
        ( A ) LENGTH: 33 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:17:

```
Gly Ala Pro Gly Ala Pro Gly Ser Gln Gly Ala Pro Gly Leu Gln Gly
  1           5                  10                  15
Ala Pro Gly Ala Pro Gly Ser Gln Gly Ala Pro Gly Leu Gln Tyr Met
            20                  25                  30
Lys
```

( 2 ) INFORMATION FOR SEQ ID NO:18:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:18:

GGTGCGGGCG CAGGAAGT                                            18

( 2 ) INFORMATION FOR SEQ ID NO:19:

( i ) SEQUENCE CHARACTERISTICS:
        ( A ) LENGTH: 18 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:19:

ACCACTTCCT GCGCCCGC                                            18

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:20:

Ala Gly Ala Gly Ser Gly
1               5

( 2 ) INFORMATION FOR SEQ ID NO:21:

( i ) SEQUENCE CHARACTERISTICS:
( A ) LENGTH: 290 base pairs
( B ) TYPE: nucleic acid
( C ) STRANDEDNESS: unknown
( D ) TOPOLOGY: unknown ( i i ) MOLECULE TYPE: DNA (genomic)

( x i ) SEQUENCE DESCRIPTION: SEQ ID NO:21:

```
AAGCTTGGGC TGCAGGTCAC CCGGGCGGGC GCAGGAAGTG GTGCGGGCGC AGGAAGTGGT     60
GCGGGCGCAG GAAGTGGTGC GGGCGCAGGA AGTGGTGCGG GCGCAGGAAG TGGTGCGGGC    120
GCAGGAAGTG GTGCGGGCGC AGGAAGTGGT GCGGGCGCAG GAAGTGGTGC GGGCGCAGGA    180
AGTGGTGCGG GCGCAGGAAG TGGTGCGGGC GCAGGAAGTG GTGCGGGCGC AGGAAGTGGT    240
GCGGGCGCAG GAAGTGGGAC TCTAGAGGAT CCCCGGGCGA GCTCGAATTC                290
```

( 2 ) INFORMATION FOR SEQ ID NO:22:

( i ) SEQUENCE CHARACTERISTICS:
( A ) LENGTH: 98 amino acids
( B ) TYPE: amino acid
( C ) STRANDEDNESS: unknown
( D ) TOPOLOGY: unknown ( i i ) MOLECULE TYPE: protein ( i x ) FEATURE:
( A ) NAME/KEY: Modified-site
( B ) LOCATION: 88..89
( D ) OTHER INFORMATION: /note= "The 'Xaa' at position 89
represents an 'O'."

( x i ) SEQUENCE DESCRIPTION: SEQ ID NO:22:

Lys Leu Gly Leu Gln Val Thr Arg Ala Gly Ala Gly Ser Gly Ala Gly
1               5                   10                  15

Ala Gly Ser Gly Ala Gly Ala Gly Ser Gly Ala Gly Ala Gly Ser Gly
                20                  25                  30

Ala Gly Ala Gly Ser Gly Ala Gly Ala Gly Ser Gly Ala Gly Ala Gly
                35                  40                  45

Ser Gly Ala Gly Ala Gly Ser Gly Ala Gly Ala Gly Ser Gly Ala Gly
                50                  55                  60

Ala Gly Ser Gly Ala Gly Ala Gly Ser Gly Ala Gly Ala Gly Ser Gly
65                  70                  75                  80

Ala Gly Ala Gly Ser Gly Thr Leu Xaa Asp Pro Thr Arg Ala Ser Ser
                85                  90                  95

Asn Ser ( 2 ) INFORMATION FOR SEQ ID NO:23:

( i ) SEQUENCE CHARACTERISTICS:
( A ) LENGTH: 84 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:23:

```
    Arg  Ala  Gly  Ala  Gly  Ser  Gly  Ala  Gly  Ala  Gly  Ser  Gly  Ala  Gly  Ala
    1                   5                        10                       15

Gly  Ser  Gly  Ala  Gly  Ala  Gly  Ser  Gly  Ala  Gly  Ala  Gly  Ser  Gly  Ala
                        20                       25                       30

Gly  Ala  Gly  Ser  Gly  Ala  Gly  Ala  Gly  Ser  Gly  Ala  Gly  Ala  Gly  Ser
                   35                       40                       45

Gly  Ala  Gly  Ala  Gly  Ser  Gly  Ala  Gly  Ala  Gly  Ser  Gly  Ala  Gly  Ala
              50                        55                       60

Gly  Ser  Gly  Ala  Gly  Ala  Gly  Ser  Gly  Ala  Gly  Ala  Gly  Ser  Gly  Thr
    65                       70                       75                       80

Leu  Glu  Asp  Pro
```

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:24:

```
    Thr  Ala  Ala  Ala  Thr  Gly
    1                   5
```

( 2 ) INFORMATION FOR SEQ ID NO:25:

( i ) SEQUENCE CHARACTERISTICS:
        ( A ) LENGTH: 6 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:25:

```
    Cys  Ala  Thr  Ala  Thr  Gly
    1                   5
```

( 2 ) INFORMATION FOR SEQ ID NO:26:

( i ) SEQUENCE CHARACTERISTICS:
        ( A ) LENGTH: 61 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:26:

```
GGTGCCGGCA  GCGGTGCAGG  AGCCGGTTCT  GGAGCTGGCG  CGGGCTCTGG  CGCGGGCGCA      60
G                                                                          61
```

( 2 ) INFORMATION FOR SEQ ID NO:27:

( i ) SEQUENCE CHARACTERISTICS:
        ( A ) LENGTH: 65 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:27:

```
CCACGGCCGT  CGCCACGTCC  TCGGCCAAGA  CCTCGACCGC  GCCCGAGACC  GCGCCCGCGT      60
CCTAG                                                                      65
```

( 2 ) INFORMATION FOR SEQ ID NO:28:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:28:

```
Gly Ala Gly Ser Gly Ala Gly Ala Gly Ser Gly Ala Gly Ala Gly Ser
 1               5                  10                  15
Gly Ala Gly Ala Gly Ser
             20
```

( 2 ) INFORMATION FOR SEQ ID NO:29:

( i ) SEQUENCE CHARACTERISTICS:
        ( A ) LENGTH: 68 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:29:

```
GATCCGGCGC AGGCGCTGGT TCTGGCGCAG GGGCAGGCTC TGGCGCAGGA GCGGGGTCTG        60
GAGCTGCA                                                                 68
```

( 2 ) INFORMATION FOR SEQ ID NO:30:

( i ) SEQUENCE CHARACTERISTICS:
        ( A ) LENGTH: 60 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:30:

```
GCCGCGTCCG CGACCAAGAC CGCGTCCCCG TCCGAGACCG CGTCCTCGCC CCAGACCTCG        60
```

( 2 ) INFORMATION FOR SEQ ID NO:31:

( i ) SEQUENCE CHARACTERISTICS:
        ( A ) LENGTH: 23 amino acids
        ( B ) TYPE: amino acid
        ( C ) STRANDEDNESS: unknown
        ( D ) TOPOLOGY: unknown ( x i ) SEQUENCE DESCRIPTION: SEQ ID NO:31:

```
Gly Ser Gly Ala Gly Ala Gly Ser Gly Ala Gly Ala Gly Ser Gly Ala
 1               5                  10                  15
Gly Ala Gly Ser Gly Ala Ala
             20
```

( 2 ) INFORMATION FOR SEQ ID NO:32:

( i ) SEQUENCE CHARACTERISTICS:
        ( A ) LENGTH: 55 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:32:

GGCTATGGAG CTGGCGCTGG CTCAGGTGCT GGAGCAGGAA GCGGAGCGGG TGCCA    55

( 2 ) INFORMATION FOR SEQ ID NO:33:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:33:

ACGTCCGATA CCTCGACCGC GACCGAGTCC ACGACCTCGT CCTTCGCCTC GCCCACGGTT    60

CGA    63

( 2 ) INFORMATION FOR SEQ ID NO:34:

( i ) SEQUENCE CHARACTERISTICS:
        ( A ) LENGTH: 19 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:34:

Ala Gly Tyr Gly Ala Gly Ala Gly Ser Gly Ala Gly Ala Gly Ser Gly
1               5                   10                  15

Ala Gly Ala ( 2 ) INFORMATION FOR SEQ ID NO:35:

( i ) SEQUENCE CHARACTERISTICS:
        ( A ) LENGTH: 1177 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:35:

Asp Pro Val Val Leu Gln Arg Arg Asp Trp Glu Asn Pro Gly Val Thr
1               5                   10                  15

Gln Leu Asn Arg Leu Ala Ala His Pro Pro Phe Ala Ser Asp Pro Met
                20                  25                  30

Gly Ala Gly Ser Gly Ala Gly Ala Gly Ser Gly Ala Gly Ala Gly Ser
                35                  40                  45

Gly Ala Gly Ala Gly Ser Gly Ala Gly Ala Gly Ser Gly Ala Gly Ala
                50                  55                  60

Gly Ser Gly Ala Gly Ala Gly Ser Gly Ala Ala Gly Tyr Gly Ala Gly
65                  70                  75                  80

Ala Gly Ser Gly Ala Gly Ala Gly Ser Gly Ala Gly Ala Gly Ser Gly
                85                  90                  95

Ala Gly Ala Gly Ser Gly Ala Gly Ala Gly Ser Gly Ala Gly Ala Gly
                100                 105                 110

Ser Gly Ala Gly Ala Gly Ser Gly Ala Gly Ala Gly Ser Gly Ala Gly
                115                 120                 125

Ala Gly Ser Gly Ala Ala Gly Tyr Gly Ala Gly Ala Gly Ser Gly Ala
                130                 135                 140

Gly Ala Gly Ser Gly Ala Gly Ala Gly Ser Gly Ala Gly Ala Gly Ser

```
        145                 150                 155                 160
Gly Ala Gly Ala Gly Ser Gly Ala Gly Ala Gly Ser Gly Ala Gly Ala
                    165                 170                 175
Gly Ser Gly Ala Gly Ala Gly Ser Gly Ala Gly Ala Gly Ser Gly Ala
                    180                 185                 190
Ala Gly Tyr Gly Ala Gly Ala Gly Ser Gly Ala Gly Ala Gly Ser Gly
                195                 200                 205
Ala Gly Ala Gly Ser Gly Ala Gly Ala Gly Ser Gly Ala Gly Ala Gly
            210                 215                 220
Ser Gly Ala Gly Ala Gly Ser Gly Ala Gly Ala Gly Ser Gly Ala Gly
225                 230                 235                 240
Ala Gly Ser Gly Ala Gly Ala Gly Ser Gly Ala Ala Gly Tyr Gly Ala
                    245                 250                 255
Gly Ala Gly Ser Gly Ala Gly Ala Gly Ser Gly Ala Gly Ala Gly Ser
                260                 265                 270
Gly Ala Gly Ala Gly Ser Gly Ala Gly Ala Gly Ser Gly Ala Gly Ala
            275                 280                 285
Gly Ser Gly Ala Gly Ala Gly Ser Gly Ala Gly Ala Gly Ser Gly Ala
    290                 295                 300
Gly Ala Gly Ser Gly Ala Ala Gly Tyr Gly Ala Gly Ala Gly Ser Gly
305                 310                 315                 320
Ala Gly Ala Gly Ser Gly Ala Gly Ala Gly Ser Gly Ala Gly Ala Gly
                325                 330                 335
Ser Gly Ala Gly Ala Gly Ser Gly Ala Gly Ala Gly Ser Gly Ala Gly
            340                 345                 350
Ala Gly Ser Gly Ala Gly Ala Gly Ser Gly Ala Gly Ala Gly Ser Gly
        355                 360                 365
Ala Ala Gly Tyr Gly Ala Gly Ala Gly Ser Gly Ala Gly Ala Gly Ser
    370                 375                 380
Gly Ala Gly Ala Gly Ser Gly Ala Gly Ala Gly Ser Gly Ala Gly Ala
385                 390                 395                 400
Gly Ser Gly Ala Gly Ala Gly Ser Gly Ala Gly Ala Gly Ser Gly Ala
                405                 410                 415
Gly Ala Gly Ser Gly Ala Gly Ala Gly Ser Gly Ala Ala Gly Tyr Gly
            420                 425                 430
Ala Gly Ala Gly Ser Gly Ala Gly Ala Gly Ser Gly Ala Gly Ala Gly
        435                 440                 445
Ser Gly Ala Gly Ala Gly Ser Gly Ala Gly Ala Gly Ser Gly Ala Gly
    450                 455                 460
Ala Gly Ser Gly Ala Gly Ala Gly Ser Gly Ala Gly Ala Gly Ser Gly
465                 470                 475                 480
Ala Gly Ala Gly Ser Gly Ala Ala Gly Tyr Gly Ala Gly Ala Gly Ser
                485                 490                 495
Gly Ala Gly Ala Gly Ser Gly Ala Gly Ala Gly Ser Gly Ala Gly Ala
            500                 505                 510
Gly Ser Gly Ala Gly Ala Gly Ser Gly Ala Gly Ala Gly Ser Gly Ala
        515                 520                 525
Gly Ala Gly Ser Gly Ala Gly Ala Gly Ser Gly Ala Gly Ala Gly Ser
    530                 535                 540
Gly Ala Ala Gly Tyr Gly Ala Gly Ala Gly Ser Gly Ala Gly Ala Gly
545                 550                 555                 560
Ser Gly Ala Gly Ala Gly Ser Gly Ala Gly Ala Gly Ser Gly Ala Gly
                565                 570                 575
```

| | | | | | | | | | | | | | | |
|---|---|---|---|---|---|---|---|---|---|---|---|---|---|---|
| Ala | Gly | Ser | Gly | Ala | Gly | Ala | Gly | Ser | Gly | Ala | Gly | Ala | Gly | Ser | Gly |
| | | | 580 | | | | | 585 | | | | | 590 | | |
| Ala | Gly | Ala | Gly | Ser | Gly | Ala | Gly | Ala | Gly | Ser | Gly | Ala | Ala | Gly | Tyr |
| | | | 595 | | | | | 600 | | | | | 605 | | |
| Gly | Ala | Gly | Ala | Gly | Ser | Gly | Ala | Gly | Ala | Gly | Ser | Gly | Ala | Gly | Ala |
| | | | 610 | | | | | 615 | | | | | 620 | | |
| Gly | Ser | Gly | Ala | Gly | Ala | Gly | Ser | Gly | Ala | Gly | Ala | Gly | Ser | Gly | Ala |
| 625 | | | | | 630 | | | | | 635 | | | | | 640 |
| Gly | Ala | Gly | Ser | Gly | Ala | Gly | Ala | Gly | Ser | Gly | Ala | Gly | Ala | Gly | Ser |
| | | | | 645 | | | | | 650 | | | | | 655 | |
| Gly | Ala | Gly | Ala | Gly | Ser | Gly | Ala | Ala | Gly | Tyr | Gly | Ala | Gly | Ala | Gly |
| | | | 660 | | | | | 665 | | | | | 670 | | |
| Ser | Gly | Ala | Gly | Ala | Gly | Ser | Gly | Ala | Gly | Ala | Gly | Ser | Gly | Ala | Gly |
| | | 675 | | | | | 680 | | | | | 685 | | | |
| Ala | Gly | Ser | Gly | Ala | Gly | Ala | Gly | Ser | Gly | Ala | Gly | Ala | Gly | Ser | Gly |
| | 690 | | | | | 695 | | | | | 700 | | | | |
| Ala | Gly | Ala | Gly | Ser | Gly | Ala | Gly | Ala | Gly | Ser | Gly | Ala | Gly | Ala | Gly |
| 705 | | | | | 710 | | | | | 715 | | | | | 720 |
| Ser | Gly | Ala | Ala | Gly | Tyr | Gly | Ala | Gly | Ala | Gly | Ser | Gly | Ala | Gly | Ala |
| | | | | 725 | | | | | 730 | | | | | 735 | |
| Gly | Ser | Gly | Ala | Gly | Ala | Gly | Ser | Gly | Ala | Gly | Ala | Gly | Ser | Gly | Ala |
| | | | 740 | | | | | 745 | | | | | 750 | | |
| Gly | Ala | Gly | Ser | Gly | Ala | Gly | Ala | Gly | Ser | Gly | Ala | Gly | Ala | Gly | Ser |
| | | | 755 | | | | | 760 | | | | | 765 | | |
| Gly | Ala | Gly | Ala | Gly | Ser | Gly | Ala | Gly | Ala | Gly | Ser | Gly | Ala | Ala | Gly |
| | 770 | | | | | 775 | | | | | 780 | | | | |
| Tyr | Gly | Ala | Gly | Ala | Gly | Ser | Gly | Ala | Gly | Ala | Gly | Ser | Gly | Ala | Gly |
| 785 | | | | | 790 | | | | | 795 | | | | | 800 |
| Ala | Gly | Ser | Gly | Ala | Gly | Ala | Gly | Ser | Gly | Ala | Gly | Ala | Gly | Ser | Gly |
| | | | | 805 | | | | | 810 | | | | | 815 | |
| Ala | Gly | Ala | Gly | Ser | Gly | Ala | Gly | Ala | Gly | Ser | Gly | Ala | Gly | Ala | Gly |
| | | | 820 | | | | | 825 | | | | | 830 | | |
| Ser | Gly | Ala | Gly | Ala | Gly | Ser | Gly | Ala | Ala | Gly | Tyr | Gly | Ala | Gly | Ala |
| | | 835 | | | | | 840 | | | | | 845 | | | |
| Gly | Ser | Gly | Ala | Gly | Ala | Gly | Ser | Gly | Ala | Gly | Ala | Gly | Ser | Gly | Ala |
| | 850 | | | | | 855 | | | | | 860 | | | | |
| Gly | Ala | Gly | Ser | Gly | Ala | Gly | Ala | Gly | Ser | Gly | Ala | Gly | Ala | Gly | Ser |
| 865 | | | | | 870 | | | | | 875 | | | | | 880 |
| Gly | Ala | Gly | Ala | Gly | Ser | Gly | Ala | Gly | Ala | Gly | Ser | Gly | Ala | Gly | Ala |
| | | | | 885 | | | | | 890 | | | | | 895 | |
| Gly | Ser | Gly | Ala | Ala | Gly | Tyr | Gly | Ala | Gly | Ala | Gly | Ser | Gly | Ala | Gly |
| | | | 900 | | | | | 905 | | | | | 910 | | |
| Ala | Gly | Ser | Gly | Ala | Gly | Ala | Gly | Ser | Gly | Ala | Gly | Ala | Gly | Ser | Gly |
| | | | 915 | | | | | 920 | | | | | 925 | | |
| Ala | Gly | Ala | Gly | Ser | Gly | Ala | Gly | Ala | Gly | Ser | Gly | Ala | Gly | Ala | Gly |
| | | | 930 | | | | | 935 | | | | | 940 | | |
| Ser | Gly | Ala | Gly | Ala | Gly | Ser | Gly | Ala | Gly | Ala | Gly | Ser | Gly | Ala | Ala |
| 945 | | | | | 950 | | | | | 955 | | | | | 960 |
| Gly | Tyr | Gly | Ala | Gly | Ala | Gly | Ser | Gly | Ala | Gly | Ala | Gly | Ser | Gly | Ala |
| | | | | 965 | | | | | 970 | | | | | 975 | |
| Gly | Ala | Gly | Ser | Gly | Ala | Gly | Ala | Gly | Ser | Gly | Ala | Gly | Ala | Gly | Ser |
| | | | 980 | | | | | 985 | | | | | 990 | | |
| Gly | Ala | Gly | Ala | Gly | Ser | Gly | Ala | Gly | Ala | Gly | Ser | Gly | Ala | Gly | Ala |
| | | | 995 | | | | | 1000 | | | | | 1005 | | |

```
    Gly  Ser  Gly  Ala  Gly  Ala  Gly  Ser  Gly  Ala  Ala  Gly  Tyr  Gly  Ala  Gly
              1010                     1015                    1020

Ala  Gly  Ser  Gly  Ala  Gly  Ala  Gly  Ser  Gly  Ala  Gly  Ala  Gly  Ser  Gly
    1025                     1030                    1035                         1040

Ala  Gly  Ala  Gly  Ser  Gly  Ala  Gly  Ala  Gly  Ser  Gly  Ala  Gly  Ala  Gly
                        1045                    1050                    1055

Ser  Gly  Ala  Gly  Ala  Gly  Ser  Gly  Ala  Gly  Ala  Gly  Ser  Gly  Ala  Gly
              1060                     1065                    1070

Ala  Gly  Ser  Gly  Ala  Ala  Gly  Tyr  Gly  Ala  Gly  Ala  Gly  Ser  Gly  Ala
              1075                     1080                    1085

Gly  Ala  Gly  Ser  Gly  Ala  Gly  Ala  Gly  Ser  Gly  Ala  Gly  Ala  Gly  Ser
              1090                     1095                    1100

Gly  Ala  Gly  Ala  Gly  Ser  Gly  Ala  Gly  Ala  Gly  Ser  Gly  Ala  Gly  Ala
    1105                     1110                    1115                         1120

Gly  Ser  Gly  Ala  Gly  Ala  Gly  Ser  Gly  Ala  Gly  Ala  Gly  Ser  Gly  Ala
                        1125                    1130                    1135

Ala  Gly  Tyr  Gly  Ala  Gly  Ala  Gly  Ser  Gly  Ala  Gly  Ala  Gly  Ser  Gly
              1140                     1145                    1150

Ala  Gly  Ala  Met  Asp  Pro  Gly  Arg  Tyr  Gln  Leu  Ser  Ala  Gly  Arg  Tyr
              1155                     1160                    1165

His  Tyr  Gln  Leu  Val  Trp  Cys  Gln  Lys
              1170                     1175
```

( 2 ) INFORMATION FOR SEQ ID NO:36:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:36:

```
AGCTGGGCTC  TGGAGTAGGC  CTG                                                    23
```

( 2 ) INFORMATION FOR SEQ ID NO:37:

( i ) SEQUENCE CHARACTERISTICS:
        ( A ) LENGTH: 23 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:37:

```
AATTCAGGCC  TACTCCAGAG  CCC                                                    23
```

( 2 ) INFORMATION FOR SEQ ID NO:38:

( i ) SEQUENCE CHARACTERISTICS:
        ( A ) LENGTH: 85 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:38:

```
AGCTTGGTGC  CAGGTGTAGG  AGTTCCGGGT  GTAGGCGTTC  CGGGAGTTGG  TGTACCTGGA          60

GTGGGTGTTC  CAGGCGTAGG  TGTGC                                                  85
```

( 2 ) INFORMATION FOR SEQ ID NO:39:

( i ) SEQUENCE CHARACTERISTICS:
        ( A ) LENGTH: 85 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:39:

```
CCGGGCACAC  CTACGCCTGG  AACACCCACT  CCAGGTACAC  CAACTCCCGG  AACGCCTACA        60

CCCGGAACTC  CTACACCTGG  CACCA                                                 85
```

( 2 ) INFORMATION FOR SEQ ID NO:40:

( i ) SEQUENCE CHARACTERISTICS:
        ( A ) LENGTH: 83 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:40:

```
CCGGGGTAGG  AGTACCAGGG  GTAGGCGTCC  CTGGAGCGGG  TGCTGGTAGC  GGCGCAGGCG        60

CGGGCTCCGG  AGTAGGGGTG  CCG                                                   83
```

( 2 ) INFORMATION FOR SEQ ID NO:41:

( i ) SEQUENCE CHARACTERISTICS:
        ( A ) LENGTH: 83 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:41:

```
AATTCGGCAC  CCCTACTCCG  GAGCCCGCGC  CTGCGCCGCT  ACCAGCACCC  GCTCCAGGGA        60

CGCCTACCCC  TGGTACTCCT  ACC                                                   83
```

( 2 ) INFORMATION FOR SEQ ID NO:42:

( i ) SEQUENCE CHARACTERISTICS:
        ( A ) LENGTH: 187 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:42:

```
AGCTGGGCTC  TGGAGTAGGT  GTGCCAGGTG  TAGGAGTTCC  GGGTGTAGGC  GTTCCGGGAG        60

TTGGTGTACC  TGGAGTGGGT  GTTCCAGGCG  TAGGTGTGCC  CGGGGTAGGA  GTACCAGGGG       120

TAGGCGTCCC  TGGAGCGGGT  GCTGGTAGCG  GCGCAGGCGC  GGGCTCCGGA  GTAGGGGTGC       180

CGAATTC                                                                      187
```

( 2 ) INFORMATION FOR SEQ ID NO:43:

( i ) SEQUENCE CHARACTERISTICS:
        ( A ) LENGTH: 75 base pairs
        ( B ) TYPE: nucleic acid
        ( C ) STRANDEDNESS: unknown ( D ) TOPOLOGY: unknown ( i i ) MOLECULE TYPE: DNA (genomic)

( x i ) SEQUENCE DESCRIPTION: SEQ ID NO:43:

GATCCTATGT TTAAATATTC TCGCGAACGT TTTTCTATGG GCTCGATGTG TTACCGTGCG    60

CATGGATATC AGCTG    75

( 2 ) INFORMATION FOR SEQ ID NO:44:

( i ) SEQUENCE CHARACTERISTICS:
        ( A ) LENGTH: 74 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:44:

GATCCAGCTG ATACCATGCG CAGGGTAACA CATCGAGCCC ATACAAAAAC GTTCGCGAGA    60

ATATTTAAAC ATAG    74

( 2 ) INFORMATION FOR SEQ ID NO:45:

( i ) SEQUENCE CHARACTERISTICS:
        ( A ) LENGTH: 1413 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:45:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Glu Arg
            20                  25                  30

Phe Cys Met Gly Ser Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Ala Gly
65                  70                  75                  80

Ala Gly Ser Gly Ala Gly Ala Gly Ser Gly Val Gly Val Pro Gly Val
                85                  90                  95

Gly Val Pro Gly Val Gly Val Pro Gly Val Gly Val Pro Gly Val Gly
                100                 105                 110

Val Pro Gly Val Gly Val Pro Gly Val Gly Val Pro Gly Val Gly Val
                115                 120                 125

Pro Gly Ala Gly Ala Gly Ser Gly Ala Gly Ala Gly Ser Gly Val Gly
            130                 135                 140

Val Pro Gly Val Gly Val Pro Gly Val Gly Val Pro Gly Val Gly Val
145                 150                 155                 160

Pro Gly Val Gly Val Pro Gly Val Gly Val Pro Gly Val Gly Val Pro
                165                 170                 175

Gly Val Gly Val Pro Gly Ala Gly Ala Gly Ser Gly Ala Gly Ala Gly
                180                 185                 190

Ser Gly Val Gly Val Pro Gly Val Gly Val Pro Gly Val Gly Val Pro
            195                 200                 205

Gly Val Gly Val Pro Gly Val Gly Val Pro Gly Val Gly Val Pro Gly
```

|     | 210 |     |     |     | 215 |     |     |     | 220 |     |     |     |
| --- | --- | --- | --- | --- | --- | --- | --- | --- | --- | --- | --- | --- |

Val Gly Val Pro Gly Val Gly Val Pro Gly Ala Gly Ala Gly Ser Gly
225                     230                     235                     240

Ala Gly Ala Gly Ser Gly Val Gly Val Pro Gly Val Gly Val Pro Gly
                    245                     250                     255

Val Gly Val Pro Gly Val Gly Val Pro Gly Val Gly Val Pro Gly Val
                    260                     265                     270

Gly Val Pro Gly Val Gly Val Pro Gly Val Gly Val Pro Gly Ala Gly
                275                     280                     285

Ala Gly Ser Gly Ala Gly Ala Gly Ser Gly Val Gly Val Pro Gly Val
        290                     295                     300

Gly Val Pro Gly Val Gly Val Pro Gly Val Gly Val Pro Gly Val Gly
305                     310                     315                     320

Val Pro Gly Val Gly Val Pro Gly Val Gly Val Pro Gly Val Gly Val
                    325                     330                     335

Pro Gly Ala Gly Ala Gly Ser Gly Ala Gly Ala Gly Ser Gly Val Gly
                340                     345                     350

Val Pro Gly Val Gly Val Pro Gly Val Gly Val Pro Gly Val Gly Val
            355                     360                     365

Pro Gly Val Gly Val Pro Gly Val Gly Val Pro Gly Val Gly Val Pro
        370                     375                     380

Gly Val Gly Val Pro Gly Ala Gly Ala Gly Ser Gly Ala Gly Ala Gly
385                     390                     395                     400

Ser Gly Val Gly Val Pro Gly Val Gly Val Pro Gly Val Gly Val Pro
                    405                     410                     415

Gly Val Gly Val Pro Gly Val Gly Val Pro Gly Val Gly Val Pro Gly
                420                     425                     430

Val Gly Val Pro Gly Val Gly Val Pro Gly Ala Gly Ala Gly Ser Gly
        435                     440                     445

Ala Gly Ala Gly Ser Gly Val Gly Val Pro Gly Val Gly Val Pro Gly
    450                     455                     460

Val Gly Val Pro Gly Val Gly Val Pro Gly Val Gly Val Pro Gly Val
465                     470                     475                     480

Gly Val Pro Gly Val Gly Val Pro Gly Val Gly Val Pro Gly Ala Gly
                485                     490                     495

Ala Gly Ser Gly Ala Gly Ala Gly Ser Gly Val Gly Val Pro Gly Val
            500                     505                     510

Gly Val Pro Gly Val Gly Val Pro Gly Val Gly Val Pro Gly Val Gly
        515                     520                     525

Val Pro Gly Val Gly Val Pro Gly Val Gly Val Pro Gly Val Gly Val
    530                     535                     540

Pro Gly Ala Gly Ala Gly Ser Gly Ala Gly Ala Gly Ser Gly Val Gly
545                     550                     555                     560

Val Pro Gly Val Gly Val Pro Gly Val Gly Val Pro Gly Val Gly Val
                565                     570                     575

Pro Gly Val Gly Val Pro Gly Val Gly Val Pro Gly Val Gly Val Pro
            580                     585                     590

Gly Val Gly Val Pro Gly Ala Gly Ala Gly Ser Gly Ala Gly Ala Gly
        595                     600                     605

Ser Gly Val Gly Val Pro Gly Val Gly Val Pro Gly Val Gly Val Pro
    610                     615                     620

Gly Val Gly Val Pro Gly Val Gly Val Pro Gly Val Gly Val Pro Gly
625                     630                     635                     640

```
Val Gly Val Pro Gly Val Gly Val Pro Gly Ala Gly Ala Gly Ser Gly
                645                 650                     655
Ala Gly Ala Gly Ser Gly Val Gly Val Pro Gly Val Gly Val Pro Gly
            660                 665                 670
Val Gly Val Pro Gly Val Gly Val Pro Gly Val Gly Val Pro Gly Val
        675                 680                 685
Gly Val Pro Gly Val Gly Val Pro Gly Val Gly Val Pro Gly Ala Gly
    690                 695                 700
Ala Gly Ser Gly Ala Gly Ala Gly Ser Gly Val Gly Val Pro Gly Val
705             710             715                     720
Gly Val Pro Gly Val Gly Val Pro Gly Val Gly Val Pro Gly Val Gly
                725                 730                     735
Val Pro Gly Val Gly Val Pro Gly Val Gly Val Pro Gly Val Gly Val
            740                 745                 750
Pro Gly Ala Gly Ala Gly Ser Gly Ala Gly Ala Gly Ser Gly Val Gly
        755                 760                 765
Val Pro Gly Val Gly Val Pro Gly Val Gly Val Pro Gly Val Gly Val
    770                 775                 780
Pro Gly Val Gly Val Pro Gly Val Gly Val Pro Gly Val Gly Val Pro
785             790                 795                     800
Gly Val Gly Val Pro Gly Ala Gly Ala Gly Ser Gly Ala Gly Ala Gly
                805                 810                     815
Ser Gly Val Gly Val Pro Gly Val Gly Val Pro Gly Val Gly Val Pro
            820                 825                 830
Gly Val Gly Val Pro Gly Val Gly Val Pro Gly Val Gly Val Pro Gly
        835                 840                 845
Val Gly Val Pro Gly Val Gly Val Pro Gly Ala Gly Ala Gly Ser Gly
    850                 855                 860
Ala Gly Ala Gly Ser Gly Val Gly Val Pro Gly Val Gly Val Pro Gly
865             870                 875                     880
Val Gly Val Pro Gly Val Gly Val Pro Gly Val Gly Val Pro Gly Val
                885                 890                     895
Gly Val Pro Gly Val Gly Val Pro Gly Val Gly Val Pro Gly Ala Gly
            900                 905                 910
Ala Gly Ser Gly Ala Gly Ala Gly Ser Gly Val Gly Val Pro Gly Val
        915                 920                 925
Gly Val Pro Gly Val Gly Val Pro Gly Val Gly Val Pro Gly Val Gly
    930                 935                 940
Val Pro Gly Val Gly Val Pro Gly Val Gly Val Pro Gly Val Gly Val
945             950                 955                     960
Pro Gly Ala Gly Ala Gly Ser Gly Ala Gly Ala Gly Ser Gly Val Gly
                965                 970                     975
Val Pro Gly Val Gly Val Pro Gly Val Gly Val Pro Gly Val Gly Val
            980                 985                 990
Pro Gly Val Gly Val Pro Gly Val Gly Val Pro Gly Val Gly Val Pro
        995                 1000                1005
Gly Val Gly Val Pro Gly Ala Gly Ala Gly Ser Gly Ala Gly Ala Gly
    1010                1015                1020
Ser Gly Val Gly Val Pro Gly Val Gly Val Pro Gly Val Gly Val Pro
1025            1030                1035                    1040
Gly Val Gly Val Pro Gly Val Gly Val Pro Gly Val Gly Val Pro Gly
                1045                1050                    1055
Val Gly Val Pro Gly Val Gly Val Pro Gly Ala Gly Ala Gly Ser Gly
            1060                1065                1070
```

Ala Gly Ala Gly Ser Gly Val Gly Val Pro Gly Val Gly Val Pro Gly
         1075                1080               1085

Val Gly Val Pro Gly Val Gly Val Pro Gly Val Gly Val Pro Gly Val
         1090                1095               1100

Gly Val Pro Gly Val Gly Val Pro Gly Val Gly Val Pro Gly Ala Gly
1105                1110               1115                    1120

Ala Gly Ser Gly Ala Gly Ala Gly Ser Gly Val Gly Val Pro Gly Val
            1125               1130                    1135

Gly Val Pro Gly Val Gly Val Pro Gly Val Gly Val Pro Gly Val Gly
            1140               1145                    1150

Val Pro Gly Val Gly Val Pro Gly Val Gly Val Pro Gly Val Gly Val
            1155               1160                    1165

Pro Gly Ala Gly Ala Gly Ser Gly Ala Gly Ala Gly Ser Gly Val Gly
        1170                1175                1180

Val Pro Gly Val Gly Val Pro Gly Val Gly Val Pro Gly Val Gly Val
1185                1190               1195                    1200

Pro Gly Val Gly Val Pro Gly Val Gly Val Pro Gly Val Gly Val Pro
            1205               1210                    1215

Gly Val Gly Val Pro Gly Ala Gly Ala Gly Ser Gly Ala Gly Ala Gly
            1220               1225                    1230

Ser Gly Val Gly Val Pro Gly Val Gly Val Pro Gly Val Gly Val Pro
            1235               1240                    1245

Gly Val Gly Val Pro Gly Val Gly Val Pro Gly Val Gly Val Pro Gly
            1250               1255                    1260

Val Gly Val Pro Gly Val Gly Val Pro Gly Ala Gly Ala Gly Ser Gly
1265                1270               1275                    1280

Ala Gly Ala Gly Ser Gly Val Gly Val Pro Gly Val Gly Val Pro Gly
            1285               1290                    1295

Val Gly Val Pro Gly Val Gly Val Pro Gly Val Gly Val Pro Gly Val
            1300               1305                    1310

Gly Val Pro Gly Val Gly Val Pro Gly Val Gly Val Pro Gly Ala Gly
            1315               1320                    1325

Ala Gly Ser Gly Ala Gly Ala Gly Ser Gly Val Gly Val Pro Gly Val
    1330                1335               1340

Gly Val Pro Gly Val Gly Val Pro Gly Val Gly Val Pro Gly Val Gly
1345                1350               1355                    1360

Val Pro Gly Val Gly Val Pro Gly Val Gly Val Pro Gly Val Gly Val
            1365               1370                    1375

Pro Gly Ala Gly Ala Gly Ser Gly Ala Gly Ala Gly Ser Met Cys Tyr
            1380               1385                    1390

Arg Ala His Gly Tyr Gln Leu Ser Ala Gly Arg Tyr His Tyr Gln Leu
            1395               1400                    1405

Val Trp Cys Gln Lys
            1410

( 2 ) INFORMATION FOR SEQ ID NO:46:

( i ) SEQUENCE CHARACTERISTICS:
        ( A ) LENGTH: 72 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:46:

```
AATTCGGTGC  CCGGTGTAGG  AGTTCCGGGT  GTAGGCGTTC  CCGGGGTAGG  CGTTCCGGGA      60

GTAGGGGTGC  CA                                                              72
```

(2) INFORMATION FOR SEQ ID NO:47:

(i) SEQUENCE CHARACTERISTICS:
        (A) LENGTH: 72 base pairs
        (B) TYPE: nucleic acid
        (C) STRANDEDNESS: unknown
        (D) TOPOLOGY: unknown (ii) MOLECULE TYPE: DNA (genomic)

(xi) SEQUENCE DESCRIPTION: SEQ ID NO:47:

```
GCCACGGGCC  ACATCCTCAA  GGCCCACATC  CGCCAGGGCC  CCATCCGCAA  GGCCCTCATC      60

CCCACGGTTC  GA                                                              72
```

(2) INFORMATION FOR SEQ ID NO:48:

(i) SEQUENCE CHARACTERISTICS:
        (A) LENGTH: 859 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:48:

```
Met  Asp  Pro  Val  Val  Leu  Gln  Arg  Arg  Asp  Trp  Glu  Asn  Pro  Gly  Val
 1                   5                        10                       15

Thr  Gln  Leu  Asn  Arg  Leu  Ala  Ala  His  Pro  Pro  Phe  Ala  Arg  Asn  Ile
               20                        25                       30

Leu  Ala  Ile  Arg  Trp  Val  Pro  Gly  Val  Gly  Val  Pro  Gly  Val  Gly  Val
                35                       40                       45

Pro  Gly  Val  Gly  Val  Pro  Gly  Val  Gly  Val  Pro  Gly  Val  Gly  Val  Pro
          50                        55                       60

Gly  Val  Gly  Val  Pro  Gly  Val  Gly  Val  Pro  Gly  Val  Gly  Val  Pro  Gly
 65                            70                       75                   80

Val  Gly  Val  Pro  Gly  Val  Gly  Val  Pro  Gly  Val  Gly  Val  Pro  Gly  Val
                     85                       90                       95

Gly  Val  Pro  Gly  Val  Gly  Val  Pro  Gly  Val  Gly  Val  Pro  Gly  Val  Gly
               100                      105                      110

Val  Pro  Gly  Val  Gly  Val  Pro  Gly  Val  Gly  Val  Pro  Gly  Val  Gly  Val
               115                      120                      125

Pro  Gly  Val  Gly  Val  Pro  Gly  Val  Gly  Val  Pro  Gly  Val  Gly  Val  Pro
          130                      135                      140

Gly  Val  Gly  Val  Pro  Gly  Val  Gly  Val  Pro  Gly  Val  Gly  Val  Pro  Gly
145                           150                      155                 160

Val  Gly  Val  Pro  Gly  Val  Gly  Val  Pro  Gly  Val  Gly  Val  Pro  Gly  Val
                     165                      170                      175

Gly  Val  Pro  Gly  Val  Gly  Val  Pro  Gly  Val  Gly  Val  Pro  Gly  Val  Gly
               180                      185                      190

Val  Pro  Gly  Val  Gly  Val  Pro  Gly  Val  Gly  Val  Pro  Gly  Val  Gly  Val
               195                      200                      205

Pro  Gly  Val  Gly  Val  Pro  Gly  Val  Gly  Val  Pro  Gly  Val  Gly  Val  Pro
          210                      215                      220

Gly  Val  Gly  Val  Pro  Gly  Val  Gly  Val  Pro  Gly  Val  Gly  Val  Pro  Gly
225                           230                      235                 240

Val  Gly  Val  Pro  Gly  Val  Gly  Val  Pro  Gly  Val  Gly  Val  Pro  Gly  Val
```

-continued

|   |   |   | 245 |   |   |   | 250 |   |   |   | 255 |   |   |
|---|---|---|---|---|---|---|---|---|---|---|---|---|---|
| Gly | Val | Pro | Gly 260 | Val | Gly | Val | Pro 265 | Gly | Val | Gly | Pro 270 | Val | Gly |
| Val | Pro | Gly 275 | Val | Gly | Val | Pro 280 | Gly | Val | Gly | Pro 285 | Val | Gly | Val |
| Pro | Gly | Val 290 | Gly | Val | Pro | Gly 295 | Val | Gly | Val | Pro 300 | Gly | Val | Pro |
| Gly 305 | Val | Gly | Val | Pro | Gly 310 | Val | Gly | Val | Pro 315 | Gly | Val | Pro | Gly 320 |
| Val | Gly | Val | Pro | Gly 325 | Val | Gly | Val | Pro 330 | Gly | Val | Gly | Pro 335 | Val |
| Gly | Val | Pro | Gly 340 | Val | Gly | Val | Pro 345 | Gly | Val | Gly | Pro 350 | Val | Gly |
| Val | Pro | Gly 355 | Val | Gly | Val | Pro 360 | Gly | Val | Gly | Pro 365 | Val | Gly | Val |
| Pro | Gly | Val 370 | Gly | Val | Pro | Gly 375 | Val | Gly | Val | Pro 380 | Gly | Val | Pro |
| Gly 385 | Val | Gly | Val | Pro | Gly 390 | Val | Gly | Val | Pro 395 | Gly | Val | Pro | Gly 400 |
| Val | Gly | Val | Pro | Gly 405 | Val | Gly | Val | Pro 410 | Gly | Val | Gly | Pro 415 | Val |
| Gly | Val | Pro | Gly 420 | Val | Gly | Val | Pro 425 | Gly | Val | Gly | Pro 430 | Val | Gly |
| Val | Pro | Gly 435 | Val | Gly | Val | Pro 440 | Gly | Val | Gly | Pro 445 | Val | Gly | Val |
| Pro | Gly | Val 450 | Gly | Val | Pro | Gly 455 | Val | Gly | Val | Pro 460 | Gly | Val | Pro |
| Gly 465 | Val | Gly | Val | Pro | Gly 470 | Val | Gly | Val | Pro 475 | Gly | Val | Pro | Gly 480 |
| Val | Gly | Val | Pro | Gly 485 | Val | Gly | Val | Pro 490 | Gly | Val | Gly | Pro 495 | Val |
| Gly | Val | Pro | Gly 500 | Val | Gly | Val | Pro 505 | Gly | Val | Gly | Pro 510 | Val | Gly |
| Val | Pro | Gly 515 | Val | Gly | Val | Pro 520 | Gly | Val | Gly | Pro 525 | Val | Gly | Val |
| Pro | Gly | Val 530 | Gly | Val | Pro | Gly 535 | Val | Gly | Val | Pro 540 | Gly | Val | Pro |
| Gly 545 | Val | Gly | Val | Pro | Gly 550 | Val | Gly | Val | Pro 555 | Gly | Val | Pro | Gly 560 |
| Val | Gly | Val | Pro | Gly 565 | Val | Gly | Val | Pro 570 | Gly | Val | Gly | Pro 575 | Val |
| Gly | Val | Pro | Gly 580 | Val | Gly | Val | Pro 585 | Gly | Val | Gly | Pro 590 | Val | Gly |
| Val | Pro | Gly 595 | Val | Gly | Val | Pro 600 | Gly | Val | Gly | Pro 605 | Val | Gly | Val |
| Pro | Gly | Val 610 | Gly | Val | Pro | Gly 615 | Val | Gly | Val | Pro 620 | Gly | Val | Pro |
| Gly 625 | Val | Gly | Val | Pro | Gly 630 | Val | Gly | Val | Pro 635 | Gly | Val | Pro | Gly 640 |
| Val | Gly | Val | Pro | Gly 645 | Val | Gly | Val | Pro 650 | Gly | Val | Gly | Pro 655 | Val |
| Gly | Val | Pro | Gly 660 | Val | Gly | Val | Pro 665 | Gly | Val | Gly | Pro 670 | Val | Gly |

|   |   |   |   |   |   |   |   |   |   |   |   |   |   |   |
|---|---|---|---|---|---|---|---|---|---|---|---|---|---|---|
| Val | Pro | Gly 675 | Val | Gly | Val | Pro | Gly 680 | Val | Gly | Val | Pro | Gly 685 | Val | Gly | Val |
| Pro | Gly 690 | Val | Gly | Val | Pro | Gly 695 | Val | Gly | Val | Pro | Gly 700 | Val | Gly | Val | Pro |
| Gly 705 | Val | Gly | Val | Pro | Gly 710 | Val | Gly | Val | Pro | Gly 715 | Val | Gly | Val | Pro | Gly 720 |
| Val | Gly | Val | Pro | Gly 725 | Val | Gly | Val | Pro | Gly 730 | Val | Gly | Val | Pro | Gly 735 | Val |
| Gly | Val | Pro | Gly 740 | Val | Gly | Val | Pro | Gly 745 | Val | Gly | Val | Pro | Gly 750 | Val | Gly |
| Val | Pro | Gly 755 | Val | Gly | Val | Pro | Gly 760 | Val | Gly | Val | Pro | Gly 765 | Val | Gly | Val |
| Pro | Gly 770 | Val | Gly | Val | Pro | Gly 775 | Val | Gly | Val | Pro | Gly 780 | Val | Gly | Val | Pro |
| Gly 785 | Val | Gly | Val | Pro | Gly 790 | Val | Gly | Val | Pro | Gly 795 | Val | Gly | Val | Pro | Gly 800 |
| Val | Gly | Val | Pro | Gly 805 | Val | Gly | Val | Pro | Gly 810 | Val | Gly | Val | Pro | Gly 815 | Val |
| Gly | Val | Pro | Gly 820 | Val | Gly | Val | Pro | Gly 825 | Val | Gly | Val | Pro | Gly 830 | Val | Gly |
| Val | Pro | Gly 835 | Val | Gly | Val | Pro | Trp 840 | Thr | Arg | Val | Asp | Leu 845 | Ser | Ala | Gly |
| Arg | Tyr 850 | His | Tyr | Gln | Leu | Val 855 | Trp | Cys | Gln | Lys |   |   |   |   |   |

( 2 ) INFORMATION FOR SEQ ID NO:49:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:49:

GTGCGCAGCT GGTACGTAGC TGCA    24

( 2 ) INFORMATION FOR SEQ ID NO:50:

( i ) SEQUENCE CHARACTERISTICS:
        ( A ) LENGTH: 24 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:50:

GCTACGTACC AGCTGCGCAC TGCA    24

( 2 ) INFORMATION FOR SEQ ID NO:51:

( i ) SEQUENCE CHARACTERISTICS:
        ( A ) LENGTH: 2107 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:51:

|   |   |   |   |   |   |   |   |   |   |   |   |   |   |   |
|---|---|---|---|---|---|---|---|---|---|---|---|---|---|---|
| Met | Asp | Pro | Val | Val | Leu | Gln | Arg | Arg | Asp | Trp | Glu | Asn | Pro | Gly | Val |

-continued

```
          1                   5                       10                      15

Thr  Gln  Leu  Asn  Arg  Leu  Ala  Ala  His  Pro  Pro  Phe  Ala  Ser  Asp  Pro
                            20                  25                      30

Met  Gly  Ala  Gly  Ser  Gly  Ala  Gly  Ala  Gly  Ser  Gly  Ala  Gly  Ala  Gly
                       35                  40                  45

Ser  Gly  Ala  Gly  Ala  Gly  Ser  Gly  Ala  Gly  Ala  Gly  Ser  Gly  Ala  Gly
                  50                  55                  60

Ala  Gly  Ser  Gly  Ala  Gly  Ala  Gly  Ser  Gly  Ala  Ala  Val  Pro  Gly  Val
        65                       70                  75                           80

Gly  Val  Pro  Gly  Val  Gly  Val  Pro  Gly  Val  Gly  Val  Pro  Gly  Val  Gly
                            85                  90                      95

Val  Ala  Ala  Gly  Tyr  Gly  Ala  Gly  Ala  Gly  Ser  Gly  Ala  Gly  Ala  Gly
                       100                 105                 110

Ser  Gly  Ala  Gly  Ala  Gly  Ser  Gly  Ala  Gly  Ala  Gly  Ser  Gly  Ala  Gly
                       115                 120                 125

Ala  Gly  Ser  Gly  Ala  Gly  Ala  Gly  Ser  Gly  Ala  Gly  Ala  Gly  Ser  Gly
                  130                 135                 140

Ala  Gly  Ala  Gly  Ser  Gly  Ala  Gly  Ala  Gly  Ser  Gly  Ala  Ala  Val  Pro
        145                      150                 155                           160

Gly  Val  Gly  Val  Pro  Gly  Val  Gly  Val  Pro  Gly  Val  Gly  Val  Pro  Gly
                            165                 170                     175

Val  Gly  Val  Ala  Ala  Gly  Tyr  Gly  Ala  Gly  Ala  Gly  Ser  Gly  Ala  Gly
                       180                 185                     190

Ala  Gly  Ser  Gly  Ala  Gly  Ala  Gly  Ser  Gly  Ala  Gly  Ala  Gly  Ser  Gly
                  195                 200                 205

Ala  Gly  Ala  Gly  Ser  Gly  Ala  Gly  Ala  Gly  Ser  Gly  Ala  Gly  Ala  Gly
                  210                 215                 220

Ser  Gly  Ala  Gly  Ala  Gly  Ser  Gly  Ala  Gly  Ala  Gly  Ser  Gly  Ala  Ala
        225                      230                 235                           240

Val  Pro  Gly  Val  Gly  Val  Pro  Gly  Val  Gly  Val  Pro  Gly  Val  Gly  Val
                            245                 250                     255

Pro  Gly  Val  Gly  Val  Ala  Ala  Gly  Tyr  Gly  Ala  Gly  Ala  Gly  Ser  Gly
                       260                 265                     270

Ala  Gly  Ala  Gly  Ser  Gly  Ala  Gly  Ala  Gly  Ser  Gly  Ala  Gly  Ala  Gly
                       275                 280                     285

Ser  Gly  Ala  Gly  Ala  Gly  Ser  Gly  Ala  Gly  Ala  Gly  Ser  Gly  Ala  Gly
                  290                 295                 300

Ala  Gly  Ser  Gly  Ala  Gly  Ala  Gly  Ser  Gly  Ala  Gly  Ala  Gly  Ser  Gly
        305                 310                 315                           320

Ala  Ala  Val  Pro  Gly  Val  Gly  Val  Pro  Gly  Val  Gly  Val  Pro  Gly  Val
                            325                 330                     335

Gly  Val  Pro  Gly  Val  Gly  Val  Ala  Ala  Gly  Tyr  Gly  Ala  Gly  Ala  Gly
                       340                 345                     350

Ser  Gly  Ala  Gly  Ala  Gly  Ser  Gly  Ala  Gly  Ala  Gly  Ser  Gly  Ala  Gly
                       355                 360                     365

Ala  Gly  Ser  Gly  Ala  Gly  Ala  Gly  Ser  Gly  Ala  Gly  Ala  Gly  Ser  Gly
                  370                 375                 380

Ala  Gly  Ala  Gly  Ser  Gly  Ala  Gly  Ala  Gly  Ser  Gly  Ala  Gly  Ala  Gly
        385                      390                 395                           400

Ser  Gly  Ala  Ala  Val  Pro  Gly  Val  Gly  Val  Pro  Gly  Val  Gly  Val  Pro
                            405                 410                     415

Gly  Val  Gly  Val  Pro  Gly  Val  Gly  Val  Ala  Ala  Gly  Tyr  Gly  Ala  Gly
                       420                 425                     430
```

-continued

```
Ala  Gly  Ser  Gly  Ala  Gly  Ala  Gly  Ser  Gly  Ala  Gly  Ala  Gly  Ser  Gly
               435                 440                 445
Ala  Gly  Ala  Gly  Ser  Gly  Ala  Gly  Ala  Gly  Ser  Gly  Ala  Gly  Ala  Gly
          450                 455                 460
Ser  Gly  Ala  Gly  Ala  Gly  Ser  Gly  Ala  Gly  Ala  Gly  Ser  Gly  Ala  Gly
465                 470                 475                                 480
Ala  Gly  Ser  Gly  Ala  Ala  Val  Pro  Gly  Val  Gly  Val  Pro  Gly  Val  Gly
               485                 490                 495
Val  Pro  Gly  Val  Gly  Val  Pro  Gly  Val  Gly  Val  Ala  Ala  Gly  Tyr  Gly
               500                 505                 510
Ala  Gly  Ala  Gly  Ser  Gly  Ala  Gly  Ala  Gly  Ser  Gly  Ala  Gly  Ala  Gly
               515                 520                 525
Ser  Gly  Ala  Gly  Ala  Gly  Ser  Gly  Ala  Gly  Ala  Gly  Ser  Gly  Ala  Gly
     530                 535                 540
Ala  Gly  Ser  Gly  Ala  Gly  Ala  Gly  Ser  Gly  Ala  Gly  Ala  Gly  Ser  Gly
545                 550                 555                                 560
Ala  Gly  Ala  Gly  Ser  Gly  Ala  Ala  Val  Pro  Gly  Val  Gly  Val  Pro  Gly
               565                 570                 575
Val  Gly  Val  Pro  Gly  Val  Gly  Val  Pro  Gly  Val  Gly  Val  Ala  Ala  Gly
               580                 585                 590
Tyr  Gly  Ala  Gly  Ala  Gly  Ser  Gly  Ala  Gly  Ala  Gly  Ser  Gly  Ala  Gly
          595                 600                 605
Ala  Gly  Ser  Gly  Ala  Gly  Ala  Gly  Ser  Gly  Ala  Gly  Ala  Gly  Ser  Gly
          610                 615                 620
Ala  Gly  Ala  Gly  Ser  Gly  Ala  Gly  Ala  Gly  Ser  Gly  Ala  Gly  Ala  Gly
625                 630                 635                                 640
Ser  Gly  Ala  Gly  Ala  Gly  Ser  Gly  Ala  Ala  Val  Pro  Gly  Val  Gly  Val
               645                 650                 655
Pro  Gly  Val  Gly  Val  Pro  Gly  Val  Gly  Val  Pro  Gly  Val  Gly  Val  Ala
               660                 665                 670
Ala  Gly  Tyr  Gly  Ala  Gly  Ala  Gly  Ser  Gly  Ala  Gly  Ala  Gly  Ser  Gly
               675                 680                 685
Ala  Gly  Ala  Gly  Ser  Gly  Ala  Gly  Ala  Gly  Ser  Gly  Ala  Gly  Ala  Gly
          690                 695                 700
Ser  Gly  Ala  Gly  Ala  Gly  Ser  Gly  Ala  Gly  Ala  Gly  Ser  Gly  Ala  Gly
705                 710                 715                                 720
Ala  Gly  Ser  Gly  Ala  Gly  Ala  Gly  Ser  Gly  Ala  Ala  Val  Pro  Gly  Val
               725                 730                 735
Gly  Val  Pro  Gly  Val  Gly  Val  Pro  Gly  Val  Gly  Val  Pro  Gly  Val  Gly
               740                 745                 750
Val  Ala  Ala  Gly  Tyr  Gly  Ala  Gly  Ala  Gly  Ser  Gly  Ala  Gly  Ala  Gly
     755                 760                 765
Ser  Gly  Ala  Gly  Ala  Gly  Ser  Gly  Ala  Gly  Ala  Gly  Ser  Gly  Ala  Gly
     770                 775                 780
Ala  Gly  Ser  Gly  Ala  Gly  Ala  Gly  Ser  Gly  Ala  Gly  Ala  Gly  Ser  Gly
785                 790                 795                                 800
Ala  Gly  Ala  Gly  Ser  Gly  Ala  Gly  Ala  Gly  Ser  Gly  Ala  Ala  Val  Pro
               805                 810                 815
Gly  Val  Gly  Val  Pro  Gly  Val  Gly  Val  Pro  Gly  Val  Gly  Val  Pro  Gly
               820                 825                 830
Val  Gly  Val  Ala  Ala  Gly  Tyr  Gly  Ala  Gly  Ala  Gly  Ser  Gly  Ala  Gly
          835                 840                 845
Ala  Gly  Ser  Gly  Ala  Gly  Ala  Gly  Ser  Gly  Ala  Gly  Ala  Gly  Ser  Gly
     850                 855                 860
```

-continued

```
Ala  Gly  Ala  Gly  Ser  Gly  Ala  Gly  Ala  Gly  Ser  Gly  Ala  Gly  Ala  Gly
865                 870                 875                 880

Ser  Gly  Ala  Gly  Ala  Gly  Ser  Gly  Ala  Gly  Ala  Gly  Ser  Gly  Ala  Ala
                    885                 890                 895

Val  Pro  Gly  Val  Gly  Val  Pro  Gly  Val  Gly  Val  Pro  Gly  Val  Gly  Val
               900                 905                 910

Pro  Gly  Val  Gly  Val  Ala  Ala  Gly  Tyr  Gly  Ala  Gly  Ala  Gly  Ser  Gly
          915                 920                 925

Ala  Gly  Ala  Gly  Ser  Gly  Ala  Gly  Ala  Gly  Ser  Gly  Ala  Gly  Ala  Gly
          930                 935                 940

Ser  Gly  Ala  Gly  Ala  Gly  Ser  Gly  Ala  Gly  Ala  Gly  Ser  Gly  Ala  Gly
945                 950                 955                 960

Ala  Gly  Ser  Gly  Ala  Gly  Ala  Gly  Ser  Gly  Ala  Gly  Ala  Gly  Ser  Gly
                    965                 970                 975

Ala  Ala  Val  Pro  Gly  Val  Gly  Val  Pro  Gly  Val  Gly  Val  Pro  Gly  Val
               980                 985                 990

Gly  Val  Pro  Gly  Val  Gly  Val  Ala  Ala  Gly  Tyr  Gly  Ala  Gly  Ala  Gly
          995                 1000                1005

Ser  Gly  Ala  Gly  Ala  Gly  Ser  Gly  Ala  Gly  Ala  Gly  Ser  Gly  Ala  Gly
1010                1015                1020

Ala  Gly  Ser  Gly  Ala  Gly  Ala  Gly  Ser  Gly  Ala  Gly  Ala  Gly  Ser  Gly
1025                1030                1035                1040

Ala  Gly  Ala  Gly  Ser  Gly  Ala  Gly  Ala  Gly  Ser  Gly  Ala  Gly  Ala  Gly
               1045                1050                1055

Ser  Gly  Ala  Ala  Val  Pro  Gly  Val  Gly  Val  Pro  Gly  Val  Gly  Val  Pro
               1060                1065                1070

Gly  Val  Gly  Val  Pro  Gly  Val  Gly  Val  Ala  Ala  Gly  Tyr  Gly  Ala  Gly
          1075                1080                1085

Ala  Gly  Ser  Gly  Ala  Gly  Ala  Gly  Ser  Gly  Ala  Gly  Ala  Gly  Ser  Gly
          1090                1095                1100

Ala  Gly  Ala  Gly  Ser  Gly  Ala  Gly  Ala  Gly  Ser  Gly  Ala  Gly  Ala  Gly
1105                1110                1115                1120

Ser  Gly  Ala  Gly  Ala  Gly  Ser  Gly  Ala  Gly  Ala  Gly  Ser  Gly  Ala  Gly
               1125                1130                1135

Ala  Gly  Ser  Gly  Ala  Ala  Val  Pro  Gly  Val  Gly  Val  Pro  Gly  Val  Gly
               1140                1145                1150

Val  Pro  Gly  Val  Gly  Val  Pro  Gly  Val  Gly  Val  Ala  Ala  Gly  Tyr  Gly
          1155                1160                1165

Ala  Gly  Ala  Gly  Ser  Gly  Ala  Gly  Ala  Gly  Ser  Gly  Ala  Gly  Ala  Gly
          1170                1175                1180

Ser  Gly  Ala  Gly  Ala  Gly  Ser  Gly  Ala  Gly  Ala  Gly  Ser  Gly  Ala  Gly
1185                1190                1195                1200

Ala  Gly  Ser  Gly  Ala  Gly  Ala  Gly  Ser  Gly  Ala  Gly  Ala  Gly  Ser  Gly
                    1205                1210                1215

Ala  Gly  Ala  Gly  Ser  Gly  Ala  Ala  Val  Pro  Gly  Val  Gly  Val  Pro  Gly
               1220                1225                1230

Val  Gly  Val  Pro  Gly  Val  Gly  Val  Pro  Gly  Val  Gly  Val  Ala  Ala  Gly
          1235                1240                1245

Tyr  Gly  Ala  Gly  Ala  Gly  Ser  Gly  Ala  Gly  Ala  Gly  Ser  Gly  Ala  Gly
          1250                1255                1260

Ala  Gly  Ser  Gly  Ala  Gly  Ala  Gly  Ser  Gly  Ala  Gly  Ala  Gly  Ser  Gly
1265                1270                1275                1280

Ala  Gly  Ala  Gly  Ser  Gly  Ala  Gly  Ala  Gly  Ser  Gly  Ala  Gly  Ala  Gly
```

```
                              1285                      1290                    1295
         Ser  Gly  Ala  Gly  Ala  Gly  Ser  Gly  Ala  Ala  Val  Pro  Gly  Val  Gly  Val
                        1300                    1305                    1310
         Pro  Gly  Val  Gly  Val  Pro  Gly  Val  Gly  Val  Pro  Gly  Val  Gly  Val  Ala
                        1315                    1320                    1325
         Ala  Gly  Tyr  Gly  Ala  Gly  Ala  Gly  Ser  Gly  Ala  Gly  Ala  Gly  Ser  Gly
                        1330                    1335                    1340
         Ala  Gly  Ala  Gly  Ser  Gly  Ala  Gly  Ala  Gly  Ser  Gly  Ala  Gly  Ala  Gly
         1345                    1350                    1355                    1360
         Ser  Gly  Ala  Gly  Ala  Gly  Ser  Gly  Ala  Gly  Ala  Gly  Ser  Gly  Ala  Gly
                             1365                    1370                    1375
         Ala  Gly  Ser  Gly  Ala  Gly  Ala  Gly  Ser  Gly  Ala  Ala  Val  Pro  Gly  Val
                        1380                    1385                    1390
         Gly  Val  Pro  Gly  Val  Gly  Val  Pro  Gly  Val  Gly  Val  Pro  Gly  Val  Gly
                        1395                    1400                    1405
         Val  Ala  Ala  Gly  Tyr  Gly  Ala  Gly  Ala  Gly  Ser  Gly  Ala  Gly  Ala  Gly
                        1410                    1415                    1420
         Ser  Gly  Ala  Gly  Ala  Gly  Ser  Gly  Ala  Gly  Ala  Gly  Ser  Gly  Ala  Gly
         1425                    1430                    1435                    1440
         Ala  Gly  Ser  Gly  Ala  Gly  Ala  Gly  Ser  Gly  Ala  Gly  Ala  Gly  Ser  Gly
                             1445                    1450                    1455
         Ala  Gly  Ala  Gly  Ser  Gly  Ala  Gly  Ala  Gly  Ser  Gly  Ala  Ala  Val  Pro
                        1460                    1465                    1470
         Gly  Val  Gly  Val  Pro  Gly  Val  Gly  Val  Pro  Gly  Val  Gly  Val  Pro  Gly
                        1475                    1480                    1485
         Val  Gly  Val  Ala  Ala  Gly  Tyr  Gly  Ala  Gly  Ala  Gly  Ser  Gly  Ala  Gly
                        1490                    1495                    1500
         Ala  Gly  Ser  Gly  Ala  Gly  Ala  Gly  Ser  Gly  Ala  Gly  Ala  Gly  Ser  Gly
         1505                    1510                    1515                    1520
         Ala  Gly  Ala  Gly  Ser  Gly  Ala  Gly  Ala  Gly  Ser  Gly  Ala  Gly  Ala  Gly
                             1525                    1530                    1535
         Ser  Gly  Ala  Gly  Ala  Gly  Ser  Gly  Ala  Gly  Ala  Gly  Ser  Gly  Ala  Ala
                        1540                    1545                    1550
         Val  Pro  Gly  Val  Gly  Val  Pro  Gly  Val  Gly  Val  Pro  Gly  Val  Gly  Val
                        1555                    1560                    1565
         Pro  Gly  Val  Gly  Val  Ala  Ala  Gly  Tyr  Gly  Ala  Gly  Ala  Gly  Ser  Gly
                        1570                    1575                    1580
         Ala  Gly  Ala  Gly  Ser  Gly  Ala  Gly  Ala  Gly  Ser  Gly  Ala  Gly  Ala  Gly
         1585                    1590                    1595                    1600
         Ser  Gly  Ala  Gly  Ala  Gly  Ser  Gly  Ala  Gly  Ala  Gly  Ser  Gly  Ala  Gly
                             1605                    1610                    1615
         Ala  Gly  Ser  Gly  Ala  Gly  Ala  Gly  Ser  Gly  Ala  Gly  Ala  Gly  Ser  Gly
                        1620                    1625                    1630
         Ala  Ala  Val  Pro  Gly  Val  Gly  Val  Pro  Gly  Val  Gly  Val  Pro  Gly  Val
                        1635                    1640                    1645
         Gly  Val  Pro  Gly  Val  Gly  Val  Ala  Ala  Gly  Tyr  Gly  Ala  Gly  Ala  Gly
                        1650                    1655                    1660
         Ser  Gly  Ala  Gly  Ala  Gly  Ser  Gly  Ala  Gly  Ala  Gly  Ser  Gly  Ala  Gly
         1665                    1670                    1675                    1680
         Ala  Gly  Ser  Gly  Ala  Gly  Ala  Gly  Ser  Gly  Ala  Gly  Ala  Gly  Ser  Gly
                             1685                    1690                    1695
         Ala  Gly  Ala  Gly  Ser  Gly  Ala  Gly  Ala  Gly  Ser  Gly  Ala  Gly  Ala  Gly
                        1700                    1705                    1710
```

| | | | | | | | | | | | | | | |
|---|---|---|---|---|---|---|---|---|---|---|---|---|---|---|
|Ser|Gly|Ala|Ala|Val|Pro|Gly|Val|Gly|Val|Pro|Gly|Val|Gly|Val|Pro|
| | |1715| | | |1720| | | |1725| | | | | |
|Gly|Val|Gly|Val|Pro|Gly|Val|Gly|Val|Ala|Ala|Gly|Tyr|Gly|Ala|Gly|
| | |1730| | | |1735| | | |1740| | | | | |
|Ala|Gly|Ser|Gly|Ala|Gly|Ala|Gly|Ser|Gly|Ala|Gly|Ala|Gly|Ser|Gly|
|1745| | | |1750| | | |1755| | | | | | |1760|
|Ala|Gly|Ala|Gly|Ser|Gly|Ala|Gly|Ala|Gly|Ser|Gly|Ala|Gly|Ala|Gly|
| | | | |1765| | | |1770| | | | | | |1775|
|Ser|Gly|Ala|Gly|Ala|Gly|Ser|Gly|Ala|Gly|Ala|Gly|Ser|Gly|Ala|Gly|
| | | | |1780| | | |1785| | | | | | |1790|
|Ala|Gly|Ser|Gly|Ala|Ala|Val|Pro|Gly|Val|Gly|Val|Pro|Gly|Val|Gly|
| | | | |1795| | | |1800| | | | |1805| | |
|Val|Pro|Gly|Val|Gly|Val|Pro|Gly|Val|Gly|Val|Ala|Ala|Gly|Tyr|Gly|
| | |1810| | | |1815| | | |1820| | | | | |
|Ala|Gly|Ala|Gly|Ser|Gly|Ala|Gly|Ala|Gly|Ser|Gly|Ala|Gly|Ala|Gly|
|1825| | | |1830| | | |1835| | | | | | |1840|
|Ser|Gly|Ala|Gly|Ala|Gly|Ser|Gly|Ala|Gly|Ala|Gly|Ser|Gly|Ala|Gly|
| | | | |1845| | | |1850| | | | | | |1855|
|Ala|Gly|Ser|Gly|Ala|Gly|Ala|Gly|Ser|Gly|Ala|Gly|Ala|Gly|Ser|Gly|
| | | | |1860| | | |1865| | | | | | |1870|
|Ala|Gly|Ala|Gly|Ser|Gly|Ala|Ala|Val|Pro|Gly|Val|Gly|Val|Pro|Gly|
| | | | |1875| | | |1880| | | | |1885| | |
|Val|Gly|Val|Pro|Gly|Val|Gly|Val|Pro|Gly|Val|Gly|Val|Ala|Ala|Gly|
| | |1890| | | |1895| | | |1900| | | | | |
|Tyr|Gly|Ala|Gly|Ala|Gly|Ser|Gly|Ala|Gly|Ala|Gly|Ser|Gly|Ala|Gly|
|1905| | | |1910| | | |1915| | | | | | |1920|
|Ala|Gly|Ser|Gly|Ala|Gly|Ala|Gly|Ser|Gly|Ala|Gly|Ala|Gly|Ser|Gly|
| | | | |1925| | | |1930| | | | | | |1935|
|Ala|Gly|Ala|Gly|Ser|Gly|Ala|Gly|Ala|Gly|Ser|Gly|Ala|Gly|Ala|Gly|
| | | | |1940| | | |1945| | | | | | |1950|
|Ser|Gly|Ala|Gly|Ala|Gly|Ser|Gly|Ala|Ala|Val|Pro|Gly|Val|Gly|Val|
| | | | |1955| | | |1960| | | | |1965| | |
|Pro|Gly|Val|Gly|Val|Pro|Gly|Val|Gly|Val|Pro|Gly|Val|Gly|Val|Ala|
| | |1970| | | |1975| | | |1980| | | | | |
|Ala|Gly|Tyr|Gly|Ala|Gly|Ala|Gly|Ser|Gly|Ala|Gly|Ala|Gly|Ser|Gly|
|1985| | | |1990| | | |1995| | | | | | |2000|
|Ala|Gly|Ala|Gly|Ser|Gly|Ala|Gly|Ala|Gly|Ser|Gly|Ala|Gly|Ala|Gly|
| | | | |2005| | | |2010| | | | | | |2015|
|Ser|Gly|Ala|Gly|Ala|Gly|Ser|Gly|Ala|Gly|Ala|Gly|Ser|Gly|Ala|Gly|
| | | | |2020| | | |2025| | | | | | |2030|
|Ala|Gly|Ser|Gly|Ala|Gly|Ala|Gly|Ser|Gly|Ala|Ala|Val|Pro|Gly|Val|
| | | | |2035| | | |2040| | | | |2045| | |
|Gly|Val|Pro|Gly|Val|Gly|Val|Pro|Gly|Val|Gly|Val|Pro|Gly|Val|Gly|
| | |2050| | | |2055| | | |2060| | | | | |
|Val|Ala|Ala|Gly|Tyr|Gly|Ala|Gly|Ala|Gly|Ser|Gly|Ala|Gly|Ala|Gly|
|2065| | | |2070| | | |2075| | | | | | |2080|
|Ser|Gly|Ala|Gly|Ala|Met|Asp|Pro|Gly|Arg|Tyr|Gln|Leu|Ser|Ala|Gly|
| | | | |2085| | | |2090| | | | | | |2095|
|Arg|Thr|His|Tyr|Gln|Leu|Val|Trp|Cys|Gln|Lys| | | | | |
| | | | |2100| | | |2105| | | | | | | |

( 2 ) INFORMATION FOR SEQ ID NO:52:

( i ) SEQUENCE CHARACTERISTICS:
        ( A ) LENGTH: 2055 amino acids (B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:52:

| Met | Asp | Pro | Val | Val | Leu | Gln | Arg | Arg | Asp | Trp | Glu | Asn | Pro | Gly | Val |
|---|---|---|---|---|---|---|---|---|---|---|---|---|---|---|---|
| 1 | | | | 5 | | | | | 10 | | | | | 15 | |
| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |
| Met | Gly | Ala | Gly | Ser | Gly | Ala | Gly | Ala | Gly | Ser | Gly | Ala | Gly | Ala | Gly |
| | | | 35 | | | | | 40 | | | | | 45 | | |
| Ser | Gly | Val | Gly | Val | Pro | Gly | Val | Gly | Val | Pro | Gly | Val | Gly | Val | Pro |
| | | 50 | | | | | 55 | | | | | 60 | | | |
| Gly | Val | Gly | Val | Pro | Gly | Val | Gly | Val | Pro | Gly | Val | Gly | Val | Pro | Gly |
| 65 | | | | | 70 | | | | | 75 | | | | | 80 |
| Val | Gly | Val | Pro | Gly | Val | Gly | Val | Pro | Gly | Ala | Gly | Ala | Gly | Ser | Gly |
| | | | | 85 | | | | | 90 | | | | | 95 | |
| Ala | Gly | Ala | Gly | Ser | Gly | Ala | Gly | Ala | Gly | Ser | Gly | Ala | Gly | Ala | Gly |
| | | | | 100 | | | | | 105 | | | | | 110 | |
| Ser | Gly | Ala | Gly | Ala | Gly | Ser | Gly | Ala | Gly | Ala | Gly | Ser | Gly | Ala | Ala |
| | | | 115 | | | | | 120 | | | | | 125 | | |
| Gly | Tyr | Gly | Ala | Gly | Ala | Gly | Ser | Gly | Ala | Gly | Ala | Gly | Ser | Gly | Ala |
| | | 130 | | | | | 135 | | | | | 140 | | | |
| Gly | Ala | Gly | Ser | Gly | Ala | Gly | Ala | Gly | Ser | Gly | Ala | Gly | Ala | Gly | Ser |
| 145 | | | | | 150 | | | | | 155 | | | | | 160 |
| Gly | Val | Gly | Val | Pro | Gly | Val | Gly | Val | Pro | Gly | Val | Gly | Val | Pro | Gly |
| | | | | 165 | | | | | 170 | | | | | 175 | |
| Val | Gly | Val | Pro | Gly | Val | Gly | Val | Pro | Gly | Val | Gly | Val | Pro | Gly | Val |
| | | | 180 | | | | | 185 | | | | | 190 | | |
| Gly | Val | Pro | Gly | Val | Gly | Val | Pro | Gly | Ala | Gly | Ala | Gly | Ser | Gly | Ala |
| | | 195 | | | | | 200 | | | | | 205 | | | |
| Gly | Ala | Gly | Ser | Gly | Ala | Gly | Ala | Gly | Ser | Gly | Ala | Gly | Ala | Gly | Ser |
| 210 | | | | | 215 | | | | | 220 | | | | | |
| Gly | Ala | Gly | Ala | Gly | Ser | Gly | Ala | Gly | Ala | Gly | Ser | Gly | Ala | Ala | Gly |
| 225 | | | | | 230 | | | | | 235 | | | | | 240 |
| Tyr | Gly | Ala | Gly | Ala | Gly | Ser | Gly | Ala | Gly | Ala | Gly | Ser | Gly | Ala | Gly |
| | | | 245 | | | | | 250 | | | | | 255 | | |
| Ala | Gly | Ser | Gly | Ala | Gly | Ala | Gly | Ser | Gly | Ala | Gly | Ala | Gly | Ser | Gly |
| | | | 260 | | | | | 265 | | | | | 270 | | |
| Val | Gly | Val | Pro | Gly | Val | Gly | Val | Pro | Gly | Val | Gly | Val | Pro | Gly | Val |
| | | 275 | | | | | 280 | | | | | 285 | | | |
| Gly | Val | Pro | Gly | Val | Gly | Val | Pro | Gly | Val | Gly | Val | Pro | Gly | Val | Gly |
| | | 290 | | | | | 295 | | | | | 300 | | | |
| Val | Pro | Gly | Val | Gly | Val | Pro | Gly | Ala | Gly | Ala | Gly | Ser | Gly | Ala | Gly |
| 305 | | | | | 310 | | | | | 315 | | | | | 320 |
| Ala | Gly | Ser | Gly | Ala | Gly | Ala | Gly | Ser | Gly | Ala | Gly | Ala | Gly | Ser | Gly |
| | | | 325 | | | | | 330 | | | | | 335 | | |
| Ala | Gly | Ala | Gly | Ser | Gly | Ala | Gly | Ala | Gly | Ser | Gly | Ala | Ala | Gly | Tyr |
| | | | 340 | | | | | 345 | | | | | 350 | | |
| Gly | Ala | Gly | Ala | Gly | Ser | Gly | Ala | Gly | Ala | Gly | Ser | Gly | Ala | Gly | Ala |
| | | 355 | | | | | 360 | | | | | 365 | | | |
| Gly | Ser | Gly | Ala | Gly | Ala | Gly | Ser | Gly | Ala | Gly | Ala | Gly | Ser | Gly | Val |
| | | 370 | | | | | 375 | | | | | 380 | | | |

-continued

```
Gly  Val  Pro  Gly  Val  Val  Pro  Gly  Val  Gly  Val  Pro  Gly  Val  Gly
385                      390                 395                      400

Val  Pro  Gly  Val  Gly  Val  Pro  Gly  Val  Gly  Val  Pro  Gly  Val  Gly  Val
                    405                      410                      415

Pro  Gly  Val  Gly  Val  Pro  Gly  Ala  Ala  Gly  Ser  Gly  Ala  Gly  Ala
               420                 425                      430

Gly  Ser  Gly  Ala  Gly  Ala  Gly  Ser  Gly  Ala  Gly  Ala  Gly  Ser  Gly  Ala
          435                 440                      445

Gly  Ala  Gly  Ser  Gly  Ala  Gly  Ala  Gly  Ser  Gly  Ala  Ala  Gly  Tyr  Gly
450                      455                      460

Ala  Gly  Ala  Gly  Ser  Gly  Ala  Gly  Ala  Gly  Ser  Gly  Ala  Gly  Ala  Gly
465                      470                      475                      480

Ser  Gly  Ala  Gly  Ala  Gly  Ser  Gly  Ala  Gly  Ala  Gly  Ser  Gly  Val  Gly
                    485                      490                      495

Val  Pro  Gly  Val  Gly  Val  Pro  Gly  Val  Gly  Val  Pro  Gly  Val  Gly  Val
                    500                      505                      510

Pro  Gly  Val  Gly  Val  Pro  Gly  Val  Gly  Val  Pro  Gly  Val  Gly  Val  Pro
          515                      520                      525

Gly  Val  Gly  Val  Pro  Gly  Ala  Ala  Gly  Ser  Gly  Ala  Gly  Ala  Gly
530                      535                      540

Ser  Gly  Ala  Gly  Ala  Gly  Ser  Gly  Ala  Gly  Ala  Gly  Ser  Gly  Ala  Gly
545                      550                      555                      560

Ala  Gly  Ser  Gly  Ala  Gly  Ala  Gly  Ser  Gly  Ala  Ala  Gly  Tyr  Gly  Ala
               565                      570                      575

Gly  Ala  Gly  Ser  Gly  Ala  Gly  Ala  Gly  Ser  Gly  Ala  Gly  Ala  Gly  Ser
               580                      585                      590

Gly  Ala  Gly  Ala  Gly  Ser  Gly  Ala  Gly  Ala  Gly  Ser  Gly  Val  Gly  Val
               595                      600                      605

Pro  Gly  Val  Gly  Val  Pro  Gly  Val  Gly  Val  Pro  Gly  Val  Gly  Val  Pro
610                      615                      620

Gly  Val  Gly  Val  Pro  Gly  Val  Gly  Val  Pro  Gly  Val  Gly  Val  Pro  Gly
625                      630                      635                      640

Val  Gly  Val  Pro  Gly  Ala  Ala  Gly  Ser  Gly  Ala  Gly  Ala  Gly  Ser
                    645                      650                      655

Gly  Ala  Gly  Ala  Gly  Ser  Gly  Ala  Gly  Ala  Gly  Ser  Gly  Ala  Gly  Ala
               660                      665                      670

Gly  Ser  Gly  Ala  Gly  Ala  Gly  Ser  Gly  Ala  Ala  Gly  Tyr  Gly  Ala  Gly
          675                      680                      685

Ala  Gly  Ser  Gly  Ala  Gly  Ala  Gly  Ser  Gly  Ala  Gly  Ala  Gly  Ser  Gly
          690                      695                      700

Ala  Gly  Ala  Gly  Ser  Gly  Ala  Gly  Ala  Gly  Ser  Gly  Val  Gly  Val  Pro
705                      710                      715                      720

Gly  Val  Gly  Val  Pro  Gly  Val  Gly  Val  Pro  Gly  Val  Gly  Val  Pro  Gly
                    725                      730                      735

Val  Gly  Val  Pro  Gly  Val  Gly  Val  Pro  Gly  Val  Gly  Val  Pro  Gly  Val
                    740                      745                      750

Gly  Val  Pro  Gly  Val  Gly  Ala  Gly  Ser  Gly  Ala  Gly  Ala  Gly  Ser  Gly
               755                      760                      765

Ala  Gly  Ala  Gly  Ser  Gly  Ala  Gly  Ala  Gly  Ser  Gly  Ala  Gly  Ala  Gly
          770                      775                      780

Ser  Gly  Ala  Gly  Ala  Gly  Ser  Gly  Ala  Ala  Gly  Tyr  Gly  Ala  Gly  Ala
785                      790                      795                      800

Gly  Ser  Gly  Ala  Gly  Ala  Gly  Ser  Gly  Ala  Gly  Ala  Gly  Ser  Gly  Ala
                    805                      810                      815
```

| | | | | | | | | | | | | | | |
|---|---|---|---|---|---|---|---|---|---|---|---|---|---|---|
| Gly | Ala | Gly | Ser | Gly | Ala | Gly | Ala | Gly | Ser | Gly | Val | Gly | Val | Pro | Gly |
| | | | 820 | | | | 825 | | | | | 830 | | | |
| Val | Gly | Val | Pro | Gly | Val | Gly | Val | Pro | Gly | Val | Gly | Val | Pro | Gly | Val |
| | | 835 | | | | | 840 | | | | | 845 | | | |
| Gly | Val | Pro | Gly | Val | Gly | Val | Pro | Gly | Val | Gly | Val | Pro | Gly | Val | Gly |
| | 850 | | | | | 855 | | | | | | 860 | | | |
| Val | Pro | Gly | Ala | Gly | Ala | Gly | Ser | Gly | Ala | Gly | Ala | Gly | Ser | Gly | Ala |
| 865 | | | | | 870 | | | | | 875 | | | | | 880 |
| Gly | Ala | Gly | Ser | Gly | Ala | Gly | Ala | Gly | Ser | Gly | Ala | Gly | Ala | Gly | Ser |
| | | | | 885 | | | | | 890 | | | | | 895 | |
| Gly | Ala | Gly | Ala | Gly | Ser | Gly | Ala | Ala | Gly | Tyr | Gly | Ala | Gly | Ala | Gly |
| | | | | 900 | | | | 905 | | | | | | 910 | |
| Ser | Gly | Ala | Gly | Ala | Gly | Ser | Gly | Ala | Gly | Ala | Gly | Ser | Gly | Ala | Gly |
| | | | 915 | | | | | 920 | | | | | 925 | | |
| Ala | Gly | Ser | Gly | Ala | Gly | Ala | Gly | Ser | Gly | Val | Gly | Val | Pro | Gly | Val |
| | | 930 | | | | | 935 | | | | | 940 | | | |
| Gly | Val | Pro | Gly | Val | Gly | Val | Pro | Gly | Val | Gly | Val | Pro | Gly | Val | Gly |
| 945 | | | | | 950 | | | | | 955 | | | | | 960 |
| Val | Pro | Gly | Val | Gly | Val | Pro | Gly | Val | Gly | Val | Pro | Gly | Val | Gly | Val |
| | | | | 965 | | | | | 970 | | | | | 975 | |
| Pro | Gly | Ala | Gly | Ala | Gly | Ser | Gly | Ala | Gly | Ala | Gly | Ser | Gly | Ala | Gly |
| | | | 980 | | | | | 985 | | | | | | 990 | |
| Ala | Gly | Ser | Gly | Ala | Gly | Ala | Gly | Ser | Gly | Ala | Gly | Ala | Gly | Ser | Gly |
| | | | 995 | | | | | 1000 | | | | | 1005 | | |
| Ala | Gly | Ala | Gly | Ser | Gly | Ala | Ala | Gly | Tyr | Gly | Ala | Gly | Ala | Gly | Ser |
| | | 1010 | | | | | 1015 | | | | | 1020 | | | |
| Gly | Ala | Gly | Ala | Gly | Ser | Gly | Ala | Gly | Ala | Gly | Ser | Gly | Ala | Gly | Ala |
| 1025 | | | | | 1030 | | | | | 1035 | | | | | 1040 |
| Gly | Ser | Gly | Ala | Gly | Ala | Gly | Ser | Gly | Val | Gly | Val | Pro | Gly | Val | Gly |
| | | | | 1045 | | | | | 1050 | | | | | 1055 | |
| Val | Pro | Gly | Val | Gly | Val | Pro | Gly | Val | Gly | Val | Pro | Gly | Val | Gly | Val |
| | | | | 1060 | | | | | 1065 | | | | | 1070 | |
| Pro | Gly | Val | Gly | Val | Pro | Gly | Val | Gly | Val | Pro | Gly | Val | Gly | Val | Pro |
| | | | 1075 | | | | | 1080 | | | | | 1085 | | |
| Gly | Ala | Gly | Ala | Gly | Ser | Gly | Ala | Gly | Ala | Gly | Ser | Gly | Ala | Gly | Ala |
| | | | 1090 | | | | | 1095 | | | | | 1100 | | |
| Gly | Ser | Gly | Ala | Gly | Ala | Gly | Ser | Gly | Ala | Gly | Ala | Gly | Ser | Gly | Ala |
| 1105 | | | | | 1110 | | | | | 1115 | | | | | 1120 |
| Gly | Ala | Gly | Ser | Gly | Ala | Ala | Gly | Tyr | Gly | Ala | Gly | Ala | Gly | Ser | Gly |
| | | | | 1125 | | | | 1130 | | | | | | 1135 | |
| Ala | Gly | Ala | Gly | Ser | Gly | Ala | Gly | Ala | Gly | Ser | Gly | Ala | Gly | Ala | Gly |
| | | | | 1140 | | | | | 1145 | | | | | 1150 | |
| Ser | Gly | Ala | Gly | Ala | Gly | Ser | Gly | Val | Gly | Val | Pro | Gly | Val | Gly | Val |
| | | | 1155 | | | | | 1160 | | | | | 1165 | | |
| Pro | Gly | Val | Gly | Val | Pro | Gly | Val | Gly | Val | Pro | Gly | Val | Gly | Val | Pro |
| | | | 1170 | | | | | 1175 | | | | | 1180 | | |
| Gly | Val | Gly | Val | Pro | Gly | Val | Gly | Val | Pro | Gly | Val | Gly | Val | Pro | Gly |
| 1185 | | | | | 1190 | | | | | 1195 | | | | | 1200 |
| Ala | Gly | Ala | Gly | Ser | Gly | Ala | Gly | Ala | Gly | Ser | Gly | Ala | Gly | Ala | Gly |
| | | | | 1205 | | | | | 1210 | | | | | 1215 | |
| Ser | Gly | Ala | Gly | Ala | Gly | Ser | Gly | Ala | Gly | Ala | Gly | Ser | Gly | Ala | Gly |
| | | | | 1220 | | | | | 1225 | | | | | 1230 | |
| Ala | Gly | Ser | Gly | Ala | Ala | Gly | Tyr | Gly | Ala | Gly | Ala | Gly | Ser | Gly | Ala |

-continued

```
              1235                    1240                        1245
    Gly  Ala  Gly  Ser  Gly  Ala  Gly  Ala  Gly  Ser  Gly  Ala  Gly  Ser
         1250                    1255                    1260
    Gly  Ala  Gly  Ala  Gly  Ser  Gly  Val  Gly  Val  Pro  Gly  Val  Pro
1265                    1270                    1275                    1280
    Gly  Val  Gly  Val  Pro  Gly  Val  Gly  Val  Pro  Gly  Val  Gly  Val  Pro  Gly
                   1285                    1290                    1295
    Val  Gly  Val  Pro  Gly  Val  Gly  Val  Pro  Gly  Val  Gly  Val  Pro  Gly  Ala
                   1300                    1305                    1310
    Gly  Ala  Gly  Ser  Gly  Ala  Gly  Ala  Gly  Ser  Gly  Ala  Gly  Ala  Gly  Ser
                   1315                    1320                    1325
    Gly  Ala  Gly  Ala  Gly  Ser  Gly  Ala  Gly  Ala  Gly  Ser  Gly  Ala  Gly  Ala
                   1330                    1335                    1340
    Gly  Ser  Gly  Ala  Ala  Gly  Tyr  Gly  Ala  Gly  Ala  Gly  Ser  Gly  Ala  Gly
1345                    1350                    1355                    1360
    Ala  Gly  Ser  Gly  Ala  Gly  Ala  Gly  Ser  Gly  Ala  Gly  Ala  Gly  Ser  Gly
                   1365                    1370                    1375
    Ala  Gly  Ala  Gly  Ser  Gly  Val  Gly  Val  Pro  Gly  Val  Gly  Val  Pro  Gly
                   1380                    1385                    1390
    Val  Gly  Val  Pro  Gly  Val  Gly  Val  Pro  Gly  Val  Gly  Val  Pro  Gly  Val
                   1395                    1400                    1405
    Gly  Val  Pro  Gly  Val  Gly  Val  Pro  Gly  Val  Gly  Val  Pro  Gly  Ala  Gly
                   1410                    1415                    1420
    Ala  Gly  Ser  Gly  Ala  Gly  Ala  Gly  Ser  Gly  Ala  Gly  Ala  Gly  Ser  Gly
1425                    1430                    1435                    1440
    Ala  Gly  Ala  Gly  Ser  Gly  Ala  Gly  Ala  Gly  Ser  Gly  Ala  Gly  Ala  Gly
                   1445                    1450                    1455
    Ser  Gly  Ala  Ala  Gly  Tyr  Gly  Ala  Gly  Ala  Gly  Ser  Gly  Ala  Gly  Ala
                   1460                    1465                    1470
    Gly  Ser  Gly  Ala  Gly  Ala  Gly  Ser  Gly  Ala  Gly  Ala  Gly  Ser  Gly  Ala
                   1475                    1480                    1485
    Gly  Ala  Gly  Ser  Gly  Val  Gly  Val  Pro  Gly  Val  Gly  Val  Pro  Gly  Val
                   1490                    1495                    1500
    Gly  Val  Pro  Gly  Val  Gly  Val  Pro  Gly  Val  Gly  Val  Pro  Gly  Val  Gly
1505                    1510                    1515                    1520
    Val  Pro  Gly  Val  Gly  Val  Pro  Gly  Val  Gly  Val  Pro  Gly  Ala  Gly  Ala
                   1525                    1530                    1535
    Gly  Ser  Gly  Ala  Gly  Ala  Gly  Ser  Gly  Ala  Gly  Ala  Gly  Ser  Gly  Ala
                   1540                    1545                    1550
    Gly  Ala  Gly  Ser  Gly  Ala  Gly  Ala  Gly  Ser  Gly  Ala  Gly  Ala  Gly  Ser
                   1555                    1560                    1565
    Gly  Ala  Ala  Gly  Tyr  Gly  Ala  Gly  Ala  Gly  Ser  Gly  Ala  Gly  Ala  Gly
                   1570                    1575                    1580
    Ser  Gly  Ala  Gly  Ala  Gly  Ser  Gly  Ala  Gly  Ala  Gly  Ser  Gly  Ala  Gly
1585                    1590                    1595                    1600
    Ala  Gly  Ser  Gly  Val  Gly  Val  Pro  Gly  Val  Gly  Val  Pro  Gly  Val  Gly
                   1605                    1610                    1615
    Val  Pro  Gly  Val  Gly  Val  Pro  Gly  Val  Gly  Val  Pro  Gly  Val  Gly  Val
                   1620                    1625                    1630
    Pro  Gly  Val  Gly  Val  Pro  Gly  Val  Gly  Val  Pro  Gly  Ala  Gly  Ala  Gly
                   1635                    1640                    1645
    Ser  Gly  Ala  Gly  Ala  Gly  Ser  Gly  Ala  Gly  Ala  Gly  Ser  Gly  Ala  Gly
                   1650                    1655                    1660
```

```
Ala  Gly  Ser  Gly  Ala  Gly  Ala  Gly  Ser  Gly  Ala  Gly  Ala  Gly  Ser  Gly
1665                 1670                 1675                 1680

Ala  Ala  Gly  Tyr  Gly  Ala  Gly  Ala  Gly  Ser  Gly  Ala  Gly  Ala  Gly  Ser
                    1685                 1690                      1695

Gly  Ala  Gly  Ala  Gly  Ser  Gly  Ala  Gly  Ala  Gly  Ser  Gly  Ala  Gly  Ala
               1700                 1705                 1710

Gly  Ser  Gly  Val  Gly  Val  Pro  Gly  Val  Gly  Val  Pro  Gly  Val  Gly  Val
          1715                 1720                 1725

Pro  Gly  Val  Gly  Val  Pro  Gly  Val  Gly  Val  Pro  Gly  Val  Gly  Val  Pro
1730                 1735                 1740

Gly  Val  Gly  Val  Pro  Gly  Val  Gly  Val  Pro  Gly  Ala  Gly  Ala  Gly  Ser
1745                 1750                 1755                           1760

Gly  Ala  Gly  Ala  Gly  Ser  Gly  Ala  Gly  Ala  Gly  Ser  Gly  Ala  Gly  Ala
               1765                 1770                      1775

Gly  Ser  Gly  Ala  Gly  Ala  Gly  Ser  Gly  Ala  Gly  Ala  Gly  Ser  Gly  Ala
          1780                 1785                      1790

Ala  Gly  Tyr  Gly  Ala  Gly  Ala  Gly  Ser  Gly  Ala  Gly  Ala  Gly  Ser  Gly
          1795                      1800                      1805

Ala  Gly  Ala  Gly  Ser  Gly  Ala  Gly  Ala  Gly  Ser  Gly  Ala  Gly  Ala  Gly
          1810                 1815                      1820

Ser  Gly  Val  Gly  Val  Pro  Gly  Val  Gly  Val  Pro  Gly  Val  Gly  Val  Pro
1825                 1830                 1835                           1840

Gly  Val  Gly  Val  Pro  Gly  Val  Gly  Val  Pro  Gly  Val  Gly  Val  Pro  Gly
                    1845                 1850                      1855

Val  Gly  Val  Pro  Gly  Val  Gly  Val  Pro  Gly  Ala  Gly  Ala  Gly  Ser  Gly
               1860                 1865                      1870

Ala  Gly  Ala  Gly  Ser  Gly  Ala  Gly  Ala  Gly  Ser  Gly  Ala  Gly  Ala  Gly
          1875                 1880                      1885

Ser  Gly  Ala  Gly  Ala  Gly  Ser  Gly  Ala  Gly  Ala  Gly  Ser  Gly  Ala  Ala
          1890                 1895                      1900

Gly  Tyr  Gly  Ala  Gly  Ala  Gly  Ser  Gly  Ala  Gly  Ala  Gly  Ser  Gly  Ala
1905                 1910                 1915                           1920

Gly  Ala  Gly  Ser  Gly  Ala  Gly  Ala  Gly  Ser  Gly  Ala  Gly  Ala  Gly  Ser
               1925                 1930                           1935

Gly  Val  Gly  Val  Pro  Gly  Val  Gly  Val  Pro  Gly  Val  Gly  Val  Pro  Gly
               1940                 1945                      1950

Val  Gly  Val  Pro  Gly  Val  Gly  Val  Pro  Gly  Val  Gly  Val  Pro  Gly  Val
          1955                 1960                      1965

Gly  Val  Pro  Gly  Val  Gly  Val  Pro  Gly  Ala  Gly  Ala  Gly  Ser  Gly  Ala
          1970                 1975                      1980

Gly  Ala  Gly  Ser  Gly  Ala  Gly  Ala  Gly  Ser  Gly  Ala  Gly  Ala  Gly  Ser
1985                 1990                 1995                           2000

Gly  Ala  Gly  Ala  Gly  Ser  Gly  Ala  Gly  Ala  Gly  Ser  Gly  Ala  Ala  Gly
               2005                 2010                           2015

Tyr  Gly  Ala  Gly  Ala  Gly  Ser  Gly  Ala  Gly  Ala  Gly  Ser  Gly  Ala  Gly
               2020                 2025                      2030

Ala  Met  Asp  Pro  Gly  Arg  Tyr  Gln  Leu  Ser  Ala  Gly  Arg  Tyr  His  Tyr
               2035                 2040                      2045

Gln  Leu  Val  Trp  Cys  Gln  Lys
2050                     2055
```

( 2 ) INFORMATION FOR SEQ ID NO:53:

( i ) SEQUENCE CHARACTERISTICS:
        ( A ) LENGTH: 2257 amino acids ( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:53:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Ala Gly Ala Gly
        35                  40                  45

Ser Gly Val Gly Val Pro Gly Val Gly Val Pro Gly Val Gly Val Pro
    50                  55                  60

Gly Val Gly Val Pro Gly Val Gly Val Pro Gly Val Gly Val Pro Gly
65                  70                  75                  80

Val Gly Val Pro Gly Val Gly Val Pro Gly Ala Gly Ala Gly Ser Gly
                85                  90                  95

Ala Gly Ala Gly Ser Gly Ala Gly Ala Gly Ser Gly Ala Gly Ala Gly
                100                 105                 110

Ser Gly Ala Gly Ala Gly Ser Gly Ala Gly Ala Gly Ser Gly Ala Gly
            115                 120                 125

Ala Gly Ser Gly Ala Gly Ala Gly Ser Gly Val Gly Val Pro Gly Val
        130                 135                 140

Gly Val Pro Gly Val Gly Val Pro Gly Val Gly Val Pro Gly Val Gly
145                 150                 155                 160

Val Pro Gly Val Gly Val Pro Gly Val Gly Val Pro Gly Val Gly Val
                165                 170                 175

Pro Gly Ala Gly Ala Gly Ser Gly Ala Gly Ala Gly Ser Gly Ala Gly
            180                 185                 190

Ala Gly Ser Gly Ala Gly Ala Gly Ser Gly Ala Gly Ala Gly Ser Gly
        195                 200                 205

Ala Gly Ala Gly Ser Gly Ala Gly Ala Gly Ser Gly Ala Gly Ala Gly
    210                 215                 220

Ser Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Ala Gly Ala Gly Ser Gly
            260                 265                 270

Ala Gly Ala Gly Ser Gly Ala Gly Ala Gly Ser Gly Ala Gly Ala Gly
        275                 280                 285

Ser Gly Ala Gly Ala Gly Ser Gly Ala Gly Ala Gly Ser Gly Ala Gly
    290                 295                 300

Ala Gly Ser Gly Ala Gly Ala Gly Ser Gly Val Gly Val Pro Gly Val
305                 310                 315                 320

Gly Val Pro Gly Val Gly Val Pro Gly Val Gly Val Pro Gly Val Gly
                325                 330                 335

Val Pro Gly Val Gly Val Pro Gly Val Gly Val Pro Gly Val Gly Val
            340                 345                 350

Pro Gly Ala Gly Ala Gly Ser Gly Ala Gly Ala Gly Ser Gly Ala Gly
        355                 360                 365

Ala Gly Ser Gly Ala Gly Ala Gly Ser Gly Ala Gly Ala Gly Ser Gly
    370                 375                 380
```

-continued

```
Ala Gly Ala Gly Ser Gly Ala Gly Ala Gly Ser Gly Ala Gly Ala Gly
385                 390                 395                 400

Ser Gly Val Gly Val Pro Gly Val Gly Val Pro Gly Val Gly Val Pro
                405                 410                 415

Gly Val Gly Val Pro Gly Val Gly Val Pro Gly Val Gly Val Pro Gly
            420                 425                 430

Val Gly Val Pro Gly Val Gly Val Pro Gly Ala Gly Ala Gly Ser Gly
        435                 440                 445

Ala Gly Ala Gly Ser Gly Ala Gly Ala Gly Ser Gly Ala Gly Ala Gly
    450                 455                 460

Ser Gly Ala Gly Ala Gly Ser Gly Ala Gly Ala Gly Ser Gly Ala Gly
465                 470                 475                 480

Ala Gly Ser Gly Ala Gly Ala Gly Ser Gly Val Gly Val Pro Gly Val
                485                 490                 495

Gly Val Pro Gly Val Gly Val Pro Gly Val Gly Val Pro Gly Val Gly
            500                 505                 510

Val Pro Gly Val Gly Val Pro Gly Val Gly Val Pro Gly Val Gly Val
        515                 520                 525

Pro Gly Ala Gly Ala Gly Ser Gly Ala Gly Ala Gly Ser Gly Ala Gly
    530                 535                 540

Ala Gly Ser Gly Ala Gly Ala Gly Ser Gly Ala Gly Ala Gly Ser Gly
545                 550                 555                 560

Ala Gly Ala Gly Ser Gly Ala Gly Ala Gly Ser Gly Ala Gly Ala Gly
                565                 570                 575

Ser Gly Val Gly Val Pro Gly Val Gly Val Pro Gly Val Gly Val Pro
            580                 585                 590

Gly Val Gly Val Pro Gly Val Gly Val Pro Gly Val Gly Val Pro Gly
        595                 600                 605

Val Gly Val Pro Gly Val Gly Val Pro Gly Ala Gly Ala Gly Ser Gly
    610                 615                 620

Ala Gly Ala Gly Ser Gly Ala Gly Ala Gly Ser Gly Ala Gly Ala Gly
625                 630                 635                 640

Ser Gly Ala Gly Ala Gly Ser Gly Ala Gly Ala Gly Ser Gly Ala Gly
                645                 650                 655

Ala Gly Ser Gly Ala Gly Ala Gly Ser Gly Val Gly Val Pro Gly Val
            660                 665                 670

Gly Val Pro Gly Val Gly Val Pro Gly Val Gly Val Pro Gly Val Gly
        675                 680                 685

Val Pro Gly Val Gly Val Pro Gly Val Gly Val Pro Gly Val Gly Val
    690                 695                 700

Pro Gly Ala Gly Ala Gly Ser Gly Ala Gly Ala Gly Ser Gly Ala Gly
705                 710                 715                 720

Ala Gly Ser Gly Ala Gly Ala Gly Ser Gly Ala Gly Ala Gly Ser Gly
                725                 730                 735

Ala Gly Ala Gly Ser Gly Ala Gly Ala Gly Ser Gly Ala Gly Ala Gly
            740                 745                 750

Ser Gly Val Gly Val Pro Gly Val Gly Val Pro Gly Val Gly Val Pro
        755                 760                 765

Gly Val Gly Val Pro Gly Val Gly Val Pro Gly Val Gly Val Pro Gly
    770                 775                 780

Val Gly Val Pro Gly Val Gly Val Pro Gly Ala Gly Ala Gly Ser Gly
785                 790                 795                 800

Ala Gly Ala Gly Ser Gly Ala Gly Ala Gly Ser Gly Ala Gly Ala Gly
                805                 810                 815
```

| | | | | | | | | | | | | | | |
|---|---|---|---|---|---|---|---|---|---|---|---|---|---|---|
| Ser | Gly | Ala | Gly | Ala | Gly | Ser | Gly | Ala | Gly | Ala | Gly | Ser | Gly | Ala | Gly |
| | | | 820 | | | | 825 | | | | 830 | | | | |
| Ala | Gly | Ser | Gly | Ala | Gly | Ala | Gly | Ser | Gly | Val | Gly | Val | Pro | Gly | Val |
| | | | 835 | | | | 840 | | | | 845 | | | | |
| Gly | Val | Pro | Gly | Val | Gly | Val | Pro | Gly | Val | Gly | Val | Pro | Gly | Val | Gly |
| | | | 850 | | | | 855 | | | | 860 | | | | |
| Val | Pro | Gly | Val | Gly | Val | Pro | Gly | Val | Gly | Val | Pro | Gly | Val | Gly | Val |
| 865 | | | | | 870 | | | | | 875 | | | | | 880 |
| Pro | Gly | Ala | Gly | Ala | Gly | Ser | Gly | Ala | Gly | Ala | Gly | Ser | Gly | Ala | Gly |
| | | | | 885 | | | | | 890 | | | | | 895 | |
| Ala | Gly | Ser | Gly | Ala | Gly | Ala | Gly | Ser | Gly | Ala | Gly | Ala | Gly | Ser | Gly |
| | | | | 900 | | | | | 905 | | | | | 910 | |
| Ala | Gly | Ala | Gly | Ser | Gly | Ala | Gly | Ala | Gly | Ser | Gly | Ala | Gly | Ala | Gly |
| | | | | 915 | | | | | 920 | | | | | 925 | |
| Ser | Gly | Val | Gly | Val | Pro | Gly | Val | Gly | Val | Pro | Gly | Val | Gly | Val | Pro |
| | 930 | | | | | | 935 | | | | | | 940 | | |
| Gly | Val | Gly | Val | Pro | Gly | Val | Gly | Val | Pro | Gly | Val | Gly | Val | Pro | Gly |
| 945 | | | | | | 950 | | | | | 955 | | | | 960 |
| Val | Gly | Val | Pro | Gly | Val | Gly | Val | Pro | Gly | Ala | Gly | Ala | Gly | Ser | Gly |
| | | | | 965 | | | | | 970 | | | | | 975 | |
| Ala | Gly | Ala | Gly | Ser | Gly | Ala | Gly | Ala | Gly | Ser | Gly | Ala | Gly | Ala | Gly |
| | | | 980 | | | | | 985 | | | | | 990 | | |
| Ser | Gly | Ala | Gly | Ala | Gly | Ser | Gly | Ala | Gly | Ala | Gly | Ser | Gly | Ala | Gly |
| | | 995 | | | | | 1000 | | | | | 1005 | | | |
| Ala | Gly | Ser | Gly | Ala | Gly | Ala | Gly | Ser | Gly | Val | Gly | Val | Pro | Gly | Val |
| | | 1010 | | | | | 1015 | | | | | 1020 | | | |
| Gly | Val | Pro | Gly | Val | Gly | Val | Pro | Gly | Val | Gly | Val | Pro | Gly | Val | Gly |
| 1025 | | | | | 1030 | | | | | 1035 | | | | | 1040 |
| Val | Pro | Gly | Val | Gly | Val | Pro | Gly | Val | Gly | Val | Pro | Gly | Val | Gly | Val |
| | | | | 1045 | | | | | 1050 | | | | | 1055 | |
| Pro | Gly | Ala | Gly | Ala | Gly | Ser | Gly | Ala | Gly | Ala | Gly | Ser | Gly | Ala | Gly |
| | | | | 1060 | | | | | 1065 | | | | | 1070 | |
| Ala | Gly | Ser | Gly | Ala | Gly | Ala | Gly | Ser | Gly | Ala | Gly | Ala | Gly | Ser | Gly |
| | | | 1075 | | | | | 1080 | | | | | 1085 | | |
| Ala | Gly | Ala | Gly | Ser | Gly | Ala | Gly | Ala | Gly | Ser | Gly | Ala | Gly | Ala | Gly |
| | | | 1090 | | | | | 1095 | | | | | 1100 | | |
| Ser | Gly | Val | Gly | Val | Pro | Gly | Val | Gly | Val | Pro | Gly | Val | Gly | Val | Pro |
| 1105 | | | | | | | 1110 | | | | | 1115 | | | 1120 |
| Gly | Val | Gly | Val | Pro | Gly | Val | Gly | Val | Pro | Gly | Val | Gly | Val | Pro | Gly |
| | | | | 1125 | | | | | 1130 | | | | | 1135 | |
| Val | Gly | Val | Pro | Gly | Val | Gly | Val | Pro | Gly | Ala | Gly | Ala | Gly | Ser | Gly |
| | | | | 1140 | | | | | 1145 | | | | | 1150 | |
| Ala | Gly | Ala | Gly | Ser | Gly | Ala | Gly | Ala | Gly | Ser | Gly | Ala | Gly | Ala | Gly |
| | | | 1155 | | | | | 1160 | | | | | 1165 | | |
| Ser | Gly | Ala | Gly | Ala | Gly | Ser | Gly | Ala | Gly | Ala | Gly | Ser | Gly | Ala | Gly |
| | | | 1170 | | | | | 1175 | | | | | 1180 | | |
| Ala | Gly | Ser | Gly | Ala | Gly | Ala | Gly | Ser | Gly | Val | Gly | Val | Pro | Gly | Val |
| 1185 | | | | | 1190 | | | | | 1195 | | | | | 1200 |
| Gly | Val | Pro | Gly | Val | Gly | Val | Pro | Gly | Val | Gly | Val | Pro | Gly | Val | Gly |
| | | | | 1205 | | | | | 1210 | | | | | 1215 | |
| Val | Pro | Gly | Val | Gly | Val | Pro | Gly | Val | Gly | Val | Pro | Gly | Val | Gly | Val |
| | | | 1220 | | | | | 1225 | | | | | 1230 | | |
| Pro | Gly | Ala | Gly | Ala | Gly | Ser | Gly | Ala | Gly | Ala | Gly | Ser | Gly | Ala | Gly |

-continued

```
                   1235                    1240                         1245
     Ala  Gly  Ser  Gly  Ala  Gly  Ala  Gly  Ser  Gly  Ala  Gly  Ala  Gly  Ser  Gly
                    1250                    1255                   1260
     Ala  Gly  Ala  Gly  Ser  Gly  Ala  Gly  Ala  Gly  Ser  Gly  Ala  Gly  Ala  Gly
     1265                    1270                    1275                         1280
     Ser  Gly  Val  Gly  Val  Pro  Gly  Val  Gly  Val  Pro  Gly  Val  Gly  Val  Pro
                         1285                    1290                    1295
     Gly  Val  Gly  Val  Pro  Gly  Val  Gly  Val  Pro  Gly  Val  Gly  Val  Pro  Gly
                    1300                    1305                         1310
     Val  Gly  Val  Pro  Gly  Val  Gly  Val  Pro  Gly  Ala  Gly  Ala  Gly  Ser  Gly
                    1315                    1320                    1325
     Ala  Gly  Ala  Gly  Ser  Gly  Ala  Gly  Ala  Gly  Ser  Gly  Ala  Gly  Ala  Gly
                    1330                    1335                    1340
     Ser  Gly  Ala  Gly  Ala  Gly  Ser  Gly  Ala  Gly  Ala  Gly  Ser  Gly  Ala  Gly
     1345                    1350                    1355                         1360
     Ala  Gly  Ser  Gly  Ala  Gly  Ala  Gly  Ser  Gly  Val  Gly  Val  Pro  Gly  Val
                         1365                    1370                         1375
     Gly  Val  Pro  Gly  Val  Gly  Val  Pro  Gly  Val  Gly  Val  Pro  Gly  Val  Gly
                    1380                    1385                         1390
     Val  Pro  Gly  Val  Gly  Val  Pro  Gly  Val  Gly  Val  Pro  Gly  Val  Gly  Val
                    1395                    1400                    1405
     Pro  Gly  Ala  Gly  Ala  Gly  Ser  Gly  Ala  Gly  Ala  Gly  Ser  Gly  Ala  Gly
     1410                    1415                    1420
     Ala  Gly  Ser  Gly  Ala  Gly  Ala  Gly  Ser  Gly  Ala  Gly  Ala  Gly  Ser  Gly
     1425                    1430                    1435                         1440
     Ala  Gly  Ala  Gly  Ser  Gly  Ala  Gly  Ala  Gly  Ser  Gly  Ala  Gly  Ala  Gly
                         1445                    1450                         1455
     Ser  Gly  Val  Gly  Val  Pro  Gly  Val  Gly  Val  Pro  Gly  Val  Gly  Val  Pro
                         1460                    1465                    1470
     Gly  Val  Gly  Val  Pro  Gly  Val  Gly  Val  Pro  Gly  Val  Gly  Val  Pro  Gly
                    1475                    1480                         1485
     Val  Gly  Val  Pro  Gly  Val  Gly  Val  Pro  Gly  Ala  Gly  Ala  Gly  Ser  Gly
                    1490                    1495                    1500
     Ala  Gly  Ala  Gly  Ser  Gly  Ala  Gly  Ala  Gly  Ser  Gly  Ala  Gly  Ala  Gly
     1505                    1510                    1515                         1520
     Ser  Gly  Ala  Gly  Ala  Gly  Ser  Gly  Ala  Gly  Ala  Gly  Ser  Gly  Ala  Gly
                         1525                    1530                         1535
     Ala  Gly  Ser  Gly  Ala  Gly  Ala  Gly  Ser  Gly  Val  Gly  Val  Pro  Gly  Val
                    1540                    1545                    1550
     Gly  Val  Pro  Gly  Val  Gly  Val  Pro  Gly  Val  Gly  Val  Pro  Gly  Val  Gly
                    1555                    1560                    1565
     Val  Pro  Gly  Val  Gly  Val  Pro  Gly  Val  Gly  Val  Pro  Gly  Val  Gly  Val
                    1570                    1575                    1580
     Pro  Gly  Ala  Gly  Ala  Gly  Ser  Gly  Ala  Gly  Ala  Gly  Ser  Gly  Ala  Gly
     1585                    1590                    1595                         1600
     Ala  Gly  Ser  Gly  Ala  Gly  Ala  Gly  Ser  Gly  Ala  Gly  Ala  Gly  Ser  Gly
                         1605                    1610                         1615
     Ala  Gly  Ala  Gly  Ser  Gly  Ala  Gly  Ala  Gly  Ser  Gly  Ala  Gly  Ala  Gly
                    1620                    1625                    1630
     Ser  Gly  Val  Gly  Val  Pro  Gly  Val  Gly  Val  Pro  Gly  Val  Gly  Val  Pro
                    1635                    1640                         1645
     Gly  Val  Gly  Val  Pro  Gly  Val  Gly  Val  Pro  Gly  Val  Gly  Val  Pro  Gly
                    1650                    1655                    1660
```

-continued

```
Val Gly Val Pro Gly Val Gly Val Pro Gly Ala Gly Ala Gly Ser Gly
1665                1670                1675                1680

Ala Gly Ala Gly Ser Gly Ala Gly Ala Gly Ser Gly Ala Gly Ala Gly
            1685                1690                1695

Ser Gly Ala Gly Ala Gly Ser Gly Ala Gly Ala Gly Ser Gly Ala Gly
        1700                1705                1710

Ala Gly Ser Gly Ala Gly Ala Gly Ser Gly Val Gly Val Pro Gly Val
    1715                1720                1725

Gly Val Pro Gly Val Gly Val Pro Gly Val Gly Val Pro Gly Val Gly
1730                1735                1740

Val Pro Gly Val Gly Val Pro Gly Val Gly Val Pro Gly Val Gly Val
1745                1750                1755                1760

Pro Gly Ala Gly Ala Gly Ser Gly Ala Gly Ala Gly Ser Gly Ala Gly
        1765                1770                1775

Ala Gly Ser Gly Ala Gly Ala Gly Ser Gly Ala Gly Ala Gly Ser Gly
    1780                1785                1790

Ala Gly Ala Gly Ser Gly Ala Gly Ala Gly Ser Gly Ala Gly Ala Gly
    1795                1800                1805

Ser Gly Val Gly Val Pro Gly Val Gly Val Pro Gly Val Gly Val Pro
    1810                1815                1820

Gly Val Gly Val Pro Gly Val Gly Val Pro Gly Val Gly Val Pro Gly
1825                1830                1835                1840

Val Gly Val Pro Gly Val Gly Val Pro Gly Ala Gly Ala Gly Ser Gly
            1845                1850                1855

Ala Gly Ala Gly Ser Gly Ala Gly Ala Gly Ser Gly Ala Gly Ala Gly
        1860                1865                1870

Ser Gly Ala Gly Ala Gly Ser Gly Ala Gly Ala Gly Ser Gly Ala Gly
    1875                1880                1885

Ala Gly Ser Gly Ala Gly Ala Gly Ser Gly Val Gly Val Pro Gly Val
    1890                1895                1900

Gly Val Pro Gly Val Gly Val Pro Gly Val Gly Val Pro Gly Val Gly
1905                1910                1915                1920

Val Pro Gly Val Gly Val Pro Gly Val Gly Val Pro Gly Val Gly Val
            1925                1930                1935

Pro Gly Ala Gly Ala Gly Ser Gly Ala Gly Ala Gly Ser Gly Ala Gly
        1940                1945                1950

Ala Gly Ser Gly Ala Gly Ala Gly Ser Gly Ala Gly Ala Gly Ser Gly
    1955                1960                1965

Ala Gly Ala Gly Ser Gly Ala Gly Ala Gly Ser Gly Ala Gly Ala Gly
    1970                1975                1980

Ser Gly Val Gly Val Pro Gly Val Gly Val Pro Gly Val Gly Val Pro
1985                1990                1995                2000

Gly Val Gly Val Pro Gly Val Gly Val Pro Gly Val Gly Val Pro Gly
            2005                2010                2015

Val Gly Val Pro Gly Val Gly Val Pro Gly Ala Gly Ala Gly Ser Gly
        2020                2025                2030

Ala Gly Ala Gly Ser Gly Ala Gly Ala Gly Ser Gly Ala Gly Ala Gly
    2035                2040                2045

Ser Gly Ala Gly Ala Gly Ser Gly Ala Gly Ala Gly Ser Gly Ala Gly
    2050                2055                2060

Ala Gly Ser Gly Ala Gly Ala Gly Ser Gly Val Gly Val Pro Gly Val
2065                2070                2075                2080

Gly Val Pro Gly Val Gly Val Pro Gly Val Gly Val Pro Gly Val Gly
            2085                2090                2095
```

| | | | | | | | | | | | | | | |
|---|---|---|---|---|---|---|---|---|---|---|---|---|---|---|
| Val | Pro | Gly | Val | Gly | Val | Pro | Gly | Val | Gly | Val | Pro | Gly | Val | Gly | Val |
| | | | 2100 | | | | 2105 | | | | 2110 | | | |
| Pro | Gly | Ala | Gly | Ala | Gly | Ser | Gly | Ala | Gly | Ala | Gly | Ser | Gly | Ala | Gly |
| | | | 2115 | | | | 2120 | | | | 2125 | | | |
| Ala | Gly | Ser | Gly | Ala | Gly | Ala | Gly | Ser | Gly | Ala | Gly | Ala | Gly | Ser | Gly |
| | | | 2130 | | | | 2135 | | | | 2140 | | | |
| Ala | Gly | Ala | Gly | Ser | Gly | Ala | Gly | Ala | Gly | Ser | Gly | Ala | Gly | Ala | Gly |
| 2145 | | | | | | 2150 | | | | | 2155 | | | | 2160 |
| Ser | Gly | Val | Gly | Val | Pro | Gly | Val | Gly | Val | Pro | Gly | Val | Gly | Val | Pro |
| | | | | 2165 | | | | | 2170 | | | | | 2175 | |
| Gly | Val | Gly | Val | Pro | Gly | Val | Gly | Val | Pro | Gly | Val | Gly | Val | Pro | Gly |
| | | | | 2180 | | | | | 2185 | | | | | 2190 | |
| Val | Gly | Val | Pro | Gly | Val | Gly | Val | Pro | Gly | Ala | Gly | Ala | Gly | Ser | Gly |
| | | | 2195 | | | | | 2200 | | | | | 2205 | | |
| Ala | Gly | Ala | Gly | Ser | Gly | Ala | Gly | Ala | Gly | Ser | Gly | Ala | Gly | Ala | Gly |
| | | | 2210 | | | | | 2215 | | | | | 2220 | | |
| Ser | Gly | Ala | Gly | Ala | Gly | Ser | Gly | Ala | Gly | Ala | Met | Asp | Pro | Gly | Arg |
| 2225 | | | | | 2230 | | | | | | 2235 | | | | 2240 |
| Tyr | Gln | Leu | Ser | Ala | Gly | Arg | Tyr | His | Tyr | Gln | Leu | Val | Trp | Cys | Gln |
| | | | | 2245 | | | | | 2250 | | | | | 2255 | |
| Lys | | | | | | | | | | | | | | | |

( 2 ) INFORMATION FOR SEQ ID NO:54:

( i ) SEQUENCE CHARACTERISTICS:
        ( A ) LENGTH: 1059 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:54:

| | | | | | | | | | | | | | | |
|---|---|---|---|---|---|---|---|---|---|---|---|---|---|---|
| Met | Asp | Pro | Val | Val | Leu | Gln | Arg | Arg | Asp | Trp | Glu | Asn | Pro | Gly | Val |
| 1 | | | | 5 | | | | | 10 | | | | | 15 | |
| Thr | Gln | Leu | Asn | Arg | Leu | Ala | Ala | His | Pro | Pro | Phe | Ala | Ser | Asp | Pro |
| | | | 20 | | | | | 25 | | | | | 30 | | |
| Met | Gly | Ala | Gly | Ser | Gly | Ala | Gly | Ala | Gly | Ser | Gly | Ala | Gly | Ala | Gly |
| | | | 35 | | | | | 40 | | | | | 45 | | |
| Ser | Gly | Ala | Gly | Ala | Gly | Ser | Gly | Ala | Gly | Ala | Gly | Ser | Gly | Ala | Gly |
| | | 50 | | | | | 55 | | | | | 60 | | | |
| Ala | Gly | Ser | Gly | Ala | Gly | Ala | Gly | Ser | Gly | Ala | Gly | Ala | Gly | Ser | Gly |
| 65 | | | | | 70 | | | | | 75 | | | | | 80 |
| Ala | Gly | Ala | Gly | Ser | Gly | Ala | Gly | Ala | Gly | Ser | Gly | Ala | Gly | Ala | Gly |
| | | | | 85 | | | | | 90 | | | | | 95 | |
| Ser | Gly | Ala | Gly | Ala | Gly | Ser | Gly | Ala | Gly | Ala | Gly | Ser | Gly | Ala | Gly |
| | | | 100 | | | | | 105 | | | | | 110 | | |
| Ala | Gly | Ser | Gly | Ala | Gly | Ala | Gly | Ser | Gly | Ala | Gly | Ala | Gly | Ser | Gly |
| | | | 115 | | | | | 120 | | | | | 125 | | |
| Ala | Gly | Ala | Gly | Ser | Gly | Ala | Gly | Ala | Gly | Ser | Gly | Ala | Gly | Ala | Gly |
| | | | 130 | | | | | 135 | | | | | 140 | | |
| Ser | Gly | Ala | Gly | Ala | Gly | Ser | Gly | Ala | Gly | Ala | Gly | Ser | Gly | Ala | Gly |
| 145 | | | | | 150 | | | | | 155 | | | | | 160 |
| Ala | Gly | Ser | Gly | Ala | Gly | Ala | Gly | Ser | Gly | Ala | Gly | Ala | Gly | Ser | Gly |
| | | | | 165 | | | | | 170 | | | | | 175 | |
| Ala | Gly | Ala | Gly | Ser | Gly | Ala | Gly | Ala | Gly | Ser | Gly | Ala | Gly | Ala | Gly |

-continued

|     |     |     | 180 |     |     |     | 185 |     |     |     | 190 |     |     |
|---|---|---|---|---|---|---|---|---|---|---|---|---|---|

Ser Gly Ala Gly Ala Gly Ser Gly Ala Gly Ala Gly Ser Gly Ala Gly
            195                     200                     205

Ala Gly Ser Gly Ala Gly Ala Gly Ser Gly Ala Gly Ala Gly Ser Gly
            210                     215                     220

Ala Gly Ala Gly Ser Gly Ala Gly Ala Gly Ser Gly Ala Gly Ala Gly
225                     230                     235                     240

Ser Gly Ala Gly Ala Gly Ser Gly Ala Gly Ala Gly Ser Gly Ala Gly
                        245                     250                     255

Ala Gly Ser Gly Ala Gly Ala Gly Ser Gly Ala Gly Ala Gly Ser Gly
            260                     265                     270

Ala Gly Ala Gly Ser Gly Ala Gly Ala Gly Ser Gly Ala Gly Ala Gly
            275                     280                     285

Ser Gly Ala Gly Ala Gly Ser Gly Ala Gly Ala Gly Ser Gly Ala Gly
            290                     295                     300

Ala Gly Ser Gly Ala Gly Ala Gly Ser Gly Ala Gly Ala Gly Ser Gly
305                     310                     315                     320

Ala Gly Ala Gly Ser Gly Ala Gly Ala Gly Ser Gly Ala Gly Ala Gly
                        325                     330                     335

Ser Gly Ala Gly Ala Gly Ser Gly Ala Gly Ala Gly Ser Gly Ala Gly
            340                     345                     350

Ala Gly Ser Gly Ala Gly Ala Gly Ser Gly Ala Gly Ala Gly Ser Gly
            355                     360                     365

Ala Gly Ala Gly Ser Gly Ala Gly Ala Gly Ser Gly Ala Gly Ala Gly
            370                     375                     380

Ser Gly Ala Gly Ala Gly Ser Gly Ala Gly Ala Gly Ser Gly Ala Gly
385                     390                     395                     400

Ala Gly Ser Gly Ala Gly Ala Gly Ser Gly Ala Gly Ala Gly Ser Gly
                        405                     410                     415

Ala Gly Ala Gly Ser Gly Ala Gly Ala Gly Ser Gly Ala Gly Ala Gly
            420                     425                     430

Ser Gly Ala Gly Ala Gly Ser Gly Ala Gly Ala Gly Ser Gly Ala Gly
            435                     440                     445

Ala Gly Ser Gly Ala Gly Ala Gly Ser Gly Ala Gly Ala Gly Ser Gly
            450                     455                     460

Ala Gly Ala Gly Ser Gly Ala Gly Ala Gly Ser Gly Ala Gly Ala Gly
465                     470                     475                     480

Ser Gly Ala Gly Ala Gly Ser Gly Ala Gly Ala Gly Ser Gly Ala Gly
                        485                     490                     495

Ala Gly Ser Gly Ala Gly Ala Gly Ser Gly Ala Gly Ala Gly Ser Gly
            500                     505                     510

Ala Gly Ala Gly Ser Gly Ala Gly Ala Gly Ser Gly Ala Gly Ala Gly
            515                     520                     525

Ser Gly Ala Gly Ala Gly Ser Gly Ala Gly Ala Gly Ser Gly Ala Gly
            530                     535                     540

Ala Gly Ser Gly Ala Gly Ala Gly Ser Gly Ala Gly Ala Gly Ser Gly
545                     550                     555                     560

Ala Gly Ala Gly Ser Gly Ala Gly Ala Gly Ser Gly Ala Gly Ala Gly
                        565                     570                     575

Ser Gly Ala Gly Ala Gly Ser Gly Ala Gly Ala Gly Ser Gly Ala Gly
            580                     585                     590

Ala Gly Ser Gly Ala Gly Ala Gly Ser Gly Ala Gly Ala Gly Ser Gly
            595                     600                     605

| | | | | | | | | | | | | | | |
|---|---|---|---|---|---|---|---|---|---|---|---|---|---|---|
| Ala | Gly | Ala | Gly | Ser | Gly | Ala | Gly | Ala | Gly | Ser | Gly | Ala | Gly | Ala | Gly |
| | 610 | | | | 615 | | | | | 620 | | | | | |
| Ser | Gly | Ala | Gly | Ala | Gly | Ser | Gly | Ala | Gly | Ala | Gly | Ser | Gly | Ala | Gly |
| 625 | | | | | 630 | | | | | 635 | | | | | 640 |
| Ala | Gly | Ser | Gly | Ala | Gly | Ala | Gly | Ser | Gly | Ala | Gly | Ala | Gly | Ser | Gly |
| | | | | 645 | | | | | 650 | | | | | 655 | |
| Ala | Gly | Ala | Gly | Ser | Gly | Ala | Gly | Ala | Gly | Ser | Gly | Ala | Gly | Ala | Gly |
| | | | 660 | | | | | 665 | | | | | 670 | | |
| Ser | Gly | Ala | Gly | Ala | Gly | Ser | Gly | Ala | Gly | Ala | Gly | Ser | Gly | Ala | Gly |
| | | 675 | | | | | 680 | | | | | 685 | | | |
| Ala | Gly | Ser | Gly | Ala | Gly | Ala | Gly | Ser | Gly | Ala | Gly | Ala | Gly | Ser | Gly |
| | 690 | | | | | 695 | | | | | 700 | | | | |
| Ala | Gly | Ala | Gly | Ser | Gly | Ala | Gly | Ala | Gly | Ser | Gly | Ala | Gly | Ala | Gly |
| 705 | | | | | 710 | | | | | 715 | | | | | 720 |
| Ser | Gly | Ala | Gly | Ala | Gly | Ser | Gly | Ala | Gly | Ala | Gly | Ser | Gly | Ala | Gly |
| | | | | 725 | | | | | 730 | | | | | 735 | |
| Ala | Gly | Ser | Gly | Ala | Gly | Ala | Gly | Ser | Gly | Ala | Gly | Ala | Gly | Ser | Gly |
| | | | 740 | | | | | 745 | | | | | 750 | | |
| Ala | Gly | Ala | Gly | Ser | Gly | Ala | Gly | Ala | Gly | Ser | Gly | Ala | Gly | Ala | Gly |
| | | 755 | | | | | 760 | | | | | 765 | | | |
| Ser | Gly | Ala | Gly | Ala | Gly | Ser | Gly | Ala | Gly | Ala | Gly | Ser | Gly | Ala | Gly |
| | 770 | | | | | 775 | | | | | 780 | | | | |
| Ala | Gly | Ser | Gly | Ala | Gly | Ala | Gly | Ser | Gly | Ala | Gly | Ala | Gly | Ser | Gly |
| 785 | | | | | 790 | | | | | 795 | | | | | 800 |
| Ala | Gly | Ala | Gly | Ser | Gly | Ala | Gly | Ala | Gly | Ser | Gly | Ala | Gly | Ala | Gly |
| | | | | 805 | | | | | 810 | | | | | 815 | |
| Ser | Gly | Ala | Gly | Ala | Gly | Ser | Gly | Ala | Gly | Ala | Gly | Ser | Gly | Ala | Gly |
| | | | 820 | | | | | 825 | | | | | 830 | | |
| Ala | Gly | Ser | Gly | Ala | Gly | Ala | Gly | Ser | Gly | Ala | Gly | Ala | Gly | Ser | Gly |
| | | 835 | | | | | 840 | | | | | 845 | | | |
| Ala | Gly | Ala | Gly | Ser | Gly | Ala | Gly | Ala | Gly | Ser | Gly | Ala | Gly | Ala | Gly |
| | 850 | | | | | 855 | | | | | 860 | | | | |
| Ser | Gly | Ala | Gly | Ala | Gly | Ser | Gly | Ala | Gly | Ala | Gly | Ser | Gly | Ala | Gly |
| 865 | | | | | 870 | | | | | 875 | | | | | 880 |
| Ala | Gly | Ser | Gly | Ala | Gly | Ala | Gly | Ser | Gly | Ala | Gly | Ala | Gly | Ser | Gly |
| | | | | 885 | | | | | 890 | | | | | 895 | |
| Ala | Gly | Ala | Gly | Ser | Gly | Ala | Gly | Ala | Gly | Ser | Gly | Ala | Gly | Ala | Gly |
| | | | 900 | | | | | 905 | | | | | 910 | | |
| Ser | Gly | Ala | Gly | Ala | Gly | Ser | Gly | Ala | Gly | Ala | Gly | Ser | Gly | Ala | Gly |
| | | 915 | | | | | 920 | | | | | 925 | | | |
| Ala | Gly | Ser | Gly | Ala | Gly | Ala | Gly | Ser | Gly | Ala | Gly | Ala | Gly | Ser | Gly |
| | 930 | | | | | 935 | | | | | 940 | | | | |
| Ala | Gly | Ala | Gly | Ser | Gly | Ala | Gly | Ala | Gly | Ser | Gly | Ala | Gly | Ala | Gly |
| 945 | | | | | 950 | | | | | 955 | | | | | 960 |
| Ser | Gly | Ala | Gly | Ala | Gly | Ser | Gly | Ala | Gly | Ala | Gly | Ser | Gly | Ala | Gly |
| | | | | 965 | | | | | 970 | | | | | 975 | |
| Ala | Gly | Ser | Gly | Ala | Gly | Ala | Gly | Ser | Gly | Ala | Gly | Ala | Gly | Ser | Gly |
| | | | 980 | | | | | 985 | | | | | 990 | | |
| Ala | Gly | Ala | Gly | Ser | Gly | Ala | Gly | Ala | Gly | Ser | Gly | Ala | Gly | Ala | Gly |
| | | 995 | | | | | 1000 | | | | | 1005 | | | |
| Ser | Gly | Ala | Gly | Ala | Gly | Ser | Gly | Ala | Gly | Ala | Gly | Ser | Gly | Ala | Gly |
| | 1010 | | | | | 1015 | | | | | 1020 | | | | |
| Ala | Gly | Ser | Gly | Ala | Gly | Ala | Gly | Ser | Gly | Ala | Gly | Ala | Met | Asp | Pro |
| 1025 | | | | | 1030 | | | | | 1035 | | | | | 1040 |

Gly Arg Tyr Gln Leu Ser Ala Gly Arg Tyr His Tyr Gln Leu Val Trp
                    1045                    1050                    1055

Cys Gln Lys ( 2 ) INFORMATION FOR SEQ ID NO:55:

( i ) SEQUENCE CHARACTERISTICS:
        ( A ) LENGTH: 5 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:55:

Gly Ala Ala Gly Tyr
1                 5

( 2 ) INFORMATION FOR SEQ ID NO:56:

( i ) SEQUENCE CHARACTERISTICS:
        ( A ) LENGTH: 54 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:56:

Gly Ala Gly Ala Gly Ser Gly Ala Gly Ala Gly Ser Gly Ala Gly Ala
1               5                   10                  15
Gly Ser Gly Ala Gly Ala Gly Ser Gly Ala Gly Ala Gly Ser Gly Ala
                20                  25                  30
Gly Ala Gly Ser Gly Ala Gly Ala Gly Ser Gly Ala Gly Ala Gly Ser
            35                  40                  45
Gly Ala Gly Ala Gly Ser
        50

( 2 ) INFORMATION FOR SEQ ID NO:57:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:57:

GTGACTGGCC GTGGTGATAG CCCGGCTAGC GCTGCA                              36

( 2 ) INFORMATION FOR SEQ ID NO:58:

( i ) SEQUENCE CHARACTERISTICS:
        ( A ) LENGTH: 36 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:58:

GCGCTAGCCG GGCTATCACC ACGGCCAGTC ACTGCA                              36

( 2 ) INFORMATION FOR SEQ ID NO:59:

( i ) SEQUENCE CHARACTERISTICS:
  ( A ) LENGTH: 219 base pairs
  ( B ) TYPE: nucleic acid
  ( C ) STRANDEDNESS: unknown
  ( D ) TOPOLOGY: unknown ( i i ) MOLECULE TYPE: DNA (genomic)

( i x ) FEATURE:
  ( A ) NAME/KEY: CDS
  ( B ) LOCATION: 1..216

( x i ) SEQUENCE DESCRIPTION: SEQ ID NO:59:

| GGT | GCC | GGC | AGC | GGT | GCA | GGA | GCC | GGT | TCT | GGA | GCT | GGC | GCG | GGC | TCT | 48 |
|---|---|---|---|---|---|---|---|---|---|---|---|---|---|---|---|---|
| Gly | Ala | Gly | Ser | Gly | Ala | Gly | Ala | Gly | Ser | Gly | Ala | Gly | Ala | Gly | Ser | |
| 1 | | | | 5 | | | | | 10 | | | | | 15 | | |

| GGC | GCG | GGC | GCA | GGA | TCC | GGC | GCA | GGC | GCT | GGT | TCT | GGC | GCA | GGG | GCA | 96 |
|---|---|---|---|---|---|---|---|---|---|---|---|---|---|---|---|---|
| Gly | Ala | Gly | Ala | Gly | Ser | Gly | Ala | Gly | Ala | Gly | Ser | Gly | Ala | Gly | Ala | |
| | | 20 | | | | | 25 | | | | | 30 | | | | |

| GGC | TCT | GGC | GCA | GGA | GCG | GGG | TCT | GGA | GCT | GCA | GTG | ACT | GGC | CGT | GGT | 144 |
|---|---|---|---|---|---|---|---|---|---|---|---|---|---|---|---|---|
| Gly | Ser | Gly | Ala | Gly | Ala | Gly | Ser | Gly | Ala | Ala | Val | Thr | Gly | Arg | Gly | |
| | | 35 | | | | | 40 | | | | | 45 | | | | |

| GAT | AGC | CCG | GCT | AGC | GCT | GCA | GGC | TAT | GGA | GCT | GGC | GCT | GGC | TCA | GGT | 192 |
|---|---|---|---|---|---|---|---|---|---|---|---|---|---|---|---|---|
| Asp | Ser | Pro | Ala | Ser | Ala | Ala | Gly | Tyr | Gly | Ala | Gly | Ala | Gly | Ser | Gly | |
| | 50 | | | | | 55 | | | | | | 60 | | | | |

| GCT | GGA | GCA | GGA | AGC | GGA | GCG | GGT | GCC | | | | | | | | 219 |
|---|---|---|---|---|---|---|---|---|---|---|---|---|---|---|---|---|
| Ala | Gly | Ala | Gly | Ser | Gly | Ala | Gly | | | | | | | | | |
| 65 | | | | 70 | | | | | | | | | | | | |

( 2 ) INFORMATION FOR SEQ ID NO:60:

( i ) SEQUENCE CHARACTERISTICS:
    ( A ) LENGTH: 72 amino acids
    ( B ) TYPE: amino acid
    ( D ) TOPOLOGY: linear ( i i ) MOLECULE TYPE: protein ( x i ) SEQUENCE DESCRIPTION: SEQ ID NO:60:

| Gly | Ala | Gly | Ser | Gly | Ala | Gly | Ala | Gly | Ser | Gly | Ala | Gly | Ala | Gly | Ser |
|---|---|---|---|---|---|---|---|---|---|---|---|---|---|---|---|
| 1 | | | | 5 | | | | | 10 | | | | | 15 | |

| Gly | Ala | Gly | Ala | Gly | Ser | Gly | Ala | Gly | Ala | Gly | Ser | Gly | Ala | Gly | Ala |
|---|---|---|---|---|---|---|---|---|---|---|---|---|---|---|---|
| | | 20 | | | | | 25 | | | | | 30 | | | |

| Gly | Ser | Gly | Ala | Gly | Ala | Gly | Ser | Gly | Ala | Ala | Val | Thr | Gly | Arg | Gly |
|---|---|---|---|---|---|---|---|---|---|---|---|---|---|---|---|
| | | 35 | | | | | 40 | | | | | 45 | | | |

| Asp | Ser | Pro | Ala | Ser | Ala | Ala | Gly | Tyr | Gly | Ala | Gly | Ala | Gly | Ser | Gly |
|---|---|---|---|---|---|---|---|---|---|---|---|---|---|---|---|
| | 50 | | | | | 55 | | | | | | 60 | | | |

| Ala | Gly | Ala | Gly | Ser | Gly | Ala | Gly |
|---|---|---|---|---|---|---|---|
| 65 | | | | 70 | | | |

( 2 ) INFORMATION FOR SEQ ID NO:61:

( i ) SEQUENCE CHARACTERISTICS:
    ( A ) LENGTH: 766 amino acids
    ( B ) TYPE: amino acid
    ( C ) STRANDEDNESS: unknown
    ( D ) TOPOLOGY: unknown ( i i ) MOLECULE TYPE: protein ( x i ) SEQUENCE DESCRIPTION: SEQ ID NO:61:

| Asp | Pro | Val | Val | Leu | Gln | Arg | Arg | Asp | Trp | Glu | Asn | Pro | Gly | Val | Thr |
|---|---|---|---|---|---|---|---|---|---|---|---|---|---|---|---|
| 1 | | | | 5 | | | | | 10 | | | | | 15 | |

| Gln | Leu | Asn | Arg | Leu | Ala | Ala | His | Pro | Pro | Phe | Ala | Ser | Asp | Pro | Met |
|---|---|---|---|---|---|---|---|---|---|---|---|---|---|---|---|
| | | 20 | | | | | 25 | | | | | 30 | | | |

-continued

```
Gly Ala Gly Ser Gly Ala Gly Ala Gly Ser Gly Ala Gly Ala Gly Ser
         35                  40                  45
Gly Ala Gly Ala Gly Ser Gly Ala Gly Ala Gly Ser Gly Ala Gly Ala
         50                  55                  60
Gly Ser Gly Ala Gly Ala Gly Ser Gly Ala Ala Val Thr Gly Arg Gly
 65                  70                  75                  80
Asp Ser Pro Ala Ser Ala Ala Gly Tyr Gly Ala Gly Ala Gly Ser Gly
                 85                  90                  95
Ala Gly Ala Gly Ser Gly Ala Gly Ala Gly Ser Gly Ala Gly Ala Gly
                100                 105                 110
Ser Gly Ala Gly Ala Gly Ser Gly Ala Gly Ala Gly Ser Gly Ala Gly
                115                 120                 125
Ala Gly Ser Gly Ala Gly Ala Gly Ser Gly Ala Gly Ala Gly Ser Gly
            130                 135                 140
Ala Ala Val Thr Gly Arg Gly Asp Ser Pro Ala Ser Ala Ala Gly Tyr
145                 150                 155                 160
Gly Ala Gly Ala Gly Ser Gly Ala Gly Ala Gly Ser Gly Ala Gly Ala
                    165                 170                 175
Gly Ser Gly Ala Gly Ala Gly Ser Gly Ala Gly Ala Gly Ser Gly Ala
            180                 185                 190
Gly Ala Gly Ser Gly Ala Gly Ala Gly Ser Gly Ala Gly Ala Gly Ser
        195                 200                 205
Gly Ala Gly Ala Gly Ser Gly Ala Ala Val Thr Gly Arg Gly Asp Ser
        210                 215                 220
Pro Ala Ser Ala Ala Gly Tyr Gly Ala Gly Ala Gly Ser Gly Ala Gly
225                 230                 235                 240
Ala Gly Ser Gly Ala Gly Ala Gly Ser Gly Ala Gly Ala Gly Ser Gly
            245                 250                 255
Ala Gly Ala Gly Ser Gly Ala Gly Ala Gly Ser Gly Ala Gly Ala Gly
            260                 265                 270
Ser Gly Ala Gly Ala Gly Ser Gly Ala Gly Ala Gly Ser Gly Ala Ala
        275                 280                 285
Val Thr Gly Arg Gly Asp Ser Pro Ala Ser Ala Ala Gly Tyr Gly Ala
        290                 295                 300
Gly Ala Gly Ser Gly Ala Gly Ala Gly Ser Gly Ala Gly Ala Gly Ser
305                 310                 315                 320
Gly Ala Gly Ala Gly Ser Gly Ala Gly Ala Gly Ser Gly Ala Gly Ala
                325                 330                 335
Gly Ser Gly Ala Gly Ala Gly Ser Gly Ala Gly Ala Gly Ser Gly Ala
            340                 345                 350
Gly Ala Gly Ser Gly Ala Ala Val Thr Gly Arg Gly Asp Ser Pro Ala
        355                 360                 365
Ser Ala Ala Gly Tyr Gly Ala Gly Ala Gly Ser Gly Ala Gly Ala Gly
    370                 375                 380
Ser Gly Ala Gly Ala Gly Ser Gly Ala Gly Ala Gly Ser Gly Ala Gly
385                 390                 395                 400
Ala Gly Ser Gly Ala Gly Ala Gly Ser Gly Ala Gly Ala Gly Ser Gly
                405                 410                 415
Ala Gly Ala Gly Ser Gly Ala Gly Ala Gly Ser Gly Ala Ala Val Thr
            420                 425                 430
Gly Arg Gly Asp Ser Pro Ala Ser Ala Ala Gly Tyr Gly Ala Gly Ala
        435                 440                 445
Gly Ser Gly Ala Gly Ala Gly Ser Gly Ala Gly Ala Gly Ser Gly Ala
    450                 455                 460
```

| | | | | | | | | | | | | | | | |
|---|---|---|---|---|---|---|---|---|---|---|---|---|---|---|---|
| Gly | Ala | Gly | Ser | Gly | Ala | Gly | Ala | Gly | Ser | Gly | Ala | Gly | Ala | Gly | Ser |
| 465 | | | | 470 | | | | 475 | | | | | | | 480 |
| Gly | Ala | Gly | Ala | Gly | Ser | Gly | Ala | Gly | Ala | Gly | Ser | Gly | Ala | Gly | Ala |
| | | | | 485 | | | | 490 | | | | | | 495 | |
| Gly | Ser | Gly | Ala | Ala | Val | Thr | Gly | Arg | Gly | Asp | Ser | Pro | Ala | Ser | Ala |
| | | | 500 | | | | | 505 | | | | | 510 | | |
| Ala | Gly | Tyr | Gly | Ala | Gly | Ala | Gly | Ser | Gly | Ala | Gly | Ala | Gly | Ser | Gly |
| | | 515 | | | | | 520 | | | | | | 525 | | |
| Ala | Gly | Ala | Gly | Ser | Gly | Ala | Gly | Ala | Gly | Ser | Gly | Ala | Gly | Ala | Gly |
| | 530 | | | | | | 535 | | | | | 540 | | | |
| Ser | Gly | Ala | Gly | Ala | Gly | Ser | Gly | Ala | Gly | Ala | Gly | Ser | Gly | Ala | Gly |
| 545 | | | | | 550 | | | | | 555 | | | | | 560 |
| Ala | Gly | Ser | Gly | Ala | Gly | Ala | Gly | Ser | Gly | Ala | Ala | Val | Thr | Gly | Arg |
| | | | | 565 | | | | | 570 | | | | | 575 | |
| Gly | Asp | Ser | Pro | Ala | Ser | Ala | Ala | Gly | Tyr | Gly | Ala | Gly | Ala | Gly | Ser |
| | | | 580 | | | | | 585 | | | | | | 590 | |
| Gly | Ala | Gly | Ala | Gly | Ser | Gly | Ala | Gly | Ala | Gly | Ser | Gly | Ala | Gly | Ala |
| | | 595 | | | | | | 600 | | | | | 605 | | |
| Gly | Ser | Gly | Ala | Gly | Ala | Gly | Ser | Gly | Ala | Gly | Ala | Gly | Ser | Gly | Ala |
| | 610 | | | | | 615 | | | | | 620 | | | | |
| Gly | Ala | Gly | Ser | Gly | Ala | Gly | Ala | Gly | Ser | Gly | Ala | Gly | Ala | Gly | Ser |
| 625 | | | | | 630 | | | | | 635 | | | | | 640 |
| Gly | Ala | Ala | Val | Thr | Gly | Arg | Gly | Asp | Ser | Pro | Ala | Ser | Ala | Ala | Gly |
| | | | | 645 | | | | | 650 | | | | | 655 | |
| Tyr | Gly | Ala | Gly | Ala | Gly | Ser | Gly | Ala | Gly | Ala | Gly | Ser | Gly | Ala | Gly |
| | | | 660 | | | | | 665 | | | | | 670 | | |
| Ala | Gly | Ser | Gly | Ala | Gly | Ala | Gly | Ser | Gly | Ala | Gly | Ala | Gly | Ser | Gly |
| | | 675 | | | | | 680 | | | | | 685 | | | |
| Ala | Gly | Ala | Gly | Ser | Gly | Ala | Gly | Ala | Gly | Ser | Gly | Ala | Gly | Ala | Gly |
| | 690 | | | | | | 695 | | | | | 700 | | | |
| Ser | Gly | Ala | Gly | Ala | Gly | Ser | Gly | Ala | Ala | Val | Thr | Gly | Arg | Gly | Asp |
| 705 | | | | | 710 | | | | | 715 | | | | | 720 |
| Ser | Pro | Ala | Ser | Ala | Ala | Gly | Tyr | Gly | Ala | Gly | Ala | Gly | Ser | Gly | Ala |
| | | | | 725 | | | | | 730 | | | | | 735 | |
| Gly | Ala | Gly | Ser | Gly | Ala | Gly | Ala | Met | Asp | Pro | Gly | Arg | Tyr | Gln | Leu |
| | | | 740 | | | | | 745 | | | | | 750 | | |
| Ser | Ala | Gly | Arg | Tyr | His | Tyr | Gln | Leu | Val | Trp | Cys | Gln | Lys | | |
| | | 755 | | | | | 760 | | | | | 765 | | | |

( 2 ) INFORMATION FOR SEQ ID NO:62:

( i ) SEQUENCE CHARACTERISTICS:
        ( A ) LENGTH: 51 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:62:

GTGCTGCGGA TGCTCGAGAT GGTGCATGCA TGTACATCCG AGTACTTCGA T    51

( 2 ) INFORMATION FOR SEQ ID NO:63:

( i ) SEQUENCE CHARACTERISTICS:
        ( A ) LENGTH: 47 base pairs
        ( B ) TYPE: nucleic acid
        ( C ) STRANDEDNESS: unknown (D) TOPOLOGY: unknown (ii) MOLECULE TYPE: DNA (genomic)

(xi) SEQUENCE DESCRIPTION: SEQ ID NO:63:

ATCGAAGTAC TCGGATGTAC ATGCATGCAC CATCTCGAGC ATCCGCA 47

(2) INFORMATION FOR SEQ ID NO:64:

(i) SEQUENCE CHARACTERISTICS:
(A) LENGTH: 24 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:64:

CTACATGTGT TACACATCCC GTGC 24

(2) INFORMATION FOR SEQ ID NO:65:

(i) SEQUENCE CHARACTERISTICS:
(A) LENGTH: 28 base pairs
(B) TYPE: nucleic acid
(C) STRANDEDNESS: unknown
(D) TOPOLOGY: unknown (ii) MOLECULE TYPE: DNA (genomic)

(xi) SEQUENCE DESCRIPTION: SEQ ID NO:65:

GCACGGGATG TGTAACACAT GTAGAGCC 28

(2) INFORMATION FOR SEQ ID NO:66:

(i) SEQUENCE CHARACTERISTICS:
(A) LENGTH: 1170 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:66:

```
Met  Asp  Pro  Val  Val  Leu  Gln  Arg  Arg  Asp  Trp  Glu  Asn  Pro  Gly  Val
 1                  5                        10                       15
Thr  Gln  Leu  Asn  Arg  Leu  Ala  Ala  His  Pro  Pro  Phe  Ala  Ser  Asp  Pro
               20                   25                        30
Met  Gly  Ala  Gly  Ser  Gly  Ala  Gly  Ala  Gly  Ser  Gly  Ala  Gly  Ala  Gly
          35                        40                   45
Ser  Gly  Val  Gly  Val  Pro  Gly  Val  Gly  Val  Pro  Gly  Val  Gly  Val  Pro
     50                             55                   60
Gly  Val  Gly  Val  Pro  Gly  Val  Gly  Val  Pro  Gly  Val  Gly  Val  Pro  Gly
 65                        70                        75                       80
Val  Gly  Val  Pro  Gly  Val  Gly  Val  Pro  Gly  Ala  Gly  Ala  Gly  Ser  Gly
                    85                        90                        95
Ala  Gly  Ala  Gly  Ser  Gly  Ala  Gly  Ala  Gly  Ser  Gly  Ala  Gly  Ala  Gly
              100                       105                       110
Ser  Gly  Ala  Gly  Ala  Gly  Ser  Gly  Ala  Gly  Ala  Gly  Ser  Gly  Ala  Gly
          115                       120                       125
Ala  Gly  Ser  Gly  Ala  Gly  Ala  Gly  Ser  Gly  Ala  Gly  Ala  Gly  Ser  Gly
          130                       135                       140
Ala  Gly  Ala  Gly  Ser  Gly  Ala  Gly  Ala  Gly  Ser  Gly  Ala  Gly  Ala  Gly
          145                       150                       155                 160
```

-continued

```
Ser  Gly  Ala  Ala  Val  Thr  Gly  Arg  Gly  Asp  Ser  Pro  Ala  Ser  Ala  Ala
                         165                 170                      175
Gly  Tyr  Gly  Ala  Gly  Ala  Gly  Ser  Gly  Ala  Gly  Ala  Gly  Ser  Gly  Ala
               180                 185                      190
Gly  Ala  Gly  Ser  Gly  Ala  Gly  Ala  Gly  Ser  Gly  Ala  Gly  Ala  Gly  Ser
               195                 200                      205
Gly  Val  Gly  Val  Pro  Gly  Val  Gly  Val  Pro  Gly  Val  Gly  Val  Pro  Gly
     210                      215                      220
Val  Gly  Val  Pro  Gly  Val  Gly  Val  Pro  Gly  Val  Gly  Val  Pro  Gly  Val
225                      230                      235                      240
Gly  Val  Pro  Gly  Val  Gly  Val  Pro  Gly  Ala  Gly  Ala  Gly  Ser  Gly  Ala
               245                      250                      255
Gly  Ala  Gly  Ser  Gly  Ala  Gly  Ala  Gly  Ser  Gly  Ala  Gly  Ala  Gly  Ser
               260                 265                      270
Gly  Ala  Gly  Ala  Gly  Ser  Gly  Ala  Gly  Ala  Gly  Ser  Gly  Ala  Gly  Ala
               275                 280                      285
Gly  Ser  Gly  Ala  Gly  Ala  Gly  Ser  Gly  Ala  Gly  Ala  Gly  Ser  Gly  Ala
     290                 295                      300
Gly  Ala  Gly  Ser  Gly  Ala  Gly  Ala  Gly  Ser  Gly  Ala  Gly  Ala  Gly  Ser
305                      310                 315                      320
Gly  Ala  Ala  Val  Thr  Gly  Arg  Gly  Asp  Ser  Pro  Ala  Ser  Ala  Ala  Gly
                    325                 330                      335
Tyr  Gly  Ala  Gly  Ala  Gly  Ser  Gly  Ala  Gly  Ala  Gly  Ser  Gly  Ala  Gly
               340                 345                      350
Ala  Gly  Ser  Gly  Ala  Gly  Ala  Gly  Ser  Gly  Ala  Gly  Ala  Gly  Ser  Gly
          355                 360                      365
Val  Gly  Val  Pro  Gly  Val  Gly  Val  Pro  Gly  Val  Gly  Val  Pro  Gly  Val
     370                      375                      380
Gly  Val  Pro  Gly  Val  Gly  Val  Pro  Gly  Val  Gly  Val  Pro  Gly  Val  Gly
385                      390                      395                      400
Val  Pro  Gly  Val  Gly  Val  Pro  Gly  Ala  Gly  Ala  Gly  Ser  Gly  Ala  Gly
               405                      410                      415
Ala  Gly  Ser  Gly  Ala  Gly  Ala  Gly  Ser  Gly  Ala  Gly  Ala  Gly  Ser  Gly
          420                 425                      430
Ala  Gly  Ala  Gly  Ser  Gly  Ala  Gly  Ala  Gly  Ser  Gly  Ala  Gly  Ala  Gly
          435                 440                      445
Ser  Gly  Ala  Gly  Ala  Gly  Ser  Gly  Ala  Gly  Ala  Gly  Ser  Gly  Ala  Gly
     450                 455                      460
Ala  Gly  Ser  Gly  Ala  Gly  Ala  Gly  Ser  Gly  Ala  Gly  Ala  Gly  Ser  Gly
465                      470                 475                      480
Ala  Ala  Val  Thr  Gly  Arg  Gly  Asp  Ser  Pro  Ala  Ser  Ala  Ala  Gly  Tyr
               485                 490                      495
Gly  Ala  Gly  Ala  Gly  Ser  Gly  Ala  Gly  Ala  Gly  Ser  Gly  Ala  Gly  Ala
               500                 505                      510
Gly  Ser  Gly  Ala  Gly  Ala  Gly  Ser  Gly  Ala  Gly  Ala  Gly  Ser  Gly  Val
          515                 520                      525
Gly  Val  Pro  Gly  Val  Gly  Val  Pro  Gly  Val  Gly  Val  Pro  Gly  Val  Gly
     530                      535                      540
Val  Pro  Gly  Val  Gly  Val  Pro  Gly  Val  Gly  Val  Pro  Gly  Val  Gly  Val
545                      550                      555                      560
Pro  Gly  Val  Gly  Val  Pro  Gly  Ala  Gly  Ala  Gly  Ser  Gly  Ala  Gly  Ala
               565                      570                      575
Gly  Ser  Gly  Ala  Gly  Ala  Gly  Ser  Gly  Ala  Gly  Ala  Gly  Ser  Gly  Ala
```

|     |     |     |     |     |     |     |     |     |     |     |     |     |
| --- | --- | --- | --- | --- | --- | --- | --- | --- | --- | --- | --- | --- |
|     |     | 580 |     |     |     | 585 |     |     |     | 590 |     |     |
| Gly | Ala | Gly | Ser | Gly | Ala | Gly | Ala | Gly | Ser | Gly | Ala | Gly | Ser |
|     |     |     | 595 |     |     |     | 600 |     |     |     | 605 |     |
| Gly | Ala | Gly | Ala | Gly | Ser | Gly | Ala | Gly | Ala | Gly | Ser | Gly | Ala | Gly | Ala |
|     |     | 610 |     |     |     | 615 |     |     |     | 620 |     |     |
| Gly | Ser | Gly | Ala | Gly | Ala | Gly | Ser | Gly | Ala | Gly | Ala | Gly | Ser | Gly | Ala |
| 625 |     |     |     | 630 |     |     |     | 635 |     |     |     | 640 |
| Ala | Val | Thr | Gly | Arg | Gly | Asp | Ser | Pro | Ala | Ser | Ala | Ala | Gly | Tyr | Gly |
|     |     |     |     | 645 |     |     |     | 650 |     |     |     |     | 655 |
| Ala | Gly | Ala | Gly | Ser | Gly | Ala | Gly | Ala | Gly | Ser | Gly | Ala | Gly | Ala | Gly |
|     |     |     | 660 |     |     |     | 665 |     |     |     | 670 |     |
| Ser | Gly | Ala | Gly | Ala | Gly | Ser | Gly | Ala | Gly | Ala | Gly | Ser | Gly | Val | Gly |
|     |     | 675 |     |     |     | 680 |     |     |     | 685 |     |     |
| Val | Pro | Gly | Val | Gly | Val | Pro | Gly | Val | Gly | Val | Pro | Gly | Val | Gly | Val |
|     | 690 |     |     |     | 695 |     |     |     | 700 |     |     |     |
| Pro | Gly | Val | Gly | Val | Pro | Gly | Val | Gly | Val | Pro | Gly | Val | Gly | Val | Pro |
| 705 |     |     |     | 710 |     |     |     | 715 |     |     |     | 720 |
| Gly | Val | Gly | Val | Pro | Gly | Ala | Gly | Ala | Gly | Ser | Gly | Ala | Gly | Ala | Gly |
|     |     |     |     | 725 |     |     |     | 730 |     |     |     | 735 |
| Ser | Gly | Ala | Gly | Ala | Gly | Ser | Gly | Ala | Gly | Ala | Gly | Ser | Gly | Ala | Gly |
|     |     |     | 740 |     |     |     | 745 |     |     |     | 750 |     |
| Ala | Gly | Ser | Gly | Ala | Gly | Ala | Gly | Ser | Gly | Ala | Gly | Ala | Gly | Ser | Gly |
|     |     | 755 |     |     |     | 760 |     |     |     | 765 |     |     |
| Ala | Gly | Ala | Gly | Ser | Gly | Ala | Gly | Ala | Gly | Ser | Gly | Ala | Gly | Ala | Gly |
|     |     | 770 |     |     |     | 775 |     |     |     | 780 |     |     |
| Ser | Gly | Ala | Gly | Ala | Gly | Ser | Gly | Ala | Gly | Ala | Gly | Ser | Gly | Ala | Ala |
| 785 |     |     |     | 790 |     |     |     | 795 |     |     |     | 800 |
| Val | Thr | Gly | Arg | Gly | Asp | Ser | Pro | Ala | Ser | Ala | Ala | Gly | Tyr | Gly | Ala |
|     |     |     | 805 |     |     |     | 810 |     |     |     | 815 |
| Gly | Ala | Gly | Ser | Gly | Ala | Gly | Ala | Gly | Ser | Gly | Ala | Gly | Ala | Gly | Ser |
|     |     |     | 820 |     |     |     | 825 |     |     |     | 830 |     |
| Gly | Ala | Gly | Ala | Gly | Ser | Gly | Ala | Gly | Ala | Gly | Ser | Gly | Val | Gly | Val |
|     |     | 835 |     |     |     | 840 |     |     |     | 845 |     |     |
| Pro | Gly | Val | Gly | Val | Pro | Gly | Val | Gly | Val | Pro | Gly | Val | Gly | Val | Pro |
| 850 |     |     |     | 855 |     |     |     | 860 |     |     |     |
| Gly | Val | Gly | Val | Pro | Gly | Val | Gly | Val | Pro | Gly | Val | Gly | Val | Pro | Gly |
| 865 |     |     |     | 870 |     |     |     | 875 |     |     |     | 880 |
| Val | Gly | Val | Pro | Gly | Ala | Gly | Ala | Gly | Ser | Gly | Ala | Gly | Ala | Gly | Ser |
|     |     |     | 885 |     |     |     | 890 |     |     |     | 895 |
| Gly | Ala | Gly | Ala | Gly | Ser | Gly | Ala | Gly | Ala | Gly | Ser | Gly | Ala | Gly | Ala |
|     |     |     | 900 |     |     |     | 905 |     |     |     | 910 |
| Gly | Ser | Gly | Ala | Gly | Ala | Gly | Ser | Gly | Ala | Gly | Ala | Gly | Ser | Gly | Ala |
|     |     |     | 915 |     |     |     | 920 |     |     |     | 925 |
| Gly | Ala | Gly | Ser | Gly | Ala | Gly | Ala | Gly | Ser | Gly | Ala | Gly | Ala | Gly | Ser |
|     |     | 930 |     |     |     | 935 |     |     |     | 940 |     |
| Gly | Ala | Gly | Ala | Gly | Ser | Gly | Ala | Gly | Ala | Gly | Ser | Gly | Ala | Ala | Val |
| 945 |     |     |     | 950 |     |     |     | 955 |     |     |     | 960 |
| Thr | Gly | Arg | Gly | Asp | Ser | Pro | Ala | Ser | Ala | Ala | Gly | Tyr | Gly | Ala | Gly |
|     |     |     | 965 |     |     |     | 970 |     |     |     | 975 |
| Ala | Gly | Ser | Gly | Ala | Gly | Ala | Gly | Ser | Gly | Ala | Gly | Ala | Gly | Ser | Gly |
|     |     |     | 980 |     |     |     | 985 |     |     |     | 990 |
| Ala | Gly | Ala | Gly | Ser | Gly | Ala | Gly | Ala | Gly | Ser | Gly | Val | Gly | Val | Pro |
|     |     | 995 |     |     |     | 1000|     |     |     | 1005|     |     |

Gly Val Gly Val Pro Gly Val Gly Val Pro Gly Val Gly Val Pro Gly
                1010                    1015                    1020

Val Gly Val Pro Gly Val Gly Val Pro Gly Val Gly Val Pro Gly Val
1025                    1030                    1035                    1040

Gly Val Pro Gly Ala Gly Ala Gly Ser Gly Ala Gly Ala Gly Ser Gly
                1045                    1050                    1055

Ala Gly Ala Gly Ser Gly Ala Gly Ala Gly Ser Gly Ala Gly Ala Gly
                1060                    1065                    1070

Ser Gly Ala Gly Ala Gly Ser Gly Ala Gly Ala Gly Ser Gly Ala Gly
                1075                    1080                    1085

Ala Gly Ser Gly Ala Gly Ala Gly Ser Gly Ala Gly Ala Gly Ser Gly
                1090                    1095                    1100

Ala Gly Ala Gly Ser Gly Ala Gly Ala Gly Ser Gly Ala Ala Val Thr
1105                    1110                    1115                    1120

Gly Arg Gly Asp Ser Pro Ala Ser Ala Ala Gly Tyr Gly Ala Gly Ala
                1125                    1130                    1135

Gly Ser Gly Ala Gly Ala Gly Ser Gly Ala Gly Ala Met Asp Pro Gly
                1140                    1145                    1150

Arg Tyr Gln Leu Ser Ala Gly Arg Tyr His Tyr Gln Leu Val Trp Cys
                1155                    1160                    1165

Gln Lys
1170

( 2 ) INFORMATION FOR SEQ ID NO:67:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:67:

GCTATGTTTA AACCACGTGT TCGCGATCCG GGTGCCGATC CAGGCCTGCG ATATCAGTAC     60

GTA     63

( 2 ) INFORMATION FOR SEQ ID NO:68:

( i ) SEQUENCE CHARACTERISTICS:
        ( A ) LENGTH: 63 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:68:

TACGTACTGA TATCGCAGGC CTGGATCGGC ACCCGGATCG CGAACACGTG GTTTAAACAT     60

AGC     63

( 2 ) INFORMATION FOR SEQ ID NO:69:

( i ) SEQUENCE CHARACTERISTICS:
        ( A ) LENGTH: 21 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:69:

| Ala | Met | Phe | Lys | Pro | Arg | Val | Arg | Asp | Pro | Gly | Ala | Asp | Pro | Gly | Leu |
|---|---|---|---|---|---|---|---|---|---|---|---|---|---|---|---|
| 1 | | | | 5 | | | | | 10 | | | | | 15 | |

| Arg | Tyr | Gln | Tyr | Val |
|---|---|---|---|---|
| | | | | 20 |

( 2 ) INFORMATION FOR SEQ ID NO:70:

( i ) SEQUENCE CHARACTERISTICS:
        ( A ) LENGTH: 226 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:70:

```
ATGGCAGCGA   AAGGGGACCG   GTGCCCCGGG   TACTCCTGGT   CCACAAGGTC   TGCCGGGAAG        60
CCCAGGGGCT   CCGGGTACTC   CAGGTCCGCA   AGGCCTGCCG   GGTTCACCGG   GTGCTCCGGG       120
AACTCCTGGC   CCGCAGGGCT   TGCCGGGATC   CCCAGGTGCA   CCAGGAACGC   CGGGACCTCA       180
GGGTCTTCCG   GGTAGCCCTG   GTGCCTTTCC   GCTAAAGTCC   TGCCGT                        226
```

( 2 ) INFORMATION FOR SEQ ID NO:71:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:71:

```
AAGAAGGAGA   TATCATATGG   CAGCGAAAGG   GGACC                                       35
```

( 2 ) INFORMATION FOR SEQ ID NO:72:

( i ) SEQUENCE CHARACTERISTICS:
        ( A ) LENGTH: 37 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:72:

```
CGCAGATCTT   TAAATTACGG   CAGGACTTTA   GCGGAAA                                     37
```

( 2 ) INFORMATION FOR SEQ ID NO:73:

( i ) SEQUENCE CHARACTERISTICS:
        ( A ) LENGTH: 186 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:73:

```
GGTGCCCCGG   GTACTCCTGG   TCCACAAGGT   CTGCCGGGAA   GCCCAGGGGC   TCCGGGTACT        60
CCAGGTCCGC   AAGGCCTGCC   GGGTTCACCG   GGTGCTCCGG   GAACTCCTGG   CCCGCAGGGC       120
TTGCCGGGAT   CCCCAGGTGC   ACCAGGAACG   CCGGGACCTC   AGGGTCTTCC   GGGTAGCCCT       180
GGTGCC                                                                             186
```

( 2 ) INFORMATION FOR SEQ ID NO:74:

(  i  ) SEQUENCE CHARACTERISTICS:
    ( A ) LENGTH: 61 amino acids
    ( B ) TYPE: amino acid
    ( C ) STRANDEDNESS: unknown
    ( D ) TOPOLOGY: unknown (  i i  ) MOLECULE TYPE: protein (  i x  ) FEATURE:
    ( A ) NAME/KEY: Modified-site
    ( B ) LOCATION: 60..61
    ( D ) OTHER INFORMATION: /note= "The 'X'at position 61
        represents either Glycine or Alanine."

( x i ) SEQUENCE DESCRIPTION: SEQ ID NO:74:

```
Gly Ala Pro Gly Thr Pro Gly Pro Gln Gly Leu Pro Gly Ser Pro Gly
 1               5                  10                  15

Ala Pro Gly Thr Pro Gly Pro Gln Gly Leu Pro Gly Ser Pro Gly Ala
             20                  25                  30

Pro Gly Thr Pro Gly Pro Gln Gly Leu Pro Gly Ser Pro Gly Ala Pro
         35                  40                  45

Gly Thr Pro Gly Pro Gln Gly Leu Pro Gly Ser Pro Xaa
     50                  55                  60
```

( 2 ) INFORMATION FOR SEQ ID NO:75:

(  i  ) SEQUENCE CHARACTERISTICS:
    ( A ) LENGTH: 837 amino acids
    ( B ) TYPE: amino acid
    ( C ) STRANDEDNESS: unknown
    ( D ) TOPOLOGY: unknown (  i i  ) MOLECULE TYPE: protein ( x i ) SEQUENCE DESCRIPTION: SEQ ID NO:75:

```
Met Asp Pro Val Val Leu Gln Arg Arg Asp Trp Glu Asn Pro Gly Val
 1               5                  10                  15

Thr Gln Leu Asn Arg Leu Ala Ala His Pro Pro Phe Ala Ser Asp Pro
             20                  25                  30

Met Gly Ala Pro Gly Thr Pro Gly Pro Gln Gly Leu Pro Gly Ser Pro
         35                  40                  45

Gly Ala Pro Gly Thr Pro Gly Pro Gln Gly Leu Pro Gly Ser Pro Gly
     50                  55                  60

Ala Pro Gly Thr Pro Gly Pro Gln Gly Leu Pro Gly Ser Pro Gly Ala
 65                  70                  75                  80

Pro Gly Thr Pro Gly Pro Gln Gly Leu Pro Gly Ser Pro Gly Ala Pro
             85                  90                  95

Gly Thr Pro Gly Pro Gln Gly Leu Pro Gly Ser Pro Gly Ala Pro Gly
         100                 105                 110

Thr Pro Gly Pro Gln Gly Leu Pro Gly Ser Pro Gly Ala Pro Gly Thr
     115                 120                 125

Pro Gly Pro Gln Gly Leu Pro Gly Ser Pro Gly Ala Pro Gly Thr Pro
     130                 135                 140

Gly Pro Gln Gly Leu Pro Gly Ser Pro Gly Ala Pro Gly Thr Pro Gly
145                 150                 155                 160

Pro Gln Gly Leu Pro Gly Ser Pro Gly Ala Pro Gly Thr Pro Gly Pro
             165                 170                 175

Gln Gly Leu Pro Gly Ser Pro Gly Ala Pro Gly Thr Pro Gly Pro Gln
         180                 185                 190

Gly Leu Pro Gly Ser Pro Gly Ala Pro Gly Thr Pro Gly Pro Gln Gly
     195                 200                 205
```

-continued

| | | | | | | | | | | | | | |
|---|---|---|---|---|---|---|---|---|---|---|---|---|---|
| Leu | Pro 210 | Gly | Ser | Pro | Gly | Ala 215 | Pro | Gly | Thr | Pro | Gly 220 | Pro | Gln | Gly | Leu |
| Pro 225 | Gly | Ser | Pro | Gly | Ala 230 | Pro | Gly | Thr | Pro | Gly 235 | Pro | Gln | Gly | Leu | Pro 240 |
| Gly | Ser | Pro | Gly | Ala 245 | Pro | Gly | Thr | Pro | Gly 250 | Pro | Gln | Gly | Leu | Pro | Gly 255 |
| Ser | Pro | Gly | Ala 260 | Pro | Gly | Thr | Pro | Gly 265 | Pro | Gln | Gly | Leu | Pro 270 | Gly | Ser |
| Pro | Gly | Ala 275 | Pro | Gly | Thr | Pro | Gly 280 | Pro | Gln | Gly | Leu | Pro 285 | Gly | Ser | Pro |
| Gly | Ala 290 | Pro | Gly | Thr | Pro | Gly 295 | Pro | Gln | Gly | Leu | Pro 300 | Gly | Ser | Pro | Gly |
| Ala 305 | Pro | Gly | Thr | Pro | Gly 310 | Pro | Gln | Gly | Leu | Pro 315 | Gly | Ser | Pro | Gly | Ala 320 |
| Pro | Gly | Thr | Pro | Gly 325 | Pro | Gln | Gly | Leu | Pro 330 | Gly | Ser | Pro | Gly | Ala | Pro 335 |
| Gly | Thr | Pro | Gly 340 | Pro | Gln | Gly | Leu | Pro 345 | Gly | Ser | Pro | Gly | Ala | Pro | Gly 350 |
| Thr | Pro | Gly 355 | Pro | Gln | Gly | Leu | Pro 360 | Gly | Ser | Pro | Gly | Ala | Pro 365 | Gly | Thr |
| Pro | Gly 370 | Pro | Gln | Gly | Leu | Pro 375 | Gly | Ser | Pro | Gly | Ala | Pro 380 | Gly | Thr | Pro |
| Gly 385 | Pro | Gln | Gly | Leu | Pro 390 | Gly | Ser | Pro | Gly | Ala | Pro 395 | Gly | Thr | Pro | Gly 400 |
| Pro | Gln | Gly | Leu | Pro 405 | Gly | Ser | Pro | Gly | Ala | Pro 410 | Gly | Thr | Pro | Gly | Pro 415 |
| Gln | Gly | Leu | Pro 420 | Gly | Ser | Pro | Gly | Ala | Pro 425 | Gly | Thr | Pro | Gly | Pro | Gln 430 |
| Gly | Leu | Pro 435 | Gly | Ser | Pro | Gly | Ala | Pro 440 | Gly | Thr | Pro | Gly | Pro | Gln 445 | Gly |
| Leu | Pro 450 | Gly | Ser | Pro | Gly | Ala 455 | Pro | Gly | Thr | Pro | Gly 460 | Pro | Gln | Gly | Leu |
| Pro 465 | Gly | Ser | Pro | Gly | Ala 470 | Pro | Gly | Thr | Pro | Gly 475 | Pro | Gln | Gly | Leu | Pro 480 |
| Gly | Ser | Pro | Gly | Ala 485 | Pro | Gly | Thr | Pro | Gly 490 | Pro | Gln | Gly | Leu | Pro | Gly 495 |
| Ser | Pro | Gly | Ala 500 | Pro | Gly | Thr | Pro | Gly 505 | Pro | Gln | Gly | Leu | Pro 510 | Gly | Ser |
| Pro | Gly | Ala 515 | Pro | Gly | Thr | Pro | Gly 520 | Pro | Gln | Gly | Leu | Pro 525 | Gly | Ser | Pro |
| Gly | Ala 530 | Pro | Gly | Thr | Pro | Gly 535 | Pro | Gln | Gly | Leu | Pro 540 | Gly | Ser | Pro | Gly |
| Ala 545 | Pro | Gly | Thr | Pro | Gly 550 | Pro | Gln | Gly | Leu | Pro 555 | Gly | Ser | Pro | Gly | Ala 560 |
| Pro | Gly | Thr | Pro | Gly 565 | Pro | Gln | Gly | Leu | Pro 570 | Gly | Ser | Pro | Gly | Ala | Pro 575 |
| Gly | Thr | Pro | Gly 580 | Pro | Gln | Gly | Leu | Pro 585 | Gly | Ser | Pro | Gly | Ala | Pro | Gly 590 |
| Thr | Pro | Gly 595 | Pro | Gln | Gly | Leu | Pro 600 | Gly | Ser | Pro | Gly | Ala | Pro 605 | Gly | Thr |
| Pro | Gly 610 | Pro | Gln | Gly | Leu | Pro 615 | Gly | Ser | Pro | Gly | Ala | Pro 620 | Gly | Thr | Pro |
| Gly | Pro | Gln | Gly | Leu | Pro | Gly | Ser | Pro | Gly | Ala | Pro | Gly | Thr | Pro | Gly |

-continued

```
        625                     630                      635                      640
    Pro  Gln  Gly  Leu  Pro  Gly  Ser  Pro  Gly  Ala  Pro  Gly  Thr  Pro  Gly  Pro
                        645                      650                      655
    Gln  Gly  Leu  Pro  Gly  Ser  Pro  Gly  Ala  Pro  Gly  Thr  Pro  Gly  Pro  Gln
                   660                      665                      670
    Gly  Leu  Pro  Gly  Ser  Pro  Gly  Ala  Pro  Gly  Thr  Pro  Gly  Pro  Gln  Gly
              675                      680                      685
    Leu  Pro  Gly  Ser  Pro  Gly  Ala  Pro  Gly  Thr  Pro  Gly  Pro  Gln  Gly  Leu
         690                      695                      700
    Pro  Gly  Ser  Pro  Gly  Ala  Pro  Gly  Thr  Pro  Gly  Pro  Gln  Gly  Leu  Pro
    705                      710                      715                      720
    Gly  Ser  Pro  Gly  Ala  Pro  Gly  Thr  Pro  Gly  Pro  Gln  Gly  Leu  Pro  Gly
                        725                      730                      735
    Ser  Pro  Gly  Ala  Pro  Gly  Thr  Pro  Gly  Pro  Gln  Gly  Leu  Pro  Gly  Ser
                   740                      745                      750
    Pro  Gly  Ala  Pro  Gly  Thr  Pro  Gly  Pro  Gln  Gly  Leu  Pro  Gly  Ser  Pro
              755                      760                      765
    Gly  Ala  Pro  Gly  Thr  Pro  Gly  Pro  Gln  Gly  Leu  Pro  Gly  Ser  Pro  Gly
         770                      775                      780
    Ala  Pro  Gly  Thr  Pro  Gly  Pro  Gln  Gly  Leu  Pro  Gly  Ser  Pro  Gly  Ala
    785                      790                      795                      800
    Pro  Gly  Thr  Pro  Gly  Pro  Gln  Gly  Leu  Pro  Gly  Ser  Pro  Gly  Ala  Met
                        805                      810                      815
    Asp  Pro  Gly  Arg  Tyr  Gln  Leu  Ser  Ala  Gly  Arg  Tyr  His  Tyr  Gln  Leu
                   820                      825                      830
    Val  Trp  Cys  Gln  Lys
                   835
```

( 2 ) INFORMATION FOR SEQ ID NO:76:

( i ) SEQUENCE CHARACTERISTICS:
        ( A ) LENGTH: 417 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:76:

```
    Met  Asp  Pro  Val  Val  Leu  Gln  Arg  Arg  Asp  Trp  Glu  Asn  Pro  Gly  Val
    1                   5                        10                       15
    Thr  Gln  Leu  Asn  Arg  Leu  Ala  Ala  His  Pro  Pro  Phe  Ala  Ser  Asp  Pro
                   20                       25                       30
    Met  Gly  Ala  Pro  Gly  Thr  Pro  Gly  Pro  Gln  Gly  Leu  Pro  Gly  Ser  Pro
              35                       40                       45
    Gly  Ala  Pro  Gly  Thr  Pro  Gly  Pro  Gln  Gly  Leu  Pro  Gly  Ser  Pro  Gly
         50                       55                       60
    Ala  Pro  Gly  Thr  Pro  Gly  Pro  Gln  Gly  Leu  Pro  Gly  Ser  Pro  Gly  Ala
    65                       70                       75                       80
    Pro  Gly  Thr  Pro  Gly  Pro  Gln  Gly  Leu  Pro  Gly  Ser  Pro  Gly  Ala  Pro
                        85                       90                       95
    Gly  Thr  Pro  Gly  Pro  Gln  Gly  Leu  Pro  Gly  Ser  Pro  Gly  Ala  Pro  Gly
                   100                      105                      110
    Thr  Pro  Gly  Pro  Gln  Gly  Leu  Pro  Gly  Ser  Pro  Gly  Ala  Pro  Gly  Thr
              115                      120                      125
    Pro  Gly  Pro  Gln  Gly  Leu  Pro  Gly  Ser  Pro  Gly  Ala  Pro  Gly  Thr  Pro
         130                      135                      140
```

Gly Pro Gln Gly Leu Pro Gly Ser Pro Gly Ala Pro Gly Thr Pro Gly
145                 150                 155                 160

Pro Gln Gly Leu Pro Gly Ser Pro Gly Ala Pro Gly Thr Pro Gly Pro
            165                 170                 175

Gln Gly Leu Pro Gly Ser Pro Gly Ala Pro Gly Thr Pro Gly Pro Gln
        180                 185                 190

Gly Leu Pro Gly Ser Pro Gly Ala Pro Gly Thr Pro Gly Pro Gln Gly
    195                 200                 205

Leu Pro Gly Ser Pro Gly Ala Pro Gly Thr Pro Gly Pro Gln Gly Leu
    210                 215                 220

Pro Gly Ser Pro Gly Ala Pro Gly Thr Pro Gly Pro Gln Gly Leu Pro
225                 230                 235                 240

Gly Ser Pro Gly Ala Pro Gly Thr Pro Gly Pro Gln Gly Leu Pro Gly
            245                 250                 255

Ser Pro Gly Ala Pro Gly Thr Pro Gly Pro Gln Gly Leu Pro Gly Ser
        260                 265                 270

Pro Gly Ala Pro Gly Thr Pro Gly Pro Gln Gly Leu Pro Gly Ser Pro
    275                 280                 285

Gly Ala Pro Gly Thr Pro Gly Pro Gln Gly Leu Pro Gly Ser Pro Gly
290                 295                 300

Ala Pro Gly Thr Pro Gly Pro Gln Gly Leu Pro Gly Ser Pro Gly Ala
305                 310                 315                 320

Pro Gly Thr Pro Gly Pro Gln Gly Leu Pro Gly Ser Pro Gly Ala Pro
            325                 330                 335

Gly Thr Pro Gly Pro Gln Gly Leu Pro Gly Ser Pro Gly Ala Pro Gly
        340                 345                 350

Thr Pro Gly Pro Gln Gly Leu Pro Gly Ser Pro Gly Ala Pro Gly Thr
    355                 360                 365

Pro Gly Pro Gln Gly Leu Pro Gly Ser Pro Gly Ala Pro Gly Thr Pro
    370                 375                 380

Gly Pro Gln Gly Leu Pro Gly Ser Pro Gly Ala Met Asp Pro Gly Arg
385                 390                 395                 400

Tyr Gln Leu Ser Ala Gly Arg Tyr His Tyr Gln Leu Val Trp Cys Gln
                405                 410                 415

Lys ( 2 ) INFORMATION FOR SEQ ID NO:77:

( i ) SEQUENCE CHARACTERISTICS:
        ( A ) LENGTH: 15 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:77:

Gly Ala Pro Gly Thr Pro Gly Pro Gln Gly Leu Pro Gly Ser Pro
1               5                   10                  15

( 2 ) INFORMATION FOR SEQ ID NO:78:

( i ) SEQUENCE CHARACTERISTICS:
        ( A ) LENGTH: 71 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:78:

```
Gly Ala Pro Gly Thr Pro Gly Pro Gln Gly Leu Pro Gly Ser Pro Gly
1               5                   10                  15

Ala Pro Gly Thr Pro Gly Pro Gln Gly Leu Pro Gly Ser Pro Gly Ala
                20                  25                  30

Pro Gly Thr Pro Gly Pro Gln Gly Leu Pro Gly Ser Pro Gly Ala Pro
            35                  40                  45

Gly Thr Pro Gly Glu Gly Gln Gln His His Leu Gly Gly Ala Lys Gln
        50              55                  60

Ala Gly Asp Val Gly Ser Pro
65              70
```

( 2 ) INFORMATION FOR SEQ ID NO:79:

( i ) SEQUENCE CHARACTERISTICS:
        ( A ) LENGTH: 123 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:79:

```
ATGGCAGCGA AAGGGGACCG TGCACCAGGA ACGCCGGGAG AAGGTCAACA GCACCATCTT        60
GGTGGAGCGA AACAGGCAGG CGACGTCGGT AGCCCTGGTG CCTTTCCGCT AAAGTCCTGC       120
CGT                                                                    123
```

( 2 ) INFORMATION FOR SEQ ID NO:80:

( i ) SEQUENCE CHARACTERISTICS:
        ( A ) LENGTH: 219 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:80:

```
GGTGCCCCGG GTACTCCTGG TCCACAAGGT CTGCCGGGAA GCCCAGGGGC TCCGGGTACT        60
CCAGGTCCGC AAGGCCTGCC GGGTTCACCG GGTGCTCCGG GAACTCCTGG CCCGCAGGGC       120
TTGCCGGGAT CCCCAGGTGC ACCAGGAACG CCGGGAGAAG GTCAACAGCA CCATCTTGGT       180
GGAGCGAAAC AGGCAGGCGA CGTCGGTAGC CCTGGTGCC                              219
```

( 2 ) INFORMATION FOR SEQ ID NO:81:

( i ) SEQUENCE CHARACTERISTICS:
        ( A ) LENGTH: 72 amino acids
        ( B ) TYPE: amino acid
        ( C ) STRANDEDNESS: unknown
        ( D ) TOPOLOGY: unknown ( i i ) MOLECULE TYPE: protein ( i x ) FEATURE:
        ( A ) NAME/KEY: Modified-site
        ( B ) LOCATION: 71..72
        ( D ) OTHER INFORMATION: /note= "The 'X'at position 72
            represents either Glycine or Alanine."

( x i ) SEQUENCE DESCRIPTION: SEQ ID NO:81:

```
Gly Ala Pro Gly Thr Pro Gly Pro Gln Gly Leu Pro Gly Ser Pro Gly
1               5                   10                  15
```

| Ala | Pro | Gly | Thr | Pro | Gly | Pro | Gln | Gly | Leu | Pro | Gly | Ser | Pro | Gly | Ala |
|---|---|---|---|---|---|---|---|---|---|---|---|---|---|---|---|
| | | | 20 | | | | 25 | | | | | | 30 | | |

| Pro | Gly | Thr | Pro | Gly | Pro | Gln | Gly | Leu | Pro | Gly | Ser | Pro | Gly | Ala | Pro |
|---|---|---|---|---|---|---|---|---|---|---|---|---|---|---|---|
| | | 35 | | | | 40 | | | | | | 45 | | | |

| Gly | Thr | Pro | Gly | Glu | Gly | Gln | Gln | His | His | Leu | Gly | Gly | Ala | Lys | Gln |
|---|---|---|---|---|---|---|---|---|---|---|---|---|---|---|---|
| | 50 | | | | | 55 | | | | | 60 | | | | |

| Ala | Gly | Asp | Val | Gly | Ser | Pro | Xaa |
|---|---|---|---|---|---|---|---|
| 65 | | | | | 70 | | |

( 2 ) INFORMATION FOR SEQ ID NO:82:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:82:

GATCTTCGAT CTCATCACCA TCACCATCAC TA         32

( 2 ) INFORMATION FOR SEQ ID NO:83:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:83:

AGTTAGTGAT GGTGATGGTG ATGAGATCGA A         31

( 2 ) INFORMATION FOR SEQ ID NO:84:

( i ) SEQUENCE CHARACTERISTICS:
        ( A ) LENGTH: 761 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:84:

| Met | Asp | Pro | Val | Val | Leu | Gln | Arg | Arg | Asp | Trp | Glu | Asn | Pro | Gly | Val |
|---|---|---|---|---|---|---|---|---|---|---|---|---|---|---|---|
| 1 | | | | 5 | | | | | 10 | | | | | 15 | |

| Thr | Gln | Asn | Arg | Leu | Ala | Ala | His | Pro | Pro | Phe | Ala | Ser | Asp | Pro | Met |
|---|---|---|---|---|---|---|---|---|---|---|---|---|---|---|---|
| | | | 20 | | | | 25 | | | | | | 30 | | |

| Gly | Ala | Pro | Gly | Thr | Pro | Gly | Pro | Gln | Gly | Leu | Pro | Gly | Ser | Pro | Gly |
|---|---|---|---|---|---|---|---|---|---|---|---|---|---|---|---|
| | | | 35 | | | | 40 | | | | | 45 | | | |

| Ala | Pro | Gly | Thr | Pro | Gly | Pro | Gln | Gly | Leu | Pro | Gly | Ser | Pro | Gly | Ala |
|---|---|---|---|---|---|---|---|---|---|---|---|---|---|---|---|
| | | 50 | | | | | 55 | | | | | 60 | | | |

| Pro | Gly | Thr | Pro | Gly | Pro | Gln | Gly | Leu | Pro | Gly | Ser | Pro | Gly | Ala | Pro |
|---|---|---|---|---|---|---|---|---|---|---|---|---|---|---|---|
| 65 | | | | | 70 | | | | | 75 | | | | | 80 |

| Gly | Thr | Pro | Gly | Glu | Gly | Gln | Gln | His | His | Leu | Gly | Gly | Ala | Lys | Gln |
|---|---|---|---|---|---|---|---|---|---|---|---|---|---|---|---|
| | | | | 85 | | | | | 90 | | | | | 95 | |

| Ala | Gly | Asp | Val | Gly | Ser | Pro | Gly | Ala | Pro | Gly | Thr | Pro | Gly | Pro | Gln |
|---|---|---|---|---|---|---|---|---|---|---|---|---|---|---|---|
| | | | | 100 | | | | | 105 | | | | | 110 | |

| Gly | Leu | Pro | Gly | Ser | Pro | Gly | Ala | Pro | Gly | Thr | Pro | Gly | Pro | Gln | Gly |
|---|---|---|---|---|---|---|---|---|---|---|---|---|---|---|---|
| | | | 115 | | | | | 120 | | | | | 125 | | |

| Leu | Pro | Gly | Ser | Pro | Gly | Ala | Pro | Gly | Thr | Pro | Gly | Pro | Gln | Gly | Leu |
|---|---|---|---|---|---|---|---|---|---|---|---|---|---|---|---|

-continued

|     |     |     |     | 130 |     |     |     | 135 |     |     |     | 140 |     |     |
| --- | --- | --- | --- | --- | --- | --- | --- | --- | --- | --- | --- | --- | --- | --- |
| Pro<br>145 | Gly | Ser | Pro | Gly<br>150 | Ala | Pro | Gly | Thr<br>155 | Pro | Gly | Glu | Gly<br>160 | Gln | Gln | His |
| His | Leu | Gly | Gly | Ala<br>165 | Lys | Gln | Ala | Gly<br>170 | Asp | Val | Gly | Ser | Pro<br>175 | Gly | Ala |
| Pro | Gly | Thr | Pro<br>180 | Gly | Pro | Gln | Gly | Leu<br>185 | Pro | Gly | Ser | Pro | Gly<br>190 | Ala | Pro |
| Gly | Thr | Pro<br>195 | Gly | Pro | Gln | Gly | Leu<br>200 | Pro | Gly | Ser | Pro | Gly<br>205 | Ala | Pro | Gly |
| Thr | Pro<br>210 | Gly | Pro | Gln | Gly | Leu<br>215 | Pro | Gly | Ser | Pro | Gly<br>220 | Ala | Pro | Gly | Thr |
| Pro<br>225 | Gly | Glu | Gly | Gln | Gln<br>230 | His | His | Leu | Gly | Gly<br>235 | Ala | Lys | Gln | Ala | Gly<br>240 |
| Asp | Val | Gly | Ser | Pro<br>245 | Gly | Ala | Pro | Gly | Thr<br>250 | Pro | Gly | Pro | Gln | Gly<br>255 | Leu |
| Pro | Gly | Ser | Pro<br>260 | Gly | Ala | Pro | Gly | Thr<br>265 | Pro | Gly | Pro | Gln | Gly<br>270 | Leu | Pro |
| Gly | Ser | Pro<br>275 | Gly | Ala | Pro | Gly | Thr<br>280 | Pro | Gly | Pro | Gln | Gly<br>285 | Leu | Pro | Gly |
| Ser | Pro<br>290 | Gly | Ala | Pro | Gly | Thr<br>295 | Pro | Gly | Glu | Gly | Gln<br>300 | Gln | His | His | Leu |
| Gly<br>305 | Gly | Ala | Lys | Gln | Ala<br>310 | Gly | Asp | Val | Gly | Ser<br>315 | Pro | Gly | Ala | Pro | Gly<br>320 |
| Thr | Pro | Gly | Pro | Gln<br>325 | Gly | Leu | Pro | Gly | Ser<br>330 | Pro | Gly | Ala | Pro | Gly<br>335 | Thr |
| Pro | Gly | Pro | Gln<br>340 | Gly | Leu | Pro | Gly | Ser<br>345 | Pro | Gly | Ala | Pro | Gly<br>350 | Thr | Pro |
| Gly | Pro | Gln<br>355 | Gly | Leu | Pro | Gly | Ser<br>360 | Pro | Gly | Ala | Pro | Gly<br>365 | Thr | Pro | Gly |
| Glu | Gly<br>370 | Gln | Gln | His | His | Leu<br>375 | Gly | Gly | Ala | Lys | Gln<br>380 | Ala | Gly | Asp | Val |
| Gly<br>385 | Ser | Pro | Gly | Ala | Pro<br>390 | Gly | Thr | Pro | Gly | Pro<br>395 | Gln | Gly | Leu | Pro | Gly<br>400 |
| Ser | Pro | Gly | Ala | Pro<br>405 | Gly | Thr | Pro | Gly | Pro<br>410 | Gln | Gly | Leu | Pro | Gly<br>415 | Ser |
| Pro | Gly | Ala | Pro<br>420 | Gly | Thr | Pro | Gly | Pro<br>425 | Gln | Gly | Leu | Pro | Gly<br>430 | Ser | Pro |
| Gly | Ala | Pro<br>435 | Gly | Thr | Pro | Gly | Glu<br>440 | Gly | Gln | Gln | His | His<br>445 | Leu | Gly | Gly |
| Ala | Lys<br>450 | Gln | Ala | Gly | Asp | Val<br>455 | Gly | Ser | Pro | Gly | Ala<br>460 | Pro | Gly | Thr | Pro |
| Gly<br>465 | Pro | Gln | Gly | Leu | Pro<br>470 | Gly | Ser | Pro | Gly | Ala<br>475 | Pro | Gly | Thr | Pro | Gly<br>480 |
| Pro | Gln | Gly | Leu | Pro<br>485 | Gly | Ser | Pro | Gly | Ala<br>490 | Pro | Gly | Thr | Pro | Gly<br>495 | Pro |
| Gln | Gly | Leu | Pro<br>500 | Gly | Ser | Pro | Gly | Ala<br>505 | Pro | Gly | Thr | Pro | Gly<br>510 | Glu | Gly |
| Gln | Gln | His | His<br>515 | Leu | Gly | Gly | Ala | Lys<br>520 | Gln | Ala | Gly | Asp | Val<br>525 | Gly | Ser |
| Pro | Gly | Ala<br>530 | Pro | Gly | Thr | Pro | Gly<br>535 | Pro | Gln | Gly | Leu | Pro<br>540 | Gly | Ser | Pro |
| Gly<br>545 | Ala | Pro | Gly | Thr | Pro<br>550 | Gly | Pro | Gln | Gly | Leu<br>555 | Pro | Gly | Ser | Pro | Gly<br>560 |

-continued

```
Ala Pro Gly Thr Pro Gly Pro Gln Gly Leu Pro Gly Ser Pro Gly Ala
            565             570                 575

Pro Gly Thr Pro Gly Glu Gly Gln Gln His His Leu Gly Gly Ala Lys
            580             585                 590

Gln Ala Gly Asp Val Gly Ser Pro Gly Ala Pro Gly Thr Pro Gly Pro
            595             600             605

Gln Gly Leu Pro Gly Ser Pro Gly Ala Pro Gly Thr Pro Gly Pro Gln
        610             615             620

Gly Leu Pro Gly Ser Pro Gly Ala Pro Gly Thr Pro Gly Pro Gln Gly
625                 630             635                 640

Leu Pro Gly Ser Pro Gly Ala Pro Gly Thr Pro Gly Glu Gly Gln Gln
                645             650                 655

His His Leu Gly Gly Ala Lys Gln Ala Gly Asp Val Gly Ser Pro Gly
            660             665             670

Ala Pro Gly Thr Pro Gly Pro Gln Gly Leu Pro Gly Ser Pro Gly Ala
            675             680             685

Pro Gly Thr Pro Gly Pro Gln Gly Leu Pro Gly Ser Pro Gly Ala Pro
    690             695             700

Gly Thr Pro Gly Pro Gln Gly Leu Pro Gly Ser Pro Gly Ala Pro Gly
705             710             715                 720

Thr Pro Gly Glu Gly Gln Gln His His Leu Gly Gly Ala Lys Gln Ala
            725             730                 735

Gly Asp Val Gly Ser Pro Gly Ala Met Asp Pro Gly Arg Tyr Gln Asp
            740             745             750

Leu Arg Ser His His His His His His
            755             760
```

(2) INFORMATION FOR SEQ ID NO:85:

(i) SEQUENCE CHARACTERISTICS:
(A) LENGTH: 64 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:85:

```
Gly Ala Gly Ala Gly Ser Gly Ala Gly Ala Gly Ser Gly Ala Gly Ala
1               5                   10                  15

Gly Ser Gly Ala Gly Ala Gly Ser Gly Val Gly Val Pro Gly Val Gly
            20              25              30

Val Pro Gly Val Gly Val Pro Gly Val Gly Val Pro Gly Lys Gly Val
            35              40              45

Pro Gly Val Gly Val Pro Gly Val Gly Val Pro Gly Val Gly Val Pro
    50              55              60
```

(2) INFORMATION FOR SEQ ID NO:86:

(i) SEQUENCE CHARACTERISTICS:
(A) LENGTH: 64 amino acids
(B) TYPE: amino acid
(C) STRANDEDNESS: unknown
(D) TOPOLOGY: unknown (ii) MOLECULE TYPE: protein (xi) SEQUENCE DESCRIPTION: SEQ ID NO:86:

```
Gly Ala Gly Ala Gly Ser Gly Ala Gly Ala Gly Ser Gly Ala Gly Ala
1               5                   10                  15
```

```
        Gly  Ser  Gly  Ala  Gly  Ala  Gly  Ser  Gly  Val  Gly  Val  Pro  Gly  Val  Gly
                       2 0                      2 5                      3 0

Val  Pro  Gly  Val  Gly  Val  Pro  Gly  Val  Gly  Val  Pro  Gly  Glu  Gly  Val
                       3 5                      4 0                      4 5

Pro  Gly  Val  Gly  Val  Pro  Gly  Val  Gly  Val  Pro  Gly  Val  Gly  Val  Pro
                  5 0                      5 5                      6 0
```

( 2 ) INFORMATION FOR SEQ ID NO:87:

( i ) SEQUENCE CHARACTERISTICS:
        ( A ) LENGTH: 31 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:87:

```
CTGGAGCGGG  TGCCTGCATG  TACATCCGAG  T                                    3 1
```

( 2 ) INFORMATION FOR SEQ ID NO:88:

( i ) SEQUENCE CHARACTERISTICS:
        ( A ) LENGTH: 35 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:88:

```
ACTCGGATGT  ACATGCAGGC  ACCCGCTCCA  GAGCC                                3 5
```

( 2 ) INFORMATION FOR SEQ ID NO:89:

( i ) SEQUENCE CHARACTERISTICS:
        ( A ) LENGTH: 192 base pairs
        ( B ) TYPE: nucleic acid
        ( C ) STRANDEDNESS: unknown
        ( D ) TOPOLOGY: unknown ( i i ) MOLECULE TYPE: DNA (genomic)

( i x ) FEATURE:
        ( A ) NAME/KEY: CDS
        ( B ) LOCATION: 1..192

( x i ) SEQUENCE DESCRIPTION: SEQ ID NO:89:

```
GGT  GCC  GGT  TCT  GGA  GCT  GGC  GCG  GGC  TCT  GGA  GTA  GGT  GTG  CCA  GGT        4 8
Gly  Ala  Gly  Ser  Gly  Ala  Gly  Ala  Gly  Ser  Gly  Val  Gly  Val  Pro  Gly
  1                 5                           1 0                    1 5

GTA  GGA  GTT  CCG  GGT  GTA  GGC  GTT  CCG  GGA  GTT  GGT  GTA  CCT  GGA  GTG        9 6
Val  Gly  Val  Pro  Gly  Val  Gly  Val  Pro  Gly  Val  Gly  Val  Pro  Gly  Val
                2 0                      2 5                      3 0

GGT  GTT  CCA  GGC  GTA  GGT  GTG  CCC  GGG  GTA  GGA  GTA  CCA  GGG  GTA  GGC       1 4 4
Gly  Val  Pro  Gly  Val  Gly  Val  Pro  Gly  Val  Gly  Val  Pro  Gly  Val  Gly
                3 5                      4 0                      4 5

GTC  CCT  GGA  GCG  GGT  GCT  GGT  AGC  GGC  GCA  GGC  GCG  GGC  TCT  GGA  GCG       1 9 2
Val  Pro  Gly  Ala  Gly  Ala  Gly  Ser  Gly  Ala  Gly  Ala  Gly  Ser  Gly  Ala
                5 0                      5 5                      6 0
```

( 2 ) INFORMATION FOR SEQ ID NO:90:

( i ) SEQUENCE CHARACTERISTICS:
        ( A ) LENGTH: 64 amino acids
        ( B ) TYPE: amino acid
        ( D ) TOPOLOGY: linear (  i i  ) MOLECULE TYPE: protein (  x i  ) SEQUENCE DESCRIPTION: SEQ ID NO:90:

| Gly | Ala | Gly | Ser | Gly | Ala | Gly | Ala | Gly | Ser | Gly | Val | Gly | Val | Pro | Gly |
|---|---|---|---|---|---|---|---|---|---|---|---|---|---|---|---|
| 1 | | | | 5 | | | | | 10 | | | | | 15 | |
| Val | Gly | Val | Pro | Gly | Val | Gly | Val | Pro | Gly | Val | Gly | Val | Pro | Gly | Val |
| | | | 20 | | | | | 25 | | | | | 30 | | |
| Gly | Val | Pro | Gly | Val | Gly | Val | Pro | Gly | Val | Gly | Val | Pro | Gly | Val | Gly |
| | | 35 | | | | | 40 | | | | | 45 | | | |
| Val | Pro | Gly | Ala | Gly | Ala | Gly | Ser | Gly | Ala | Gly | Ala | Gly | Ser | Gly | Ala |
| | | 50 | | | | 55 | | | | | 60 | | | | |

( 2 ) INFORMATION FOR SEQ ID NO:91:

(  i  ) SEQUENCE CHARACTERISTICS:
        ( A ) LENGTH: 202 base pairs
        ( B ) TYPE: nucleic acid
        ( C ) STRANDEDNESS: unknown
        ( D ) TOPOLOGY: unknown (  i i  ) MOLECULE TYPE: DNA (genomic)

(  x i  ) SEQUENCE DESCRIPTION: SEQ ID NO:91:

| ATGGCAGCGA | AAGGGGACCG | GGCTCTGGTG | TTGGAGTGCC | AGGTGTCGGT | GTTCCGGGTG | 60 |
|---|---|---|---|---|---|---|
| TAGGCGTTCC | GGGAGTTGGT | GTACCTGGAR | AAGGTGTTCC | GGGGGTAGGT | GTGCCGGGCG | 120 |
| TTGGAGTACC | AGGTGTAGGC | GTCCCGGGAG | CGGGTGCTGG | TAGCGGCGCA | GGCGCGGGCT | 180 |
| CTTTCCGCTA | AAGTCCTGCC | GT | | | | 202 |

( 2 ) INFORMATION FOR SEQ ID NO:92:

(  i  ) SEQUENCE CHARACTERISTICS:
        ( A ) LENGTH: 192 base pairs
        ( B ) TYPE: nucleic acid
        ( C ) STRANDEDNESS: unknown
        ( D ) TOPOLOGY: unknown (  i i  ) MOLECULE TYPE: DNA (genomic)

(  i x  ) FEATURE:
        ( A ) NAME/KEY: CDS
        ( B ) LOCATION: 1..192

(  x i  ) SEQUENCE DESCRIPTION: SEQ ID NO:92:

| GGT | GCC | GGT | TCT | GGA | GCT | GGC | GCG | GGC | TCT | GGT | GTT | GGA | GTG | CCA | GGT | 48 |
|---|---|---|---|---|---|---|---|---|---|---|---|---|---|---|---|---|
| Gly | Ala | Gly | Ser | Gly | Ala | Gly | Ala | Gly | Ser | Gly | Val | Gly | Val | Pro | Gly | |
| 1 | | | | 5 | | | | | 10 | | | | | 15 | | |
| GTC | GGT | GTT | CCG | GGT | GTA | GGC | GTT | CCG | GGA | GTT | GGT | GTA | CCT | GGA | AAA | 96 |
| Val | Gly | Val | Pro | Gly | Val | Gly | Val | Pro | Gly | Val | Gly | Val | Pro | Gly | Lys | |
| | | | 20 | | | | | 25 | | | | | 30 | | | |
| GGT | GTT | CCG | GGG | GTA | GGT | GTG | CCG | GGC | GTT | GGA | GTA | CCA | GGT | GTA | GGC | 144 |
| Gly | Val | Pro | Gly | Val | Gly | Val | Pro | Gly | Val | Gly | Val | Pro | Gly | Val | Gly | |
| | | 35 | | | | | 40 | | | | | 45 | | | | |
| GTC | CCG | GGA | GCG | GGT | GCT | GGT | AGC | GGC | GCA | GGC | GCG | GGC | TCT | GGA | GCG | 192 |
| Val | Pro | Gly | Ala | Gly | Ala | Gly | Ser | Gly | Ala | Gly | Ala | Gly | Ser | Gly | Ala | |
| | | 50 | | | | 55 | | | | | 60 | | | | | |

( 2 ) INFORMATION FOR SEQ ID NO:93:

(  i  ) SEQUENCE CHARACTERISTICS:
        ( A ) LENGTH: 64 amino acids
        ( B ) TYPE: amino acid
        ( D ) TOPOLOGY: linear (  i i  ) MOLECULE TYPE: protein ( x i ) SEQUENCE DESCRIPTION: SEQ ID NO:93:

| Gly | Ala | Gly | Ser | Gly | Ala | Gly | Ala | Gly | Ser | Gly | Val | Gly | Val | Pro | Gly |
|---|---|---|---|---|---|---|---|---|---|---|---|---|---|---|---|
| 1 | | | | 5 | | | | | 10 | | | | | 15 | |

| Val | Gly | Val | Pro | Gly | Val | Gly | Val | Pro | Gly | Val | Gly | Val | Pro | Gly | Lys |
|---|---|---|---|---|---|---|---|---|---|---|---|---|---|---|---|
| | | | 20 | | | | | 25 | | | | | 30 | | |

| Gly | Val | Pro | Gly | Val | Gly | Val | Pro | Gly | Val | Gly | Val | Pro | Gly | Val | Gly |
|---|---|---|---|---|---|---|---|---|---|---|---|---|---|---|---|
| | | 35 | | | | | 40 | | | | | 45 | | | |

| Val | Pro | Gly | Ala | Gly | Ala | Gly | Ser | Gly | Ala | Gly | Ala | Gly | Ser | Gly | Ala |
|---|---|---|---|---|---|---|---|---|---|---|---|---|---|---|---|
| | 50 | | | | | 55 | | | | | 60 | | | | |

( 2 ) INFORMATION FOR SEQ ID NO:94:

( i ) SEQUENCE CHARACTERISTICS:
( A ) LENGTH: 192 base pairs
( B ) TYPE: nucleic acid
( C ) STRANDEDNESS: unknown
( D ) TOPOLOGY: unknown ( i i ) MOLECULE TYPE: DNA (genomic)

( i x ) FEATURE:
( A ) NAME/KEY: CDS
( B ) LOCATION: 1..192

( x i ) SEQUENCE DESCRIPTION: SEQ ID NO:94:

| GGT | GCC | GGT | TCT | GGA | GCT | GGC | GCG | GGC | TCT | GGT | GTT | GGA | GTG | CCA | GGT | 48 |
|---|---|---|---|---|---|---|---|---|---|---|---|---|---|---|---|---|
| Gly | Ala | Gly | Ser | Gly | Ala | Gly | Ala | Gly | Ser | Gly | Val | Gly | Val | Pro | Gly | |
| 1 | | | | 5 | | | | | 10 | | | | | 15 | | |

| GTC | GGT | GTT | CCG | GGT | GTA | GGC | GTT | CCG | GGA | GTT | GGT | GTA | CCT | GGA | GAA | 96 |
|---|---|---|---|---|---|---|---|---|---|---|---|---|---|---|---|---|
| Val | Gly | Val | Pro | Gly | Val | Gly | Val | Pro | Gly | Val | Gly | Val | Pro | Gly | Glu | |
| | | | 20 | | | | | 25 | | | | | 30 | | | |

| GGT | GTT | CCG | GGG | GTA | GGT | GTG | CCG | GGC | GTT | GGA | GTA | CCA | GGT | GTA | GGC | 144 |
|---|---|---|---|---|---|---|---|---|---|---|---|---|---|---|---|---|
| Gly | Val | Pro | Gly | Val | Gly | Val | Pro | Gly | Val | Gly | Val | Pro | Gly | Val | Gly | |
| | | 35 | | | | | 40 | | | | | 45 | | | | |

| GTC | CCG | GGA | GCG | GGT | GCT | GGT | AGC | GGC | GCA | GGC | GCG | GGC | TCT | GGA | GCG | 192 |
|---|---|---|---|---|---|---|---|---|---|---|---|---|---|---|---|---|
| Val | Pro | Gly | Ala | Gly | Ala | Gly | Ser | Gly | Ala | Gly | Ala | Gly | Ser | Gly | Ala | |
| | 50 | | | | | 55 | | | | | 60 | | | | | |

( 2 ) INFORMATION FOR SEQ ID NO:95:

( i ) SEQUENCE CHARACTERISTICS:
( A ) LENGTH: 64 amino acids
( B ) TYPE: amino acid
( D ) TOPOLOGY: linear ( i i ) MOLECULE TYPE: protein ( x i ) SEQUENCE DESCRIPTION: SEQ ID NO:95:

| Gly | Ala | Gly | Ser | Gly | Ala | Gly | Ala | Gly | Ser | Gly | Val | Gly | Val | Pro | Gly |
|---|---|---|---|---|---|---|---|---|---|---|---|---|---|---|---|
| 1 | | | | 5 | | | | | 10 | | | | | 15 | |

| Val | Gly | Val | Pro | Gly | Val | Gly | Val | Pro | Gly | Val | Gly | Val | Pro | Gly | Glu |
|---|---|---|---|---|---|---|---|---|---|---|---|---|---|---|---|
| | | | 20 | | | | | 25 | | | | | 30 | | |

| Gly | Val | Pro | Gly | Val | Gly | Val | Pro | Gly | Val | Gly | Val | Pro | Gly | Val | Gly |
|---|---|---|---|---|---|---|---|---|---|---|---|---|---|---|---|
| | | 35 | | | | | 40 | | | | | 45 | | | |

| Val | Pro | Gly | Ala | Gly | Ala | Gly | Ser | Gly | Ala | Gly | Ala | Gly | Ser | Gly | Ala |
|---|---|---|---|---|---|---|---|---|---|---|---|---|---|---|---|
| | 50 | | | | | 55 | | | | | 60 | | | | |

( 2 ) INFORMATION FOR SEQ ID NO:96:

( i ) SEQUENCE CHARACTERISTICS:
( A ) LENGTH: 884 amino acids
( B ) TYPE: amino acid
( C ) STRANDEDNESS: unknown
( D ) TOPOLOGY: unknown ( i i ) MOLECULE TYPE: protein ( x i ) SEQUENCE DESCRIPTION: SEQ ID NO:96:

```
Met Asp Pro Val Val Leu Gln Arg Arg Asp Trp Glu Asn Pro Gly Val
1               5                   10                  15

Thr Gln Leu Asn Arg Leu Ala Ala His Pro Pro Phe Ala Ser Asp Pro
            20                  25                  30

Met Gly Ala Gly Ser Gly Ala Gly Ala Gly Ser Gly Val Gly Val Pro
        35                  40                  45

Gly Val Gly Val Pro Gly Val Gly Val Pro Gly Val Gly Val Pro Gly
    50                  55                  60

Lys Gly Val Pro Gly Val Gly Val Pro Gly Val Gly Val Pro Gly Val
65                  70                  75                  80

Gly Val Pro Gly Ala Gly Ala Gly Ser Gly Ala Gly Ala Gly Ser Gly
            85                  90                  95

Ala Gly Ala Gly Ser Gly Ala Gly Ala Gly Ser Gly Val Gly Val Pro
            100                 105                 110

Gly Val Gly Val Pro Gly Val Gly Val Pro Gly Val Gly Val Pro Gly
        115                 120                 125

Lys Gly Val Pro Gly Val Gly Val Pro Gly Val Gly Val Pro Gly Val
    130                 135                 140

Gly Val Pro Gly Ala Gly Ala Gly Ser Gly Ala Gly Ala Gly Ser Gly
145                 150                 155                 160

Ala Gly Ala Gly Ser Gly Ala Gly Ala Gly Ser Gly Val Gly Val Pro
                165                 170                 175

Gly Val Gly Val Pro Gly Val Gly Val Pro Gly Val Gly Val Pro Gly
            180                 185                 190

Lys Gly Val Pro Gly Val Gly Val Pro Gly Val Gly Val Pro Gly Val
        195                 200                 205

Gly Val Pro Gly Ala Gly Ala Gly Ser Gly Ala Gly Ala Gly Ser Gly
    210                 215                 220

Ala Gly Ala Gly Ser Gly Ala Gly Ala Gly Ser Gly Val Gly Val Pro
225                 230                 235                 240

Gly Val Gly Val Pro Gly Val Gly Val Pro Gly Val Gly Val Pro Gly
                245                 250                 255

Lys Gly Val Pro Gly Val Gly Val Pro Gly Val Gly Val Pro Gly Val
            260                 265                 270

Gly Val Pro Gly Ala Gly Ala Gly Ser Gly Ala Gly Ala Gly Ser Gly
        275                 280                 285

Ala Gly Ala Gly Ser Gly Ala Gly Ala Gly Ser Gly Val Gly Val Pro
    290                 295                 300

Gly Val Gly Val Pro Gly Val Gly Val Pro Gly Val Gly Val Pro Gly
305                 310                 315                 320

Lys Gly Val Pro Gly Val Gly Val Pro Gly Val Gly Val Pro Gly Val
                325                 330                 335

Gly Val Pro Gly Ala Gly Ala Gly Ser Gly Ala Gly Ala Gly Ser Gly
            340                 345                 350

Ala Gly Ala Gly Ser Gly Ala Gly Ala Gly Ser Gly Val Gly Val Pro
        355                 360                 365

Gly Val Gly Val Pro Gly Val Gly Val Pro Gly Val Gly Val Pro Gly
    370                 375                 380

Lys Gly Val Pro Gly Val Gly Val Pro Gly Val Gly Val Pro Gly Val
385                 390                 395                 400

Gly Val Pro Gly Ala Gly Ala Gly Ser Gly Ala Gly Ala Gly Ser Gly
```

-continued

```
                        405                         410                         415
Ala  Gly  Ala  Gly  Ser  Gly  Ala  Gly  Gly  Ser  Gly  Val  Gly  Val  Pro
               420                      425                      430
Gly  Val  Gly  Val  Pro  Gly  Val  Gly  Val  Pro  Gly  Val  Gly  Val  Pro  Gly
               435                      440                      445
Lys  Gly  Val  Pro  Gly  Val  Gly  Val  Pro  Gly  Val  Gly  Val  Pro  Gly  Val
     450                      455                      460
Gly  Val  Pro  Gly  Ala  Gly  Ala  Gly  Ser  Gly  Ala  Gly  Ala  Gly  Ser  Gly
465                      470                      475                      480
Ala  Gly  Ala  Gly  Ser  Gly  Ala  Gly  Ala  Gly  Ser  Gly  Val  Gly  Val  Pro
               485                      490                      495
Gly  Val  Gly  Val  Pro  Gly  Val  Gly  Val  Pro  Gly  Val  Gly  Val  Pro  Gly
               500                      505                      510
Lys  Gly  Val  Pro  Gly  Val  Gly  Val  Pro  Gly  Val  Gly  Val  Pro  Gly  Val
     515                      520                      525
Gly  Val  Pro  Gly  Ala  Gly  Ala  Gly  Ser  Gly  Ala  Gly  Ala  Gly  Ser  Gly
     530                      535                      540
Ala  Gly  Ala  Gly  Ser  Gly  Ala  Gly  Ala  Gly  Ser  Gly  Val  Gly  Val  Pro
545                      550                      555                      560
Gly  Val  Gly  Val  Pro  Gly  Val  Gly  Val  Pro  Gly  Val  Gly  Val  Pro  Gly
               565                      570                      575
Lys  Gly  Val  Pro  Gly  Val  Gly  Val  Pro  Gly  Val  Gly  Val  Pro  Gly  Val
               580                      585                      590
Gly  Val  Pro  Gly  Ala  Gly  Ala  Gly  Ser  Gly  Ala  Gly  Ala  Gly  Ser  Gly
          595                      600                      605
Ala  Gly  Ala  Gly  Ser  Gly  Ala  Gly  Ala  Gly  Ser  Gly  Val  Gly  Val  Pro
     610                      615                      620
Gly  Val  Gly  Val  Pro  Gly  Val  Gly  Val  Pro  Gly  Val  Gly  Val  Pro  Gly
625                      630                      635                      640
Lys  Gly  Val  Pro  Gly  Val  Gly  Val  Pro  Gly  Val  Gly  Val  Pro  Gly  Val
               645                      650                      655
Gly  Val  Pro  Gly  Ala  Gly  Ala  Gly  Ser  Gly  Ala  Gly  Ala  Gly  Ser  Gly
               660                      665                      670
Ala  Gly  Ala  Gly  Ser  Gly  Ala  Gly  Ala  Gly  Ser  Gly  Val  Gly  Val  Pro
     675                      680                      685
Gly  Val  Gly  Val  Pro  Gly  Val  Gly  Val  Pro  Gly  Val  Gly  Val  Pro  Gly
     690                      695                      700
Lys  Gly  Val  Pro  Gly  Val  Gly  Val  Pro  Gly  Val  Gly  Val  Pro  Gly  Val
705                      710                      715                      720
Gly  Val  Pro  Gly  Ala  Gly  Ala  Gly  Ser  Gly  Ala  Gly  Ala  Gly  Ser  Gly
               725                      730                      735
Ala  Gly  Ala  Gly  Ser  Gly  Ala  Gly  Ala  Gly  Ser  Gly  Val  Gly  Val  Pro
               740                      745                      750
Gly  Val  Gly  Val  Pro  Gly  Val  Gly  Val  Pro  Gly  Val  Gly  Val  Pro  Gly
          755                      760                      765
Lys  Gly  Val  Pro  Gly  Val  Gly  Val  Pro  Gly  Val  Gly  Val  Pro  Gly  Val
     770                      775                      780
Gly  Val  Pro  Gly  Ala  Gly  Ala  Gly  Ser  Gly  Ala  Gly  Ala  Gly  Ser  Gly
785                      790                      795                      800
Ala  Gly  Ala  Gly  Ser  Gly  Ala  Gly  Ala  Gly  Ser  Gly  Val  Gly  Val  Pro
               805                      810                      815
Gly  Val  Gly  Val  Pro  Gly  Val  Gly  Val  Pro  Gly  Val  Gly  Val  Pro  Gly
               820                      825                      830
```

```
    Lys  Gly  Val  Pro  Gly  Val  Gly  Val  Pro  Gly  Val  Gly  Val  Pro  Gly  Val
              835                 840                 845

Gly  Val  Pro  Gly  Ala  Gly  Ala  Gly  Ser  Gly  Ala  Gly  Ala  Gly  Ser  Gly
              850                 855                 860

Ala  Gly  Ala  Met  Asp  Pro  Gly  Arg  Tyr  Gln  Asp  Leu  Arg  Ser  His  His
    865                      870                 875                           880

His  His  His  His
```

( 2 ) INFORMATION FOR SEQ ID NO:97:

( i ) SEQUENCE CHARACTERISTICS:
        ( A ) LENGTH: 4 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:97:

```
    Pro  Leu  Gly  Pro
    1
```

( 2 ) INFORMATION FOR SEQ ID NO:98:

( i ) SEQUENCE CHARACTERISTICS:
        ( A ) LENGTH: 22 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:98:

```
    Gly  Ala  Gly  Ala  Gly  Ser  Gly  Val  Gly  Val  Pro  Leu  Gly  Pro  Leu  Gly
    1                   5                   10                  15

Pro  Gly  Val  Gly  Val  Pro
                    20
```

( 2 ) INFORMATION FOR SEQ ID NO:99:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:99:

```
TGCTTAGTGA  TGGTGATGGT  GATGAGATCG  AA                                              3 2
```

( 2 ) INFORMATION FOR SEQ ID NO:100:

( i ) SEQUENCE CHARACTERISTICS:
        ( A ) LENGTH: 93 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:100:

```
ATGGCAGCGA  AAGGGACCG   GTGCCGGCGC  AGGTAGCGGA  GCCGGTGCGG  GCTCAAAAAG              6 0

GGCTCTGGTG  CCTTTCCGCT  AAAGTCCTGC  CGT                                             9 3
```

( 2 ) INFORMATION FOR SEQ ID NO:101:

( i ) SEQUENCE CHARACTERISTICS:
- ( A ) LENGTH: 162 base pairs
- ( B ) TYPE: nucleic acid
- ( C ) STRANDEDNESS: unknown
- ( D ) TOPOLOGY: unknown ( i i ) MOLECULE TYPE: DNA (genomic)

( x i ) SEQUENCE DESCRIPTION: SEQ ID NO:101:

```
GGGCTCTGGT GTTGGAGTGC CAGGTGTCGG TGTTCCGGGT GTAGGCGTTC CGGGAGTTGG        60
TGTACCTGGA AAAGGTGTTC CGGGGGTAGG TGTGCCGGGC GTTGGAGTAC CAGGTGTAGG       120
CGTCCCGGGA GCGGGTGCTG GTAGCGGCGC AGGCGCGGGC TC                         162
```

( 2 ) INFORMATION FOR SEQ ID NO:102:

( i ) SEQUENCE CHARACTERISTICS:
- ( A ) LENGTH: 54 amino acids
- ( B ) TYPE: amino acid
- ( C ) STRANDEDNESS: unknown
- ( D ) TOPOLOGY: unknown ( i i ) MOLECULE TYPE: protein ( x i ) SEQUENCE DESCRIPTION: SEQ ID NO:102:

```
Gly Ser Gly Val Gly Val Pro Gly Val Gly Val Pro Gly Val Gly Val
1               5                   10                  15
Pro Gly Val Gly Val Pro Gly Lys Gly Val Pro Gly Val Gly Val Pro
                20                  25                  30
Gly Val Gly Val Pro Gly Val Gly Val Pro Gly Ala Gly Ala Gly Ser
                35                  40                  45
Gly Ala Gly Ala Gly Ser
                50
```

( 2 ) INFORMATION FOR SEQ ID NO:103:

( i ) SEQUENCE CHARACTERISTICS:
- ( A ) LENGTH: 1002 amino acids
- ( B ) TYPE: amino acid
- ( C ) STRANDEDNESS: unknown
- ( D ) TOPOLOGY: unknown ( i i ) MOLECULE TYPE: protein ( x i ) SEQUENCE DESCRIPTION: SEQ ID NO:103:

```
Met Asp Pro Val Val Leu Gln Arg Arg Asp Trp Glu Asn Pro Gly Val
1               5                   10                  15
Thr Gln Leu Asn Arg Leu Ala Ala His Pro Pro Phe Ala Ser Asp Pro
                20                  25                  30
Met Gly Ala Gly Ala Gly Ser Gly Ala Gly Ala Gly Ser Gly Val Gly
                35                  40                  45
Val Pro Gly Val Gly Val Pro Gly Val Gly Val Pro Gly Val Gly Val
                50                  55                  60
Pro Gly Lys Gly Val Pro Gly Val Gly Val Pro Gly Val Gly Val Pro
65                  70                  75                  80
Gly Val Gly Val Pro Gly Ala Gly Ala Gly Ser Gly Ala Gly Ala Gly
                85                  90                  95
Ser Gly Val Gly Val Pro Gly Val Gly Val Pro Gly Val Gly Val Pro
                100                 105                 110
Gly Val Gly Val Pro Gly Lys Gly Val Pro Gly Val Gly Val Pro Gly
                115                 120                 125
Val Gly Val Pro Gly Val Gly Val Pro Gly Ala Gly Ala Gly Ser Gly
```

-continued

```
                    130                           135                           140
Ala   Gly   Ala   Gly   Ser   Gly   Val   Gly   Val   Pro   Gly   Val   Gly   Val   Pro   Gly
145                           150                           155                           160
Val   Gly   Val   Pro   Gly   Val   Gly   Val   Pro   Gly   Lys   Gly   Val   Pro   Gly   Val
                              165                           170                           175
Gly   Val   Pro   Gly   Val   Gly   Val   Pro   Gly   Val   Gly   Val   Pro   Gly   Ala   Gly
                  180                           185                           190
Ala   Gly   Ser   Gly   Ala   Gly   Ala   Gly   Ser   Gly   Val   Gly   Val   Pro   Gly   Val
            195                           200                           205
Gly   Val   Pro   Gly   Val   Gly   Val   Pro   Gly   Val   Gly   Val   Pro   Gly   Lys   Gly
            210                           215                           220
Val   Pro   Gly   Val   Gly   Val   Pro   Gly   Val   Gly   Val   Pro   Gly   Val   Gly   Val
225                           230                           235                           240
Pro   Gly   Ala   Gly   Ala   Gly   Ser   Gly   Ala   Gly   Ala   Gly   Ser   Gly   Val   Gly
                        245                           250                           255
Val   Pro   Gly   Val   Gly   Val   Pro   Gly   Val   Gly   Val   Pro   Gly   Val   Gly   Val
                  260                           265                           270
Pro   Gly   Lys   Gly   Val   Pro   Gly   Val   Gly   Val   Pro   Gly   Val   Gly   Val   Pro
            275                           280                           285
Gly   Val   Gly   Val   Pro   Gly   Ala   Gly   Ala   Gly   Ser   Gly   Ala   Gly   Ala   Gly
            290                           295                           300
Ser   Gly   Val   Gly   Val   Pro   Gly   Val   Gly   Val   Pro   Gly   Val   Gly   Val   Pro
305                           310                           315                           320
Gly   Val   Gly   Val   Pro   Gly   Lys   Gly   Val   Pro   Gly   Val   Gly   Val   Pro   Gly
                        325                           330                           335
Val   Gly   Val   Pro   Gly   Val   Gly   Val   Pro   Gly   Ala   Gly   Ala   Gly   Ser   Gly
                  340                           345                           350
Ala   Gly   Ala   Gly   Ser   Gly   Val   Gly   Val   Pro   Gly   Val   Gly   Val   Pro   Gly
            355                           360                           365
Val   Gly   Val   Pro   Gly   Val   Gly   Val   Pro   Gly   Lys   Gly   Val   Pro   Gly   Val
            370                           375                           380
Gly   Val   Pro   Gly   Val   Gly   Val   Pro   Gly   Val   Gly   Val   Pro   Gly   Ala   Gly
385                           390                           395                           400
Ala   Gly   Ser   Gly   Ala   Gly   Ala   Gly   Ser   Gly   Val   Gly   Val   Pro   Gly   Val
                        405                           410                           415
Gly   Val   Pro   Gly   Val   Gly   Val   Pro   Gly   Val   Gly   Val   Pro   Gly   Lys   Gly
                  420                           425                           430
Val   Pro   Gly   Val   Gly   Val   Pro   Gly   Val   Gly   Val   Pro   Gly   Val   Gly   Val
            435                           440                           445
Pro   Gly   Ala   Gly   Ala   Gly   Ser   Gly   Ala   Gly   Ala   Gly   Ser   Gly   Val   Gly
            450                           455                           460
Val   Pro   Gly   Val   Gly   Val   Pro   Gly   Val   Gly   Val   Pro   Gly   Val   Gly   Val
465                           470                           475                           480
Pro   Gly   Lys   Gly   Val   Pro   Gly   Val   Gly   Val   Pro   Gly   Val   Gly   Val   Pro
                        485                           490                           495
Gly   Val   Gly   Val   Pro   Gly   Ala   Gly   Ala   Gly   Ser   Gly   Ala   Gly   Ala   Gly
                  500                           505                           510
Ser   Gly   Val   Gly   Val   Pro   Gly   Val   Gly   Val   Pro   Gly   Val   Gly   Val   Pro
            515                           520                           525
Gly   Val   Gly   Val   Pro   Gly   Lys   Gly   Val   Pro   Gly   Val   Gly   Val   Pro   Gly
            530                           535                           540
Val   Gly   Val   Pro   Gly   Val   Gly   Val   Pro   Gly   Ala   Gly   Ala   Gly   Ser   Gly
545                           550                           555                           560
```

-continued

```
Ala Gly Ala Gly Ser Gly Val Gly Val Pro Gly Val Gly Val Pro Gly
             565             570             575
Val Gly Val Pro Gly Val Gly Val Pro Gly Lys Gly Val Pro Gly Val
             580             585             590
Gly Val Pro Gly Val Gly Val Pro Gly Val Gly Val Pro Gly Ala Gly
             595             600             605
Ala Gly Ser Gly Ala Gly Ala Gly Ser Gly Val Gly Val Pro Gly Val
             610             615             620
Gly Val Pro Gly Val Gly Val Pro Gly Val Gly Val Pro Gly Lys Gly
625             630             635             640
Val Pro Gly Val Gly Val Pro Gly Val Gly Val Pro Gly Val Gly Val
             645             650             655
Pro Gly Ala Gly Ala Gly Ser Gly Ala Gly Ala Gly Ser Gly Val Gly
             660             665             670
Val Pro Gly Val Gly Val Pro Gly Val Gly Val Pro Gly Val Gly Val
             675             680             685
Pro Gly Lys Gly Val Pro Gly Val Gly Val Pro Gly Val Gly Val Pro
             690             695             700
Gly Val Gly Val Pro Gly Ala Gly Ala Gly Ser Gly Ala Gly Ala Gly
705             710             715             720
Ser Gly Val Gly Val Pro Gly Val Gly Val Pro Gly Val Gly Val Pro
             725             730             735
Gly Val Gly Val Pro Gly Lys Gly Val Pro Gly Val Gly Val Pro Gly
             740             745             750
Val Gly Val Pro Gly Val Gly Val Pro Gly Ala Gly Ala Gly Ser Gly
             755             760             765
Ala Gly Ala Gly Ser Gly Val Gly Val Pro Gly Val Gly Val Pro Gly
             770             775             780
Val Gly Val Pro Gly Val Gly Val Pro Gly Lys Gly Val Pro Gly Val
785             790             795             800
Gly Val Pro Gly Val Gly Val Pro Gly Val Gly Val Pro Gly Ala Gly
             805             810             815
Ala Gly Ser Gly Ala Gly Ala Gly Ser Gly Val Gly Val Pro Gly Val
             820             825             830
Gly Val Pro Gly Val Gly Val Pro Gly Val Gly Val Pro Gly Lys Gly
             835             840             845
Val Pro Gly Val Gly Val Pro Gly Val Gly Val Pro Gly Val Gly Val
             850             855             860
Pro Gly Ala Gly Ala Gly Ser Gly Ala Gly Ala Gly Ser Gly Val Gly
865             870             875             880
Val Pro Gly Val Gly Val Pro Gly Val Gly Val Pro Gly Val Gly Val
             885             890             895
Pro Gly Lys Gly Val Pro Gly Val Gly Val Pro Gly Val Gly Val Pro
             900             905             910
Gly Val Gly Val Pro Gly Ala Gly Ala Gly Ser Gly Ala Gly Ala Gly
             915             920             925
Ser Gly Val Gly Val Pro Gly Val Gly Val Pro Gly Val Gly Val Pro
             930             935             940
Gly Val Gly Val Pro Gly Lys Gly Val Pro Gly Val Gly Val Pro Gly
945             950             955             960
Val Gly Val Pro Gly Val Gly Val Pro Gly Ala Gly Ala Gly Ser Gly
             965             970             975
Ala Gly Ala Gly Ser Gly Ala Gly Ala Met Asp Pro Gly Arg Tyr Gln
             980             985             990
```

```
            Asp  Leu  Arg  Ser  His  His  His  His  His
                           995                      1000
```

(2) INFORMATION FOR SEQ ID NO:104:

(i) SEQUENCE CHARACTERISTICS:
        (A) LENGTH: 378 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:104:

```
Met  Asp  Pro  Val  Val  Leu  Gln  Arg  Arg  Asp  Trp  Glu  Asn  Pro  Gly  Val
1                   5                        10                       15

Thr  Gln  Leu  Asn  Arg  Leu  Ala  Ala  His  Pro  Pro  Phe  Ala  Ser  Asp  Pro
               20                  25                       30

Met  Gly  Ala  Gly  Ala  Gly  Ser  Gly  Ala  Gly  Ala  Gly  Ser  Gly  Val  Gly
          35                  40                       45

Val  Pro  Gly  Val  Gly  Val  Pro  Gly  Val  Gly  Val  Pro  Gly  Val  Gly  Val
     50                       55                       60

Pro  Gly  Lys  Gly  Val  Pro  Gly  Val  Gly  Val  Pro  Gly  Val  Gly  Val  Pro
65                       70                       75                       80

Gly  Val  Gly  Val  Pro  Gly  Ala  Gly  Ala  Gly  Ser  Gly  Ala  Gly  Ala  Gly
                    85                       90                       95

Ser  Gly  Val  Gly  Val  Pro  Gly  Val  Gly  Val  Pro  Gly  Val  Gly  Val  Pro
               100                      105                      110

Gly  Val  Gly  Val  Pro  Gly  Lys  Gly  Val  Pro  Gly  Val  Gly  Val  Pro  Gly
          115                      120                      125

Val  Gly  Val  Pro  Gly  Val  Gly  Val  Pro  Gly  Ala  Gly  Ala  Gly  Ser  Gly
     130                      135                      140

Ala  Gly  Ala  Gly  Ser  Gly  Val  Gly  Val  Pro  Gly  Val  Gly  Val  Pro  Gly
145                      150                      155                      160

Val  Gly  Val  Pro  Gly  Val  Gly  Val  Pro  Gly  Lys  Gly  Val  Pro  Gly  Val
                    165                      170                      175

Gly  Val  Pro  Gly  Val  Gly  Val  Pro  Gly  Val  Gly  Val  Pro  Gly  Ala  Gly
               180                      185                      190

Ala  Gly  Ser  Gly  Ala  Gly  Ala  Gly  Ser  Gly  Val  Gly  Val  Pro  Gly  Val
          195                      200                      205

Gly  Val  Pro  Gly  Val  Gly  Val  Pro  Gly  Val  Gly  Val  Pro  Gly  Lys  Gly
     210                      215                      220

Val  Pro  Gly  Val  Gly  Val  Pro  Gly  Val  Gly  Val  Pro  Gly  Val  Gly  Val
225                      230                      235                      240

Pro  Gly  Ala  Gly  Ala  Gly  Ser  Gly  Ala  Gly  Ala  Gly  Ser  Gly  Val  Gly
                    245                      250                      255

Val  Pro  Gly  Val  Gly  Val  Pro  Gly  Val  Gly  Val  Pro  Gly  Val  Gly  Val
               260                      265                      270

Pro  Gly  Lys  Gly  Val  Pro  Gly  Val  Gly  Val  Pro  Gly  Val  Gly  Val  Pro
          275                      280                      285

Gly  Val  Gly  Val  Pro  Gly  Ala  Gly  Ala  Gly  Ser  Gly  Ala  Gly  Ala  Gly
     290                      295                      300

Ser  Gly  Val  Gly  Val  Pro  Gly  Val  Gly  Val  Pro  Gly  Val  Gly  Val  Pro
305                      310                      315                      320

Gly  Val  Gly  Val  Pro  Gly  Lys  Gly  Val  Pro  Gly  Val  Gly  Val  Pro  Gly
                    325                      330                      335
```

```
      Val  Gly  Val  Pro  Gly  Val  Gly  Val  Pro  Gly  Ala  Gly  Ala  Gly  Ser  Gly
                     340                      345                      350

Ala  Gly  Ala  Gly  Ser  Gly  Ala  Gly  Ala  Met  Asp  Pro  Gly  Arg  Tyr  Gln
                     355                      360                      365

Asp  Leu  Arg  Ser  His  His  His  His  His  His
                     370                      375
```

( 2 ) INFORMATION FOR SEQ ID NO:105:

( i ) SEQUENCE CHARACTERISTICS:
        ( A ) LENGTH: 141 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:105:

```
ATGGCAGCGA   AAGGGGACCG   CCGGTGCGGG   CTCTGGTGTT   GGAGTGCCGC   TGGGTCCTCT        60

TGGCCCAGGT   GTCGGTGTTC   CGGGTGTAGG   CGTTCCGGGA   GTTGGTGTAC   CTGGAAAAGG       120

TTTCCGCTAA   AGTCCTGCCG   T                                                      141
```

( 2 ) INFORMATION FOR SEQ ID NO:106:

( i ) SEQUENCE CHARACTERISTICS:
        ( A ) LENGTH: 181 base pairs
        ( B ) TYPE: nucleic acid
        ( C ) STRANDEDNESS: unknown
        ( D ) TOPOLOGY: unknown ( i i ) MOLECULE TYPE: DNA (genomic)

( x i ) SEQUENCE DESCRIPTION: SEQ ID NO:106:

```
GGGCTCTGGT   GTTGGAGTGC   CGCTGGGTCC   TCTTGGCCCA   GGTGTCGGTG   TTCCGGGTGT        60

AGGCGTTCCG   GGAGTTGGTG   TACCTGGAAA   AGGTGTTCCG   GGGGTAGGTG   TGCCGGGCGT       120

TGGAGTACCA   GGTGTAGGCG   TCCCGGGAGC   GGGTGCTGGT   AGCGGCGCAG   GCGCGGGCTC       180

T                                                                                181
```

( 2 ) INFORMATION FOR SEQ ID NO:107:

( i ) SEQUENCE CHARACTERISTICS:
        ( A ) LENGTH: 60 amino acids
        ( B ) TYPE: amino acid
        ( C ) STRANDEDNESS: unknown
        ( D ) TOPOLOGY: unknown ( i i ) MOLECULE TYPE: protein ( x i ) SEQUENCE DESCRIPTION: SEQ ID NO:107:

```
      Gly  Ser  Gly  Val  Gly  Val  Pro  Leu  Gly  Pro  Leu  Gly  Pro  Gly  Val  Gly
      1                    5                     10                      15

Val  Pro  Gly  Val  Gly  Val  Pro  Gly  Val  Gly  Val  Pro  Gly  Lys  Gly  Val
                     20                      25                      30

Pro  Gly  Val  Gly  Val  Pro  Gly  Val  Gly  Val  Pro  Gly  Val  Gly  Val  Pro
                     35                      40                      45

Gly  Ala  Gly  Ala  Gly  Ser  Gly  Ala  Gly  Ala  Gly  Ser
                     50                      55                      60
```

( 2 ) INFORMATION FOR SEQ ID NO:108:

( i ) SEQUENCE CHARACTERISTICS:
        ( A ) LENGTH: 936 amino acids
        ( B ) TYPE: amino acid -continued ( C ) STRANDEDNESS: unknown
( D ) TOPOLOGY: unknown ( i i ) MOLECULE TYPE: protein ( x i ) SEQUENCE DESCRIPTION: SEQ ID NO:108:

```
Met Asp Pro Val Val Leu Gln Arg Arg Asp Trp Glu Asn Pro Gly Val
 1               5                  10                  15
Thr Gln Leu Asn Arg Leu Ala Ala His Pro Pro Phe Ala Ser Asp Pro
            20                  25                  30
Met Gly Ala Gly Ala Gly Ser Gly Ala Gly Ala Gly Ser Gly Val Gly
         35                  40                  45
Val Pro Leu Gly Pro Leu Gly Pro Gly Val Gly Val Pro Gly Val Gly
     50                  55                  60
Val Pro Gly Val Gly Val Pro Gly Lys Gly Val Pro Gly Val Gly Val
 65                  70                  75                  80
Pro Gly Val Gly Val Pro Gly Val Gly Val Pro Gly Ala Gly Ala Gly
             85                  90                  95
Ser Gly Ala Gly Ala Gly Ser Gly Val Gly Val Pro Leu Gly Pro Leu
            100                 105                 110
Gly Pro Gly Val Gly Val Pro Gly Val Gly Val Pro Gly Val Gly Val
            115                 120                 125
Pro Gly Lys Gly Val Pro Gly Val Gly Val Pro Gly Val Gly Val Pro
        130                 135                 140
Gly Val Gly Val Pro Gly Ala Gly Ala Gly Ser Gly Ala Gly Ala Gly
145                 150                 155                 160
Ser Gly Val Gly Val Pro Leu Gly Pro Leu Gly Pro Gly Val Gly Val
                165                 170                 175
Pro Gly Val Gly Val Pro Gly Val Gly Val Pro Gly Lys Gly Val Pro
            180                 185                 190
Gly Val Gly Val Pro Gly Val Gly Val Pro Gly Val Gly Val Pro Gly
        195                 200                 205
Ala Gly Ala Gly Ser Gly Ala Gly Ala Gly Ser Gly Val Gly Val Pro
        210                 215                 220
Leu Gly Pro Leu Gly Pro Gly Val Gly Val Pro Gly Val Gly Val Pro
225                 230                 235                 240
Gly Val Gly Val Pro Gly Lys Gly Val Pro Gly Val Gly Val Pro Gly
                245                 250                 255
Val Gly Val Pro Gly Val Gly Val Pro Gly Ala Gly Ala Gly Ser Gly
            260                 265                 270
Ala Gly Ala Gly Ser Gly Val Gly Val Pro Leu Gly Pro Leu Gly Pro
        275                 280                 285
Gly Val Gly Val Pro Gly Val Gly Val Pro Gly Val Gly Val Pro Gly
    290                 295                 300
Lys Gly Val Pro Gly Val Gly Val Pro Gly Val Gly Val Pro Gly Val
305                 310                 315                 320
Gly Val Pro Gly Ala Gly Ala Gly Ser Gly Ala Gly Ala Gly Ser Gly
                325                 330                 335
Val Gly Val Pro Leu Gly Pro Leu Gly Pro Gly Val Gly Val Pro Gly
            340                 345                 350
Val Gly Val Pro Gly Val Gly Val Pro Gly Lys Gly Val Pro Gly Val
        355                 360                 365
Gly Val Pro Gly Val Gly Val Pro Gly Val Gly Val Pro Gly Ala Gly
    370                 375                 380
Ala Gly Ser Gly Ala Gly Ala Gly Ser Gly Val Gly Val Pro Leu Gly
```

```
        385                     390                     395                     400
Pro   Leu   Gly   Pro   Gly   Val   Gly   Val   Pro   Val   Gly   Val   Pro   Gly   Val
                        405                     410                     415
Gly   Val   Pro   Gly   Lys   Gly   Val   Pro   Gly   Val   Gly   Val   Pro   Gly   Val   Gly
                        420                     425                     430
Val   Pro   Gly   Val   Gly   Val   Pro   Gly   Ala   Gly   Ala   Gly   Ser   Gly   Ala   Gly
            435                     440                     445
Ala   Gly   Ser   Gly   Val   Gly   Val   Pro   Leu   Gly   Pro   Leu   Gly   Pro   Gly   Val
      450                     455                     460
Gly   Val   Pro   Gly   Val   Gly   Val   Pro   Gly   Val   Gly   Val   Pro   Gly   Lys   Gly
465                     470                     475                     480
Val   Pro   Gly   Val   Gly   Val   Pro   Gly   Val   Gly   Val   Pro   Gly   Val   Gly   Val
                        485                     490                     495
Pro   Gly   Ala   Gly   Ala   Gly   Ser   Gly   Ala   Gly   Ala   Gly   Ser   Gly   Val   Gly
                  500                     505                     510
Val   Pro   Leu   Gly   Pro   Leu   Gly   Pro   Gly   Val   Gly   Val   Pro   Gly   Val   Gly
            515                     520                     525
Val   Pro   Gly   Val   Gly   Val   Pro   Gly   Lys   Gly   Val   Pro   Gly   Val   Gly   Val
      530                     535                     540
Pro   Gly   Val   Gly   Val   Pro   Gly   Val   Gly   Val   Pro   Gly   Ala   Gly   Ala   Gly
545                     550                     555                     560
Ser   Gly   Ala   Gly   Ala   Gly   Ser   Gly   Val   Gly   Val   Pro   Leu   Gly   Pro   Leu
                  565                     570                     575
Gly   Pro   Gly   Val   Gly   Val   Pro   Gly   Val   Gly   Val   Pro   Gly   Val   Gly   Val
                        580                     585                     590
Pro   Gly   Lys   Gly   Val   Pro   Gly   Val   Gly   Val   Pro   Gly   Val   Gly   Val   Pro
            595                     600                     605
Gly   Val   Gly   Val   Pro   Gly   Ala   Gly   Ala   Gly   Ser   Gly   Ala   Gly   Ala   Gly
      610                     615                     620
Ser   Gly   Val   Gly   Val   Pro   Leu   Gly   Pro   Leu   Gly   Pro   Gly   Val   Gly   Val
625                     630                     635                     640
Pro   Gly   Val   Gly   Val   Pro   Gly   Val   Gly   Val   Pro   Gly   Lys   Gly   Val   Pro
                        645                     650                     655
Gly   Val   Gly   Val   Pro   Gly   Val   Gly   Val   Pro   Gly   Val   Gly   Val   Pro   Gly
                        660                     665                     670
Ala   Gly   Ala   Gly   Ser   Gly   Ala   Gly   Ala   Gly   Ser   Gly   Val   Gly   Val   Pro
                  675                     680                     685
Leu   Gly   Pro   Leu   Gly   Pro   Gly   Val   Gly   Val   Pro   Gly   Val   Gly   Val   Pro
            690                     695                     700
Gly   Val   Gly   Val   Pro   Gly   Lys   Gly   Val   Pro   Gly   Val   Gly   Val   Pro   Gly
705                     710                     715                     720
Val   Gly   Val   Pro   Gly   Val   Gly   Val   Pro   Gly   Ala   Gly   Ala   Gly   Ser   Gly
                        725                     730                     735
Ala   Gly   Ala   Gly   Ser   Gly   Val   Gly   Val   Pro   Leu   Gly   Pro   Leu   Gly   Pro
                  740                     745                     750
Gly   Val   Gly   Val   Pro   Gly   Val   Gly   Val   Pro   Gly   Val   Gly   Val   Pro   Gly
            755                     760                     765
Lys   Gly   Val   Pro   Gly   Val   Gly   Val   Pro   Gly   Val   Gly   Val   Pro   Gly   Val
      770                     775                     780
Gly   Val   Pro   Gly   Ala   Gly   Ala   Gly   Ser   Gly   Ala   Gly   Ala   Gly   Ser   Gly
785                     790                     795                     800
Val   Gly   Val   Pro   Leu   Gly   Pro   Leu   Gly   Pro   Gly   Val   Gly   Val   Pro   Gly
                        805                     810                     815
```

```
Val  Gly  Val  Pro  Gly  Val  Gly  Val  Pro  Gly  Lys  Gly  Val  Pro  Gly  Val
               820                          825                    830

Gly  Val  Pro  Gly  Val  Gly  Val  Pro  Gly  Val  Gly  Val  Pro  Gly  Ala  Gly
          835                          840                    845

Ala  Gly  Ser  Gly  Ala  Gly  Ala  Gly  Ser  Gly  Val  Gly  Val  Pro  Leu  Gly
     850                       855                     860

Pro  Leu  Gly  Pro  Gly  Val  Gly  Val  Pro  Gly  Val  Gly  Val  Pro  Gly  Val
865                      870                     875                      880

Gly  Val  Pro  Gly  Lys  Gly  Val  Pro  Gly  Val  Gly  Val  Pro  Gly  Val  Gly
               885                     890                          895

Val  Pro  Gly  Val  Gly  Val  Pro  Gly  Ala  Gly  Ala  Gly  Ser  Gly  Ala  Gly
               900                     905                          910

Ala  Gly  Ser  Gly  Ala  Gly  Ala  Met  Asp  Pro  Gly  Arg  Tyr  Gln  Asp  Leu
          915                      920                      925

Arg  Ser  His  His  His  His  His  His
     930                      935
```